US012303544B2

(12) United States Patent
Winters et al.

(10) Patent No.: US 12,303,544 B2
(45) Date of Patent: *May 20, 2025

(54) CYTOTOXIC AND ANTI-MITOTIC COMPOUNDS, AND METHODS OF USING THE SAME

(71) Applicant: ZYMEWORKS BC INC., Vancouver (CA)

(72) Inventors: Geoffrey C. Winters, Vancouver (CA); Alexander Laurence Mandel, Vancouver (CA); James R. Rich, Vancouver (CA); Bradley John Hedberg, Vancouver (CA); Tom Han Hsiao Hsieh, Vancouver (CA); Elyse Marie Josée Bourque, L'Etang-du-Nord (CA); John Babcook, Vancouver (CA)

(73) Assignee: ZYMEWORKS BC INC., Vancouver (CA)

( * ) Notice: Subject to any disclaimer, the term of this patent is extended or adjusted under 35 U.S.C. 154(b) by 0 days.

This patent is subject to a terminal disclaimer.

(21) Appl. No.: 18/112,402

(22) Filed: Feb. 21, 2023

(65) Prior Publication Data
US 2023/0390354 A1 Dec. 7, 2023

Related U.S. Application Data

(63) Continuation of application No. 16/273,045, filed on Feb. 11, 2019, now Pat. No. 11,617,777, which is a
(Continued)

(51) Int. Cl.
A61K 38/05 (2006.01)
A61K 31/445 (2006.01)
A61K 38/06 (2006.01)
A61K 39/395 (2006.01)
A61K 47/54 (2017.01)
A61K 47/64 (2017.01)
A61K 47/68 (2017.01)
A61P 35/00 (2006.01)
C07C 311/51 (2006.01)
C07C 317/28 (2006.01)
C07C 317/32 (2006.01)
(Continued)

(52) U.S. Cl.
CPC ............ *A61K 38/05* (2013.01); *A61K 31/445* (2013.01); *A61K 38/06* (2013.01); *A61K 39/3955* (2013.01); *A61K 47/54* (2017.08); *A61K 47/64* (2017.08); *A61K 47/6415* (2017.08); *A61K 47/6803* (2017.08); *A61P 35/00* (2018.01); *C07C 311/51* (2013.01); *C07C 323/12* (2013.01); *C07C 323/67* (2013.01); *C07C 327/06* (2013.01); *C07C 381/08* (2013.01); *C07D 207/08* (2013.01); *C07D 207/452* (2013.01); *C07D 211/34* (2013.01); *C07D 211/60* (2013.01); *C07D 213/56* (2013.01); *C07D 213/71* (2013.01); *C07D 333/34* (2013.01); *C07K 5/0205* (2013.01); *C07K 5/06078* (2013.01); *C07C 317/28* (2013.01); *C07C 317/32* (2013.01); *C07C 317/50* (2013.01); *C07C 2601/02* (2017.05); *C07C 2601/08* (2017.05); *C07C 2601/14* (2017.05); *C07K 16/2863* (2013.01); *C07K 16/32* (2013.01); *Y02A 50/30* (2018.01)

(58) Field of Classification Search
CPC ...... A61K 38/05; A61K 38/06; A61K 31/445; A61K 39/3955; A61K 47/54; A61K 47/64; A61K 47/6415; A61K 47/6803; A61K 47/6855; A61P 35/00; C07C 2601/02; C07C 2601/08; C07C 2601/14; C07C 311/51; C07C 323/12; C07C 323/67; C07C 327/06; C07C 381/08; C07C 317/28; C07C 317/32; C07C 317/50; C07D 207/08; C07D 207/452; C07D 211/34; C07D 211/60; C07D 213/56; C07D 213/71; C07D 333/34; Y02A 50/30; C07K 5/0205; C07K 5/06078; C07K 5/162863; C07K 5/32
See application file for complete search history.

(56) References Cited

U.S. PATENT DOCUMENTS 5,349,066 A 9/1994 Kaneko et al.
5,502,032 A 3/1996 Haupt et al.
(Continued)

FOREIGN PATENT DOCUMENTS

CN 101039701 A 9/2007
EP 2620433 A1 7/2013
(Continued)

OTHER PUBLICATIONS

U.S. Appl. No. 14/776,654, entitled, "Cytotoxic and Anti-Mitotic Compounds, and Methods of Using the Same," filed Sep. 14, 2015, of Zymeworks BC Inc. (Issued as U.S. Pat. No. 10,201,614 on Feb. 12, 2019).
(Continued)

Primary Examiner — Sun Jae Yoo
(74) Attorney, Agent, or Firm — Todd Lorenz

(57) ABSTRACT

Compounds having cytotoxic and/or anti-mitotic activity are disclosed. Methods associated with preparation and use of such compounds, as well as pharmaceutical compositions comprising such compounds, are also disclosed. Also disclosed are compositions having the structure: (T)-(L)-(D), wherein (T) is a targeting moiety, (L) is an optional linker, and (D) is a compound having cytotoxic and/or anti-mitotic activity.

24 Claims, 19 Drawing Sheets

Related U.S. Application Data continuation of application No. 14/776,654, filed as application No. PCT/US2014/029463 on Mar. 14, 2014, now Pat. No. 10,201,614.

(60) Provisional application No. 61/792,020, filed on Mar. 15, 2013, provisional application No. 61/792,066, filed on Mar. 15, 2013.

(51) Int. Cl.

| | |
|---|---|
| C07C 317/50 | (2006.01) |
| C07C 323/12 | (2006.01) |
| C07C 323/67 | (2006.01) |
| C07C 327/06 | (2006.01) |
| C07C 381/08 | (2006.01) |
| C07D 207/02 | (2006.01) |
| C07D 207/08 | (2006.01) |
| C07D 207/452 | (2006.01) |
| C07D 211/34 | (2006.01) |
| C07D 211/60 | (2006.01) |
| C07D 213/56 | (2006.01) |
| C07D 213/71 | (2006.01) |
| C07D 333/34 | (2006.01) |
| C07K 5/02 | (2006.01) |
| C07K 5/065 | (2006.01) |
| C07K 16/32 | (2006.01) |
| C07K 16/28 | (2006.01) |

(56) References Cited

U.S. PATENT DOCUMENTS

| | | |
|---|---|---|
| 5,635,483 A | 6/1997 | Pettit et al. |
| 5,663,149 A | 9/1997 | Pettit et al. |
| 5,780,588 A | 7/1998 | Pettit et al. |
| 6,124,431 A | 9/2000 | Sakakibara et al. |
| 6,153,590 A | 11/2000 | Anderson et al. |
| 6,214,345 B1 | 4/2001 | Firestone et al. |
| 6,323,315 B1 | 11/2001 | Pettit et al. |
| 6,569,834 B1 | 5/2003 | Pettit et al. |
| 6,870,028 B1 | 3/2005 | Anderson et al. |
| 6,884,869 B2 | 4/2005 | Pettit et al. |
| 7,064,211 B2 | 6/2006 | Kowalczyk et al. |
| 7,078,562 B2 | 7/2006 | Furukawa et al. |
| 7,078,572 B2 | 7/2006 | Kendall |
| 7,192,972 B2 | 3/2007 | Kowalczyk et al. |
| 7,211,696 B2 | 5/2007 | Werbovetz et al. |
| 7,390,910 B2 | 6/2008 | Zask et al. |
| 7,410,951 B2 | 8/2008 | Anderson et al. |
| 7,528,152 B2 | 5/2009 | Kowalczyk et al. |
| 7,553,969 B1 | 6/2009 | Matsuoka et al. |
| 7,579,323 B1 | 8/2009 | Anderson et al. |
| 7,585,976 B2 | 9/2009 | Campagna et al. |
| 7,626,023 B2 | 12/2009 | Zask et al. |
| 7,659,241 B2 | 2/2010 | Senter et al. |
| 7,772,397 B2 | 8/2010 | Anderson et al. |
| 7,851,437 B2 | 12/2010 | Senter et al. |
| 7,994,135 B2 | 8/2011 | Doronina et al. |
| 8,097,648 B2 | 1/2012 | Littlefield et al. |
| 8,129,407 B2 | 3/2012 | Kowalczyk et al. |
| 8,394,922 B2 | 3/2013 | Cheng et al. |
| 8,609,105 B2 | 12/2013 | Senter et al. |
| 8,633,224 B2 | 1/2014 | Kowalczyk et al. |
| 8,992,932 B2 | 3/2015 | Lerchen et al. |
| 9,522,876 B2 | 12/2016 | Winters et al. |
| 9,801,951 B2 | 10/2017 | Miao et al. |
| 9,879,086 B2 | 1/2018 | Winters et al. |
| 10,201,614 B2 | 2/2019 | Winters et al. |
| 2004/0121965 A1 | 6/2004 | Greenberger et al. |
| 2005/0171014 A1 | 8/2005 | Tarasova et al. |
| 2005/0180972 A1 | 8/2005 | Wahl et al. |
| 2006/0106082 A1 | 5/2006 | Del Soldato et al. |
| 2007/0026478 A1 | 2/2007 | Greenberger et al. |
| 2008/0300192 A1 | 2/2008 | Doronina et al. |
| 2008/0108820 A1 | 5/2008 | Campagna et al. |
| 2008/0305044 A1 | 12/2008 | McDonagh et al. |
| 2009/0155289 A1 | 6/2009 | Roberts et al. |
| 2009/0264487 A1 | 10/2009 | Anderson et al. |
| 2011/0020343 A1 | 1/2011 | Senter et al. |
| 2011/0027274 A1 | 2/2011 | Cheng et al. |
| 2011/0293704 A1 | 12/2011 | Holst et al. |
| 2012/0041196 A1 | 2/2012 | Raffaella et al. |
| 2013/0095123 A1 | 4/2013 | Lerchen et al. |
| 2013/0129753 A1 | 5/2013 | Doroski et al. |
| 2013/0190248 A1 | 7/2013 | Mendelsohn et al. |
| 2013/0231320 A1 | 9/2013 | Kawaminami et al. |
| 2015/0105540 A1 | 4/2015 | Miao et al. |
| 2015/0141646 A1 | 5/2015 | Miao et al. |
| 2015/0250896 A1 | 9/2015 | Zhao |
| 2015/0284416 A1 | 10/2015 | Zhao |
| 2016/0038606 A1 | 2/2016 | Winters et al. |
| 2016/0311853 A1 | 10/2016 | Geirstanger et al. |
| 2017/0029490 A1 | 2/2017 | Winters et al. |
| 2017/0246310 A1 | 8/2017 | Rich et al. |
| 2017/0247408 A1 | 8/2017 | Winters et al. |
| 2018/0117163 A9 | 5/2018 | Rich et al. |

FOREIGN PATENT DOCUMENTS

| | | |
|---|---|---|
| WO | WO 1996/14856 A1 | 5/1996 |
| WO | WO 1996/33211 A1 | 10/1996 |
| WO | WO 1999/32509 A2 | 7/1999 |
| WO | WO 2000/044770 A1 | 8/2000 |
| WO | WO 2001/18032 A2 | 3/2001 |
| WO | WO 2003/072754 A2 | 9/2003 |
| WO | WO 2003/082268 A2 | 10/2003 |
| WO | WO 2004/010957 A2 | 2/2004 |
| WO | WO 2004/026293 A2 | 4/2004 |
| WO | WO 2004/026814 A2 | 4/2004 |
| WO | WO 2005/021558 A2 | 3/2005 |
| WO | WO 2005/026169 A1 | 3/2005 |
| WO | WO 2005/030794 A2 | 4/2005 |
| WO | WO 2005/039492 A2 | 5/2005 |
| WO | WO 2005/082023 A2 | 9/2005 |
| WO | WO 2006/027711 A2 | 3/2006 |
| WO | WO 2006/065533 A2 | 6/2006 |
| WO | WO 2006/132670 A2 | 12/2006 |
| WO | WO 2007/008603 A1 | 1/2007 |
| WO | WO 2007/008848 A2 | 1/2007 |
| WO | WO 2009/047264 A2 | 4/2009 |
| WO | WO 2009/059309 A2 | 5/2009 |
| WO | WO 2009/095447 A1 | 8/2009 |
| WO | WO 2009/117531 A1 | 9/2009 |
| WO | WO 2010/033207 A1 | 3/2010 |
| WO | WO 2010/115981 A1 | 10/2010 |
| WO | WO 2011/154359 A1 | 12/2011 |
| WO | WO 2012/059882 A2 | 5/2012 |
| WO | WO 2012/113847 A1 | 8/2012 |
| WO | WO 2012/123957 A1 | 9/2012 |
| WO | WO 2012/135440 A1 | 10/2012 |
| WO | WO 2013/068874 A1 | 5/2013 |
| WO | WO 2013/071035 A1 | 5/2013 |
| WO | WO 2013/173391 A1 | 11/2013 |
| WO | WO 2013/173392 A1 | 11/2013 |
| WO | WO 2013/173393 A1 | 11/2013 |
| WO | WO 2013/185117 A1 | 12/2013 |
| WO | WO 2013/192360 A1 | 12/2013 |
| WO | WO 2014/004376 A2 | 1/2014 |
| WO | WO 2014/074658 A1 | 5/2014 |
| WO | WO 2014/080251 A1 | 5/2014 |
| WO | WO 2014/100762 A1 | 6/2014 |
| WO | WO 2014/144871 A1 | 9/2014 |
| WO | WO 2015/095301 A2 | 6/2015 |
| WO | WO 2015/095952 A1 | 7/2015 |
| WO | WO 2015/095953 A1 | 7/2015 |

OTHER PUBLICATIONS

U.S. Appl. No. 16/273,045, entitled, "Cytotoxic and Anti-Mitotic Compounds, and Methods of Using the Same," filed Feb. 11, 2019,

(56) References Cited

OTHER PUBLICATIONS of Zymeworks BC Inc. (Issued as U.S. Pat. No. 11,617,777 on Apr. 4, 2023).
U.S. Appl. No. 14/213,504, entitled, "Cytotoxic and Anti-Mitotic Compounds, and Methods of Using the Same," filed Mar. 14, 2014, of Zymeworks BC Inc. (Issued as U.S. Pat. No. 9,522,876 on Dec. 20, 2016).
U.S. Appl. No. 15/108,247, entitled, "Sulfonaminde-Containing Linkage Systems for Drug Conjugates," filed Jun. 24, 2016, of Zymeworks BC Inc. (Issued as U.S. Pat. No. 11,560,422 on Jan. 24, 2023).
U.S. Appl. No. 17/990,485, entitled, "Sulfonaminde-Containing Linkage Systems for Drug Conjugates," filed Nov. 18, 2022, of Zymeworks BC Inc.
U.S. Appl. No. 14/857,733, entitled, "Cytotoxic and Anti-Mitotic Compounds, and Methods of Using the Same," filed Sep. 17, 2015, of Zymeworks BC Inc. (Issued as U.S. Pat. No. 9,879,086 on Jan. 30, 2018).
U.S. Appl. No. 15/872,642, entitled, "Cytotoxic and Anti-Mitotic Compounds, and Methods of Using the Same," filed Jan. 16, 2018, of Zymeworks BC Inc. (Issued as U.S. Pat. No. 10,414,822 on Sep. 17, 2019).
U.S. Appl. No. 16/523,942, entitled, "Cytotoxic and Anti-Mitotic Compounds, and Methods of Using the Same," filed Jul. 26, 2019, of Zymeworks BC Inc. (Issued as U.S. Pat. No. 11,591,405 on Feb. 28, 2023).
U.S. Appl. No. 18/099,875, entitled, "Cytotoxic and Anti-Mitotic Compounds, and Methods of Using the Same," filed Jan. 20, 2023, of Zymeworks BC Inc.
U.S. Appl. No. 15/512,030, entitled, "Cytotoxic and Anti-Mitotic Compounds, and Methods of Using the Same," filed Mar. 16, 2017, of Zymeworks BC Inc. (Issued as U.S. Pat. No. 10,450,378 on Oct. 22, 2019).
U.S. Appl. No. 15/108,258, entitled, "VAR2CSA-Drug Conjugates," filed Jun. 24, 2016, of Zymeworks BC Inc. (Issued as U.S. Pat. No. 10,675,355 on Jun. 9, 2020).
Alexander-Bryant et al., "Bioengineering Strategies for Designing Targeted Cancer Therapies," Adv Cancer Res, vol. 118, pp. 1-59 (2013).
Alley et al., "Contribution of Linker Stability to the Activities of Anticancer Immunoconjugates," Bioconjugate Chem., vol. 19, pp. 759-765 (2008).
Badescu et al, "Bridging Disulfides for Stable and Defined Antibody Drug Conjugates," Bioconjugate Chem., vol. 25 (6), pp. 1124-1136 (2014).
Bai et al., "Interactions of the Sponge-Derived Antimitotic Tripeptide Hemiasterlin with Tubulin: Comparison with Dolastatin 10 and Cyrpotphycin 1," Biochemistry, vol. 38, pp. 14302-14310 (1999).
Baldwin, A. D. and Kiick, K. L., "Tunable Degradation of Maleimide-Thiol Adducts in Reducing Environments," Bioconjugate Chem., Vo. 22, pp. 1946-1953 (2011).
Beaulieu, P.L. et al., "Allosteric N-acetamide-indole-6-carboxylic acid thumb pocket 1 inhibitors of hepatitis C virus NS5B polymerase—Acylsulfonamides and acylsulfamides as carboxylic acid replacements," Can J. Chem., vol. 91, pp. 66-81 (2013).
Bongo et al., "Efficient approach for profiling photoaffinity labeled peptides with a cleavable biotinyl photoprobe," Bioorganic & Medicinal Chemistry Letters, vol. 20, pp. 1834-1836 (2010).
Burke et al., "Design, Synthesis and Biological Evaluation of Antibody-Drug Conjugates Comprised of Potent Camptothecin Analogues," Bioconjugate Chem., vol. 20, pp. 1242-1250 (2009).
Burke et al., "Novel immunoconjugates comprised of streptonigrin and 17-amino-geldanamycin attached via dipeptide-p-aminobenzyl-amine linker system," Biorg. Med. Chem. Lett., vol. 19, pp. 2650-2653 (2009).
Cancer-Prevention, http://www.mcancer.org/cancer-prevention, downloaded Nov. 10, 2017.
Cancer-Prevention, http://www.cancerresearchuk.org/about-cancer/causes-of-cancer-be-prevented, downloaded Jan. 8, 2018.
CAS RN 1350253-85-8, STN Entry Date: Dec. 7, 2011.
Chakraborty et al., "Nucleation of B-Hairpin Structures with Cis Amide Bonds in E-Vinylogous Proline-Containing Peptides," J. Org. Chem., vol. 68, pp. 6459-6462 (2003).
Chan et al., "Mitosis-targeted anti-cancer therapies: where they stand," Cell Death and Disease, vol. 3, pp. 1-11 (2012).
Chen, J. et al., "The Bcl-2/Bcl-XL/Bcl-w Inhibitor, Navitoclax, Enhances the Activity of Chemotherapeutic Agents In Vitro and In Vivo," Mol Cancer Ther, 10(12), pp. 2340-2349, (2011).
Chen, X. et al., "Fusion protein linkers: property, design and funtionality,", Adv Drug Deliv Rev., vol. 65(10), pp. 1357-1369 (2013).
Cheng-Bin Yim et al., "Spacer Effects on in vivo Properties of DOTA-Conjugated Dimeric [Tyr3]Octreotate Peptides Synthesized by a "Cul-Click" and "Sulfo-Click" Ligation Method," Chembiochem, vol. 12, No. 5, pp. 750-760 (2011).
Choi, K.Y., "Protease-Activated Drug Development," Theranostics, 2(2), pp. 156-178, (2012).
Coleman et al., "Cytotoxic Peptides from the Marine Sponge *Cymbastella* sp.," Tetrahedron vol. 51, No. 39, pp. 10653-10662 (1995).
Doronina et al., "Development of potent monoclonal antibody auristatin conjugates for cancer therapy," Nature Biotechnology, vol. 21, No. 7, pp. 778-784 (2003).
Doronina et al., "Enhanced Activity of Monomethylauristatin F through Monoclonal Antibody Delivery: Effects of Linker Technology on Efficacy and Toxicity," Bioconjugate Chem., vol. 17, pp. 114-124 (2006).
Doronina et al., "Novel Peptide Linkers for Highly Potent Antibody—Auristatin Conjugate," Bioconjugate Chem., vol. 19, pp. 1960-1963 (2008).
Dosio et al., "Immunotoxins and Anticancer Drug Conjugates Assemblies: The role of the linkage between components", Toxinsm vol. 3(7), pp. 848-883 (2011).
Dubowchik et al., "Cathepsin B-Labile Dipeptide Linkers for Lysosomal Release of Doxorubicin from Internalizing Immunoconjugates: Model Studies of Enzymatic Drug Release and Antigen-Specific In Vitro Anticancer Activity," Bioconjugate Chem., vol. 13, pp. 855-869 (2002).
Ducry, L. and Stump, B., "Antibody-Drug Conjugates: Linking cytotoxic payloads to Monoclonal Antibodies," Bioconjugate Chem, vol. 21, pp. 5-13 (2010).
"Expert Scientific Group on Phase One Clinical Trails Final Report" 30th Nov. 2006, pp. C1, C35-C38.
Fennell et al., "Effects of the antimitotic natural product dolastatin 10, and related peptides, on the human malarial parasite Plasmodium falciparum," Antimicrob. Chemother., vol. 51, pp. 833-841 (2003).
Francisco et al., "cAC10-vcMMAE, and anti-CD30-monomethyl auristatin E conjugate with potent and selective antitumor activity," Blood, vol. 102, No. 4, pp. 1458-1465 (2003).
Gajula et al., "A Synthetic Dolastatin 10 Analgoue Supresses Microtubule Dynamics, Inhibits Cell Proliferation, and Induces Apoptotic Cell Death," J. Med. Chem, vol. 56, pp. 2235-2245 (2013).
Govindaraju et al., "Supporting Information Surface Immobilization of Biomolecules by Click Sulfonamide Reaction," Supplemental Material (ESI) for Chemical Communications, The Royal Society of Chemistry (2008) Downloaded from: (http://www.rsc.org/suppdata/cc/b8/b80674c/b806764c.pdf).
Grison, C. et al., "Stereoselective synthesis of vinylogous peptides," Tetrahedron, 57, pp. 4903-4923 (2001).
Grison et al., "Structural Investigation of "cis" and "trans" Vinylogous Peptides: cis-Vinylog Turn in Folded cis-Vinylogous Peptides, an Excelletn Mimic of the Natural β-Turn," J. Org. Chem. vol. 70, pp. 10753-10764 (2005).
Gura, T., "Cancer Models: Systems for Identifiying New Drugs Are Often Faulty," Science 7, vol. 278, No. 5340, pp. 1041-1042 (2007).
Haba, K., "Single-Triggered Trimeric Prodrugs," Angew. Chem. Int. Ed., vol. 44, pp. 716-720 (2005).

(56) References Cited

OTHER PUBLICATIONS

Hadaschik, B.A. et al., "Intravesical Chemotherapy of High-Grade Bladder Cancer with HTI-286, A Synthetic Analogue of the Marine Sponge Product Hemiasterlin," Clin Cancer Res., vol. 14, pp. 1510-1518 (2008).
Hamada et al., caplus an 2008:324765.
Huang, S. et al., "Synthesis and evaluation of N-acyl sulfonamides as potential prodrugs of cyclin-dependent kinase inhibitor JNJ-7706621," Bioorganic & Medicinal Chemistry Letters, vol. 16, pp. 3639-3641 (2006).
Ishikawa et al., "Preparation of endothelin antagonistic peptide derivatives," caplus an Eur. Pat. Appl., p. 121, 1992:256053.
Jeffrey et al., "Design, Synthesis, and in Vitro Evaluation of Dipeptide-Based Antibody Minor Groove Binder Conjugates," J. Med. Chem., vol. 48, pp. 1344-1358 (2005).
Jeffrey et al., "Dipeptide-based highly potent doxorubicin antibody conjugates," Biorg. Med. Chem. Lett. vol. 16, pp. 358-362 (2006).
Jeffrey et al., "Expanded Utility of the β-Glucuronide Linker: ADCs That Deliver Phenolic Cytotoxic Agents," ACS Med. Chem. lett., vol. 1, pp. 277-280 (2010).
Jiang, Y. et al., "Discovery of Danoprevir (ITMN-191/R7227), a Highly Selective and Potent Inhibitor of Hepatitis C Virus (HCV) NS3/4A Protease," J. Med. Chem., vol. 57, pp. 1753-1769 (2014).
Johansson, A. et al., "Acyl Sulfonamides as Potent Protease Inhibitors of the Hepatitis C Virus Full-Length NS3 (Protease-Helicase/NTPase): A Comparative Study of Different C-Terminals," Bioorganic & Medicinal Chemistry, 11, pp. 2551-2568 (2003).
Kamb, A., "What's wrong with our cancer models?," Nature Reviews Drug Discovery 4, vol. 4, pp. 161-165 (2005).
Koniev, O. et al., "Selective Irreversible Chemical Tagging of Cysteine with 3-Arylpropiolonitriles," Bioconjugate Chem., vol. 25 (2), pp. 202-206 (2014).
Kuznetsov et al., "Tubulin-based antimitotic mechanism of E7974, a novel analogue of the marine sponge natural product hemiasterlin," Mol Cancer Ther , 8(10), pp. 2852-2860 (2009).
Leaf, C., "Why Are We Losing The War On Cancer (And How To Win It)," Health Administrator vol. XVII, No. 1, pp. 172-183 (2005).
Lesma, et al., "Hemiasterlin Analogues Incorporating an Aromatic, and Heterocyclic Type C-terminus: Design, Synthesis and Biological Evaluation," Mol Divers.,18(2), pp. 357-373 (2004).
Li et al., "Immunotoxins and Cancer Therapy," Cellular & Molecular Immunology, vol. 6, No. 2, pp. 106-112 (2005).
Loganzo et al., "HTI-286 , a Synthetic Analogue of the Tripeptide Hemiasterlin, Is a Potent Antimicrotubule Agent that Circumvents p. Glycoprotein-mediated Resistance in Vitro and in Vivo," Cancer Res, 63, pp. 1838-1845 (2003).
Luo et al., "Principle of Cancer Therapy: Oncogen and Non-oncogene Addiction," Cell vol. 136, pp. 823-837 (2009).
Mader, M.M. et al., "Acyl sulfonamide anti-proliferatives. Part 2: Activity of heterocyclic sulfonamide derivatives," Bioorganic & Medicinal Chemistry Letters, 15, pp. 617-620 (2005).
Marzo et al., "Antimitotic drugs in cancer chemotherapy: Promises and pitfalls, " Biochemical Pharmacology, Vo. 86, pp. 703-710 (2013).
Matsuoka et al., caplus an 2000:535162 (WO2000044770)—Chugai.
Melnyk, O. et al., "Phenylthiocarbamate or N-Carbothiophenyl Group Chemistry in Peptide Synthesis and Bioconjugation," Bioconjugate Chem., vol. 25, pp. 629-639 (2014).
Merkx et al., "Resin-bound sulfonyl-azides: Efficient loading and activation strategy for the preparation of the N-acyl sulfonamide linker," J. Org. Chem., vol. 72, pp. 4574-4577 (2007).
Milton et al., "Mapping the bound conformation and protein interactions of microtubule destabilizing peptides by STD-NMR spectroscopy," Bioorganic & medicinal Chemistry Letters, Pergamon, Amsterdam, NL, vol. 16, No. 16 (2006).
Mitra, A. and Sept D., "Localization of the Antimitotic Peptide and Depsipeptide Binding Site on B-tubulin," Biochemistry, 43, pp. 13955-13962 (2004).

Miyazawa, T. et al., "Effect of copper(II) chloride on suppression of racemization in peptide synthesis by the carbodiimide method," Int. J. Peptide Protein Res., vol. 39, pp. 237-244 (1992).
Neidle, S., "Failure Modes in Clinical Development," Cancer Drug Design and Discovery, ed. (Elsevier/Academic Press) pp. 427-431 (2008).
Neiman et al., "Synthesis and Antimitotic/Cytotoxic Activity of Hemiasterlin Analogues," J. Nat. Prod. Vol. 66, pp. 183-199 (2003).
Niu et al., "Absolute configurations of tubulin inhibitors taltobulin (HTI-286) and HTI-042 characterized by X-ray diffraction analysis and NMR studies," Bioorganic & Medicinal Chmistry Letters, 20, pp. 1535-1538 (2010).
Olsen et al., caplus an 2010:213501.
Otani et al., "TZT-1027, an antimicrotubule agent, attacks tumor vasculature and induces tumor cell death," Jpn. J. Cancer Res., vol. 91, pp. 837-844 (2000).
Papisov et al., "Semisynthetic Hydrophilic Polyals," Biomacromolecules, vol. 6, pp. 2659-2670 (2005).
Pettit et al., "Antineoplastic agents 337. Synthesis of dolastatin 10 structural modifications," Anti-Cancer Drug Des., vol. 10, pp. 529-544 (1995).
Pettit et al., "Specific activities of dolastatin 10 and peptide derivatives against *Cryptococcus neoformans*," Antimicrob. Agents Chemother., vol. 42, pp. 2961-2965 (1998).
Pettit et al., "Antineoplastic agents 365. Dolastatin 10 SAR probes," Anti-Cancer Drug Des., vol. 13, pp. 243-277 (1998).
Pettit et al., "Antineoplastic agents. 592. Highly effective cancer cell growth inhibitory structural modifications of dolastatin 10," J. Nat. Prod., vol. 74, pp. 962-968 (2011).
Ratain et al., "Phase I and pharmacological study of HTI-286, a novel antimicrotubule agent: correlation of neutropenia with time above a threshold serum concentration," Proc. Am. Soc. Clin. Oncol., vol. 22, p. 129 (2003).
Ravi M. et al., "Structure-Based Identification of the Binding Site for the Hemiasterlin Analogue HTI-286 on Tubulin," Biochemistry, 44, pp. 15871-15879 (2005).
Rich, J.R., et al., CAPLUS AN 2015:1087487.
Rocha-Lima et al., "A Phase 1 Trial of E7974 Administrated on Day 1 of a 21 Day Cycle in Patients with Advanced Solid Tumors," Cancer, pp. 4262-4270, Sep. 1, 2012.
Scola, P.M. et al., "The Discovery of Asunaprevir (BMS-650032), An Orally Efficacious NS3 Protease Inhibitor for the Treatment of Hepatitis C Virus Infection," J. Med. Chem., 57, pp. 1730-1752 (2014).
Schumacher, F.F. et al., "In Situ Maleimide Bridging of Disulfides and a New Approach to Protein Pegylation," Bioconjugate Chem., vol. 22, pp. 132-136 (2011).
Shabat et al., "In vivo activity in a catalytic antibody-prodrug system: Antibody catalyzed etoposide prodrug activation for selective chemotherapy," PNAS, vol. 98, No. 13, pp. 7528-7533 (2001).
Shannon et al., "Investigating the Proteome Reactivity and Selectivity of Aryl Halides," J. Am. Chem. Soc., vol. 136, pp. 3330-3333 (2014).
Shnyder et al., "Auristatin PYE, a novel synthetic derivative of dolastatin 10, is highly effective in human colon tumour models," Int. J. Oncol., vol. 31, pp. 353-360 (2007).
Sigmund, F. and Wesseley, F., "Untersuchungen über α-Amino-N-Carbonsäureanhydride. II.," Z. Physiol. Chem, vol. 157, pp. 91-105 (1926).
Steiner, M. et al., "Spacer length shapes drug release and therapeutic efficacy of traceless disulfide-linked ADCs targeting the tumor neovasculature," Chem. Sci., vol. 4, pp. 297-302 (2013).
Sutherland, M.S.K., et al., "Lysosomal Trafficking and Cysteine Protease Metabolism Confer Target-specific Cytotoxicity by Peptide-linked Anti-CD30-Auristatin Conjugates," Journal of Biological Chemistry, Vo. 281, No. 15, pp. 10540-10547 (2006).
Talpir et al., "Hemiasterlin and Geodiamolide TA; Two New Cytotoxic Peptides from the Marine Sponge Hemiasterella Minor (Kirkpatrick)," Tetrahedron Letters, vol. 35, No. 25, pp. 4453-4456 (1994).
Temming et al., "Improved Efficacy of αvβ3-Targeted Albumin Conjugates by Conjugation of a Novel Auristatin Derivative," Molecular Pharmaceutics, vol. 4, No. 5, pp. 686-694 (2007).

(56) References Cited

OTHER PUBLICATIONS

Thomssen et al., "Prognostic value of the cysteine proteases cathepsins B and cathepsin L in human breast cancer," Clinical Cancer Research, vol. 1, pp. 741-746 (1995).
Toki et al., "Protease-Mediated Fragmentation of p-Aminobenzyl Ethers: A New Strategy for the Activation of Anticancer Prodrugs," J. Org. Chem., vol. 67, pp. 1866-1872 (2002).
Toure, B.C. et al., "The Role of the Acidity of N-Heteroaryl Sulfonamides as Inhibitors of Bcl-2 Family Protein-Protein Interactions," ACS Med. Chem. Lett., vol. 4, pp. 186-190 (2013).
Uehling, D.E. et al., "Synthesis and Evaluation of Potent and Selective β3 Adrenergic Receptor Agonists Containing Acylsulfonamide, Sulfonylsulfonamide, and Sulfonylurea Carboxylic Acid Isosteres," J. Med. Chem., vol. 45, pp. 567-583 (2002).
Vedejs, et al., "A Total Synthesis of (−)-Hemiasterlin Using N-Bts Methodology," J. Org. Chem., vol. 66, pp. 7355-7364 (2001).
Walker et al., "Monoclonal antibody mediated intracellular targeting of tallysomycin S10b," Bioorganic & Medicinal Chemistry Letters, vol. 14, pp. 4323-4327 (2004).
Werboretz et al., "Selective Antimicrotubule Activity of N1-Phenyl-3-5-dinitro- 4,N-4-di-n-propylsulfanilamide (GB-II-5) against Kinetoplastid Parasites," Mol. Pharmacol., vol. 64, pp. 1325-1333 (2003).
Wilkinson et al., "Synthesis of MUC1 glycopeptide thioesters and ligation via direct aminolysis," Biopolymers, vol. 96(2), pp. 137-146 (2011).
Winters, G., et al., CAPLUS AN 2015:1087672.
Woyke et al., "In vitro activities and postantifungal effects of the potent dolastatin 10 derivative Auristatin PHE," Antimicrob. Agents Chemother., vol. 45, pp. 3580-3584 (2001).
Yamashita et al., "Synthesis and Activity of Novel Analogs of Hemiasterlin as Inhibitors of Tubulin Polymerization: Modification of the A Segment," Bioorganic and Medicinal Chemistry Letters, vol. 14, pp. 5317-5322 (2004).
Yan, S. et al., "Thiazolone-acylsulfonamides as novel HCV NS5B polymerase allosteric inhibitors: convergence of structure-based drug design and X-ray crystallographic study," Bioorganic & Medicinal Chemistry Letters, vol. 17, pp. 1991-1995 (2007).
Yurkovestkiy et al., "Synthesis of a Macromolecular Camptothecin Conjugate with Dual Phase Drug Release," Mol Pharm., vol. 1:5, pp. 375-382 (2004).
Zask et al., "D-piece Modifications of the Hemiasterlin Analog HTI-286 Produce Potent Tubulin Inhibitors," Bioorganic & Medicinal Chemistry Letters, vol. 14, pp. 4353-4358 (2004).
Zask et al., "Synthesis and Biological Activity of Analogues of the Antimicrotubule Agent N,β,β-Trimethyl-I-phenylalanyl-N1-[(1S,2E)-3-carboxy-1-isopropylbut-2-enyl]-N1,3-dimethyl-l-valinamide (HTI-286)," J. Med. Chem., vol. 47, pp. 4774-4786 (2004).
Zubovych et al., "A missense mutation in Caenorhabditis elegans prohibitin 2 confers an atypical mltidrug resistance," PNAS, vol. 102, No. 42, pp. 15523-15528 (2006).
Non-final Office Action issued Oct. 2, 2015 in U.S. Appl. No. 14/213,504.
Final Office Action issued May 18, 2016 in U.S. Appl. No. 14/213,504.
Notice of Allowance issued Aug. 23, 2016 in U.S. Appl. No. 14/213,504.
Restriction Requirement issued Aug. 29, 2016 in U.S. Appl. No. 14/776,654.
Non-final Office Action issued Nov. 16, 2016 in U.S. Appl. No. 14/776,654.
Final Office Action issued May 9, 2017 in U.S. Appl. No. 14/776,654.
Advisory Action issued Jul. 14, 2017 in U.S. Appl. No. 14/776,654.
Non-final Office Action issued Sep. 15, 2017 in U.S. Appl. No. 14/776,654.
Notice of Allowance issued Feb. 5, 2018 in U.S. Appl. No. 14/776,654.
Restriction Requirement issued Jun. 4, 2018 in U.S. Appl. No. 15/108,247.
Non-final Office Action issued Dec. 14, 2018 in U.S. Appl. No. 15/108,247.
Final Office Action issued Jul. 29, 2019 in U.S. Appl. No. 15/108,247.
Office Action issued Apr. 13, 2020 in U.S. Appl. No. 15/108,247.
Office Action issued Jan. 14, 2021 in U.S. Appl. No. 15/108,247.
Office Action issued Jul. 15, 2021 in U.S. Appl. No. 15/108,247.
Office Action issued Jan. 19, 2022 in U.S. Appl. No. 15/108,247.
Notice of Allowance issued Aug. 2, 2022 in U.S. Appl. No. 15/108,247.
Restriction Requirement issued Oct. 5, 2017 in U.S. Appl. No. 15/108,258.
Non-final Office Action issued May 18, 2018 in U.S. Appl. No. 15/108,258.
Non-final Office Action issued Mar. 19, 2019 in U.S. Appl. No. 15/108,258.
Notice of Allowance issued Dec. 12, 2019 in U.S. Appl. No. 15/108,258.
Restriction Requirement mail Dec. 18, 2019 in U.S. Appl. No. 16/273,045.
Office Action mailed Jun. 24, 2020 in U.S. Appl. No. 16/273,045.
Office Action mailed Feb. 25, 2021 in U.S. Appl. No. 16/273,045.
Office Action mailed Jan. 24, 2022 in U.S. Appl. No. 16/273,045.
Final Office Action mailed Aug. 22, 2022 in U.S. Appl. No. 16/273,045.
Notice of Allowance mailed in U.S. Appl. No. 16/273,045.
Restriction Requirement issued Jul. 8, 2020 in U.S. Appl. No. 16/523,942.
Non-final Office Action issued Jan. 21, 2021 in U.S. Appl. No. 16/523,942.
Final Office Action issued Jul. 20, 2021 in U.S. Appl. No. 16/523,942.
Non-final Office Action issued Mar. 2, 2022 in U.S. Appl. No. 16/523,942.
Notice of Allowance issued Oct. 1, 2022 in U.S. Appl. No. 16/523,942.

CYTOTOXIC AND ANTI-MITOTIC COMPOUNDS, AND METHODS OF USING THE SAME

REFERENCE TO PRIOR APPLICATION

This application claims the benefit of U.S. Provisional Application No. 61/792,020, filed Mar. 15, 2013, and U.S. Provisional Application No. 61/792,066, filed Mar. 15, 2013, the disclosure of each of which is incorporated by reference herein in its entirety.

BACKGROUND

Field

The invention relates to biologically active compounds, compositions comprising the same, and methods of using such biologically active compounds and compositions for the treatment of cancer and other diseases.

Description of the Related Art

Talpir, R. et al. (1994) Tetrahedron Lett. 35:4453-6, describe the naturally occurring compound hemiasterlin, a stable tripeptide obtained from marine sponges that causes microtubule depolymerization and mitotic arrest in cells. Hemisasterlin consists of unusual and highly congested amino acids, features thought to contribute to its activity. A number of groups have modified particular structural elements of hemiasterlin to evaluate structure-activity relationships and assess the activity of hemiasterlin analogs. See for example Zask et al., Bioorganic & Medicinal Chemistry Letters, 14:4353-4358, 2004; Zask et al., J Med Chem, 47:4774-4786, 2004; Yamashita et al., Bioorganic & Medicinal Chemistry Letters, 14:5317-5322, 2004; PCT/GB96/00942; WO 2004/026293; WO96/33211; and U.S. Pat. No. 7,579,323.

Analogs of hemiasterlin with modifications in the "A-segment", or the amino terminal segment, have been described (see for example, Zask et al., J Med Chem, 47:4774-4786, 2004; Yamashita et al., Bioorganic & Medicinal Chemistry Letters, 14:5317-5322, 2004; U.S. Pat. No. 7,579,323). U.S. Pat. No. 7,579,323 discloses an analog of hemiasterlin, referred to as HTI-286, in which the indole moiety is replaced by a phenyl group. HTI-286 exhibits potent anti-mitotic activity and has been assessed in clinical trials for the treatment of cancer (Ratain et al., Proc Am Soc Clin Oncol, 22:129, 2003).

Analogs of hemiasterlin with modifications in the "D-segment", or the carboxy terminal segment, have also been reported (see, for example, WO 2004/026293; Zask et al., Bioorganic & Medicinal Chemistry Letters, 14:4353-4358, 2004; Zask et al., J Med Chem, 47:4774-4786, 2004). The majority of modifications at the carboxy terminus result in compounds with substantially decreased potency compared to parent carboxylic acids. See, for example, WO 2004/026293, particularly Table 12. Zask et al., (J Med Chem, 47:4774-4786, 2004) also report that amide analogs prepared using simple cyclic and acyclic amines exhibit significantly reduced potency (reductions of one to three orders of magnitude). Among the few tolerated modifications, Zask et al., (Bioorganic & Medicinal Chemistry Letters, 14:4353-4358, 2004) report that the addition of esterified cyclic amino acids at the carboxy-terminus yields tetrapeptide analogs with prolyl-like ester-containing termini, some of which exhibit potency comparable to parent compound in a tested cancer cell line.

Potent cytotoxic and anti-mitotic compositions are highly desired for the treatment of a number of devastating disorders, including cancer. While a wide variety of hemiasterlin analogs have been generated, many, including a wide variety of compounds with modifications at the carboxy terminus, exhibit reduced potency that limits utility in methods of medical treatment.

For the foregoing reasons, while progress has been made in this field, there is a need for additional potent anti-mitotic and cytotoxic compounds having preferred characteristics that render them suitable for the treatment of a variety of disorders, including cancer. The present disclosure fulfills these needs and provides further related advantages.

BRIEF SUMMARY

In brief, the present disclosure is directed to biologically active compounds, compositions comprising the same, and methods of using such compounds and compositions.

In one embodiment, compounds having the following structure (I) are provided:

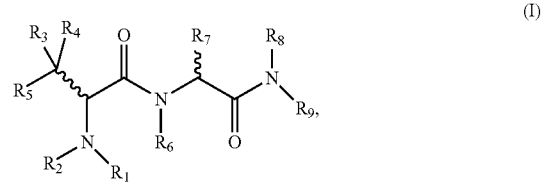

wherein:
$R_1$ and $R_2$ are independently selected from the group consisting of: H and a saturated or unsaturated moiety having a linear, branched, or non-aromatic cyclic skeleton containing one to ten carbon atoms, and the carbon atoms are optionally substituted with: —OH, —I, —Br, —Cl, —F, —CN, —$CO_2$H, —CHO, —COSH, or —$NO_2$; or $R_2$ and $R_5$ are fused and form a ring;
$R_3$ and $R_4$ are independently selected from the group consisting of: H, R, ArR—, or $R_3$ and $R_4$ are joined to form a ring;
$R_5$ is selected from the group consisting of: H, R, ArR—, and Ar;
or $R_5$ and $R_2$ are fused and form a ring;
$R_6$ is selected from the group consisting of: H, R, and ArR—;
$R_7$ and $R_8$ are independently selected from the group consisting of: H, R, and ArR—; and
$R_9$ is:

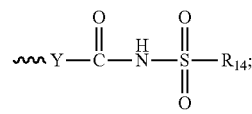

wherein,
R is defined as a saturated or unsaturated moiety having a linear, branched, or non-aromatic cyclic skeleton containing one to ten carbon atoms, zero to four nitrogen atoms, zero to four oxygen atoms, and zero to four sulfur atoms, and the carbon atoms are optionally substituted with: =O, =S, OH, —OR$_{10}$, —O$_2$CR$_{10}$, —SH, —SR$_{10}$, —SOCR$_{10}$, —NH$_2$, —NHR$_{10}$, —N(R$_{10}$)$_2$, —NHCOR$_{10}$, —NR$_{10}$COR$_{10}$, —I, —Br, —Cl, —F, —CN, —CO$_2$H, —CO$_2$R$_{10}$, —CHO, —COR$_{10}$, —CONH$_2$, —CONHR$_{10}$, —CON(R$_{10}$)$_2$, —COSH, —COSR$_{10}$, —NO$_2$, —SO$_3$H, —SOR$_{10}$, —SO$_2$R$_{10}$, wherein R$_{10}$ is a linear, branched or cyclic, one to ten carbon saturated or unsaturated alkyl group;

the ring formed by joining R$_3$ and R$_4$ is a three to seven member non-aromatic cyclic skeleton within the definition of R, Y is defined as a moiety selected from the group consisting of: a linear, saturated or unsaturated, one to six carbon alkyl group, optionally substituted with R, ArR—, or X; and, X is defined as a moiety selected from the group consisting of: —OH, —OR, =O, =S, —O$_2$CR, —SH, —SR, —SOCR, —NH$_2$, —NHR, —N(R)$_2$, —NHCOR, —NRCOR, —I, —Br, —Cl, —F, —CN, —CO$_2$H, —CO$_2$R, —CHO, —COR, —CONH$_2$, —CONHR, —CON(R)$_2$, —COSH, —COSR, —NO$_2$, —SO$_3$H, —SOR, and —SO$_2$R;

R$_{14}$ is selected from the group consisting of optionally substituted alkyl, optionally substituted alkylamino, optionally substituted cycloalkyl, optionally substituted aryl, optionally substituted heterocyclyl and optionally substituted heteroaryls, COR$_{24}$, —CSR$_{24}$, —OR$_{24}$, and —NHR$_{24}$, wherein each R$_{24}$ is, independently, alkyl optionally substituted with halogen, —OH or —SH;

or a stereoisomer, prodrug or pharmaceutically acceptable salt thereof.

In one embodiment, Ar is an aromatic ring selected from the group consisting of: phenyl, naphthyl, anthracyl, pyrrolyl.

In one embodiment, compounds having the following structure (Ia) are provided:

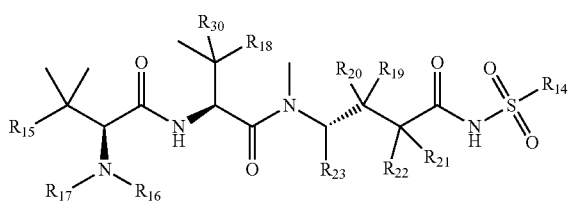

(Ia)

wherein:

R$_{14}$ is selected from the group consisting of optionally substituted alkyl, optionally substituted alkylamino, optionally substituted cycloalkyl, optionally substituted aryl, optionally substituted heterocyclyl, optionally substituted heteroaryl, —COR$_{24}$, —CSR$_{24}$, —OR$_{24}$, and —NHR$_{24}$, wherein each R$_{24}$ is, independently, alkyl optionally substituted with halogen, —OH or —SH;

R$_{15}$ is selected from the group consisting of optionally substituted alkyl, optionally substituted alkylamino, optionally substituted cycloalkyl, optionally substituted aryl, optionally substituted heterocyclyl and optionally substituted heteroaryl;

R$_{16}$ is selected from the group consisting of H and C$_{1-6}$ alkyl;

R$_{17}$ is selected from the group consisting of H and C$_{1-6}$ alkyl;

R$_{18}$ and R$_{30}$ are independently selected from the group consisting of H, C$_{1-6}$ alkyl and —SH, with the proviso that R$_{18}$ and R$_{30}$ cannot both be H;

R$_{19}$, R$_{20}$, R$_{21}$ and R$_{22}$ are independently H and C$_{1-6}$ alkyl, at least one of R$_{19}$ and R$_{20}$ is H; or R$_{20}$ and R$_{21}$ form a double bond, R$_{19}$ is H, and R$_{22}$ is H or C$_{1-6}$ alkyl; and R$_{23}$ is selected from the group consisting of H and C$_{1-6}$ alkyl;

or a stereoisomer, prodrug or pharmaceutically acceptable salt thereof.

In a further embodiment, each optionally substituted alkyl, optionally substituted alkylamino, optionally substituted cycloalkyl, optionally substituted aryl, optionally substituted heterocyclyl and optionally substituted heteroaryl is, independently, optionally substituted with =O, =S, —OH, —OR$_{24}$, —O$_2$CR$_{24}$, —SH, —SR$_{24}$, —SOCR$_{24}$, —NH$_2$, —N$_3$, —NHR$_{24}$, —N(R$_{24}$)$_2$, —NHCOR$_{24}$, —NR$_{24}$COR$_{24}$, —I, —Br, —Cl, —F, —CN, —CO$_2$H, —CO$_2$R$_{24}$, —CHO, —COR$_{24}$, —CONH$_2$, —CONHR$_{24}$, —CON(R$_{24}$)$_2$, —COSH, —COSR$_{24}$, —NO$_2$, —SO$_3$H, —SOR$_{24}$ or —SO$_2$R$_{24}$ wherein each R$_{24}$ is, independently, alkyl optionally substituted with halogen, —OH or —SH In another further embodiment, each optionally substituted aryl and optionally substituted heteroaryl is, independently, selected from the group consisting of optionally substituted phenyl, optionally substituted naphthyl, optionally substituted anthracyl, optionally substituted phenanthryl, optionally substituted furyl, optionally substituted pyrrolyl, optionally substituted thiophenyl, optionally substituted benzofuryl, optionally substituted benzothiophenyl, optionally substituted quinolinyl, optionally substituted isoquinolinyl, optionally substituted imidazolyl, optionally substituted thiazolyl, optionally substituted oxazolyl, and optionally substituted pyridinyl.

In another further embodiment, R$_{15}$ is selected from one of the following structures (II), (III), (IV), (V):

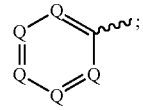

(II)

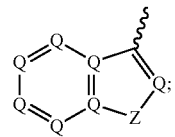

(III)

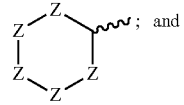

(IV)

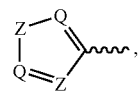

(V)

wherein:

Q is CR$_{25}$ or N;

Z is C(R$_{25}$)$_2$, NR$_{25}$, S, or O;

each R$_{25}$ is, independently, selected from the group consisting of H, —OH, —R$_{24}$, —OR$_{24}$, —O$_2$CR$_{24}$, —SH, —SR$_{24}$, —SOCR$_{24}$, —NH$_2$, —N$_3$, —NHR$_{24}$, —N(R$_{24}$)$_2$, —NHCOR$_{24}$, —NR$_{24}$COR$_{24}$, —R$_{24}$NH$_2$, —I, —Br, —Cl, —F, —CN, —CO$_2$H, —CO$_2$R$_{24}$, —CHO, —COR$_{24}$, —CONH$_2$, —CONHR$_{24}$, —CON(R$_{24}$)$_2$, —COSH, —COSR$_{24}$, —NO$_2$, —SO$_3$H, —SOR$_{24}$ or —SO$_2$R$_{24}$, wherein each R$_{24}$ is, independently, alkyl optionally substituted with halogen, —OH or —SH.

In another further embodiment, R$_{15}$ is selected from the group consisting of:

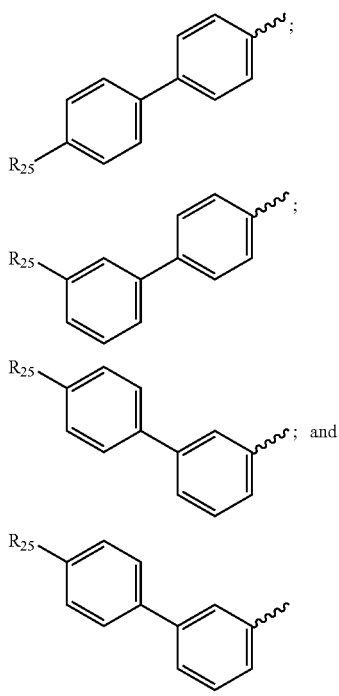

wherein each R$_{25}$ is, independently, selected from the group consisting of H, —OH, —R$_{24}$, —OR$_{24}$, —O$_2$CR$_{24}$, —SH, —SR$_{24}$, —SOCR$_{24}$, —NH$_2$, —N$_3$, —NHR$_{24}$, —N(R$_{24}$)$_2$, —NHCOR$_{24}$, —NR$_{24}$COR$_{24}$, —R$_{24}$NH$_2$, —I, —Br, —Cl, —F, —CN, —CO$_2$H, —CO$_2$R$_{24}$, —CHO, —COR$_{24}$, —CONH$_2$, —CONHR$_{24}$, —CON(R$_{24}$)$_2$, —COSH, —COSR$_{24}$, —NO$_2$, —SO$_3$H, —SOR$_{24}$ or —SO$_2$R$_{24}$, wherein each R$_{24}$ is, independently, alkyl optionally substituted with halogen, —OH or —SH.

In another further embodiment, R$_{15}$ is selected from the group consisting of:

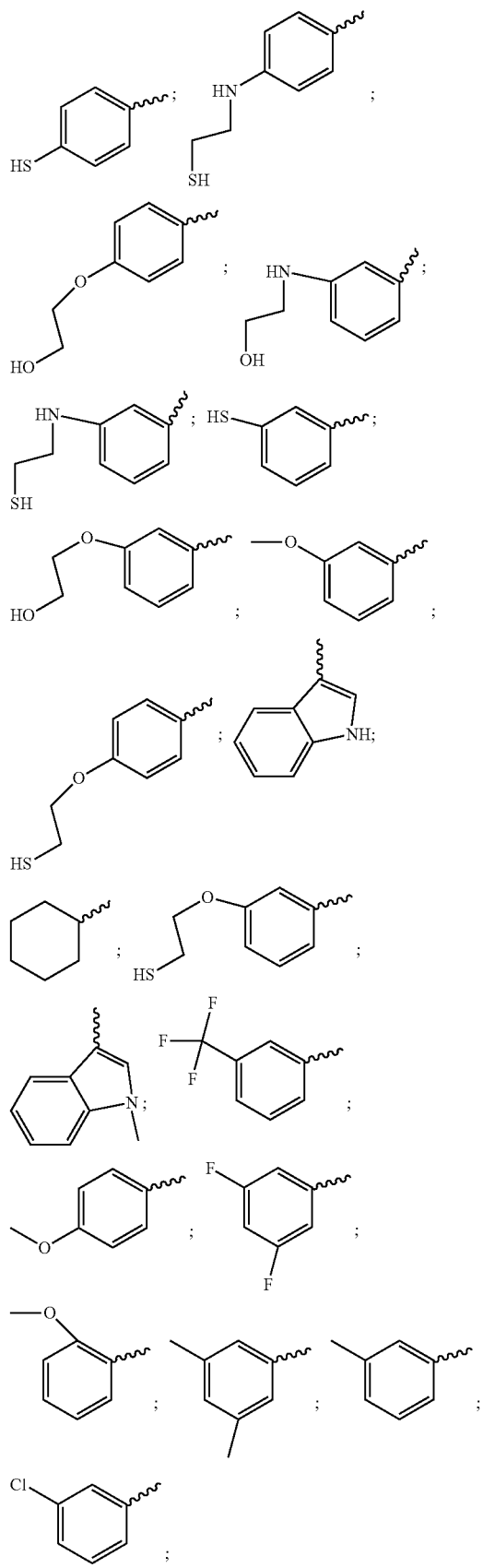

In another further embodiment, $R_{15}$ is:

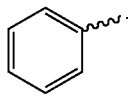

In another further embodiment, $R_{16}$, $R_{17}$, $R_{18}$, and $R_{30}$ are each methyl.

In another further embodiment, $R_{16}$ is H, $R_{17}$ is methyl, $R_{18}$ is methyl, and $R_{30}$ is methyl.

It is understood that any embodiment of the compounds of structure (Ia), as set forth above, and any specific substituent set forth herein for a $R_{14}$, $R_{15}$, $R_{16}$, $R_{17}$, $R_{18}$, $R_{19}$, $R_{20}$ and $R_{30}$ group in the compounds of structure (Ia), as set forth above, may be independently combined with other embodiments and/or substituents of compounds of structure (1) to form embodiments of the present disclosure not specifically set forth above. In addition, in the event that a list of substituents is listed for any particular $R_{14}$, $R_{15}$, $R_{16}$, $R_{17}$, $R_{18}$, $R_{19}$, $R_{20}$, and $R_{30}$ in a particular embodiment and/or claim, it is understood that each individual substituent may be deleted from the particular embodiment and/or claim and that the remaining list of substituents will be considered to be within the scope of the present disclosure.

In one embodiment, compounds having the following structure (Ib) are provided:

(Ib)

wherein:

$R_{26}$ is selected from the group consisting of optionally substituted alkyl, optionally substituted alkylamino, optionally substituted cycloalkyl, optionally substituted aryl, optionally substituted heterocyclyl and optionally substituted heteroaryl;

$R_{27}$ is selected from the group consisting of optionally substituted alkyl, optionally substituted alkylamino, optionally substituted cycloalkyl, optionally substituted aryl, optionally substituted heterocyclyl and optionally substituted heteroaryl;

$R_{16}$ is selected from the group consisting of H and $C_{1-6}$ alkyl;

$R_{17}$ is selected from the group consisting of H and $C_{1-6}$ alkyl; and $R_{18}$ is selected from the group consisting of $C_{1-6}$ alkyl and —SH, or a stereoisomer, prodrug or pharmaceutically acceptable salt thereof.

In a further embodiment, each optionally substituted alkyl, optionally substituted alkylamino, optionally substituted cycloalkyl, optionally substituted aryl, optionally substituted heterocyclyl and optionally substituted heteroaryl is, independently, optionally substituted with =O, =S, —OH, —OR$_{28}$, —O$_2$CR$_{28}$, —SH, —SR$_{28}$, —SOCR$_{28}$, —NH$_2$, —N$_3$, —NHR$_{28}$, —N(R$_{28}$)$_2$, —NHCOR$_{28}$, —NR$_{28}$COR$_{28}$, —I, —Br, —Cl, —F, —CN, —CO$_2$H, —CO$_2$R$_{28}$, —CHO, —COR$_{28}$, —CONH$_{28}$, —CONHR$_{28}$, —CON(R$_{28}$)$_2$, —COSH, —COSR$_{28}$, —NO$_2$, —SO$_3$H, —SOR$_{28}$ or —SO$_2$R$_{28}$, wherein each R$_{28}$ is, independently, alkyl optionally substituted with halogen, —OH or —SH.

In another further embodiment, each optionally substituted aryl and optionally substituted heteroaryl is, independently, selected from the group consisting of optionally substituted phenyl, optionally substituted naphthyl, optionally substituted anthracyl, optionally substituted phenanthryl, optionally substituted furyl, optionally substituted pyrrolyl, optionally substituted thiophenyl, optionally substituted benzofuryl, optionally substituted benzothiophenyl, optionally substituted quinolinyl, optionally substituted isoquinolinyl, optionally substituted imidazolyl, optionally substituted thiazolyl, optionally substituted oxazolyl, and optionally substituted pyridinyl.

In another further embodiment, $R_{27}$ is selected from one of the following structures (II), (III), (IV), (V):

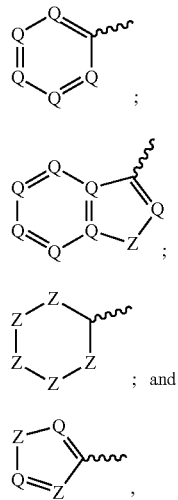

(II); (III); (IV); and (V), wherein:

Q is $CR_{29}$ or N;

Z is $C(R_{29})_2$, $NR_{29}$, S, or O;

each $R_{29}$ is, independently, selected from the group consisting of H, —OH, —$OR_{28}$, —$O_2CR_{28}$, —SH, —$SR_{28}$, —$SOCR_{28}$, —$NH_2$, —$N_3$, —$NHR_{28}$, —$N(R_{28})_2$, —$NHCOR_{28}$, —$NR_{28}COR_{28}$, —I, —Br, —Cl, —F, —CN, —$CO_2H$, —$CO_2R_{28}$, —CHO, —$COR_{28}$, —$CONH_2$, —$CONHR_{28}$, —$CON(R_{28})_2$, —COSH, —$COSR_{28}$, —$NO_2$, —$SO_3H$, —$SOR_{28}$ or —$SO_2R_{28}$, wherein each $R_{28}$ is, independently, alkyl optionally substituted with halogen, —OH or —SH.

In another further embodiment, $R_{27}$ is selected from the group consisting of:

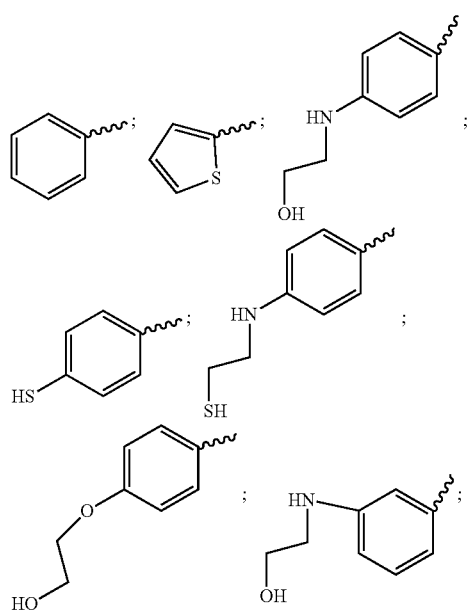

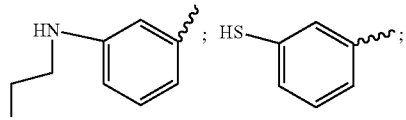

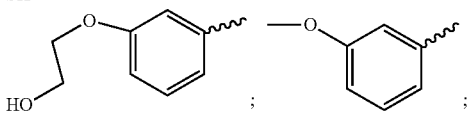

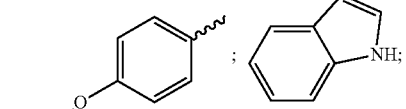

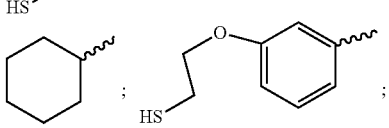

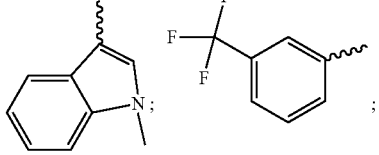

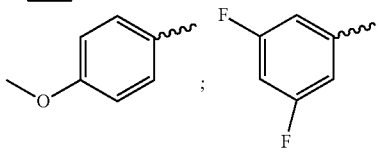

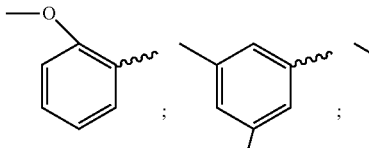

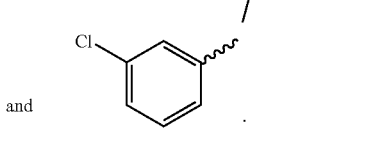

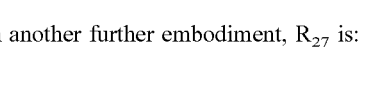

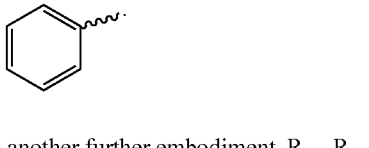

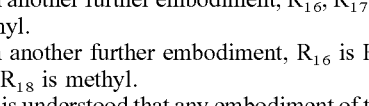

and 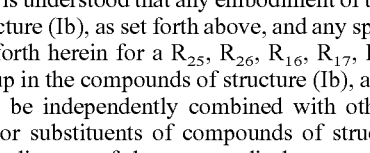.

In another further embodiment, $R_{27}$ is:

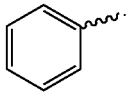

In another further embodiment, $R_{16}$, $R_{17}$ and $R_{18}$ are each methyl.

In another further embodiment, $R_{16}$ is H, $R_{17}$ is methyl, and $R_{18}$ is methyl.

It is understood that any embodiment of the compounds of structure (Ib), as set forth above, and any specific substituent set forth herein for a $R_{25}$, $R_{26}$, $R_{16}$, $R_{17}$, $R_{18}$, $R_{18}$ and $R_{20}$ group in the compounds of structure (Ib), as set forth above, may be independently combined with other embodiments and/or substituents of compounds of structure (I) to form embodiments of the present disclosure not specifically set forth above. In addition, in the event that a list of substitutents is listed for any particular $R_{25}$, $R_{26}$, $R_{16}$, $R_{17}$, $R_{18}$, $R_{18}$ and $R_{20}$ in a particular embodiment and/or claim, it is understood that each individual substituent may be deleted from the particular embodiment and/or claim and that the remaining list of substituents will be considered to be within the scope of the present disclosure.

In one embodiment, the invention provides a method of making a compound having structure (I), (Ia) or (Ib).

In another embodiment, a pharmaceutical composition is provided comprising a compound having structure (I), (Ia) or (Ib), or a stereoisomer, pharmaceutically acceptable salt or prodrug thereof, and a pharmaceutically acceptable carrier, diluent or excipient.

In another embodiment, a method of using a compound having structure (I), (Ia) or (Ib), or a stereoisomer, pharmaceutically acceptable salt or prodrug thereof, in therapy is provided. In particular, the present disclosure provides a method of treating cancer in a mammal comprising administering to a mammal in need thereof an effective amount of a compound having structure (I), (Ia) or (Ib), or a stereoisomer, pharmaceutically acceptable salt or prodrug thereof, or a pharmaceutical composition comprising a compound having structure (I), (Ia) or (Ib), or a stereoisomer, pharmaceutically acceptable salt or prodrug thereof, and a pharmaceutically acceptable carrier diluent or excipient.

In another embodiment, the present disclosure provides a method of inhibiting tumor growth in a mammal comprising administering to a mammal in need thereof an effective amount of a compound having structure (I), (Ia) or (Ib), or a stereoisomer, pharmaceutically acceptable salt or prodrug thereof, or a pharmaceutical composition comprising a compound having structure (I), (Ia) or (Ib), or a stereoisomer, pharmaceutically acceptable salt or prodrug thereof, and a pharmaceutically acceptable carrier, diluent or excipient.

In another embodiment, the present disclosure provides a method of killing cancer cells in vitro using a compound having structure (I), (Ia) or (Ib), or a stereoisomer, pharmaceutically acceptable salt or prodrug thereof. In another embodiment, the present disclosure provides a method of killing cancer cells in vivo in a mammal, comprising administering to a mammal in need thereof an effective amount of a compound having structure (I), (Ia) or (Ib), or a stereoisomer, pharmaceutically acceptable salt or prodrug thereof, or a pharmaceutical composition comprising a compound having structure (I), (Ia) or (Ib), or a stereoisomer, pharmaceutically acceptable salt or prodrug thereof, and a pharmaceutically acceptable carrier, diluent or excipient.

In another embodiment, the present disclosure provides a method of increasing the survival time of a mammal having cancer, comprising administering to such mammal an effective amount of a compound having structure (I), (Ia) or (Ib), or a stereoisomer, pharmaceutically acceptable salt or prodrug thereof, or a pharmaceutical composition comprising a compound having structure (I), (Ia) or (Ib), or a stereoisomer, pharmaceutically acceptable salt or prodrug thereof, and a pharmaceutically acceptable carrier, diluent or excipient.

In one embodiment, compositions comprising biologically active compounds having structure or (I), (Ia) or (Ib), or a stereoisomer, pharmaceutically acceptable salt or prodrug thereof, linked directly or indirectly to a targeting moiety are provided.

In one embodiment, the invention provides compositions having the following structure:

(T)-(L)-(D)         (VI)

wherein (T) is a targeting moiety, (L) is an optional linker, and (D) is a compound having structure (I), (Ia) or (Ib), or a stereoisomer, pharmaceutically acceptable salt or prodrug thereof. (D) is covalently attached to (L), if (L) is present, or (T), if (L) is not present.

In a particular embodiment, (D) is a compound having the structure (Ib).

In one embodiment, the targeting moiety is an antibody. Accordingly, in one embodiment, antibody-drug conjugates (ADCs) comprising compounds having structure (I), (Ia) or (Ib), or a stereoisomer, pharmaceutically acceptable salt or prodrug thereof, are provided.

In one embodiment, the invention provides a method of making a composition having structure (VI).

In another embodiment, a pharmaceutical composition is provided comprising a composition having structure (VI), or a stereoisomer, pharmaceutically acceptable salt or prodrug thereof, and a pharmaceutically acceptable carrier, diluent or excipient.

In another embodiment, a method of using a composition having structure (VI) in therapy is provided. In particular, the present disclosure provides a method of treating cancer in a mammal comprising administering to a mammal in need thereof an effective amount of a composition having structure (VI) or a pharmaceutical composition comprising a composition having structure (VI) and a pharmaceutically acceptable carrier diluent or excipient.

In another embodiment, the present disclosure provides a method of inhibiting tumor growth in a mammal comprising administering to a mammal in need thereof an effective amount of a composition having structure (VI) or a pharmaceutical composition comprising a composition having structure (VI) and a pharmaceutically acceptable carrier, diluent or excipient.

In another embodiment, the present disclosure provides a method of killing cancer cells in vitro using a composition having structure (VI). In another embodiment, the present disclosure provides a method of killing cancer cells in vivo in a mammal, comprising administering to a mammal in need thereof an effective amount of a composition having structure (VI) or a pharmaceutical composition comprising a composition having structure (VI) and a pharmaceutically acceptable carrier, diluent or excipient.

In another embodiment, the present disclosure provides a method of increasing the survival time of a mammal having cancer, comprising administering to a mammal in need thereof an effective amount of a composition having structure (VI) or a pharmaceutical composition comprising a composition having structure (VI) and a pharmaceutically acceptable carrier, diluent or excipient.

These and other aspects of the disclosure will be apparent upon reference to the following detailed description.

DETAILED DESCRIPTION

Figure 1:
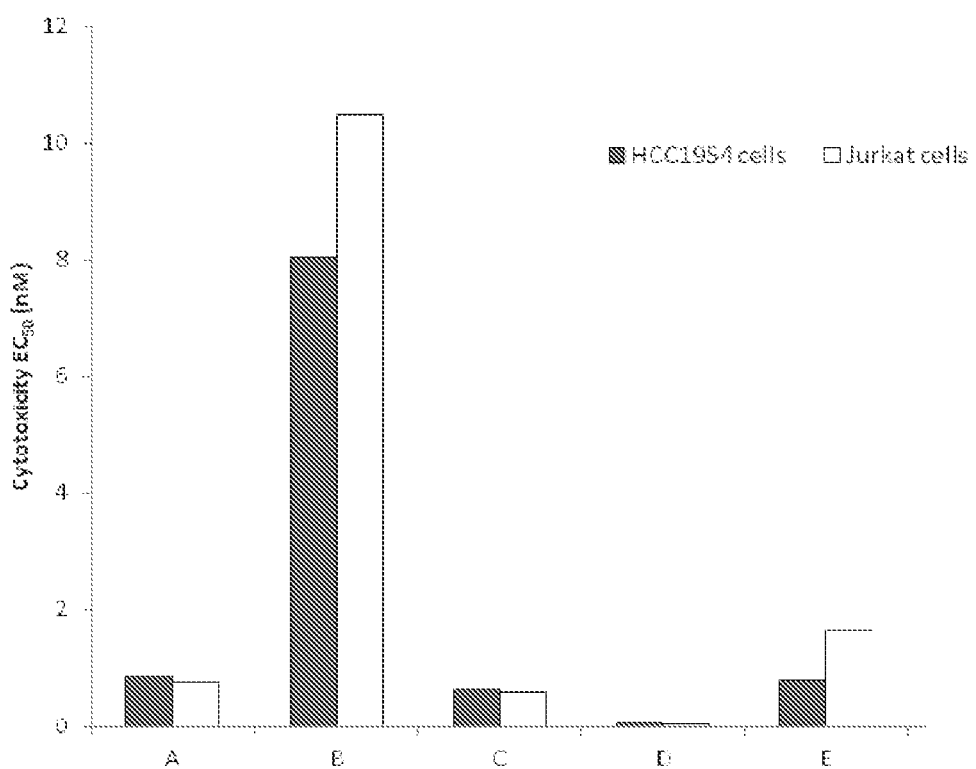
FIG. 1 shows summarized cytotoxicity data ($EC_{50}$) for each of Compounds A-E for two cell lines (HCC1954 and Jurkat).
Figure 2:
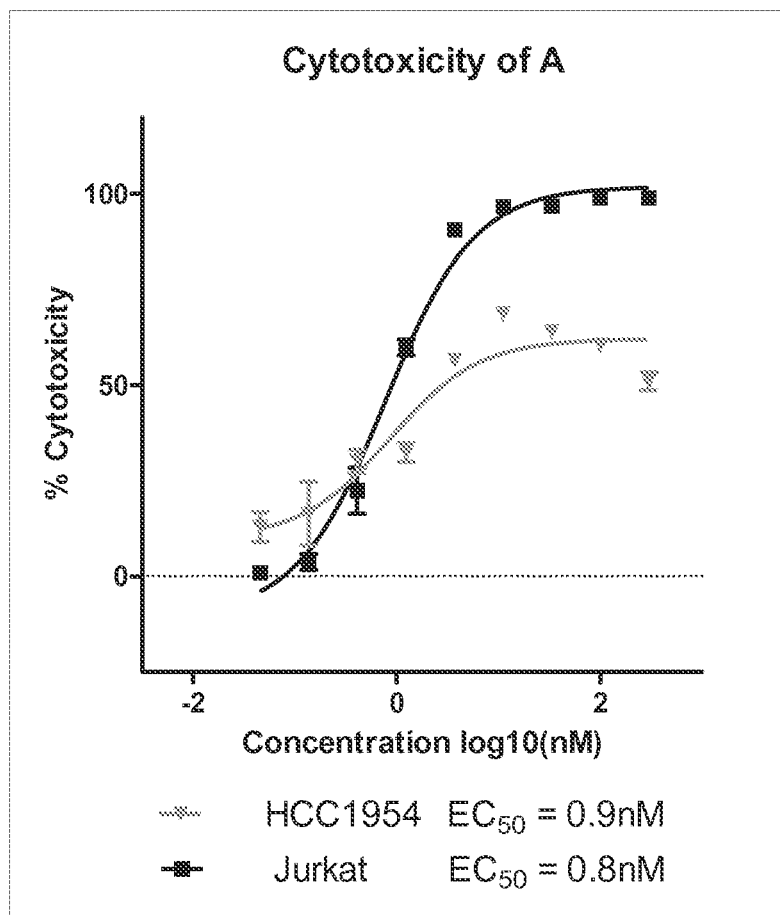
FIG. 2 shows a cytotoxicity data plot for Compound A on two cell lines (HCC1954 and Jurkat).
Figure 3:
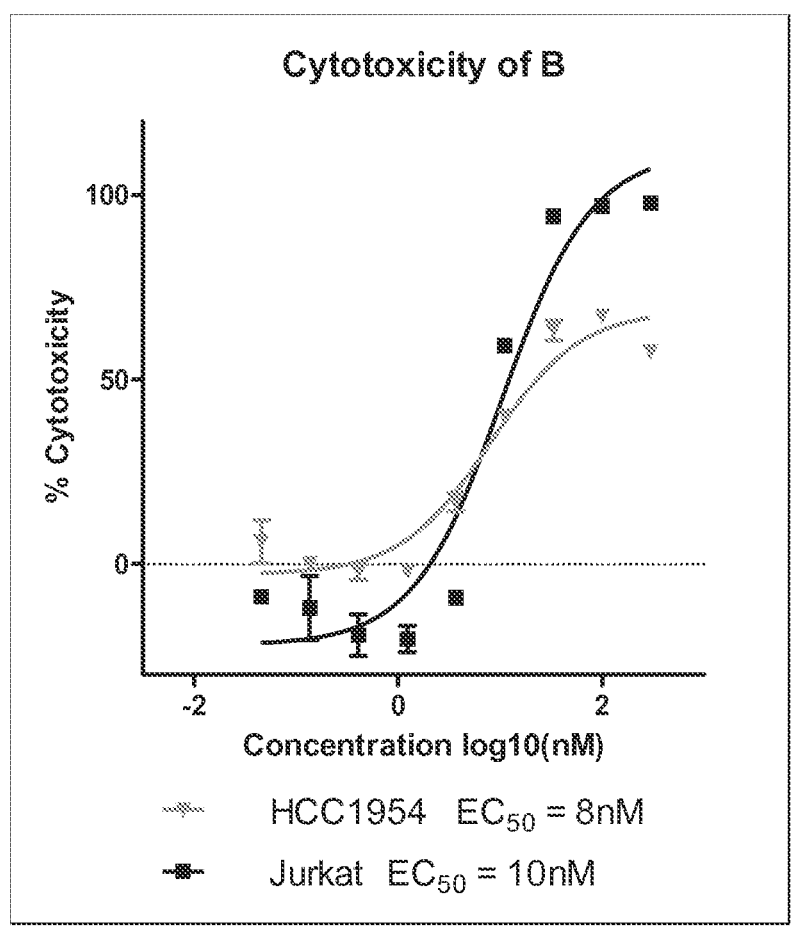
FIG. 3 shows a cytotoxicity data plot for Compound B on two cell lines (HCC1954 and Jurkat).
Figure 4:
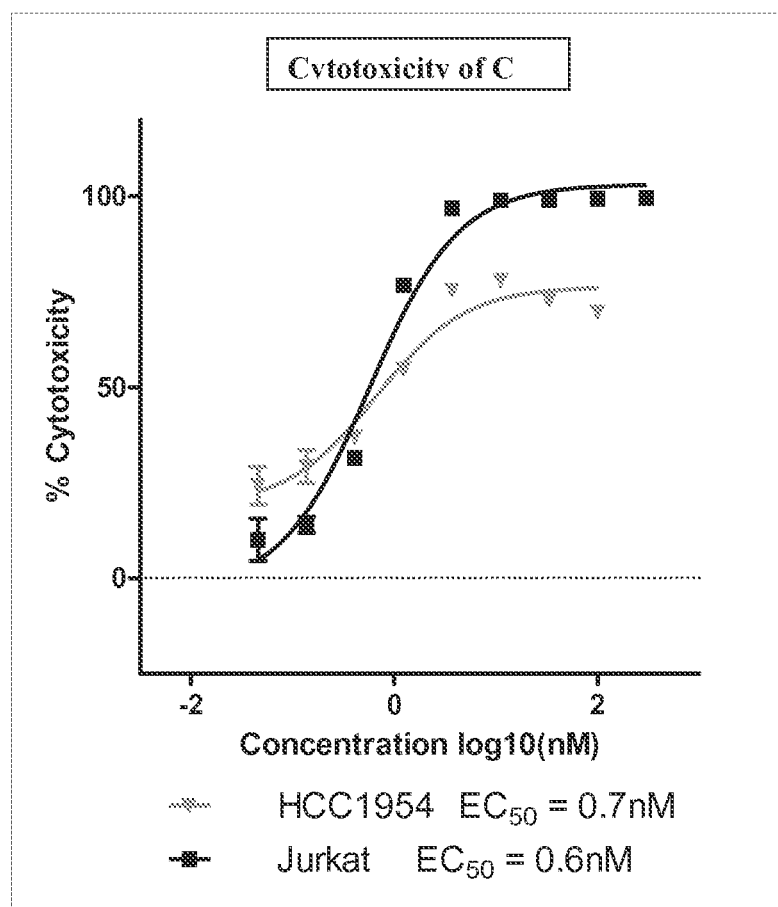
FIG. 4 shows a cytotoxicity data plot for Compound C on two cell lines (HCC1954 and Jurkat).
Figure 5:
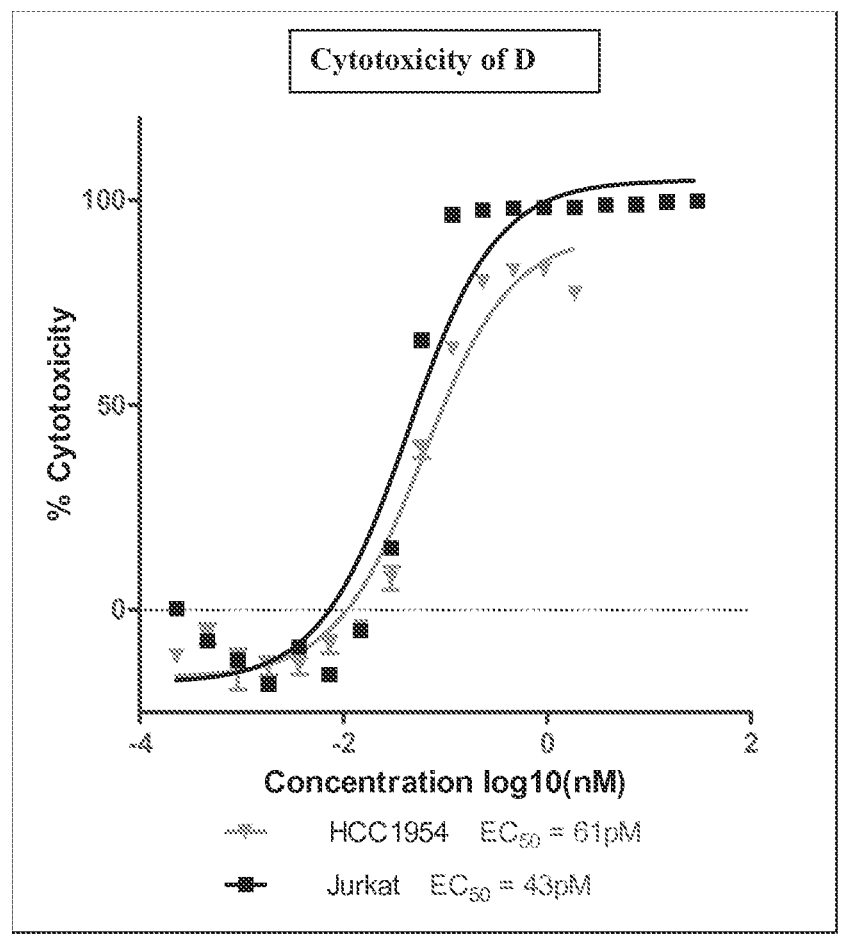
FIG. 5 shows a cytotoxicity data plot for Compound D on two cell lines (HCC1954 and Jurkat).
Figure 6:
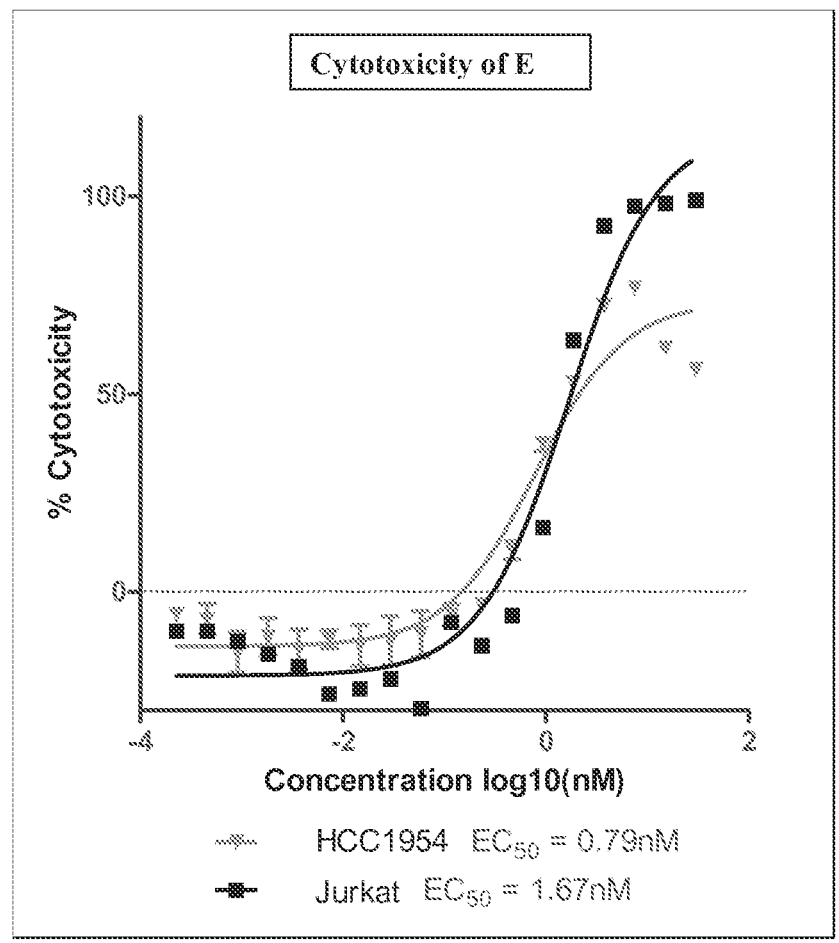
FIG. 6 shows a cytotoxicity data plot for Compound E on two cell lines (HCC1954 and Jurkat).

In the following description, certain specific details are set forth in order to provide a thorough understanding of various embodiments of the disclosure. However, one skilled in the art will understand that the disclosure may be practiced without these details.

Unless the context requires otherwise, throughout the present specification and claims, the word "comprise" and variations thereof, such as, "comprises" and "comprising" are to be construed in an open, inclusive sense, that is as "including, but not limited to".

Reference throughout this specification to "one embodiment" or "an embodiment" means that a particular feature, structure or characteristic described in connection with the embodiment is included in at least one embodiment of the present disclosure. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Unless stated otherwise, the following terms and phrases as used herein are intended to have the following meanings. When trade names are used herein, applicants intend to independently include the trade name product formulation, the generic drug, and the active pharmaceutical ingredient(s) of the trade name product.

"Amino" refers to the —$NH_2$ substituent.
"Cyano" refers to the —CN substituent.
"Hydroxy" or "hydroxyl" refers to the —OH substituent.
"Imino" refers to the =NH substituent.
"Nitro" refers to the —$NO_2$ substituent.
"Oxo" refers to the =O substituent.
"Thiol" refers to the —SH substituent.
"Thioxo" refers to the =S substituent.
"Alkyl" refers to a straight or branched hydrocarbon chain substituent consisting solely of carbon and hydrogen atoms, which is saturated or unsaturated (i.e., contains one or more double and/or triple bonds), having from one to twelve carbon atoms ($C_1$-$C_{12}$ alkyl), preferably one to eight carbon atoms ($C_1$-$C_8$ alkyl) or one to six carbon atoms ($C_1$-$C_6$ alkyl), and which is attached to the rest of the molecule by a single bond, e.g., methyl, ethyl, n-propyl, 1-methylethyl (iso-propyl), n-butyl, n-pentyl, 1,1-dimethylethyl (t-butyl), 3-methylhexyl, 2-methylhexyl, ethenyl, prop-1-enyl, but-1-enyl, pent-1-enyl, penta-1,4-dienyl, ethynyl, propynyl, butynyl, pentynyl, hexynyl, and the like. Unless stated otherwise specifically in the specification, an alkyl group may be optionally substituted.

"Alkylene" or "alkylene chain" refers to a straight or branched divalent hydrocarbon chain linking the rest of the molecule to a substituent group, consisting solely of carbon and hydrogen, which is saturated or unsaturated (i.e., contains one or more double and/or triple bonds), and having from one to twelve carbon atoms, e.g., methylene, ethylene, propylene, n-butylene, ethenylene, propenylene, n-butynylene, propynylene, n-butynylene, and the like. The alkylene chain is attached to the rest of the molecule through a single or double bond and to the substituent group through a single or double bond. The points of attachment of the alkylene chain to the rest of the molecule and to the substituent group can be through one carbon or any two carbons within the chain. Unless stated otherwise specifically in the specification, an alkylene chain may be optionally substituted.

"Alkoxy" refers to a substituent of the formula —OR, where $R_a$ is an alkyl substituent as defined above containing one to twelve carbon atoms. Unless stated otherwise specifically in the specification, an alkoxy group may be optionally substituted.

"Alkylamino" refers to a substituent of the formula —NHR$_a$ or —NR$_a$R$_a$ where each $R_a$ is, independently, an alkyl substituent as defined above containing one to twelve carbon atoms. Unless stated otherwise specifically in the specification, an alkylamino group may be optionally substituted.

"Thioalkyl" refers to a substituent of the formula —SR$_a$ where $R_a$ is an alkyl substituent as defined above containing one to twelve carbon atoms. Unless stated otherwise specifically in the specification, a thioalkyl group may be optionally substituted.

"Aryl" refers to a hydrocarbon ring system substituent comprising hydrogen, 6 to 18 carbon atoms and at least one aromatic ring. For purposes of this disclosure, the aryl substituent may be a monocyclic, bicyclic, tricyclic or tetracyclic ring system, which may include fused or bridged ring systems. Aryl substituents include, but are not limited to, aryl substituents derived from aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. Unless stated otherwise specifically in the specification, the term "aryl" or the prefix "ar-" (such as in "aralkyl") is meant to include aryl substituents that are optionally substituted.

"Aralkyl" refers to a substituent of the formula —R$_b$—R, where $R_b$ is an alkylene chain as defined above and R, is one or more aryl substituents as defined above, for example, benzyl, diphenylmethyl and the like. Unless stated otherwise specifically in the specification, an aralkyl group may be optionally substituted.

"Cycloalkyl" or "carbocyclic ring" refers to a stable non-aromatic monocyclic or polycyclic hydrocarbon substituent consisting solely of carbon and hydrogen atoms, which may include fused or bridged ring systems, having from three to fifteen carbon atoms, preferably having from three to ten carbon atoms, and which is saturated or unsaturated and attached to the rest of the molecule by a single bond. Monocyclic substituents include, for example, cyclopropyl, cyclobutyl, cyclopentyl, cyclohexyl, cycloheptyl, and cyclooctyl. Polycyclic substituents include, for example, adamantyl, norbornyl, decalinyl, 7,7-dimethyl-bicyclo [2.2.1]heptanyl, and the like. Unless otherwise stated specifically in the specification, a cycloalkyl group may be optionally substituted.

"Cycloalkylalkyl" refers to a substituent of the formula —R$_b$R$_d$ where R$_d$ is an alkylene chain as defined above and R$_g$ is a cycloalkyl substituent as defined above. Unless stated otherwise specifically in the specification, a cycloalkylalkyl group may be optionally substituted.

"Fused" refers to any ring structure described herein which is fused to an existing ring structure in the compounds of the disclosure. When the fused ring is a heterocyclyl ring or a heteroaryl ring, any carbon atom on the existing ring structure which becomes part of the fused heterocyclyl ring or the fused heteroaryl ring may be replaced with a nitrogen atom.

"Halo" or "halogen" refers to bromo, chloro, fluoro or iodo.

"Haloalkyl" refers to an alkyl substituent, as defined above, that is substituted by one or more halo substituents, as defined above, e.g., trifluoromethyl, difluoromethyl, trichloromethyl, 2,2,2-trifluoroethyl, 1,2-difluoroethyl, 3-bromo-2-fluoropropyl, 1,2-dibromoethyl, and the like. Unless stated otherwise specifically in the specification, a haloalkyl group may be optionally substituted.

"Heterocyclyl" or "heterocyclic ring" refers to a stable 3- to 18-membered non-aromatic ring substituent which consists of two to twelve carbon atoms and from one to six heteroatoms selected from the group consisting of nitrogen, oxygen and sulfur. Unless stated otherwise specifically in the specification, the heterocyclyl substituent may be a monocyclic, bicyclic, tricyclic or tetracyclic ring system, which may include fused or bridged ring systems; and the nitrogen, carbon or sulfur atoms in the heterocyclyl substituent may be optionally oxidized; the nitrogen atom may be optionally quaternized; and the heterocyclyl substituent may be partially or fully saturated. Examples of such heterocyclyl substituents include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxothiomorpholinyl. Unless stated otherwise specifically in the specification, a heterocyclyl group may be optionally substituted.

"N-heterocyclyl" refers to a heterocyclyl substituent as defined above containing at least one nitrogen and where the point of attachment of the heterocyclyl substituent to the rest of the molecule is through a nitrogen atom in the heterocyclyl substituent. Unless stated otherwise specifically in the specification, a N-heterocyclyl group may be optionally substituted.

"Heterocyclylalkyl" refers to a substituent of the formula —R$_b$R$_c$ where R$_a$, is an alkylene chain as defined above and R is a heterocyclyl substituent as defined above, and if the heterocyclyl is a nitrogen-containing heterocyclyl, the heterocyclyl may be attached to the alkyl substituent at the nitrogen atom. Unless stated otherwise specifically in the specification, a heterocyclylalkyl group may be optionally substituted.

"Heteroaryl" refers to a 5- to 14-membered ring system substituent comprising hydrogen atoms, one to thirteen carbon atoms, one to six heteroatoms selected from the group consisting of nitrogen, oxygen and sulfur, and at least one aromatic ring. For purposes of this disclosure, the heteroaryl substituent may be a monocyclic, bicyclic, tricyclic or tetracyclic ring system, which may include fused or bridged ring systems; and the nitrogen, carbon or sulfur atoms in the heteroaryl substituent may be optionally oxidized; the nitrogen atom may be optionally quaternized. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, I-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e. thienyl). Unless stated otherwise specifically in the specification, a heteroaryl group may be optionally substituted.

"N-heteroaryl" refers to a heteroaryl substituent as defined above containing at least one nitrogen and where the point of attachment of the heteroaryl substituent to the rest of the molecule is through a nitrogen atom in the heteroaryl substituent. Unless stated otherwise specifically in the specification, an N-heteroaryl group may be optionally substituted.

"Heteroarylalkyl" refers to a substituent of the formula —$R_bR_f$ where $R_b$ is an alkylene chain as defined above and $R_f$ is a heteroaryl substituent as defined above. Unless stated otherwise specifically in the specification, a heteroarylalkyl group may be optionally substituted.

The term "substituted" used herein means any of the above groups (i.e., alkyl, alkylene, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl) wherein at least one hydrogen atom is replaced by a bond to a non-hydrogen atoms such as, but not limited to: a halogen atom such as F, Cl, Br, and I; an oxygen atom in groups such as hydroxyl groups, alkoxy groups, and ester groups; a sulfur atom in groups such as thiol groups, thioalkyl groups, sulfone groups, sulfonyl groups, and sulfoxide groups; a nitrogen atom in groups such as azides, amines, amides, alkylamines, dialkylamines, arylamines, alkylarylamines, diarylamines, N-oxides, imides, and enamines; a silicon atom in groups such as trialkylsilyl groups, dialkylarylsilyl groups, alkyldiarylsilyl groups, and triarylsilyl groups; and other heteroatoms in various other groups. "Substituted" also means any of the above groups in which one or more hydrogen atoms are replaced by a higher-order bond (e.g., a double- or triple-bond) to a heteroatom such as oxygen in oxo, carbonyl, carboxyl, and ester groups; and nitrogen in groups such as imines, oximes, hydrazones, and nitriles. For example, "substituted" includes any of the above groups in which one or more hydrogen atoms are replaced with —$NR_gR_h$, —$NR_gC(=O)R_h$, —$NR_gC(=O)NR_gR_h$, —$NR_gC(=O)OR_h$, —$NR_gC(=NR_g)NR_gR_h$, —$NR_gSO_2R_h$, —$OC(=O)NR_gR_h$, —$OR_g$, —$SR_g$, —$SOR_g$, —$SO_2R_g$, —$OSO_2R_g$, —$SO_2OR_g$, =$NSO_2R_g$, and —$SO_2NR_gR_h$. "Substituted also means any of the above groups in which one or more hydrogen atoms are replaced with —$C(=O)R_g$, —$C(=O)OR_g$, —$C(=O)NR_gR_h$, —$CH_2SO_2R_g$, —$CH_2SO_2NR_BR_h$. In the foregoing, $R_g$ and $R_h$ are the same or different and independently hydrogen, alkyl, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl. "Substituted" further means any of the above groups in which one or more hydrogen atoms are replaced by a bond to an amino, cyano, hydroxyl, imino, nitro, oxo, thioxo, halo, alkyl, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl group. In addition, each of the foregoing substituents may also be optionally substituted with one or more of the above substituents.

The term "protecting group," as used herein, refers to a labile chemical moiety which is known in the art to protect reactive groups including without limitation, hydroxyl and amino groups, against undesired reactions during synthetic procedures. Hydroxyl and amino groups which protected with a protecting group are referred to herein as "protected hydroxyl groups" and "protected amino groups", respectively. Protecting groups are typically used selectively and/or orthogonally to protect sites during reactions at other reactive sites and can then be removed to leave the unprotected group as is or available for further reactions. Protecting groups as known in the art are described generally in Greene and Wuts, Protective Groups in Organic Synthesis, 3rd edition, John Wiley & Sons, New York (1999). Groups can be selectively incorporated into compounds of the present disclosure as precursors. For example an amino group can be placed into a compound of the disclosure as an azido group that can be chemically converted to the amino group at a desired point in the synthesis. Generally, groups are protected or present as a precursor that will be inert to reactions that modify other areas of the parent molecule for conversion into their final groups at an appropriate time. Further representative protecting or precursor groups are discussed in Agrawal, et al., Protocols for Oligonucleotide Conjugates, Eds, Humana Press; New Jersey, 1994; Vol. 26 pp. 1-72. Examples of "hydroxyl protecting groups" include, but are not limited to, t-butyl, t-butoxymethyl, methoxymethyl, tetrahydropyranyl, 1-ethoxyethyl, 1-(2-chloroethoxy) ethyl, 2-trimethylsilylethyl, p-chlorophenyl, 2,4-dinitrophenyl, benzyl, 2,6-dichlorobenzyl, diphenylmethyl, p-nitrobenzyl, triphenylmethyl, trimethylsilyl, triethylsilyl, t-butyldimethylsilyl, t-butyldiphenylsilyl (TBDPS), triphenylsilyl, benzoylformate, acetate, chloroacetate, trichloroacetate, tri-fluoroacetate, pivaloate, benzoate, p-phenylbenzoate, 9-fluorenylmethyl carbonate, mesylate and tosylate. Examples of "amino protecting groups" include, but are not limited to, carbamate-protecting groups, such as 2-trimethylsilylethoxycarbonyl (Teoc), 1-methyl-1-(4-biphenylyl) ethoxycarbonyl (Bpoc), t-butoxycarbonyl (BOC), allyloxycarbonyl (Alloc), 9-fluorenylmethyloxycarbonyl (Fmoc), and benzyloxycarbonyl (Cbz); amide protecting groups, such as formyl, acetyl, trihaloacetyl, benzoyl, and nitrophenylacetyl; sulfonamide-protecting groups, such as 2-nitrobenzenesulfonyl; and imine and cyclic imide protecting groups, such as phthalimido and dithiasuccinoyl.

"Prodrug" is meant to indicate a compound that may be converted under physiological conditions or by solvolysis to a biologically active compound of the disclosure. Thus, the term "prodrug" refers to a metabolic precursor of a compound of the disclosure that is pharmaceutically acceptable. A prodrug may be inactive when administered to a subject in need thereof, but is converted in vivo to an active compound of the disclosure. In one embodiment, a prodrug is rapidly transformed in vivo to yield the parent compound of the disclosure, for example, by hydrolysis in blood. In one embodiment, a prodrug may be stable in plasma or blood. In one embodiment, a prodrug may be targeted form of a compound of the invention. The prodrug compound often offers advantages of solubility, tissue compatibility or delayed release in a mammalian organism (see, Bundgard, H., Design of Prodrugs (1985), pp. 7-9, 21-24 (Elsevier, Amsterdam)). A discussion of prodrugs is provided in Higuchi, T., et al., A.C.S. Symposium Series, Vol. 14, and in Bioreversible Carriers in Drug Design, Ed. Edward B. Roche, American Pharmaceutical Association and Pergamon Press, 1987.

The term "prodrug" is meant to include any covalently bonded carriers, which release the active compound of the disclosure in vivo when such prodrug is administered to a mammalian subject. Conjugates, including ADCs, as disclosed herein, are such prodrugs of compositions having structure (I), (Ia) or (Ib). Prodrugs of a compound of the disclosure may be prepared by modifying functional groups present in the compound of the disclosure in such a way that the modifications are cleaved, either in routine manipulation or in vivo, to the parent compound of the disclosure. Prodrugs include compounds of the disclosure wherein a hydroxy, amino or mercapto group is bonded to any group that, when the prodrug of the compound of the disclosure is administered to a mammalian subject, cleaves to form a free hydroxy, free amino or free mercapto group, respectively. Examples of prodrugs include, but are not limited to, acetate, formate and benzoate derivatives of alcohol or amide derivatives of amine functional groups in the compounds of the disclosure and the like.

The present disclosure also meant to encompass all pharmaceutically acceptable compounds of structure (I), (Ia) or (Ib) being isotopically-labelled by having one or more atoms replaced by an atom having a different atomic mass or mass number. Examples of isotopes that can be incorporated into the disclosed compounds include isotopes of hydrogen, carbon, nitrogen, oxygen, phosphorous, fluorine, chlorine, and iodine, such as $^{2}H$, $^{3}H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, $^{36}Cl$, $^{123}I$, and $^{125}I$, respectively. These radiolabelled compounds could be useful to help determine or measure the effectiveness of the compounds, by characterizing, for example, the site or mode of action, or binding affinity to pharmacologically important site of action. Certain isotopically-labelled compounds of structure (I), (Ia) or (Ib), for example, those incorporating a radioactive isotope, are useful in drug and/or substrate tissue distribution studies. The radioactive isotopes tritium, i.e. $^{3}H$, and carbon-14, i.e. $^{14}C$, are particularly useful for this purpose in view of their ease of incorporation and ready means of detection.

Substitution with heavier isotopes such as deuterium, i.e. $^{2}H$, may afford certain therapeutic advantages resulting from greater metabolic stability, for example, increased in vivo half-life or reduced dosage requirements, and hence may be preferred in some circumstances.

Substitution with positron emitting isotopes, such as $^{11}C$, $^{18}F$, $^{15}O$ and $^{13}N$, can be useful in Positron Emission Topography (PET) studies for examining substrate receptor occupancy. Isotopically-labeled compounds of structure (I), (Ia) or (Ib) can generally be prepared by conventional techniques known to those skilled in the art or by processes analogous to those described in the Preparations and Examples as set out below using an appropriate isotopically-labeled reagent in place of the non-labeled reagent previously employed.

The present disclosure is also meant to encompass the in vivo metabolic products of the disclosed compounds. Such products may result from, for example, the oxidation, reduction, hydrolysis, amidation, esterification, and the like of the administered compound, primarily due to enzymatic processes. Accordingly, the present disclosure includes compounds produced by a process comprising administering a compound of this disclosure to a mammal for a period of time sufficient to yield a metabolic product thereof. Such products are typically identified by administering a radiolabelled compound of the disclosure in a detectable dose to an animal, such as rat, mouse, guinea pig, monkey, or to human, allowing sufficient time for metabolism to occur, and isolating its conversion products from the urine, blood or other biological samples.

"Stable compound" and "stable structure" are meant to indicate a compound that is sufficiently robust to survive isolation to a useful degree of purity from a reaction mixture, and formulation into an efficacious therapeutic agent.

The term "antibody" herein is used in the broadest sense and specifically covers intact monoclonal antibodies, polyclonal antibodies, multispecific antibodies (e.g., bispecific antibodies) formed from at least two intact antibodies, and antibody fragments, so long as they exhibit the desired biological activity. The term "antibody" refers to a full-length immunoglobulin molecule or a functionally active portion of a full-length immunoglobulin molecule, i.e., a molecule that contains an antigen binding site that immunospecifically binds an antigen of a target of interest or part thereof. The immunoglobulin disclosed herein can be of any type (e.g., IgG, IgE, IgM, IgD, and IgA), class (e.g., IgG1, IgG2, IgG3, IgG4, IgA1 and IgA2) or subclass of immunoglobulin molecule. The immunoglobulins can be derived from any species. In one aspect the immunoglobulin is of human, murine, or rabbit origin. In another aspect, the antibodies are polyclonal, monoclonal, multi-specific (e.g., bispecific), human, humanized or chimeric antibodies, linear antibodies, single chain antibodies, diabodies, maxibodies, minibodies, Fv, Fab fragments, F(ab') fragments, F(ab')$_2$ fragments, fragments produced by a Fab expression library, anti-idiotypic (anti-Id) antibodies, CDR's, and epitope-binding fragments of any of the above which immunospecifically bind to a target antigen.

The term "monoclonal antibody" as used herein refers to an antibody obtained from a population of substantially homogeneous antibodies, i.e., the individual antibodies comprising the population are identical except for possible naturally-occurring mutations that may be present in minor amounts. Monoclonal antibodies include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies (see, e.g., U.S. Pat. No. 4,816,567; and Morrison et al., 1984, Proc. Natl. Acad. Sci. USA 81:6851-6855). Monoclonal antibodies also include humanized antibodies may contain a completely human constant region and a CDRs from a nonhuman source.

An "intact" antibody is one which comprises an antigen-binding variable region as well as a light chain constant domain (CL) and heavy chain constant domains, $C_{H1}$, $C_{H2}$ and $C_{H3}$. The constant domains may be native sequence constant domains (e.g., human native sequence constant domains) or amino acid sequence variant thereof.

"Antibody fragments" comprise a portion of an intact antibody, preferably comprising the antigen-binding or variable region thereof. Examples of antibody fragments include Fab, Fab', F(ab')$_2$, and Fv fragments; diabodies; linear antibodies; single-chain antibody molecules; maxibodies; minibodies; and multispecific antibodies formed from antibody fragment(s).

An "isolated" antibody is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In some embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

An antibody "which binds" an antigen of interest is one capable of binding that antigen with sufficient affinity such that the antibody is useful in targeting a cell expressing the antigen.

A "native sequence" polypeptide is one which has the same amino acid sequence as a polypeptide derived from nature. Such native sequence polypeptides can be isolated from nature or can be produced by recombinant or synthetic means. Thus, a native sequence polypeptide can have the amino acid sequence of naturally-occurring human polypeptide, murine polypeptide, or polypeptide from any other mammalian species.

The term "intracellular metabolite" refers to a compound resulting from a metabolic process or reaction inside a cell on a composition of the invention (e.g., an antibody drug conjugate (ADC)). The metabolic process or reaction may be an enzymatic process such as proteolytic cleavage of a peptide linker of the subject composition, or hydrolysis of a functional group such as a hydrazone, ester, or amide within the subject composition. In the context of conjugates, including ADCs, intracellular metabolites include, but are not limited to, antibodies and free drug which have been separated intracellularly, i.e., after entry, diffusion, uptake or transport into a cell (e.g., by enzymatic cleavage of an ADC by an intracellular enzyme).

In the context of conjugates, including ADCs, the terms "intracellularly cleaved" and "intracellular cleavage" refer to metabolic processes or reactions inside a cell on a composition of the invention whereby the covalent attachment, e.g., the linker (L), between the drug moiety (D) and the targeting moiety (T) (e.g., an antibody) is broken, resulting in the free drug dissociated from (T) inside the cell. In one embodiment, the cleaved moieties of the subject compositions are thus intracellular metabolites (e.g., T, T-L fragment, D-L fragment, D). Accordingly, in one embodiment, the invention provides compositions that are cleavage products of a composition having structure (VI), which cleavage products include compositions comprising structure (I), (Ia) or (Ib), or stereoisomers thereof. Similarly, the linker (L), between microtubule disrupting peptide toxin (PT) and the targeting moiety (T) (e.g., an antibody) may be broken intracellularly, resulting in the PT dissociated from (T) inside the cell. The cleaved moieties of the subject compositions are thus intracellular metabolites (e.g., T, T-L fragment, PT-L fragment, PT). Accordingly, in one embodiment, the invention provides compositions that are cleavage products of a composition having structure (VII), which cleavage products include compositions structure (I), (Ia) or (Ib), or stereoisomers thereof.

The term "extracellular cleavage" refers a metabolic process or reaction outside a cell on a composition of the invention whereby the covalent attachment, e.g., the linker (L), between the drug moiety (D) and the targeting moiety (T) (e.g., an antibody) is broken, resulting in the free drug dissociated from (T) outside the cell. In one embodiment, the cleaved moieties of the subject compositions are thus initially extracellular metabolites (e.g., T, T-L fragment, D-L fragment, D), which may move intracellularly by diffusion and cell permeability or transport. Accordingly, in one embodiment, the invention provides compositions that are cleavage products of a composition having structure (VI), which cleavage products include compositions comprising structure (I), (Ia) or (Ib), or stereoisomers thereof. Similarly, the linker (L), between microtubule disrupting peptide toxin (PT) and the targeting moiety (T) (e.g., an antibody) may be broken extracellularly, resulting in the PT dissociated from (T) outside the cell. The cleaved moieties of the subject compositions are thus initially extracellular metabolites (e.g., T, T-L fragment, PT-L fragment, PT). Accordingly, in one embodiment, the invention provides compositions that are cleavage products of a composition having structure (VII), which cleavage products include compositions comprising structure (I), (Ia) or (Ib), or stereoisomers thereof.

"Mammal" includes humans and both domestic animals such as laboratory animals and household pets (e.g., cats, dogs, swine, cattle, sheep, goats, horses, rabbits), and non-domestic animals such as wildlife and the like.

"Optional" or "optionally" means that the subsequently described event of circumstances may or may not occur, and that the description includes instances where said event or circumstance occurs and instances in which it does not. For example, "optionally substituted aryl" means that the aryl substituent may or may not be substituted and that the description includes both substituted aryl substituents and aryl substituents having no substitution.

"Pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration (or other similar regulatory agency of another jurisdiction) as being acceptable for use in humans or domestic animals.

"Pharmaceutically acceptable salt" includes both acid and base addition salts.

"Pharmaceutically acceptable acid addition salt" refers to those salts which retain the biological effectiveness and properties of the free bases, which are not biologically or otherwise undesirable, and which are formed with inorganic acids such as, but are not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

Often crystallizations produce a solvate of the compound of the disclosure. As used herein, the term "solvate" refers to an aggregate that comprises one or more molecules of a compound of the disclosure with one or more molecules of solvent. The solvent may be water, in which case the solvate may be a hydrate. Alternatively, the solvent may be an organic solvent. Thus, the compounds of the present disclosure may exist as a hydrate, including a monohydrate, dihydrate, hemihydrate, sesquihydrate, trihydrate, tetrahydrate and the like, as well as the corresponding solvated forms. The compound of the disclosure may be true solvates, while in other cases, the compound of the disclosure may merely retain adventitious water or be a mixture of water plus some adventitious solvent.

A "pharmaceutical composition" refers to a formulation of a compound of the disclosure and a medium generally accepted in the art for the delivery of the biologically active compound to mammals, e.g., humans. Such a medium includes all pharmaceutically acceptable carriers, diluents or excipients therefor.

Non-limiting examples of disorders to be treated herein include benign and malignant tumors; leukemia and lymphoid malignancies, in particular breast, ovarian, stomach, endometrial, salivary gland, lung, kidney, colon, thyroid, pancreatic, prostate or bladder cancer; neuronal, glial, astrocytal, hypothalamic and other glandular, macrophagal, epithelial, stromal and blastocoelic disorders, autoimmune disease, inflammatory disease, fibrosis, and infectious disease. Given the characteristics, and particularly the potency of the subject compositions, it will be apparent to the artisan of reasonable skill that the compounds of the invention may be indicated for use to treat any disease where exertion of a cytotoxic or cytotoxic effect on a target cell is desirable.

In one embodiment, compositions of the invention are used to treat autoimmune disease. Antibodies immunospecific for an antigen of a cell that is responsible for producing autoimmune antibodies can be obtained from any organization (e.g., a university scientist or a company such as Genentech) or produced by any method known to one of skill in the art such as, e.g., chemical synthesis or recombinant expression techniques. In another embodiment, useful Ligand antibodies that are immunospecific for the treatment of autoimmune diseases include, but are not limited to, Anti-Nuclear Antibody; Anti ds DNA; Anti ss DNA, Anti Cardiolipin Antibody IgM, IgG; Anti Phospholipid Antibody IgM, IgG; Anti SM Antibody; Anti Mitochondrial Antibody;

Thyroid Antibody; Microsomal Antibody; Thyroglobulin Antibody; Anti SCL-70; Anti-Jo; Anti-U1RNP; Anti-La/SSB; Anti SSA; Anti SSB; Anti Perital Cells Antibody; Anti Histones; Anti RNP; C-ANCA; P-ANCA; Anti centromere; Anti-Fibrillarin, and Anti GBM Antibody. In certain preferred embodiments, antibodies useful in the present methods, can bind to both a receptor or a receptor complex expressed on an activated lymphocyte.

The receptor or receptor complex can comprise an immunoglobulin gene superfamily member, a TNF receptor superfamily member, an integrin, a cytokine receptor, a chemokine receptor, a major histocompatibility protein, a lectin, or a complement control protein. Non-limiting examples of suitable immunoglobulin superfamily members are CD2, CD3, CD4, CD8, CD19, CD22, CD28, CD79, CD90, CD152/CTLA-4, PD-1, and ICOS.

Non-limiting examples of suitable TNF receptor superfamily members are CD27, CD40, CD95/Fas, CD134/OX40, CD137/4-1BB, TNF-R1, TNFR-2, RANK, TACI, BCMA, osteoprotegerin, Apo2/TRAIL-R1, TRAIL-R2, TRAIL-R3, TRAIL-R4, and APO-3. Non-limiting examples of suitable integrins are CD11a, CD11b, CD11c, CD18, CD29, CD41, CD49a, CD49b, CD49c, CD49d, CD49e, CD49f, CD103, and CD104. Non-limiting examples of suitable lectins are C-type, S-type, and I-type lectin.

In one embodiment, the Ligand is an antibody that binds to an activated lymphocyte that is associated with an autoimmune disease.

Immunological diseases that are characterized by inappropriate activation of immune cells and that can be treated or prevented by the methods described herein can be classified, for example, by the type(s) of hypersensitivity reaction(s) that underlie the disorder. These reactions are typically classified into four types: anaphylactic reactions, cytotoxic (cytolytic) reactions, immune complex reactions, or cell-mediated immunity (CMI) reactions (also referred to as delayed-type hypersensitivity (DTH) reactions). (See, e.g., Fundamental Immunology (William E. Paul ed., Raven Press, N.Y., 3rd ed. 1993).)

Specific examples of such immunological diseases include the following: rheumatoid arthritis, autoimmune demyelinative diseases (e.g., multiple sclerosis, allergic encephalomyelitis), endocrine ophthalmopathy, uveoretinitis, systemic lupus erythematosus, myasthenia gravis, Grave's disease, glomerulonephritis, autoimmune hepatological disorder, inflammatory bowel disease (e.g., Crohn's disease), anaphylaxis, allergic reaction, Sjogren's syndrome, type I diabetes mellitus, primary biliary cirrhosis, Wegener's granulomatosis, fibromyalgia, polymyositis, dermatomyositis, multiple endocrine failure, Schmidt's syndrome, autoimmune uveitis, Addison's disease, adrenalitis, thyroiditis, Hashimoto's thyroiditis, autoimmune thyroid disease, pernicious anemia, gastric atrophy, chronic hepatitis, lupoid hepatitis, atherosclerosis, subacute cutaneous lupus erythematosus, hypoparathyroidism, Dressler's syndrome, autoimmune thrombocytopenia, idiopathic thrombocytopenic purpura, hemolytic anemia, pemphigus vulgaris, pemphigus, dermatitis herpetiformis, alopecia arcata, pemphigoid, scleroderma, progressive systemic sclerosis, CREST syndrome (calcinosis, Raynaud's phenomenon, esophageal dysmotility, sclerodactyl), and telangiectasia), male and female autoimmune infertility, ankylosing spondolytis, ulcerative colitis, mixed connective tissue disease, polyarteritis nedosa, systemic necrotizing vasculitis, atopic dermatitis, atopic rhinitis, Goodpasture's syndrome, Chagas' disease, sarcoidosis, rheumatic fever, asthma, recurrent abortion, anti-phospholipid syndrome, farmer's lung, erythema multiforme, post cardiotomy syndrome, Cushing's syndrome, autoimmune chronic active hepatitis, bird-fancier's lung, toxic epidermal necrolysis, Alport's syndrome, alveolitis, allergic alveolitis, fibrosing alveolitis, interstitial lung disease, erythema nodosum, pyoderma gangrenosum, transfusion reaction, Takayasu's arteritis, polymyalgia rheumatica, temporal arteritis, schistosomiasis, giant cell arteritis, ascariasis, aspergillosis, Sampter's syndrome, eczema, lymphomatoid granulomatosis, Behcet's disease, Caplan's syndrome, Kawasaki's disease, dengue, encephalomyelitis, endocarditis, endomyocardial fibrosis, endophthalmitis, erythema elevatum et diutinum, psoriasis, erythroblastosis fetalis, eosinophilic faciitis, Shulman's syndrome, Felty's syndrome, filariasis, cyclitis, chronic cyclitis, heterochronic cyclitis, Fuch's cyclitis, IgA nephropathy, Henoch-Schonlein purpura, graft versus host disease, transplantation rejection, cardiomyopathy, Eaton-Lambert syndrome, relapsing polychondritis, cryoglobulinemia, Waldenstrom's macroglobulemia, Evan's syndrome, and autoimmune gonadal failure. Accordingly, the methods described herein encompass treatment of disorders of B lymphocytes (e.g., systemic lupus erythematosus, Goodpasture's syndrome, rheumatoid arthritis, and type I diabetes), Th1-lymphocytes (e.g., rheumatoid arthritis, multiple sclerosis, psoriasis, Sjorgren's syndrome, Hashimoto's thyroiditis, Grave's disease, primary biliary cirrhosis, Wegener's granulomatosis, tuberculosis, or acute graft versus host disease), or Th2-lymphocytes (e.g., atopic dermatitis, systemic lupus erythematosus, atopic asthma, rhinoconjunctivitis, allergic rhinitis, Omenn's syndrome, systemic sclerosis, or chronic graft versus host disease). Generally, disorders involving dendritic cells involve disorders of Th1-lymphocytes or Th2-lymphocytes.

In certain embodiments, the immunological disorder is T cell-mediated, which may include activated T cells. ADC's or ADC derivatives can be administered to deplete such activated T cells.

In one embodiment, compositions of the invention may be used to treat fibrosis. Fibrosis can occur in many tissues within the body, typically as a result of inflammation or damage, examples include but are not limited to; Lungs, Pulmonary fibrosis, Idiopathic pulmonary fibrosis, Cystic fibrosis; Liver, Cirrhosis; Heart, Endomyocardial fibrosis, Old myocardial infarction, Atrial Fibrosis; Others, Mediastinal fibrosis (soft tissue of the mediastinum), Myelofibrosis (bone marrow), Retroperitoneal fibrosis (soft tissue of the retroperitoneum), Progressive massive fibrosis (lungs); a complication of coal workers' pneumoconiosis, Nephrogenic systemic fibrosis (skin), Crohn's Disease (intestine), Keloid (skin), Scleroderma/systemic sclerosis (skin, lungs), Arthrofibrosis (knee, shoulder, other joints), Peyronie's disease (penis), Dupuytren's contracture (hands, fingers) and some forms of adhesive capsulitis (shoulder).

With respect to infectious disease, compositions of the invention may be used directly on certain infectious agents or pathogens, or may be used to exert a cytostatic or cytotoxic effect on a host cell that harbours or otherwise provides for the infectious agent or pathogen.

"Effective amount" or "therapeutically effective amount" refers to that amount of a compound of the disclosure which, when administered to a mammal, preferably a human, is sufficient to effect treatment, as defined below, of the particular indication (e.g., cancer or tumour cells in the mammal, preferably a human). The amount of a compound of the disclosure which constitutes a "therapeutically effective amount" will vary depending on the compound, the condition and its severity, the manner of administration, and the age of the mammal to be treated, but can be determined routinely by one of ordinary skill in the art having regard to his own knowledge and to this disclosure.

"Treating" or "treatment" as used herein covers the treatment of the disease or condition of interest in a mammal, preferably a human, having the disease or condition of interest, and includes:

(i) preventing the disease or condition from occurring in a mammal, in particular, when such mammal is predisposed to the condition but has not yet been diagnosed as having it;

(ii) inhibiting the disease or condition, i.e., arresting its development;

(iii) relieving the disease or condition, i.e., causing regression of the disease or condition; or (iv) relieving the symptoms resulting from the disease or condition, i.e., relieving pain without addressing the underlying disease or condition.

A therapeutically effective amount of compound in respect of cancer treatment may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; increase survival time; and/or relieve to some extent one or more of the symptoms associated with the cancer. To the extent the drug may prevent growth and/or kill existing cancer cells, it may be cytostatic and/or cytotoxic. Compounds of the present invention are preferably cytotoxic. For cancer therapy, efficacy can, for example, be measured by assessing the time to disease progression (TTP) and/or determining the response rate (RR).

An "effective amount" in respect of a particular result to be achieved is an amount sufficient to achieve the desired result. For example, an "effective amount" of drug when referred to in respect of the killing of cancer cells, refers to an amount of drug sufficient to produce the killing effect.

Solid tumors contemplated for treatment using the presently disclosed compounds include but are not limited to:

sarcoma, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon cancer, colorectal cancer, kidney cancer, pancreatic cancer, bone cancer, breast cancer, ovarian cancer, prostate cancer, esophageal cancer, stomach cancer (e.g., gastrointestinal cancer), oral cancer, nasal cancer, throat cancer, squamous cell carcinoma (e.g., of the lung), basal cell carcinoma, adenocarcinoma (e.g., of the lung), sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma bile duct carcinoma, choriocarcinoma, seminoma, embryonal carcinoma, Wilms' tumor, cervical cancer, uterine cancer, testicular cancer, small cell lung carcinoma, bladder carcinoma, lung cancer, non-small cell lung cancer, epithelial carcinoma, glioma, glioblastoma, multiforme astrocytoma, medulloblastoma, craniopharyngioma, ependymoma, pinealoma, hemangioblastoma, acoustic neuroma, oligodendroglioma, meningioma, skin cancer, melanoma, neuroblastoma, and retinoblastoma. Blood-borne cancers contemplated for treatment using the presently disclosed compounds include but are not limited to: acute lymphoblastic leukemia "ALL", acute lymphoblastic B-cell leukemia, acute lymphoblastic T-cell leukemia, acute myeloblastic leukemia "AML", acute promyelocytic leukemia "APL", acute monoblastic leukemia, acute erythroleukemic leukemia, acute megakaryoblastic leukemia, acute myelomonocytic leukemia, acute nonlymphocytic leukemia, acute undifferentiated leukemia, chronic myelocytic leukemia "CML", chronic lymphocytic leukemia "CLL", hairy cell leukemia, and multiple myeloma. Acute and chronic leukemias contemplated for treatment using the presently disclosed compounds include but are not limited to: lymphoblastic, myelogenous, lymphocytic, and myelocytic leukemias. Lymphomas contemplated for treatment using the presently disclosed compounds include but are not limited to: Hodgkin's disease, non-Hodgkin's lymphoma, multiple myeloma, Waldenstrom's macroglobulinemia, heavy chain disease, and polycythemia vera. Other cancers contemplated for treatment using the presently disclosed compounds include but are not limited to: peritoneal cancer, hepatocellular cancer, hepatoma, salivary cancer, vulval cancer, thyroid, penile cancer, anal cancer, head and neck cancer, renal cell carcinoma, acute anaplastic large cell carcinoma, and cutaneous anaplastic large cell carcinoma.

Cancers, including, but not limited to, a tumor, metastasis, or other disease or disorder characterized by uncontrolled or undesired cell growth, can be treated or prevented by administration of the presently disclosed compounds.

In other embodiments, methods for treating or preventing cancer are provided, including administering to a patient in need thereof an effective amount of a compound disclosed herein in combination with an additional method of treatment. In one embodiment, the additional method of treatment includes treatment with a chemotherapeutic agent. In one embodiment the chemotherapeutic agent is that with which treatment of the cancer has not been found to be refractory. In another embodiment, the chemotherapeutic agent is that with which the treatment of cancer has been found to be refractory. The compound of the invention may be administered before, after, or at the same time as the chemotherapeutic agent.

In one embodiment, the additional method of treatment is radiation therapy. The compound of the invention may be administered before, after, or at the same time as the radiation.

Compounds of the invention may also be administered to a patient that has undergone or will undergo surgery as treatment for the cancer.

In a specific embodiment, the compound of the invention is administered concurrently with the chemotherapeutic agent or with radiation therapy. In another specific embodiment, the chemotherapeutic agent or radiation therapy is administered prior or subsequent to administration of compound of the invention, in one aspect at least an hour, five hours, 12 hours, a day, a week, a month, in further aspects several months (e.g., up to three months), prior or subsequent to administration of a compound of the invention.

A chemotherapeutic agent can be administered over a series of sessions. Any one or a combination of the chemotherapeutic agents listed herein or otherwise known in the art can be administered. With respect to radiation, any radiation therapy protocol can be used depending upon the type of cancer to be treated. For example, but not by way of limitation, x-ray radiation can be administered; in particular, high-energy megavoltage (radiation of greater that 1 MeV energy) can be used for deep tumors, and electron beam and orthovoltage x-ray radiation can be used for skin cancers. Gamma-ray emitting radioisotopes, such as radioactive isotopes of radium, cobalt and other elements, can also be administered.

Additionally, methods of treatment of cancer with a compound of the invention are provided as an alternative to chemotherapy or radiation therapy where the chemotherapy or the radiation therapy has proven or can prove too toxic, e.g., results in unacceptable or unbearable side effects, for the subject being treated. Additionally, methods of treatment of cancer with a compound of the invention are provided as an alternative to surgery where the surgery has proven or can prove unacceptable or unbearable for the subject being treated.

The compound of the invention can also be used in an in vitro or ex vivo fashion, such as for the treatment of certain cancers, including, but not limited to leukemias and lymphomas, such treatment involving autologous stem cell transplants. This can involve a multi-step process in which the animal's autologous hematopoietic stem cells are harvested and purged of all cancer cells, the animal's remaining bone-marrow cell population is then eradicated via the administration of a high dose of a compound of the invention with or without accompanying high dose radiation therapy, and the stem cell graft is infused back into the animal. Supportive care is then provided while bone marrow function is restored and the animal recovers.

Methods for treating cancer further include administering to a patient in need thereof an effective amount of a compound of the invention and another therapeutic agent that is an anti-cancer agent. Suitable anticancer agents include, but are not limited to, methotrexate, taxol, L-asparaginase, mercaptopurine, thioguanine, hydroxyurea, cytarabine, cyclophosphamide, ifosfamide, nitrosoureas, cisplatin, carboplatin, mitomycin, dacarbazine, procarbizine, topotecan, nitrogen mustards, cytoxan, etoposide, 5-fluorouracil, BCNU, irinotecan, camptothecins, bleomycin, doxorubicin, idarubicin, daunorubicin, actinomycin D, dactinomycin, plicamycin, mitoxantrone, asparaginase, vinblastine, vincristine, vindesine, vinorelbine, paclitaxel, and docetaxel.

Other examples of chemotherapeutic agents include alkylating agents such as thiotepa and CYTOXAN® cyclosphosphamide; alkyl sulfonates such as busulfan, treosulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; TLK 286 (TELCYTA™); acetogenins (especially bullatacin and bullatacinone); delta-9-tetrahydrocannabinol (dronabinol, MARINOL); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlomaphazine, cholophosphamide, estramustine, ifosfamide, mechlorethamine, mechlorethamine oxide hydrochloride, melphalan, novembichin, phenesterine, prednimustine, trofosfamide, and uracil mustard; triazines such as decarbazine; nitrosureas such as carmustine, chlorozotocin, fotemustine, lomustine, nimustine, and ranimnustine; epipodophyllins, such as etoposide, teniposide, topotecan, 9-aminocamptothecin, camptothecin orcrisnatol; bisphosphonates, such as clodronate; antibiotics such as the enediyne antibiotics (e.g., calicheamicin, especially calicheamicin gamma1I and calicheamicin omega1l (see, e.g., Agnew, Chem. Intl. Ed. Engl., 33:183-186 (1994)) and anthracyclines such as annamycin, AD 32, alcarubicin, daunorubicin, dexrazoxane, DX-52-1, epirubicin, GPX-100, idarubicin, KRN5500, menogaril, dynemicin, including dynemicin A, an esperamicin, neocarzinostatin chromophore and related chromoprotein enediyne antibiotic chromophores, aclacinomysins, actinomycin, authramycin, azaserine, bleomycins (e.g., A2 and B2), cactinomycin, carabicin, caminomycin, carzinophilin, chromomycinis, dactinomycin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin, liposomal doxorubicin, and deoxydoxorubicin), esorubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, and zorubicin; photodynamic therapies, such as vertoporfin (BPD-MA), phthalocyanine, photosensitizer Pc4, and demethoxy-hypocrellin A (2BA-2-DMHA); folic acid analogues such as denopterin, pteropterin, and trimetrexate; dpurine analogs such as fludarabine, 6-mercaptopurine, thiamiprine, and thioguanine; pyrimidine analogs such as ancitabine, azacitidine, 6-azauridine, carmofur, cytarabine, cytosine arabinoside, dideoxyuridine, doxifluridine, enocitabine, and floxuridine; androgens such as calusterone, dromostanolone propionate, epitiostanol, mepitiostane, and testolactone; anti-adrenals such as aminoglutethimide, mitotane, and trilostane; folic acid replenisher such as folinic acid (leucovorin); aceglatone; anti-folate anti-neoplastic agents such as ALIMTA®, LY231514 pemetrexed, dihydrofolate reductase inhibitors such as methotrexate and trimetrexate; anti-metabolites such as 5-fluorouracil (5-FU) and its prodrugs such as UFT, S-1 and capecitabine, floxuridine, doxifluridine and ratitrexed; and thymidylate synthase inhibitors and glycinamide ribonucleotide formyltransferase inhibitors such as raltitrexed (TOMUDEX®, TDX); inhibitors of dihydropyrimidine dehydrogenase such as eniluracil; aldophosphamide glycoside; aminolevulinic acid; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2''-trichlorotriethylamine; trichothecenes (especially T-2 toxin, verracurin A, roridin A and anguidine); urethan; vindesine (ELDISINE®, FILDESIN®); dacarbazine; mannomustine; mitobronitol; mitolactol; pipobroman; gacytosine; arabinoside ("Ara-C"); cyclophosphamide; thiotepa; taxoids and taxanes, e.g., TAXOL® paclitaxel (Bristol-Myers Squibb Oncology, Princeton, N.J.), ABRAXANE™ Cremophor-free, albumin-engineered nanoparticle formulation of paclitaxel (American Pharmaceutical Partners, Schaumberg, Ill.), and TAXOTERE® doxetaxel (Rhone-Poulenc Rorer, Antony, France); chloranbucil; gemcitabine (GEMZAR)); 6-thioguanine; mercaptopurine; platinum; platinum analogs or platinum-based analogs such as cisplatin, oxaliplatin and carboplatin; vinblastine (VELBAN®); etoposide (VP-16); ifosfamide; mitoxantrone; vincristine (ONCOVIN®); vinca alkaloid; vinorelbine (NAVELBINE®); velcade; revlimid; thalidomide; IMiD3; lovastatin; verapamil; thapsigargin; I-methyl-4-phenylpyridinium; cell cycle inhibitors such as staurosporine; novantrone; edatrexate; daunomycin; mtoxantrone; aminopterin; xeloda; ibandronate; topoisomerase inhibitor RFS 2000; difluoromethylornithine (DMFO); vitamin D3 analogs, such as EB 1089, CB 1093 and KH 1060; retinoids such as retinoic acid; pharmaceutically acceptable salts, acids or derivatives of any of the above; as well as combinations of two or more of the above such as CHOP, an abbreviation for a combined therapy of cyclophosphamide, doxorubicin, vincristine, and prednisolone, and FOLFOX, an abbreviation for a treatment regimen with oxaliplatin (ELOXATIN™) combined with 5-FU and leucovorin.

Anti-hormonal agents that act to regulate or inhibit hormone action on tumors such as anti-estrogens and selective estrogen receptor modulators (SERMs), including, for example, tamoxifen (including NOLVADEX® tamoxifen), raloxifene, megastrol, droloxifene, 4-hydroxytamoxifen, trioxifene, keoxifene, LY 117018, onapristone, and FARESTON® toremifene; aromatase inhibitors that inhibit the enzyme aromatase, which regulates estrogen production in the adrenal glands, such as, for example, 4(5)-imidazoles, aminoglutethimide, MEGASE) megestrol acetate, AROMASIN® exemestane, formestanie, fadrozole, RIVISOR® vorozole, FEMARA® letrozole, and ARIMIDEX® anastrozole; and anti-androgens such as flutamide, bicalutamide, nilutamide, bicalutamide, leuprolide, and goserelin; as well as troxacitabine (a 1,3-dioxolane nucleoside cytosine analog); antisense oligonucleotides, particularly those that inhibit expression of genes in signaling pathways implicated in abherant cell proliferation, such as, for example, PKC-alpha, Raf, H-Ras, and epidermal growth factor receptor (EGF-R); vaccines such as gene therapy vaccines, for example, ALLOVECTIN® vaccine, LEUVECTIN® vaccine, and VAXID® vaccine; PROLEUKIN® rIL-2; LURTOTECAN® topoisomerase 1 inhibitor; ABARELIX® rmRH; and pharmaceutically acceptable salts, acids or derivatives of any of the above.

The compounds of the disclosure, or their pharmaceutically acceptable salts may contain one or more asymmetric centers and may thus give rise to enantiomers, diastereomers, and other stereoisomeric forms that may be defined, in terms of absolute stereochemistry, as (R)- or (S)- or, as (D)- or (L)- for amino acids. The present disclosure is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centres of geometric asymmetry, and unless specified otherwise, it is intended that the compounds include both E and Z geometric isomers. Likewise, all tautomeric forms are also intended to be included.

A "stereoisomer" refers to a compound made up of the same atoms bonded by the same bonds but having different three-dimensional structures, which are not interchangeable. The present disclosure contemplates various stereoisomers and mixtures thereof and includes "enantiomers", which refers to two stereoisomers whose molecules are nonsuperimposable mirror images of one another.

A "tautomer" refers to a proton shift from one atom of a molecule to another atom of the same molecule. The present disclosure includes tautomers of any said compounds.

Novel Compounds

In one embodiment, compounds having the following structure (I) are provided:

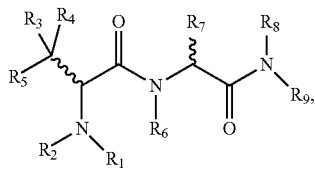

wherein:

$R_1$ and $R_2$ are independently selected from the group consisting of: H and a saturated or unsaturated moiety having a linear, branched, or non-aromatic cyclic skeleton containing one to ten carbon atoms, and the carbon atoms are optionally substituted with: —OH, —I, —Br, —Cl, —F, —CN, —CO$_2$H, —CHO, —COSH, or —NO$_2$; or $R_2$ and $R_5$ are fused and form a ring;

$R_3$ and $R_4$ are independently selected from the group consisting of: H, R, ArR—, or $R_3$ and $R_4$ are joined to form a ring;

$R_5$ is selected from the group consisting of: H, R, ATR-, and Ar;

or $R_5$ and $R_2$ are fused and form a ring;

$R_6$ is selected from the group consisting of: H, R, and ArR—;

$R_7$ and $R_8$ are independently selected from the group consisting of: H, R, and ArR—; and $R_9$ is:

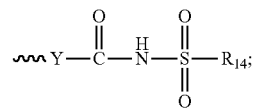

wherein,

R is defined as a saturated or unsaturated moiety having a linear, branched, or non-aromatic cyclic skeleton containing one to ten carbon atoms, zero to four nitrogen atoms, zero to four oxygen atoms, and zero to four sulfur atoms, and the carbon atoms are optionally substituted with: =O, =S, OH, —OR$_{10}$, —O$_2$CR$_{10}$, —SH, —SR$_{10}$, —SOCR$_{10}$, —NH$_2$, —NHR$_{10}$, —N(R$_{10}$)$_2$, —NHCOR$_{10}$, —NR$_{10}$COR$_{10}$, —I, —Br, —Cl, —F, —CN, —CO$_2$H, —CO$_2$R$_{10}$, —CHO, —COR$_{10}$, —CONH$_2$, —CONHR$_{10}$, —CON(R$_{10}$)$_2$, —COSH, —COSR$_{10}$, —NO$_2$, —SO$_3$H, —SOR$_{10}$, —SO$_2$R$_{10}$, wherein R$_{10}$ is a linear, branched, or cyclic, one to ten carbon saturated or unsaturated alkyl group;

the ring formed by joining $R_3$ and $R_4$ is a three to seven member non-aromatic cyclic skeleton within the definition of R, Y is defined as a moiety selected from the group consisting of: a linear, saturated or unsaturated, one to six carbon alkyl group, optionally substituted with R, ArR—, or X; and, X is defined as a moiety selected from the group consisting of: —OH, —OR, =O, =S, —O$_2$CR, —SH, —SR, —SOCR, —NH$_2$, —NHR, —N(R)$_2$, —NHCOR, —NRCOR, —I, —Br, —Cl, —F, —CN, —CO$_2$H, —CO$_2$R, —CHO, —COR, —CONH$_2$, —CONHR, —CON(R)$_2$, —COSH, —COSR, —NO$_2$, —SO$_3$H, —SOR, and —SO$_2$R;

$R_{14}$ is selected from the group consisting of optionally substituted alkyl, optionally substituted alkylamino, optionally substituted cycloalkyl, optionally substituted aryl, optionally substituted heterocyclyl and optionally substituted heteroaryls, COR$_{24}$, —CSR$_{24}$, —OR$_{24}$, and —NHR$_{24}$, wherein each R$_{24}$ is, independently, alkyl optionally substituted with halogen, —OH or —SH;

or a stereoisomer, prodrug or pharmaceutically acceptable salt thereof.

In one embodiment, Ar is an aromatic ring selected from the group consisting of: phenyl, naphthyl, anthracyl, pyrrolyl.

In one embodiment, compounds having the following structure (Ia) are provided:

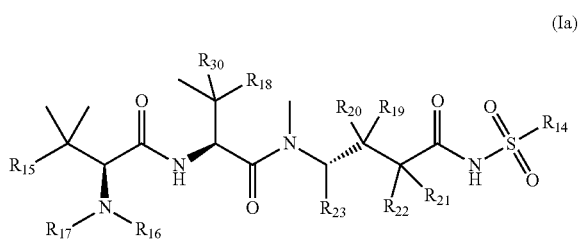

(Ia)

wherein:

$R_{14}$ is selected from the group consisting of optionally substituted alkyl, optionally substituted alkylamino, optionally substituted cycloalkyl, optionally substituted aryl, optionally substituted heterocyclyl, optionally substituted heteroaryl, —COR$_{24}$, —CSR$_{24}$, —OR$_{24}$, and —NHR$_{24}$, wherein each R$_{24}$ is, independently, alkyl optionally substituted with halogen, —OH or —SH;

R$_{15}$ is selected from the group consisting of optionally substituted alkyl, optionally substituted alkylamino, optionally substituted cycloalkyl, optionally substituted aryl, optionally substituted heterocyclyl and optionally substituted heteroaryl;

R$_{16}$ is selected from the group consisting of H and C$_{1-6}$ alkyl;

R$_{17}$ is selected from the group consisting of H and C$_{1-6}$ alkyl;

R$_{18}$ and R$_{30}$ are independently selected from the group consisting of H, C$_{1-6}$ alkyl and —SH, with the proviso that R$_{18}$ and R$_{30}$ cannot both be H;

R$_{19}$, R$_{20}$, R$_{21}$ and R$_{22}$ are independently H and C$_{1-6}$ alkyl, at least one of R$_{19}$ and R$_{20}$ is H; or R$_{20}$ and R$_{21}$ form a double bond, R$_{19}$ is H, and R$_{22}$ is H or C$_{1-6}$ alkyl; and R$_{23}$ is selected from the group consisting of H and C$_{1-6}$ alkyl;

or a stereoisomer, prodrug or pharmaceutically acceptable salt thereof.

In a further embodiment, each optionally substituted alkyl, optionally substituted alkylamino, optionally substituted cycloalkyl, optionally substituted aryl, optionally substituted heterocyclyl and optionally substituted heteroaryl is, independently, optionally substituted with =O, =S, —OH, —OR$_{24}$, —O$_2$CR$_{24}$, —SH, —SR$_{24}$, —SOCR$_{24}$, —NH$_2$, —N$_3$, —NHR$_{24}$, —N(R$_{24}$)$_2$, —NHCOR$_{24}$, —NR$_{24}$COR$_{24}$, —I, —Br, —Cl, —F, —CN, —CO$_2$H, —CO$_2$R$_{24}$, —CHO, —COR$_{24}$, —CONH$_2$, —CONHR$_{24}$, —CON(R$_{24}$)$_2$, —COSH, —COSR$_{24}$, —NO$_2$, —SO$_3$H, —SOR$_{24}$ or —SO$_2$R$_{24}$ wherein each R$_{24}$ is, independently, alkyl optionally substituted with halogen, —OH or —SH In another further embodiment, each optionally substituted aryl and optionally substituted heteroaryl is, independently, selected from the group consisting of optionally substituted phenyl, optionally substituted naphthyl, optionally substituted anthracyl, optionally substituted phenanthryl, optionally substituted furyl, optionally substituted pyrrolyl, optionally substituted thiophenyl, optionally substituted benzofuryl, optionally substituted benzothiophenyl, optionally substituted quinolinyl, optionally substituted isoquinolinyl, optionally substituted imidazolyl, optionally substituted thiazolyl, optionally substituted oxazolyl, and optionally substituted pyridinyl.

In another further embodiment, R$_{15}$ is selected from one of the following structures (II), (III), (IV), (V):

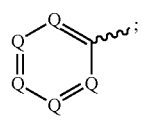

(II)

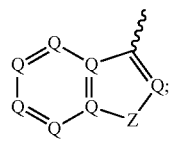

(III)

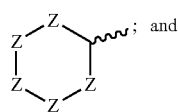

(IV)

and

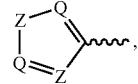

(V)

wherein:

Q is CR$_{25}$ or N;

Z is C(R$_{25}$)$_2$, NR$_{25}$, S, or O;

each R$_{25}$ is, independently, selected from the group consisting of H, —OH, —R$_{24}$, —OR$_{24}$, —O$_2$CR$_{24}$, —SH, —SR$_{24}$, —SOCR$_{24}$, —NH$_2$, —N$_3$, —NHR$_{24}$, —N(R$_{24}$)$_2$, —NHCOR$_{24}$, —NR$_{24}$COR$_{24}$, —R$_{24}$NH$_2$, —I, —Br, —Cl, —F, —CN, —CO$_2$H, —CO$_2$R$_{24}$, —CHO, —COR$_{24}$, —CONH$_2$, —CONHR$_{24}$, —CON(R$_{24}$)$_2$, —COSH, —COSR$_{24}$, —NO$_2$, —SO$_3$H, —SOR$_{24}$ or —SO$_2$R$_{24}$, wherein each R$_{24}$ is, independently, alkyl optionally substituted with halogen, —OH or —SH.

In another further embodiment, R$_{15}$ is selected from the group consisting of:

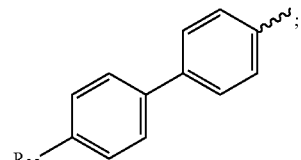

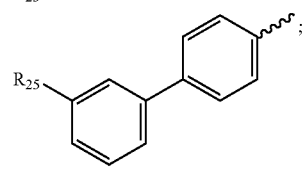

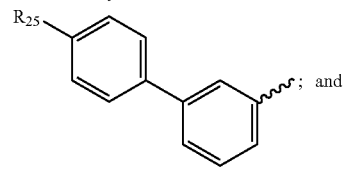

; and

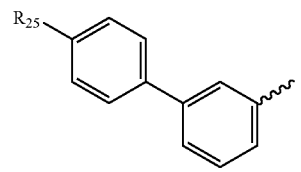

wherein each R$_{25}$ is, independently, selected from the group consisting of H, —OH, —R$_{24}$, —OR$_{24}$, —O$_2$CR$_{24}$, —SH, —SR$_{24}$, —SOCR$_{24}$, —NH$_2$, —N$_3$, —NHR$_{24}$, —N(R$_{24}$)$_2$, —NHCOR$_{24}$, —NR$_{24}$COR$_{24}$, —R$_{24}$NH$_2$, —I, —Br, —Cl, —F, —CN, —CO$_2$H, —CO$_2$R$_{24}$, —CHO, —COR$_{24}$, —CONH$_2$, —CONHR$_{24}$, —CON(R$_{24}$)$_2$, —COSH, —COSR$_{24}$, —NO$_2$, —SO$_3$H, —SOR$_{24}$ or —SO$_2$R$_{24}$, wherein each R$_{24}$ is, independently, alkyl optionally substituted with halogen, —OH or —SH.

In another further embodiment, R$_{15}$ is selected from the group consisting of:
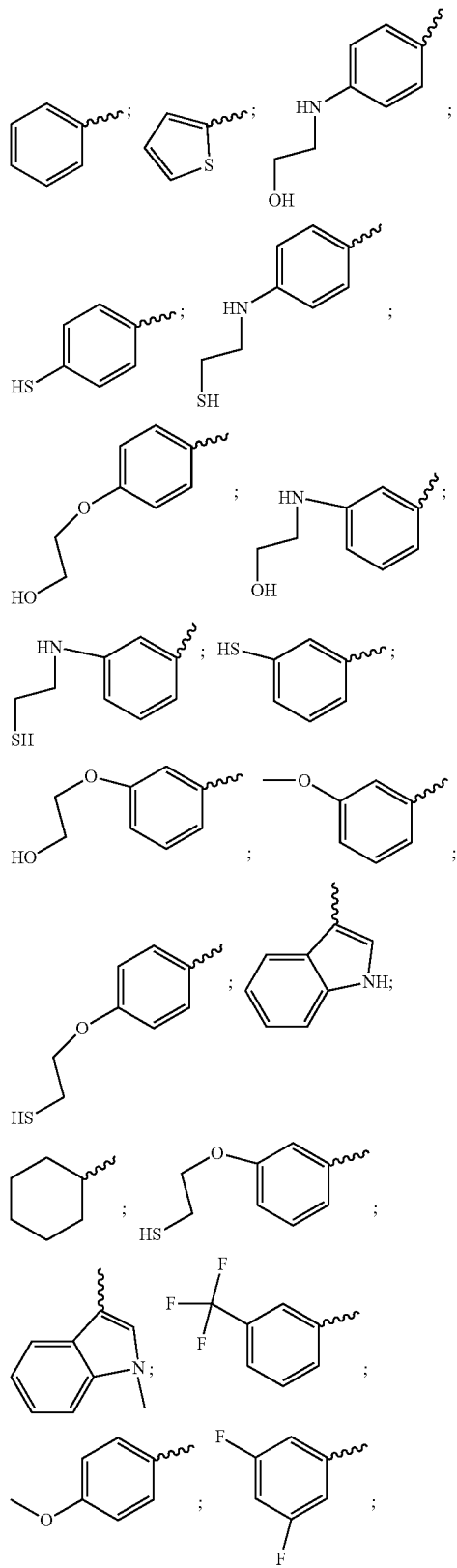
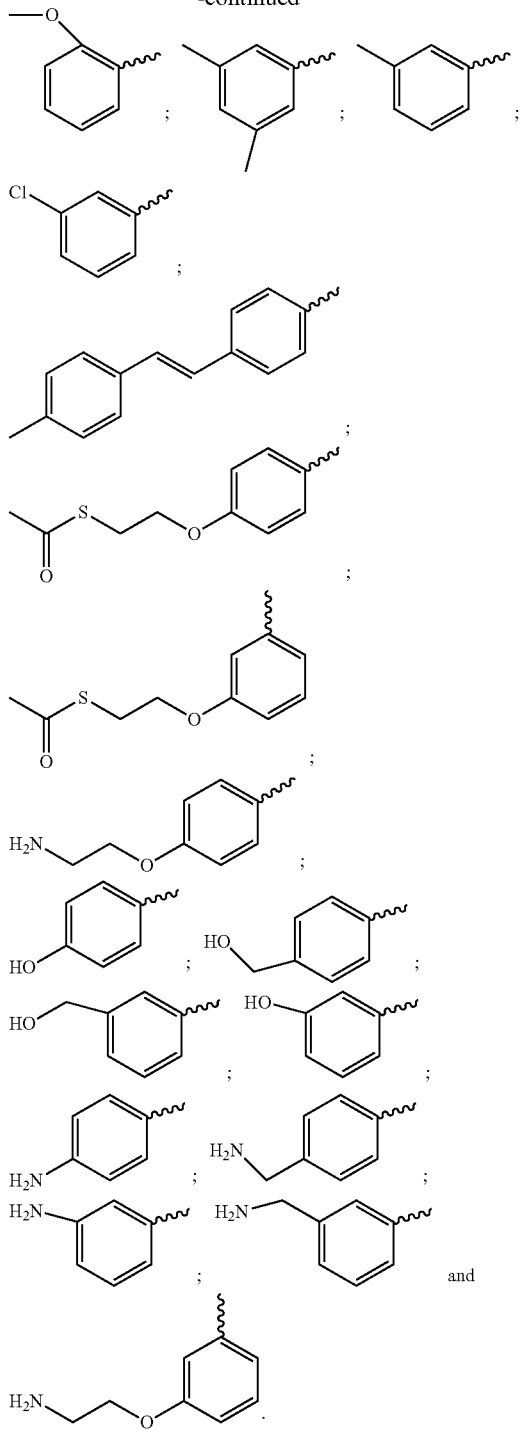
In another further embodiment, R$_{15}$ is:
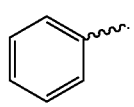
In another further embodiment, R$_{16}$, R$_{17}$, R$_{18}$, and R$_{30}$ are each methyl.

In another further embodiment, $R_{16}$ is H, $R_{17}$ is methyl, $R_{18}$ is methyl, and $R_{30}$ is methyl.

It is understood that any embodiment of the compounds of structure (Ia), as set forth above, and any specific substituent set forth herein for a $R_{14}$, $R_{15}$, $R_{16}$, $R_{17}$, $R_{18}$, $R_{19}$, $R_{20}$ and $R_{30}$ group in the compounds of structure (Ia), as set forth above, may be independently combined with other embodiments and/or substituents of compounds of structure (I) to form embodiments of the present disclosure not specifically set forth above. In addition, in the event that a list of substituents is listed for any particular $R_{14}$, $R_{15}$, $R_{16}$, $R_{17}$, $R_{18}$, $R_{19}$, $R_{20}$, and $R_{30}$ in a particular embodiment and/or claim, it is understood that each individual substituent may be deleted from the particular embodiment and/or claim and that the remaining list of substituents will be considered to be within the scope of the present disclosure.

In one embodiment, compounds having the following structure (Ib) are provided:

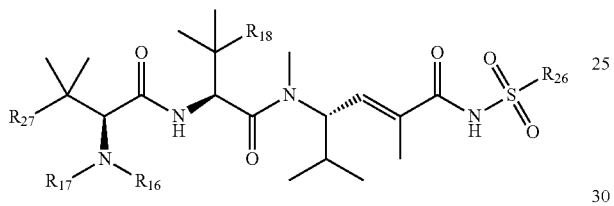

(Ib)

wherein:
$R_{26}$ is selected from the group consisting of optionally substituted alkyl, optionally substituted alkylamino, optionally substituted cycloalkyl, optionally substituted aryl, optionally substituted heterocyclyl and optionally substituted heteroaryl;
$R_{27}$ is selected from the group consisting of optionally substituted alkyl, optionally substituted alkylamino, optionally substituted cycloalkyl, optionally substituted aryl, optionally substituted heterocyclyl and optionally substituted heteroaryl;
$R_{16}$ is selected from the group consisting of H and $C_{1-6}$ alkyl;
$R_{17}$ is selected from the group consisting of H and $C_{1-6}$ alkyl; and
$R_{18}$ is selected from the group consisting of $C_{1-6}$ alkyl and —SH,
or a stereoisomer, prodrug or pharmaceutically acceptable salt thereof.

In a further embodiment, each optionally substituted alkyl, optionally substituted alkylamino, optionally substituted cycloalkyl, optionally substituted aryl, optionally substituted heterocyclyl and optionally substituted heteroaryl is, independently, optionally substituted with =O, =S, —OH, —OR$_{28}$, —O$_2$CR$_{28}$, —SH, —SR$_{28}$, —SOCR$_{28}$, —NH$_2$, —N$_3$, —NHR$_{28}$, —N(R$_{28}$)$_2$, —NHCOR$_{28}$, —NR$_{28}$COR$_{28}$, —I, —Br, —Cl, —F, —CN, —CO$_2$H, —CO$_2$R$_{28}$, —CHO, —COR$_{28}$, —CONH$_2$, —CONHR$_{28}$, —CON(R$_{28}$)$_2$, —COSH, —COSR$_{28}$, —NO$_2$, —SO$_3$H, —SOR$_{28}$ or —SO$_2$R$_{28}$, wherein each R$_{28}$ is, independently, alkyl optionally substituted with halogen, —OH or —SH.

In another further embodiment, each optionally substituted aryl and optionally substituted heteroaryl is, independently, selected from the group consisting of optionally substituted phenyl, optionally substituted naphthyl, optionally substituted anthracyl, optionally substituted phenanthryl, optionally substituted furyl, optionally substituted pyrrolyl, optionally substituted thiophenyl, optionally substituted benzofuryl, optionally substituted benzothiophenyl, optionally substituted quinolinyl, optionally substituted isoquinolinyl, optionally substituted imidazolyl, optionally substituted thiazolyl, optionally substituted oxazolyl, and optionally substituted pyridinyl.

In another further embodiment, $R_{27}$ is selected from one of the following structures (II), (III), (IV), (V):

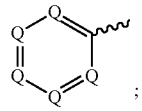

(II)

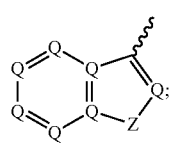

(III)

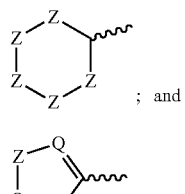

(IV)

; and

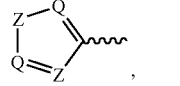

(V)

wherein:
Q is CR$_{29}$ or N;
Z is C(R$_{29}$)$_2$, NR$_{29}$, S, or O;
each R$_{29}$ is, independently, selected from the group consisting of H, —OH, —OR$_{28}$, —O$_2$CR$_{28}$, —SH, —SR$_{29}$, —SOCR$_{28}$, —NH$_2$, —N$_3$, —NHR$_{28}$, —N(R$_{28}$)$_2$, —NHCOR$_{28}$, —NR$_{28}$COR$_{28}$, —I, —Br, —Cl, —F, —CN, —CO$_2$H, —CO$_2$R$_{28}$, —CHO, —COR$_{28}$, —CONH$_2$, —CONHR$_{78}$, —CON(R$_{28}$)$_2$, —COSH, —COSR$_{28}$, —NO$_2$, —SO$_3$H, —SOR$_{28}$ or —SO$_2$R$_{28}$, wherein each R$_{28}$ is, independently, alkyl optionally substituted with halogen, —OH or —SH.

In another further embodiment, $R_{27}$ is selected from the group consisting of:

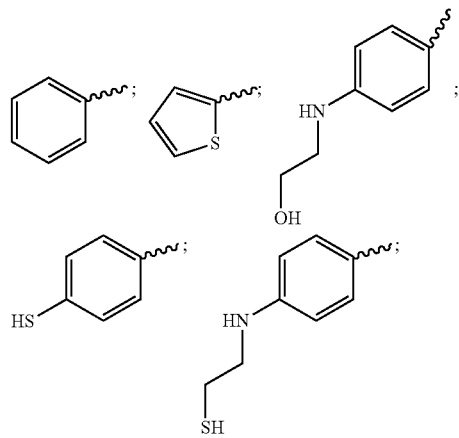

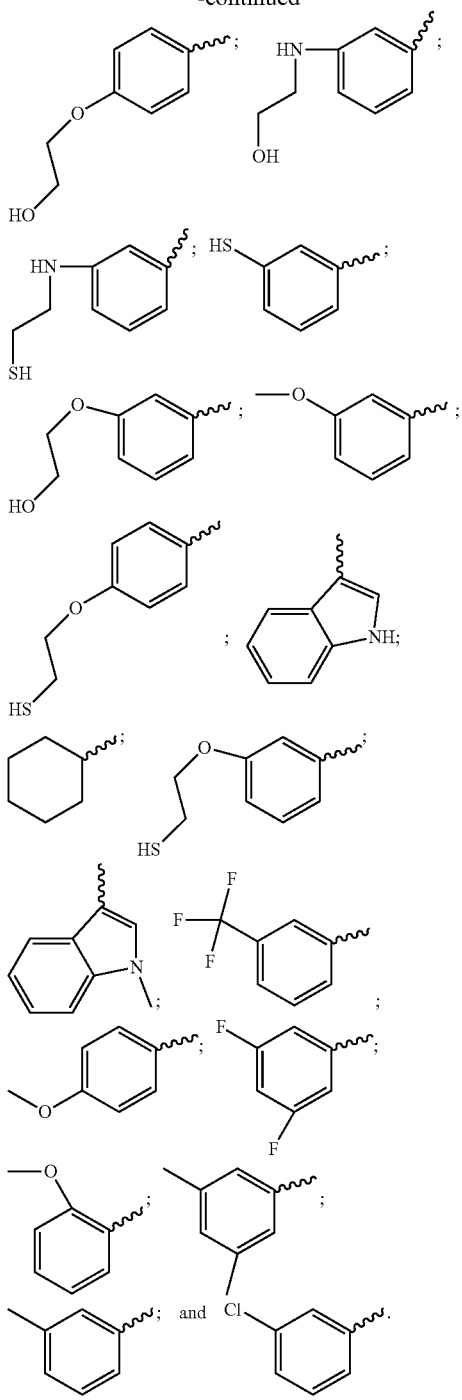

In another further embodiment, $R_{27}$ is:

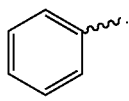

In another further embodiment, $R_{16}$, $R_{17}$ and $R_{18}$ are each methyl.

In another further embodiment, $R_{16}$ is H, $R_{17}$ is methyl, and $R_{18}$ is methyl.

It is understood that any embodiment of the compounds of structure (Ib), as set forth above, and any specific substituent set forth herein for a $R_{25}$, $R_{26}$, $R_{16}$, $R_{17}$, $R_{18}$, $R_{19}$ and $R_{20}$ group in the compounds of structure (Ib), as set forth above, may be independently combined with other embodiments and/or substituents of compounds of structure (I) to form embodiments of the present disclosure not specifically set forth above. In addition, in the event that a list of substitutents is listed for any particular $R_{25}$, $R_{26}$, $R_{16}$, $R_{17}$, $R_{18}$, $R_{19}$ and $R_{20}$ in a particular embodiment and/or claim, it is understood that each individual substituent may be deleted from the particular embodiment and/or claim and that the remaining list of substituents will be considered to be within the scope of the present disclosure.

In one embodiment, the invention provides a method of making a compound having structure (1), (Ia) or (Ib).

Conjugates Comprising Novel Compounds

Compounds having structure (I), (Ia) or (Ib) may be used to form conjugates, for example antibody-drug conjugates (ADCs). Accordingly, in one embodiment of the present disclosure, conjugate compositions having the following structure are provided:

$$(T)\text{-}(L)\text{-}(D) \tag{VI}$$

wherein (T) is a targeting moiety, (L) is an optional linker, and (D) is a compound having structure (I), (Ia) or (Ib), below. In one embodiment, (T) is an antibody. Accordingly, in one embodiment, antibody-drug conjugates (ADCs) comprising compounds (D) having structure (I), (Ia) or (Ib) are provided.

As will be appreciated by the artisan of reasonable skill, a wide variety of means are available to covalently link (T)-(L)-(D). Any known method may be used to link the conjugate components. Any known linker technology may be used to link (T) to (D). Further, (T), (L), and (D) may be modified in any suitable manner, as recognized by the artisan of reasonable skill, in order to facilitate conjugate formation.

Targeting Moiety (T)

The Targeting moiety (T) of the subject compositions includes within its scope any unit of a (T) that binds or reactively associates or complexes with a receptor, antigen or other receptive moiety associated with a given target-cell population. A (T) is a molecule that binds to, complexes with, or reacts with a moiety of a cell population sought to be targeted. In one aspect, the (T) acts to deliver the Drug (D) to the particular target cell population with which the (T) reacts. Such (T)s include, but are not limited to, large molecular weight proteins such as, for example, full-length antibodies, antibody fragments, smaller molecular weight proteins, polypeptide or peptides, lectins, glycoproteins, non-peptides, vitamins, nutrient-transport molecules (such as, but not limited to, transferrin), or any other cell binding molecule or substance.

A (T) can form a bond to a Linker unit (L) or a Drug (D). A (T) can form a bond to a (L) unit via a heteroatom of the (T). Heteroatoms that may be present on a (T) include sulfur (in one embodiment, from a sulfhydryl group of a (T)), oxygen (in one embodiment, from a carbonyl, carboxyl or hydroxyl group of a (T)) and nitrogen (in one embodiment, from a primary or secondary amino group of a (T)). These heteroatoms can be present on the (T) in the (T)'s natural state, for example a naturally-occurring antibody, or can be introduced into the (T) via chemical modification.

In one embodiment, a (T) has a sulfhydryl group and the (T) bonds to the (L) via the sulfhydryl group's sulfur atom. In another embodiment, the (T) has one or more lysine residues that can be chemically modified to introduce one or more sulfhydryl groups. The (T) bonds to the (L) unit via the sulfhydryl group. Reagents that can be used to modify lysines include, but are not limited to, N-succinimidyl S-acetylthioacetate (SATA) and 2-Iminothiolane hydrochloride (Traut's Reagent).

In another embodiment, the (L) can have one or more carbohydrate groups that can be chemically modified to have one or more sulfhydryl groups. The (T) bonds to the (L) via the sulfhydryl group's sulfur atom. In yet another embodiment, the (T) can have one or more carbohydrate groups that can be oxidized to provide an aldehyde (—CHO) group (see, e.g., Laguzza et al., 1989, J. Med. Chem. 32(3):548-55). The corresponding aldehyde can form a bond with a reactive site on a portion of a (L). Reactive sites that can react with a carbonyl group on a (T) include, but are not limited to, hydrazine and hydroxylamine. Other protocols for the modification of proteins for the attachment or association of (D) are described in Coligan et al., Current Protocols in Protein Science, vol. 2, John Wiley & Sons (2002), incorporated herein by reference.

The (T) can include, for example a protein, polypeptide, or peptide include, but are not limited to, transferrin, epidermal growth factors ("EGF"), bombesin, gastrin, gastrin-releasing peptide, platelet-derived growth factor, IL-2, IL-6, transforming growth factor ("TGF"), such as TGF-α or TGF-β, vaccinia growth factor ("VGF"), insulin and insulin-like growth factors I and II, lectins and apoprotein from low density lipoprotein.

The (T) can also include an antibody, such as polyclonal antibodies or monoclonal antibodies. The antibody can be directed to a particular antigenic determinant, including for example, a cancer cell antigen, a viral antigen, a microbial antigen, a protein, a peptide, a carbohydrate, a chemical, nucleic acid, or fragments thereof. Methods of producing polyclonal antibodies are known in the art. A monoclonal antibody (mAb) to an antigen-of-interest can be prepared by using any technique known in the art. These include, but are not limited to, the hybridoma technique originally described by Kohler and Milstein (1975, Nature 256, 495-497), the human B cell hybridoma technique (Kozbor et al., 1983, Immunology Today 4:72), and the EBV-hybridoma technique (Cole et al., 1985, Monoclonal Antibodies and Cancer Therapy, Alan R. Liss, Inc., pp. 77-96). The Selected Lymphocyte Antibody Method (SLAM) (Babcook, J. S., et al., A novel strategy for generating monoclonal antibodies from single, isolated lymphocytes producing antibodies of defined specificities. Proc Natl Acad Sci USA, 1996. 93 (15): p. 7843-8.) and (McLean G R, Olsen O A, Watt I N, Rathanaswami P. Leslie K B, Babcook J S, Schrader J W. Recognition of human cytomegalovirus by human primary immunoglobulins identifies an innate foundation to an adaptive immune response. J Immunol. 2005 Apr. 15; 174(8): 4768-78. Such antibodies may be of any immunoglobulin class including IgG, IgM, IgE, IgA, and IgD and any subclass thereof. Hybridomas producing the mAbs of use in this invention may be cultivated in vitro or in vivo.

The monoclonal antibody can be, for example, a human monoclonal antibody, a humanized monoclonal antibody, an antibody fragment, or a chimeric antibody (e.g., a human-mouse antibody). Human monoclonal antibodies may be made by any of numerous techniques known in the art (e.g., Teng et al., 1983, Proc. Natl. Acad. Sci. USA 80:7308-7312; Kozbor et al., 1983, Immunology Today 4:72-79; and Olsson et al., 1982, Meth. Enzymol. 92:3-16). See also, Huse et al., 1989, Science 246:1275-1281 and McLean et al. J Immunol. 2005 Apr. 15; 174(8):4768-78.

The antibody can also be a bispecific antibody. Methods for making bispecific antibodies are known in the art. Traditional production of full-length bispecific antibodies is based on the coexpression of two immunoglobulin heavy chain-light chain pairs, where the two chains have different specificities (see, e.g., Milstein et al., 1983, Nature 305:537-539; International Publication No. WO 93/08829, Traunecker et al., 1991, EMBO J. 10:3655-3659.

According to a different approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, $C_{H2}$, and $C_{H3}$ regions. It is preferred to have the first heavy-chain constant region ($C_{H1}$) containing the site necessary for light chain binding, present in at least one of the fusions. Nucleic acids with sequences encoding the immunoglobulin heavy chain fusions and, if desired, the immunoglobulin light chain, are inserted into separate expression vectors, and are co-transfected into a suitable host organism. This provides for flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

For example, the bispecific antibodies can have a hybrid immunoglobulin heavy chain with a first binding specificity in one arm, and a hybrid immunoglobulin heavy chain-light chain pair (providing a second binding specificity) in the other arm. This asymmetric structure facilitates the separation of the desired bispecific compound from unwanted immunoglobulin chain combinations, as the presence of an immunoglobulin light chain in only one half of the bispecific molecule provides for a facile way of separation (International Publication No. WO 94/04690) which is incorporated herein by reference in its entirety.

For further details for generating bispecific antibodies see, for example, Suresh et al., 1986, Methods in Enzymology 121:210; Rodrigues et al., 1993, J. Immunology 151:6954-6961; Carter et al., 1992, Bio/Technology 10:163-167; Carter et al., 1995, J. Hematotherapy 4:463-470; Merchant et al., 1998, Nature Biotechnology 16:677-681. Using such techniques, bispecific antibodies can be prepared for use in the treatment or prevention of disease as defined herein.

Bifunctional antibodies are also described in European Patent Publication No. EPA 0 105 360. As disclosed in this reference, hybrid or bifunctional antibodies can be derived either biologically, i.e., by cell fusion techniques, or chemically, especially with cross-linking agents or disulfide-bridge forming reagents, and may comprise whole antibodies or fragments thereof. Methods for obtaining such hybrid antibodies are disclosed for example, in International Publication WO 83/03679, and European Patent Publication No. EPA 0 217 577, both of which are incorporated herein by reference.

The antibody also can be a functionally active fragment, derivative or analog of an antibody that immunospecifically binds to a target antigen (e.g., a cancer antigen, a viral antigen, a microbial antigen, or other antibodies bound to cells or matrix). In this regard, "functionally active" means that the fragment, derivative or analog is able to recognize the same antigen that the antibody from which the fragment, derivative or analog is derived recognized. Specifically, in an exemplary embodiment the antigenicity of the idiotype of the immunoglobulin molecule can be enhanced by deletion of framework and CDR sequences that are C-terminal to the CDR sequence that specifically recognizes the antigen. To determine which CDR sequences bind the antigen, synthetic peptides containing the CDR sequences can be used in binding assays with the antigen by any binding assay method known in the art (e.g., the BIA core assay) (see, e.g., Kabat et al., 1991, Sequences of Proteins of Immunological Interest, Fifth Edition, National Institute of Health, Bethesda, Md.; Kabat et al., 1980, J. Immunology 125(3): 961-969).

Other useful antibodies include fragments of antibodies such as, but not limited to, F(ab')$_2$ fragments, Fab fragments, Fab', Fv fragments and heavy chain and light chain dimers of antibodies, or any minimal fragment thereof such as Fvs or single chain antibodies (SCAs) (e.g., as described in U.S. Pat. No. 4,946,778; Bird, 1988, Science 242:423-42; Huston et al., 1988, Proc. Natl. Acad. Sci. USA 85:5879-5883; and Ward et al., 1989, Nature 334:544-54).

Recombinant antibodies, such as chimeric and humanized monoclonal antibodies, comprising both human and non-human portions, which can be made using standard recombinant DNA techniques, also can be used. (See, e.g., U.S. Pat. Nos. 4,816,567; and 4,816,397.) Humanized antibodies are antibody molecules from non-human species having one or more complementarity determining regions (CDRs) from the non-human species and a framework region from a human immunoglobulin molecule. (See, e.g., U.S. Pat. No. 5,585,089.) Chimeric and humanized monoclonal antibodies can be produced by recombinant DNA techniques known in the art, for example using methods described in International Publication No. WO 87/02671; European Patent Publication No. 0 184 187; European Patent Publication No. 0 171 496; European Patent Publication No. 0 173 494; International Publication No. WO 86/01533; U.S. Pat. No. 4,816,567; European Patent Publication No. 012 023; Berter et al., 1988, Science 240:1041-1043; Liu et al., 1987, Proc. Natl. Acad. Sci. USA 84:3439-3443; Liu et al., 1987, J. Immunol. 139:3521-3526; Sun et al., 1987, Proc. Natl. Acad. Sci. USA 84:214-218; Nishimura et al., 1987, Cancer. Res. 47:999-1005; Wood et al., 1985, Nature 314:446-449; Shaw et al., 1988, J. Natl. Cancer Inst. 80:1553-1559; Morrison, 1985, Science 229:1202-1207; Oi et al., 1986, BioTechniques 4:214; U.S. Pat. No. 5,225,539; Jones et al., 1986, Nature 321:552-525; Verhoeyan et al., 1988, Science 239:1534; and Beidler et al., 1988, J. Immunol. 141:4053-4060.

Completely human antibodies can be used. Human antibodies can be prepared, for example, using transgenic mice that are incapable of expressing endogenous immunoglobulin heavy and light chains genes, but which can express human heavy and light chain genes. The transgenic mice are immunized in the normal fashion with a selected antigen, e.g., all or a portion of a polypeptide of the invention. Monoclonal antibodies directed against the antigen can be obtained using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar (1995, Int. Rev. Immunol. 13:65-93). For a detailed discussion of this technology for producing human antibodies and human monoclonal antibodies and protocols for producing such antibodies, see, e.g., U.S. Pat. Nos. 5,625,126; 5,633,425; 5,569,825; 5,661, 016; and 5,545,806.

Human antibodies that recognize a selected epitope also can be generated using a technique referred to as "guided selection." In this approach a selected non-human monoclonal antibody, e.g., a mouse antibody, is used to guide the selection of a completely human antibody recognizing the same epitope. (See, e.g., Jespers et al., 1994, Biotechnology 12:899-903.) Human antibodies can also be produced using various techniques known in the art, including phage display libraries (see, e.g., Hoogenboom and Winter, 1991, J. Mol. Biol. 227:381; Marks et al., 1991, J. Mol. Biol. 222:581; Quan and Carter, 2002, "The rise of monoclonal antibodies as therapeutics," in Anti-IgE and Allergic Disease, Jardieu, P. M, and Fick Jr., R. B, eds., Marcel Dekker, New York, N.Y., Chapter 20, pp. 427-469).

In other embodiments, the antibody is a fusion protein of an antibody, or a functionally active fragment thereof. For example, an antibody can be fused via a covalent bond (e.g., a peptide bond) at either the N-terminus or the C-terminus to an amino acid sequence of another protein (or portion thereof, such as at least a 10, 20 or 50 amino acid portion of the protein) that is not the antibody.

Antibodies also include analogs and derivatives that are either modified, i.e., by the covalent attachment of any type of molecule as long as such covalent attachment permits the antibody to retain its antigen binding immunospecificity. For example, but not by way of limitation, the derivatives and analogs of the antibodies include those that have been further modified, e.g., by glycosylation, acetylation, pegylation, phosphorylation, amidation, derivatization by known protecting/blocking groups, proteolytic cleavage, linkage to a cellular antibody unit or other protein, etc. Any of numerous chemical modifications can be carried out by known techniques, including but not limited to specific chemical cleavage, acetylation, formylation, metabolic synthesis in the presence of tunicamycin, etc. Additionally, the analog or derivative can contain one or more unnatural amino acids.

The antibodies can have modifications (e.g., substitutions, deletions or additions) in amino acid residues that interact with Fc receptors. In particular, antibodies include antibodies having modifications in amino acid residues identified as involved in the interaction between the anti-Fc domain and the FcRn receptor (see, e.g., International Publication No. WO 97/34631, which is incorporated herein by reference in its entirety). Antibodies immunospecific for a target antigen can be obtained commercially or other source or produced by any method known to one of skill in the art such as, e.g., chemical synthesis or recombinant expression techniques. The nucleotide sequence encoding antibodies immunospecific for a cancer cell antigen can be obtained, e.g., from the GenBank database or a database like it, the literature publications, or by routine cloning and sequencing.

Examples of antibodies available for the treatment of cancer include, but are not limited to, humanized anti HER2 monoclonal antibody, HERCEPTIN® (trastuzumab; Genentech); RITUXAN® (rituximab; Genentech) which is a chimeric anti CD20 monoclonal antibody for the treatment of patients with non-Hodgkin's lymphoma; OvaRex (AltaRex Corporation, MA) which is a murine antibody for the treatment of ovarian cancer, Panorex (Glaxo Wellcome, NC) which is a murine IgG2a antibody for the treatment of colorectal cancer; Cetuximab Erbitux (Imclone Systems Inc., NY) which is an anti-EGFR IgG chimeric antibody for the treatment of epidermal growth factor positive cancers, such as head and neck cancer; Vitaxin (MedImmune, Inc., MD) which is a humanized antibody for the treatment of sarcoma; Campath I/H (Leukosite, MA) which is a humanized IgG1 antibody for the treatment of chronic lymphocytic leukemia (CLL); Smart M 195 (Protein Design Labs, Inc., CA) which is a humanized anti-CD33 IgG antibody for the treatment of acute myeloid leukemia (AML); LymphoCide (Immunomedics, Inc., NJ) which is a humanized anti-CD22 IgG antibody for the treatment of non-Hodgkin's lymphoma; Smart ID10 (Protein Design Labs, Inc., CA) which is a humanized anti-HLA-DR antibody for the treatment of non-Hodgkin's lymphoma; Oncolym (Techniclone, Inc., CA) which is a radiolabeled murine anti-HLA-Dr10 antibody for the treatment of non-Hodgkin's lymphoma; Allomune (BioTransplant, CA) which is a humanized anti-CD2 mAb for the treatment of Hodgkin's Disease or non-Hodgkin's lymphoma; Avastin (Genentech, Inc., CA) which is an anti-VEGF humanized antibody for the treatment of lung and colorectal cancers; Epratuzamab (Immunomedics, Inc., NJ and Amgen, CA) which is an anti-CD22 antibody for the treatment of non-Hodgkin's lymphoma; and CEAcide (Immunomedics, NJ) which is a humanized anti-CEA antibody for the treatment of colorectal cancer.

Other antibodies useful in the treatment of cancer include, but are not limited to, antibodies against the following antigens (exemplary cancers are indicated in parentheses): CA125 (ovarian), CA15-3 (carcinomas), CA19-9 (carcinomas), L6 (carcinomas), Lewis Y (carcinomas), Lewis X (carcinomas), alpha fetoprotein (carcinomas), CA 242 (colorectal), placental alkaline phosphatase (carcinomas), prostate specific membrane antigen (prostate), prostatic acid phosphatase (prostate), epidermal growth factor (carcinomas), MAGE-1 (carcinomas), MAGE-2 (carcinomas), MAGE-3 (carcinomas), MAGE-4 (carcinomas), anti transferrin receptor (carcinomas), p97 (melanoma), MUC1-KLH (breast cancer), CEA (colorectal), gp100 (melanoma), MART1 (melanoma), prostate specific antigen (PSA) (prostate), IL-2 receptor (T-cell leukemia and lymphomas), CD20 (non Hodgkin's lymphoma), CD52 (leukemia), CD33 (leukemia), CD22 (lymphoma), human chorionic gonadotropin (carcinoma), CD38 (multiple myeloma), CD40 (lymphoma), mucin (carcinomas), P21 (carcinomas), MPG (melanoma), and Neu oncogene product (carcinomas). Some specific, useful antibodies include, but are not limited to, BR96 mAb (Trail et al., 1993, Science 261:212-215), BR64 (Trail et al., 1997, Cancer Research 57:100-105), mAbs against the CD40 antigen, such as S2C6 mAb (Francisco et al., 2000, Cancer Res. 60:3225-3231) and chimeric and humanized variants thereof, mabs against the cD33 antigen; mabs against the EphA2 antigen; mAbs against the CD70 antigen, such as IF6 mAb and 2F2 mAb and chimeric and humanized variants thereof, and mAbs against the CD30 antigen, such as AC10 (Bowen et al., 1993, J. Immunol. 151:5896-5906; Wahl et al., 2002, Cancer Res. 62(13):3736-42) and chimeric and humanized variants thereof. Many other internalizing antibodies that bind to tumor associated antigens can be used and have been reviewed (see, e.g., Franke et al., 2000, Cancer Biother. Radiopharm. 15:459 76; Murray, 2000, Semin. Oncol. 27:64 70; Breitling et al., Recombinant Antibodies, John Wiley, and Sons, New York, 1998).

The antibody also can be an antibody that binds to an antigen that is present on a target cell or target cell population. For example, transmembrane polypeptides and other markers can be specifically expressed on the surface of one or more particular type(s) of target cells (e.g., a cancer cell) as compared to on one or more normal (e.g., a non-cancerous cell(s)). Often, such markers are more abundantly expressed on the surface of the target cells, or exhibit greater immunogenicity, as compared to those on the surface of the normal cells. The identification of such cell surface antigen polypeptides has given rise to the ability to specifically target cells for destruction via antibody-based therapies. Thus, in some embodiments, the antibodies include, but are not limited to, antibodies against tumor-associated antigens (TAA). Such tumor-associated antigens are known in the art, and can prepared for use in generating antibodies using methods and information which are well known in the art.

See also EP2552957, WO/2012/116453, WO/2012/032080. See also Zybody™, http://www.zyngenia.com/technology.html. See also human heavy chain-only antibodies technology, http://www.crescendobiologics.com/. See also WO2010001251, yeast based human antibody yeast-based platform http://www.adimab.com/science-and-technology/technology-overview/, mAbLogix™ platform http://www.dna.com/technology, monoclonal discovery platform http://www.igenica.com/technology/, WO2009/157771, EP2560993, WO2013004842, WO2012166560.

Linker Moiety (L)

The subject compositions optionally further include a Linker moiety (L). (L) is a bifunctional compound which can be used to link a (D) and a (T) to form a conjugate composition, T-L-D. Such conjugates allow the selective delivery of drugs to target cells (e.g., tumor cells). (L)s include a divalent substituent such as an alkyldiyl, an aryldiyl, a heteroaryldiyl, moieties such as: —(CR$_2$)$_n$O (CR$_2$)$_n$—, repeating units of alkyloxy (e.g., polyethylenoxy, PEG, polymethyleneoxy) and alkylamino (e.g., polyethyleneamino, Jeffamine™); and diacid ester and amides including succinate, succinamide, diglycolate, malonate, and caproamide.

The subject compositions can be prepared using a (L) unit having a reactive site for binding to the (D) and (T). In some embodiments, (L) has a reactive site which has an electrophilic group that is reactive to a nucleophilic group present on (T). Useful nucleophilic groups on (T) include but are not limited to sulfhydryl, hydroxyl and amino groups. The heteroatom of the nucleophilic group of (T) is reactive to an electrophilic group on (L) and forms a covalent bond to (L). Useful electrophilic groups include, but are not limited to maleimide and haloacetamide groups. The nucleophilic group on (T) provides a convenient site for attachment to (L).

In another embodiment, (L) has a reactive site which has a nucleophilic group that is reactive to an electrophilic group present on (T). Useful electrophilic groups on (T) include, but are not limited to, aldehyde and ketone carbonyl groups. The heteroatom of a nucleophilic group of (L) can react with an electrophilic group on (T) and form a covalent bond to (T). Useful nucleophilic groups on (L) include, but are not limited to, hydrazide, oxime, amino, hydrazine, thiosemicarbazone, hydrazine carboxylate, and arylhydrazide. The electrophilic group on (T) provides a convenient site for attachment to (L).

Carboxylic acid functional groups and chloroformate functional groups are also useful reactive sites for (L) because they can react with amino groups of a (D) to form an amide linkage. Also useful as a reactive site is a carbonate functional group on (L), such as but not limited to p-nitrophenyl carbonate, which can react with an amino group of a (D) to form a carbamate linkage.

It will be appreciated that any linker moieties taught in the prior art, and particularly those taught for use in the context of drug delivery, may be used in the current invention. Without limiting the scope of the preceding statement, in one embodiment, (L) comprises a linker moiety disclosed in WO 2012/113847. In another embodiment, (L) comprises a linker moiety disclosed in U.S. Pat. No. 8,288,352. In another embodiment, (L) comprises a linker moiety disclosed in U.S. Pat. No. 5,028,697. In another embodiment, (L) comprises a linker moiety disclosed in U.S. Pat. No. 5,006,652. In another embodiment, (L) comprises a linker moiety disclosed in U.S. Pat. No. 5,094,849. In another embodiment, (L) comprises a linker moiety disclosed in U.S. Pat. No. 5,053,394. In another embodiment, (L) comprises a linker moiety disclosed in U.S. Pat. No. 5,122,368. In another embodiment, (L) comprises a linker moiety disclosed in U.S. Pat. No. 5,387,578. In another embodiment, (L) comprises a linker moiety disclosed in U.S. Pat. No. 5,547,667. In another embodiment, (L) comprises a linker moiety disclosed in U.S. Pat. No. 5,622,929. In another embodiment, (L) comprises a linker moiety disclosed in U.S. Pat. No. 5,708,146. In another embodiment, (L) comprises a linker moiety disclosed in U.S. Pat. No. 6,468,522. In another embodiment, (L) comprises a linker moiety disclosed in U.S. Pat. No. 6,103,236. In another embodiment, (L) comprises a linker moiety disclosed in U.S. Pat. No. 6,638,509. In another embodiment, (L) comprises a linker moiety disclosed in U.S. Pat. No. 6,214,345. In another embodiment, (L) comprises a linker moiety disclosed in U.S. Pat. No. 6,759,509. In another embodiment, (L) comprises a linker moiety disclosed in WO 2007/103288. In another embodiment, (L) comprises a linker moiety disclosed in WO 2008/083312. In another embodiment, (L) comprises a linker moiety disclosed in WO 2003/068144. In another embodiment, (L) comprises a linker moiety disclosed in WO 2004/016801. In another embodiment, (L) comprises a linker moiety disclosed in WO 2009/134976. In another embodiment, (L) comprises a linker moiety disclosed in WO 2009/134952. In another embodiment, (L) comprises a linker moiety disclosed in WO 2009/134977. In another embodiment, (L) comprises a linker moiety disclosed in WO 2002/08180. In another embodiment, (L) comprises a linker moiety disclosed in WO 2004/043493. In another embodiment, (L) comprises a linker moiety disclosed in WO 2007/018431. In another embodiment, (L) comprises a linker moiety disclosed in WO 2003/026577. In another embodiment, (L) comprises a linker moiety disclosed in WO 2005/077090. In another embodiment, (L) comprises a linker moiety disclosed in WO 2005/082023. In another embodiment, (L) comprises a linker moiety disclosed in WO 2007/011968. In another embodiment, (L) comprises a linker moiety disclosed in WO 2007/038658. In another embodiment, (L) comprises a linker moiety disclosed in WO 2007/059404. In another embodiment, (L) comprises a linker moiety disclosed in WO 2006/110476. In another embodiment, (L) comprises a linker moiety disclosed in WO 2005/112919. In another embodiment, (L) comprises a linker moiety disclosed in WO 2008/103693. In another embodiment, (L) comprises a linker moiety disclosed in U.S. Pat. No. 6,756,037. In another embodiment, (L) comprises a linker moiety disclosed in U.S. Pat. No. 7,087,229. In another embodiment, (L) comprises a linker moiety disclosed in U.S. Pat. No. 7,122,189. In another embodiment, (L) comprises a linker moiety disclosed in U.S. Pat. No. 7,332,164. In another embodiment, (L) comprises a linker moiety disclosed in U.S. Pat. No. 5,556,623. In another embodiment, (L) comprises a linker moiety disclosed in U.S. Pat. No. 5,643,573. In another embodiment, (L) comprises a linker moiety disclosed in U.S. Pat. No. 5,665,358.

Linkers (L) comprising a self-immolative component may also be used. For example, see U.S. Pat. No. 6,214,345. An example of a self-immolative component is p-aminobenzyl-carbamoyl (PABC).

Commercially available linkers may be used in the invention. For example, the commercially available cleavable linker sulfosuccinimidyl 6-[3'(2-pyridyldithio)-propionamido] hexanoate (sulfo-LC-SPDP: Thermo Pierce Cat #21650) and Non-cleavable linker succinimidyl 4-[N-maleimidomethyl]cyclohexane-1-carboxylate (SMCC: Thermo Pierce Cat #22360) may be used, as demonstrated herein.

See also, WO2012171020, WO2010138719, the range of commercially available linkers, for example, from Concortis http://www.concortis.com/home. See also Kim et al., BIOCONJUGATE CHEMISTRY, 21 (8): 1513-1519 August 2010. See also EP2326349. See also copper free click chemistry linkers, Angew. Chem. Int. Ed., 2010, 49, p. 9422-9425, ChemBioChem, 2011, 12, p. 1309-1312, http://www.synaffix.com/technology/.

Drug Moiety (D)

(D) is a compound having the structure (I), (Ia) or (Ib) as described herein. It will be recognized by the artisan of reasonable skill that compounds of structure (I), (Ia) or (Ib) may be appropriately modified to facilitate a conjugation reaction with (L), or if (L) is not present, with (T), and formation of a conjugate (T)-(L)-(D) or (T)-(D). Any point of attachment on (D) may be used. In one embodiment, the C-terminus of (D) forms the point of attachment in a (T)-(L)-(D) conjugate. In another embodiment, the N-terminus of (D) forms the point of attachment in a (T)-(L)-(D) conjugate. In another embodiment, a side chain of (D) forms the point of attachment in a (T)-(L)-(D) conjugate.

Novel Conjugates Comprising Microtubule Disrupting Peptide Toxins

In one embodiment of the present disclosure, conjugates comprising microtubule disrupting peptide toxins covalently linked in the conjugate through the side chain of the N-terminal amino acid are provided. In one embodiment, the microtubule disrupting peptide toxin is hemiasterlin or an analog thereof and the toxin is covalently linked in the conjugate through the indole moiety within the side chain of the N-terminal amino acid of the toxin peptide. In another embodiment, the microtubule disrupting peptide toxin is HTI-286 or an analog thereof and the toxin is covalently linked in the conjugate through the phenyl group within the side chain of the N-terminal amino acid of the toxin peptide. In one embodiment, the microtubule disrupting peptide toxin is a compound having structure (1), (Ia) or (Ib) as disclosed herein.

The subject compositions have anti-mitotic activity and the following structure:

$$(T)\text{-}(L)\text{-}(PT) \quad\quad\quad (VII)$$

wherein (T) is a targeting moiety as described herein, (L) is an optional linker as described herein, and (PT) is a microtubule disrupting peptide toxin that covalently linked to (L) through the side chain of the N-terminal amino acid of (PT), or if (L) is not present, (PT) is covalently linked to (T) through the side chain of the N-terminal amino acid of (PT).

In one embodiment, (T) is an antibody. Accordingly, in one embodiment, antibody-drug conjugates (ADCs) comprising microtubule disrupting peptide toxins that are linked to the conjugate through the side chain of the N-terminal amino acid are provided.

In one embodiment, (T)-(L)-(PT) has the following structure:

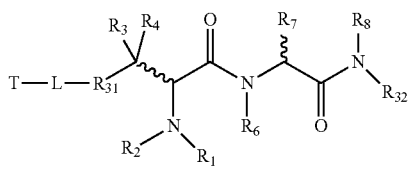

wherein, $R_1$ and $R_2$ are independently selected from the group consisting of: H and a saturated or unsaturated moiety having a linear, branched, or non-aromatic cyclic skeleton containing one to ten carbon atoms, and the carbon atoms are optionally substituted with: —OH, —I, —Br, —Cl, —F, —CN, —$CO_2H$, —CHO, —COSH, or —$NO_2$;

$R_3$ and $R_4$ are independently selected from the group consisting of: H, R, ArR—, or $R_3$ and $R_4$ are joined to form a ring;

$R_{31}$ is selected from the group consisting of: H, R', ArR—, Ar—R—Ar, R—Ar—Ar, Ar—Ar—R—, and Ar, wherein each R and each Ar may be substituted, and zero to ten heteroatoms may replace carbon atoms in the chain, for example O or S or N may be incorporated into the carbon chain; in one embodiment, wherein R' is

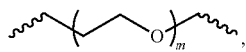

wherein m is an integer from one to fifteen;

$R_6$ is selected from the group consisting of: H, R, and ArR—;

$R_7$ and $R_8$ are independently selected from the group consisting of: H, R, and ArR—; and $R_{32}$ is selected from:

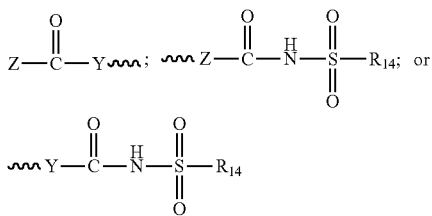

wherein,

Z is defined as a moiety selected from the group consisting of: —OH, —OR; —SH; —SR; —$NH_2$; —NRCH($R_{11}$)COOH; and —NHCH($R_{11}$)COOH, wherein $R_{11}$ is a moiety having the formula: R, or —$(CH_2)_n NR_{12}R_{13}$, wherein n=1-4 and $R_{12}$ and $R_{13}$ are independently selected from the group consisting of: H; R; and —C(NH)($NH_2$), Y is defined as a moiety selected from the group consisting of: a linear, saturated or unsaturated, one to six carbon alkyl group, optionally substituted with R, ArR—, or X; and, X is defined as a moiety selected from the group consisting of: —OH, —OR, =O, =S, —$O_2CR$, —SH, —SR, —SOCR, —$NH_2$, —NHR, —$N(R)_2$, —NHCOR, —NRCOR, —I, —Br, —Cl, —F, —CN, —$CO_2H$, —$CO_2R$, —CHO, —COR, —$CONH_2$, —CONHR, —$CON(R)_2$, —COSH, —COSR, —$NO_2$, —$SO_3H$, —SOR, and —$SO_2R$;

$R_{14}$ is selected from the group consisting of optionally substituted alkyl, optionally substituted alkylamino, optionally substituted cycloalkyl, optionally substituted aryl, optionally substituted heterocyclyl and optionally substituted heteroaryls, $COR_{24}$, —$CSR_{24}$, —$OR_{24}$, and —$NHR_{24}$, wherein each $R_{24}$ is, independently, alkyl optionally substituted with halogen, —OH or —SH, R is defined as a saturated or unsaturated moiety having a linear, branched, or non-aromatic cyclic skeleton containing one to ten carbon atoms, zero to four nitrogen atoms, zero to four oxygen atoms, and zero to four sulfur atoms, and the carbon atoms are optionally substituted with: =O, =S, OH, —$OR_{10}$, —$O_2CR_{10}$, —SH, —$SR_{10}$, —$SOCR_{10}$, —$NH_2$, —$NHR_{10}$, —$N(R_{10})_2$, —$NHCOR_{10}$, —$NR_{10}COR_{10}$, —I, —Br, —Cl, —F, —CN, —$CO_2H$, —$CO_2R_{10}$, —CHO, —$COR_{10}$, —$CONH_2$, —$CONHR_{10}$, —$CON(R_{10})_2$, —COSH, —$COSR_{10}$, —$NO_2$, —$SO_3H$, —$SOR_{10}$, —$SO_2R_{10}$, wherein $R_{10}$ is a linear, branched or cyclic, one to ten carbon saturated or unsaturated alkyl group;

the ring formed by joining $R_3$ and $R_4$ is a three to seven member non-aromatic cyclic skeleton within the definition of R, Y is defined as a moiety selected from the group consisting of: a linear, saturated or unsaturated, one to six carbon alkyl group, optionally substituted with R, ArR—, or X; and, X is defined as a moiety selected from the group consisting of: —OH, —OR, =O, =S, —$O_2CR$, —SH, —SR, —SOCR, —$NH_2$, —NHR, —$N(R)_2$, —NHCOR, —NRCOR, —I, —Br, —Cl, —F, —CN, —$CO_2H$, —$CO_2R$, —CHO, —COR, —$CONH_2$, —CONHR, —$CON(R)_2$, —COSH, —COSR, —$NO_2$, —$SO_3H$, —SOR, and —$SO_2R$;

or a stereoisomer, prodrug or pharmaceutically acceptable salt thereof.

In one embodiment, Ar is an aromatic ring selected from the group consisting of: phenyl, naphthyl, anthracyl, pyrrolyl.

In one embodiment, $R_{32}$ is:

wherein Z and Y are defined as above.

In one embodiment, $R_{32}$ is:

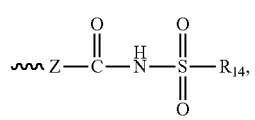

wherein Z and $R_{14}$ are defined as above.

In one embodiment, $R_{32}$ is:

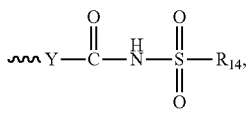

wherein y and $R_{14}$ are defined as above.

In another embodiment, (T)-(L)-(PT) has the following structure:

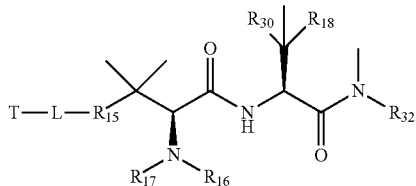

wherein,
$R_{15}$ is selected from the group consisting of optionally substituted alkyl, optionally substituted alkylamino, optionally substituted cycloalkyl, optionally substituted aryl, optionally substituted heterocyclyl and optionally substituted heteroaryl;
$R_{16}$ is selected from the group consisting of H and $C_{1-6}$ alkyl;
$R_{17}$ is selected from the group consisting of H and $C_{1-6}$ alkyl;
$R_{18}$ and $R_{30}$ are independently selected from the group consisting of H, $C_{1-6}$ alkyl and —SH, with the proviso that both the $R_{18}$ and $R_{30}$ substituents cannot be H;
$R_{32}$ is selected from:

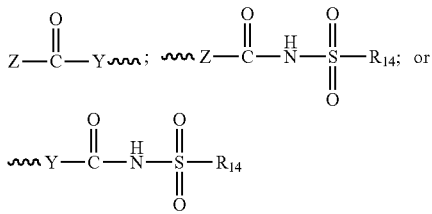

wherein,
Z is defined as a moiety selected from the group consisting of: —OH, —OR; —SH; —SR; —NH$_2$; —NRCH(R$_{11}$)COOH; and —NHCH(R$_{11}$)COOH, wherein R$_{11}$ is a moiety having the formula: R, or —(CH$_2$)$_n$NR$_{12}$R$_{13}$, wherein n=1-4 and $R_{12}$ and $R_{13}$ are independently selected from the group consisting of: H; R; and —C(NH)(NH$_2$), R is defined as a saturated or unsaturated moiety having a linear, branched, or non-aromatic cyclic skeleton containing one to ten carbon atoms, zero to four nitrogen atoms, zero to four oxygen atoms, and zero to four sulfur atoms, and the carbon atoms are optionally substituted with: =O, =S, OH, —OR$_{10}$, —O$_2$CR$_{10}$, —SH, —SR$_{10}$, —SOCR$_{10}$, —NH$_2$, —NHR$_{10}$, —N(R$_{10}$)$_2$, —NHCOR$_{10}$, —NR$_{10}$COR$_{10}$, —I, —Br, —Cl, —F, —CN, —CO$_2$H, —CO$_2$R$_{10}$, —CHO, —COR$_{10}$, —CONH$_2$, —CONHR$_{10}$, —CON(R$_{10}$)$_2$, —COSH, —COSR$_{10}$, —NO$_2$, —SO$_3$H, —SOR$_{10}$, —SO$_2$R$_{10}$, wherein R$_{10}$ is a linear, branched or cyclic, one to ten carbon saturated or unsaturated alkyl group;

the ring formed by joining $R_3$ and $R_4$ is a three to seven member non-aromatic cyclic skeleton within the definition of R, Y is defined as a moiety selected from the group consisting of: a linear, saturated or unsaturated, one to six carbon alkyl group, optionally substituted with R, ArR—, or X; and, X is defined as a moiety selected from the group consisting of: —OH, —OR, =O, =S, —O$_2$CR, —SH, —SR, —SOCR, —NH$_2$, —NHR, —N(R)$_2$, —NHCOR, —NRCOR, —I, —Br, —Cl, —F, —CN, —CO$_2$H, —CO$_2$R, —CHO, —COR, —CONH$_2$, —CONHR, —CON(R)$_2$, —COSH, —COSR, —NO$_2$, —SO$_3$H, —SOR, and —SO$_2$R;

or a stereoisomer, prodrug or pharmaceutically acceptable salt thereof.

In another embodiment, (T)-(L)-(PT) has the following structure:

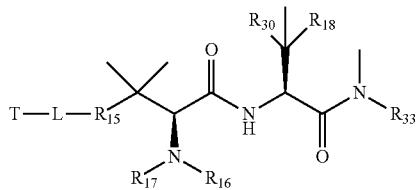

wherein,
$R_{15}$ is selected from the group consisting of optionally substituted alkyl, optionally substituted alkylamino, optionally substituted cycloalkyl, optionally substituted aryl, optionally substituted heterocyclyl and optionally substituted heteroaryl;
$R_{16}$ is selected from the group consisting of H and $C_{1-6}$ alkyl;
$R_{17}$ is selected from the group consisting of H and $C_{1-6}$ alkyl;
$R_{18}$ and $R_{30}$ are independently selected from the group consisting of H, $C_{1-6}$ alkyl and —SH, with the proviso that both the $R_{18}$ and $R_{30}$ substituents cannot be H;
$R_{33}$ is:

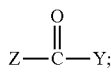

wherein,
Z is as defined above,
R is defined as a saturated or unsaturated moiety having a linear, branched, or non-aromatic cyclic skeleton containing one to ten carbon atoms, zero to four nitrogen atoms, zero to four oxygen atoms, and zero to four sulfur atoms, and the carbon atoms are optionally substituted with: =O, =S, OH, —OR$_{10}$, —O$_2$CR$_{10}$, —SH, —SR$_{10}$, —SOCR$_{10}$, —NH$_2$, —NHR$_{10}$, —N(R$_{10}$)$_2$, —NHCOR$_{10}$, —NR$_{10}$COR$_{10}$, —I, —Br, —Cl, —F, —CN, —CO$_2$H, —CO$_2$R$_{10}$, —CHO, —COR$_{10}$, —CONH$_2$, —CONHR$_{10}$, —CON(R$_{10}$)$_2$, —COSH, —COSR$_{10}$, —NO$_2$, —SO$_3$H, —SOR$_{10}$, —SO$_2$R$_{10}$, wherein R$_{10}$ is a linear, branched or cyclic, one to ten carbon saturated or unsaturated alkyl group;
the ring formed by joining $R_3$ and $R_4$ is a three to seven member non-aromatic cyclic skeleton within the definition of R, Y is defined as a moiety selected from the group consisting of: a linear, saturated or unsaturated, one to six carbon alkyl group, optionally substituted with R, ArR—, or X; and, X is defined as a moiety selected from the group consisting of: —OH, —OR, =O, =S, —O₂CR, —SH, —SR, —SOCR, —NH₂, —NHR, —N(R)₂, —NHCOR, —NRCOR, —I, —Br, —Cl, —F, —CN, —CO₂H, —CO₂R, —CHO, —COR, —CONH₂, —CONHR, —CON(R)₂, —COSH, —COSR, —NO₂, —SO₃H, —SOR, and —SO₂R;

or a stereoisomer, prodrug or pharmaceutically acceptable salt thereof.

In another embodiment, (T)-(L)-(PT) has the following structure:

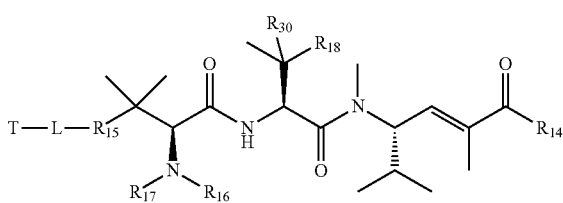

wherein, $R_{14}$ is selected from the group consisting of optionally substituted alkyl, optionally substituted alkylamino, optionally substituted cycloalkyl, optionally substituted aryl, optionally substituted heterocyclyl, optionally substituted heteroaryl, —COR$_{24}$, —CSR$_{24}$, —OR$_{24}$, —SR$_{24}$, and —NHR$_{24}$, wherein each $R_{24}$ is, independently, alkyl optionally substituted with halogen, —OH or —SH;

$R_{15}$ is selected from the group consisting of optionally substituted alkyl, optionally substituted alkylamino, optionally substituted cycloalkyl, optionally substituted aryl, optionally substituted heterocyclyl and optionally substituted heteroaryl;

$R_{16}$ is selected from the group consisting of H and $C_{1-6}$ alkyl;

$R_{17}$ is selected from the group consisting of H and $C_{1-6}$ alkyl;

$R_{18}$ and $R_{30}$ are independently selected from the group consisting of H, $C_{1-6}$ alkyl and —SH, with the proviso that both the $R_{18}$ and $R_{30}$ substituents cannot be H;

or a stereoisomer, prodrug or pharmaceutically acceptable salt thereof.

In another embodiment, (T)-(L)-(PT) has the following structure:

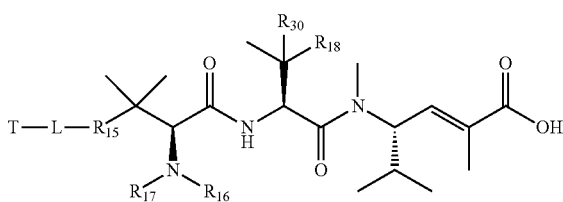

wherein, $R_{14}$ is selected from the group consisting of optionally substituted alkyl, optionally substituted alkylamino, optionally substituted cycloalkyl, optionally substituted aryl, optionally substituted heterocyclyl, optionally substituted heteroaryl, —COR$_{24}$, —CSR$_{24}$, —OR$_{24}$, —SR$_{24}$, and —NHR$_{24}$, wherein each $R_{24}$ is, independently, alkyl optionally substituted with halogen, —OH or —SH;

$R_{15}$ is selected from the group consisting of optionally substituted alkyl, optionally substituted alkylamino, optionally substituted cycloalkyl, optionally substituted aryl, optionally substituted heterocyclyl and optionally substituted heteroaryl;

$R_{16}$ is selected from the group consisting of H and $C_{1-6}$ alkyl;

$R_{17}$ is selected from the group consisting of H and $C_{1-6}$ alkyl;

$R_{18}$ and $R_{30}$ are independently selected from the group consisting of H, $C_{1-6}$ alkyl and —SH, with the proviso that both the $R_8$ and $R_{30}$ substituents cannot be H; or a stereoisomer, prodrug or pharmaceutically acceptable salt thereof.

In another embodiment, (T)-(L)-(PT) has the following structure:

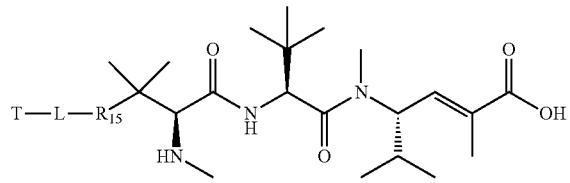

wherein, $R_{15}$ is selected from the group consisting of optionally substituted alkyl, optionally substituted alkylamino, optionally substituted cycloalkyl, optionally substituted aryl, optionally substituted heterocyclyl and optionally substituted heteroaryl;

or a stereoisomer, prodrug or pharmaceutically acceptable salt thereof.

In another embodiment, (T)-(L)-(PT) has the following structure:

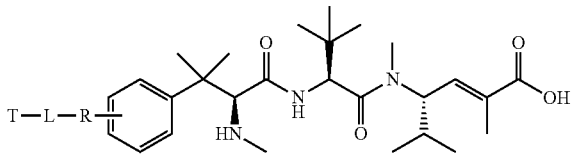

wherein,

R is defined as a saturated or unsaturated moiety having a linear, branched, or non-aromatic cyclic skeleton containing one to ten carbon atoms, zero to four nitrogen atoms, zero to four oxygen atoms, and zero to four sulfur atoms, and the carbon atoms are optionally substituted with: =O, =S, OH, —OR$_{10}$, —O₂CR$_{10}$, —SH, —SR$_{10}$, —SOCR$_{10}$, —NH₂, —NHR$_{10}$, —N(R$_{10}$)₂, —NHCOR$_{10}$, —NR$_{10}$COR$_{10}$, —I, —Br, —Cl, —F, —CN, —CO₂H, —CO₂R$_{10}$, —CHO, —COR$_{10}$, —CONH₂, —CONHR$_{10}$, —CON(R$_{10}$)₂, —COSH, —COSR$_{10}$, —NO₂, —SO₃H, —SOR$_{10}$, —SO₂R$_{10}$, wherein $R_{10}$ is a linear, branched or cyclic, one to ten carbon saturated or unsaturated alkyl group, or a stereoisomer, prodrug or pharmaceutically acceptable salt thereof.

In another embodiment, (T)-(L)-(PT) has the following structure:

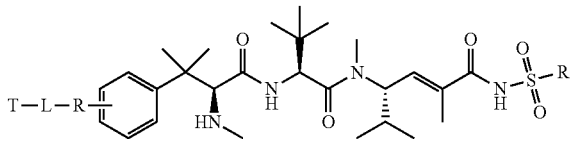

wherein,

R is defined as a saturated or unsaturated moiety having a linear, branched, or non-aromatic cyclic skeleton containing one to ten carbon atoms, zero to four nitrogen atoms, zero to four oxygen atoms, and zero to four sulfur atoms, and the carbon atoms are optionally substituted with: =O, =S, OH, —OR$_{10}$, —O$_2$CR$_{10}$, —SH, —SR$_{10}$, —SOCR$_{10}$, —NH$_2$, —NHR$_{10}$, —N(R$_{10}$)$_2$, —NHCOR$_{10}$, —NR$_{10}$COR$_{10}$, —I, —Br, —Cl, —F, —CN, —CO$_2$H, —CO$_2$R$_{10}$, —CHO, —COR$_{10}$, —CONH$_2$, —CONHR$_{10}$, —CON(R$_{10}$)$_2$, —COSH, —COSR$_{10}$, —NO$_2$, —SO$_3$H, —SOR$_{10}$, —SO$_2$R$_{10}$, wherein R$_{10}$ is a linear, branched or cyclic, one to ten carbon saturated or unsaturated alkyl group, or a stereoisomer, prodrug or pharmaceutically acceptable salt thereof.

In a further embodiment of the invention, (PT) is a hemisterlin analog, such as those disclosed in U.S. Pat. No. 7,579,323, which is hereby incorporated by reference in its entirety for all purposes.

In synthesizing conjugates, including ADCs, comprising microtubule disrupting peptide toxins, peptide linkage through the side chain of the N-terminal amino acid holds several advantages. As demonstrated herein, the side chains of such peptide toxins are ammenable to chemical modifications and manipulations that facilitate formation of covalently linked conjugates without compromising potency. As demonstrated herein, such conjugates are potent cytotoxic compositions capable of delivering peptide toxin payloads.

Administration

For the purposes of administration, the compounds of the present disclosure may be administered as a raw chemical or may be formulated as pharmaceutical compositions. Pharmaceutical compositions of the present disclosure comprise a compound of structure (I), (Ia) or (Ib) and a pharmaceutically acceptable carrier, diluent or excipient. The compound of structure (I), (Ia) or (Ib) is present in the composition in an amount which is effective to treat a particular disease or condition of interest—e.g., in an amount sufficient to treat cancer or tumour cell growth, and preferably with acceptable toxicity to the patient. The activity of compounds of structure (I), (Ia) or (Ib) can be determined by one skilled in the art, for example, as described in the Examples below. Appropriate concentrations and dosages can be readily determined by one skilled in the art.

Administration of the compounds of the disclosure, or their pharmaceutically acceptable salts, in pure form or in an appropriate pharmaceutical composition, can be carried out via any of the accepted modes of administration of agents for serving similar utilities. The pharmaceutical compositions of the disclosure can be prepared by combining a compound of the disclosure with an appropriate pharmaceutically acceptable carrier, diluent or excipient, and may be formulated into preparations in solid, semi-solid, liquid or gaseous forms, such as tablets, capsules, powders, granules, ointments, solutions, suppositories, injections, inhalants, gels, microspheres, and aerosols. Typical routes of administering such pharmaceutical compositions include, without limitation, oral, topical, transdermal, inhalation, parenteral, sublingual, buccal, rectal, vaginal, and intranasal. The term parenteral as used herein includes subcutaneous injections, intravenous, intramuscular, intrasternal injection or infusion techniques. Pharmaceutical compositions of the disclosure are formulated so as to allow the active ingredients contained therein to be bioavailable upon administration of the composition to a patient. Compositions that will be administered to a subject or patient take the form of one or more dosage units, where for example, a tablet may be a single dosage unit, and a container of a compound of the disclosure in aerosol form may hold a plurality of dosage units. Actual methods of preparing such dosage forms are known, or will be apparent, to those skilled in this art; for example, see Remington: The Science and Practice of Pharmacy, 20th Edition (Philadelphia College of Pharmacy and Science, 2000). The composition to be administered will, in any event, contain a therapeutically effective amount of a compound of the disclosure, or a pharmaceutically acceptable salt thereof, for treatment of a disease or condition of interest in accordance with the teachings of this disclosure.

A pharmaceutical composition of the disclosure may be in the form of a solid or liquid. In one aspect, the carrier(s) are particulate, so that the compositions are, for example, in tablet or powder form. The carrier(s) may be liquid, with the compositions being, for example, an oral syrup, injectable liquid or an aerosol, which is useful in, for example, inhalatory administration.

When intended for oral administration, pharmaceutical compositions of the present disclosure typically are either solid or liquid form, where semi-solid, semi-liquid, suspension and gel forms are included within the forms considered herein as either solid or liquid.

As a solid composition for oral administration, the pharmaceutical compositions may be formulated into a powder, granule, compressed tablet, pill, capsule, chewing gum, wafer or the like form. Such a solid composition will typically contain one or more inert diluents or edible carriers. In addition, one or more of the following may be present: binders such as carboxymethylcellulose, ethyl cellulose, microcrystalline cellulose, gum tragacanth or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin; a flavoring agent such as peppermint, methyl salicylate or orange flavoring; and a coloring agent.

When the pharmaceutical composition is in the form of a capsule, for example, a gelatin capsule, it may contain, in addition to materials of the above type, a liquid carrier such as polyethylene glycol or oil.

Pharmaceutical compositions of the disclosure may be in the form of a liquid, for example, an elixir, syrup, solution, emulsion or suspension. The liquid may be for oral administration or for delivery by injection, as two examples. When intended for oral administration, pharmaceutical compositions of the disclosure typically contain, in addition to the present compounds, one or more of a sweetening agent, preservatives, dye/colorant and flavor enhancer. In a composition intended to be administered by injection, one or more of a surfactant, preservative, wetting agent, dispersing agent, suspending agent, buffer, stabilizer and isotonic agent may be included.

Liquid pharmaceutical compositions of the disclosure, whether they be solutions, suspensions or other like form, may include one or more of the following adjuvants: sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. Parenteral preparations can be enclosed in ampoules, disposable syringes or multiple dose vials made of glass or plastic. Physiological saline is a preferred adjuvant. An injectable pharmaceutical composition is preferably sterile.

A liquid pharmaceutical composition of the disclosure intended for either parenteral or oral administration should contain an amount of a compound of the disclosure such that a suitable dosage will be obtained.

Pharmaceutical compositions of the disclosure may be intended for topical administration, in which case the carrier may suitably comprise a solution, emulsion, ointment or gel base. The base, for example, may comprise one or more of the following: petrolatum, lanolin, polyethylene glycols, bee wax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device.

Pharmaceutical compositions of the disclosure may be intended for rectal administration, in the form, for example, of a suppository, which will melt in the rectum and release the drug. Compositions for rectal administration may contain an oleaginous base as a suitable nonirritating excipient. Such bases include, without limitation, lanolin, cocoa butter and polyethylene glycol.

Pharmaceutical compositions of the disclosure may include various materials, which modify the physical form of a solid or liquid dosage unit. For example, the composition may include materials that form a coating shell around the active ingredients. The materials that form the coating shell are typically inert, and may be selected from, for example, sugar, shellac, and other enteric coating agents. Alternatively, the active ingredients may be encased in a gelatin capsule.

Pharmaceutical compositions of the disclosure may be prepared in dosage units that can be administered as an aerosol. The term aerosol is used to denote a variety of systems ranging from those of colloidal nature to systems consisting of pressurized packages. Delivery may be by a liquefied or compressed gas or by a suitable pump system that dispenses the active ingredients. Aerosols of compounds of the disclosure may be delivered in single phase, bi-phasic, or tri-phasic systems in order to deliver the active ingredient(s). Delivery of the aerosol includes the necessary container, activators, valves, subcontainers, and the like, which together may form a kit. One skilled in the art, without undue experimentation may determine preferred aerosols.

The pharmaceutical compositions of the disclosure may be prepared by methodology well known in the pharmaceutical art. For example, a pharmaceutical composition intended to be administered by injection can be prepared by combining a compound of the disclosure with sterile, distilled water so as to form a solution. A surfactant may be added to facilitate the formation of a homogeneous solution or suspension. Surfactants are compounds that non-covalently interact with the compound of the disclosure so as to facilitate dissolution or homogeneous suspension of the compound in the aqueous delivery system.

The compounds of the disclosure, or their pharmaceutically acceptable salts, are administered in a therapeutically effective amount, which will vary depending upon a variety of factors including the activity of the specific compound employed; the metabolic stability and length of action of the compound; the age, body weight, general health, sex, and diet of the patient; the mode and time of administration; the rate of excretion; the drug combination; the severity of the particular disorder or condition; and the subject undergoing therapy.

Compounds of the disclosure, or pharmaceutically acceptable derivatives thereof, may also be administered simultaneously with, prior to, or after administration of one or more other therapeutic agents. Such combination therapy includes administration of a single pharmaceutical dosage formulation which contains a compound of the disclosure and one or more additional active agents, as well as administration of the compound of the disclosure and each active agent in its own separate pharmaceutical dosage formulation. For example, a compound of the disclosure and the other active agent can be administered to the patient together in a single oral dosage composition such as a tablet or capsule, or each agent administered in separate oral dosage formulations. Where separate dosage formulations are used, the compounds of the disclosure and one or more additional active agents can be administered at essentially the same time, i.e., concurrently, or at separately staggered times, i.e., sequentially; combination therapy is understood to include all these regimens.

It is understood that in the present description, combinations of substituents and/or variables of the depicted formulae are permissible only if such contributions result in stable compounds.

It will also be appreciated by those skilled in the art that in the synthetic processes described herein the functional groups of intermediate compounds may need to be protected by suitable protecting groups. Such functional groups include hydroxy, amino, mercapto and carboxylic acid. As described above, suitable protecting groups for hydroxy include trialkylsilyl or diarylalkylsilyl (for example, t-butyldimethylsilyl, t-butyldiphenylsilyl or trimethylsilyl), tetrahydropyranyl, benzyl, and the like, and suitable protecting groups for amino, amidino and guanidino include t-butoxycarbonyl, benzyloxycarbonyl, and the like. Suitable protecting groups for mercapto include —C(O)—R" (where R" is alkyl, aryl or arylalkyl), p-methoxybenzyl, trityl and the like. Suitable protecting groups for carboxylic acid include alkyl, aryl or arylalkyl esters. Protecting groups may be added or removed in accordance with standard techniques, which are known to one skilled in the art and as described herein. The use of protecting groups is described in detail in Green, T. W, and P. G. M. Wutz, *Protective Groups in Organic Synthesis* (1999), 3rd Ed., Wiley. As one of skill in the art would appreciate, the protecting group may also be a polymer resin such as a Wang resin, Rink resin or a 2-chlorotrityl-chloride resin.

It will also be appreciated by those skilled in the art, although a protected derivative of compounds of this disclosure may not possess pharmacological activity as such, they may be administered to a mammal and thereafter metabolized in the body to form compounds of the disclosure which are pharmacologically active. Such derivatives may therefore be described as "prodrugs". All prodrugs of compounds of this disclosure are included within the scope of the present disclosure.

Furthermore, compounds of the disclosure which exist in free base or acid form can be converted to their pharmaceutically acceptable salts by treatment with the appropriate inorganic or organic base or acid by methods known to one skilled in the art. Salts of the compounds of the disclosure can be converted to their free base or acid form by standard techniques.

The following Examples illustrate various methods of making compounds of this disclosure, i.e., compound of structures (I), (Ia), (Ib), (VI), and (VII). It is understood that one skilled in the art may be able to make these compounds by similar methods or by combining other methods known to one skilled in the art. It is also understood that one skilled in the art would be able to make, in a similar manner as described below, other compounds of structure (I), (Ia), (Ib), (VI) or (VII) not specifically illustrated below by using the appropriate starting components and modifying the parameters of the synthesis as needed. In general, starting components may be obtained from sources such as Sigma Aldrich, Lancaster Synthesis, Inc., Maybridge, Matrix Scientific, TCI, and Fluorochem USA, etc. or synthesized according to sources known to those skilled in the art (see, for example, Advanced Organic Chemistry: Reactions, Mechanisms, and Structure, 5th edition (Wiley, December 2000)) or prepared as described herein.

The following examples are provided for purposes of illustration, not limitation.

EXAMPLES

General Synthetic Schemes

General Scheme

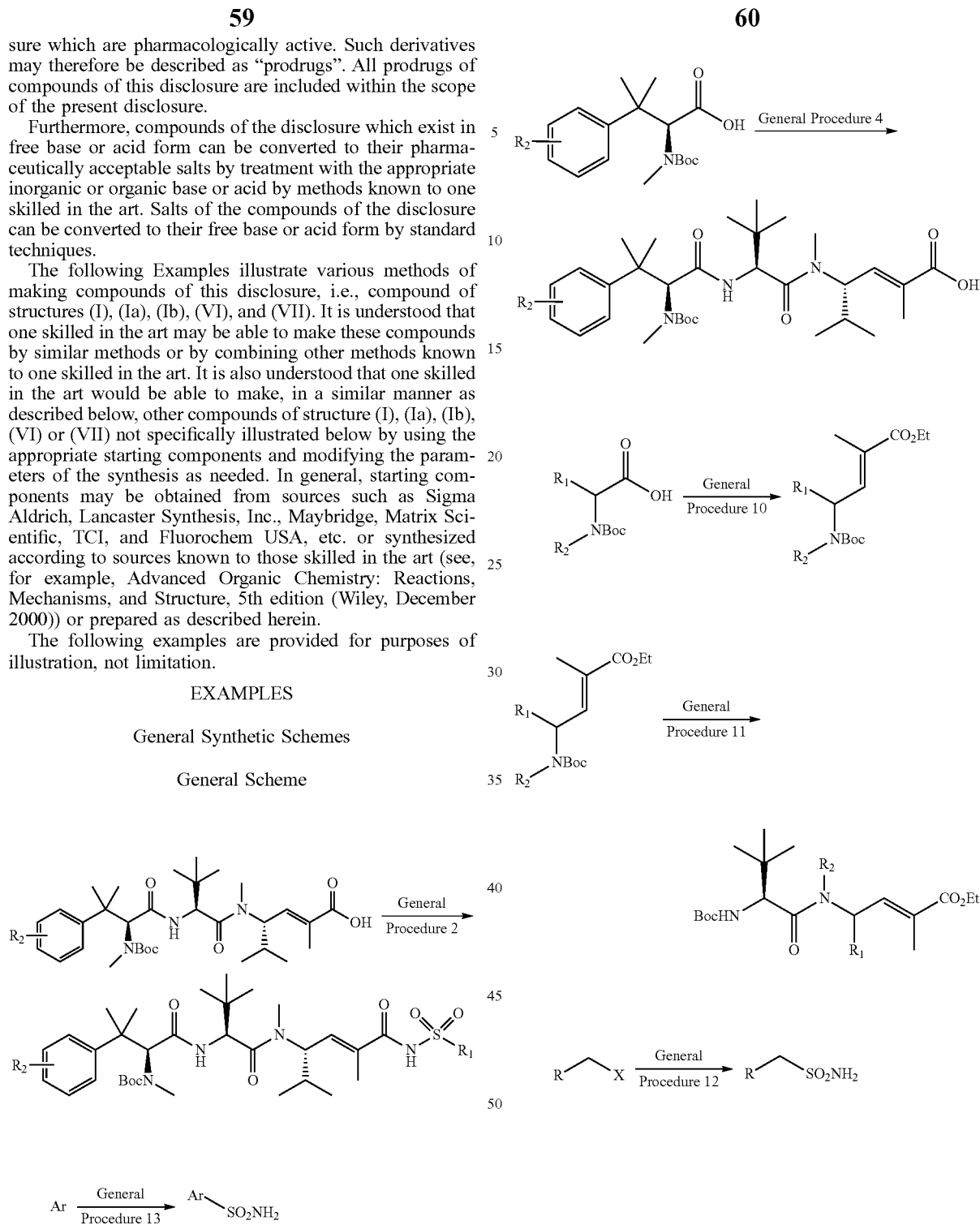

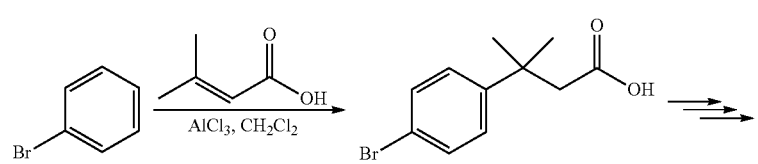

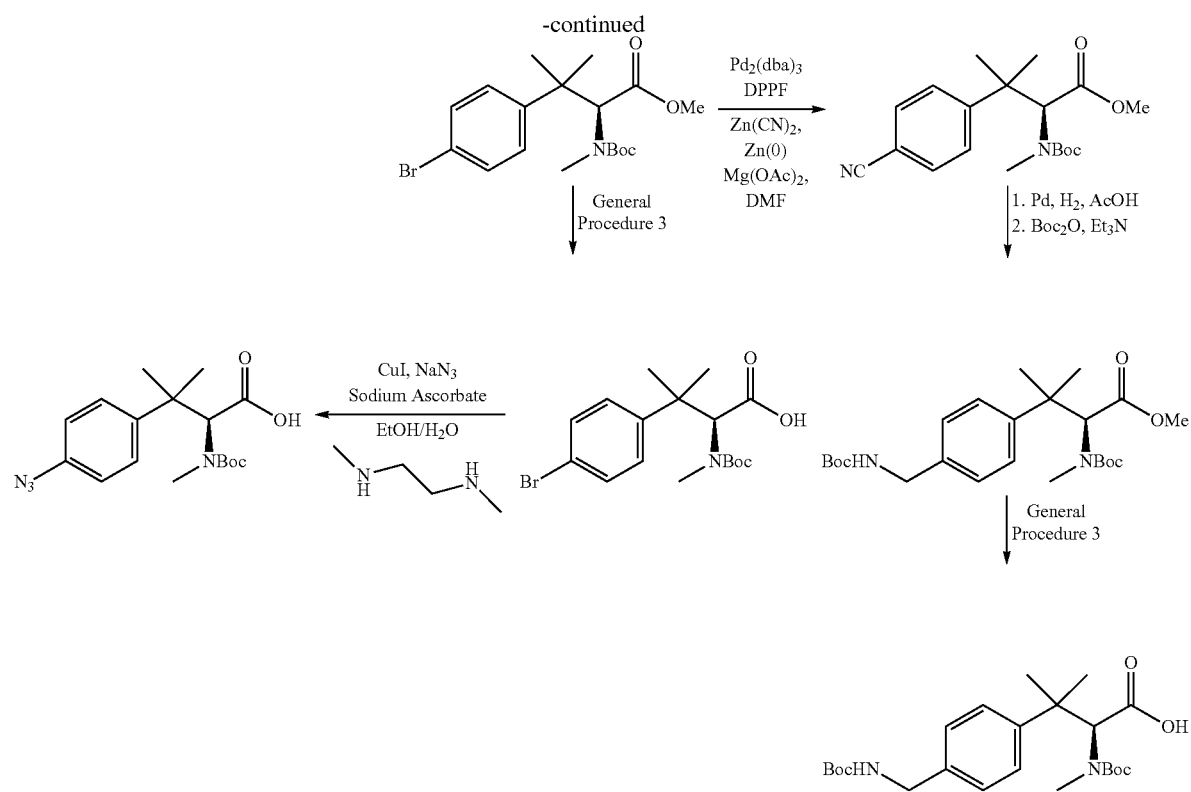
General Procedure 14
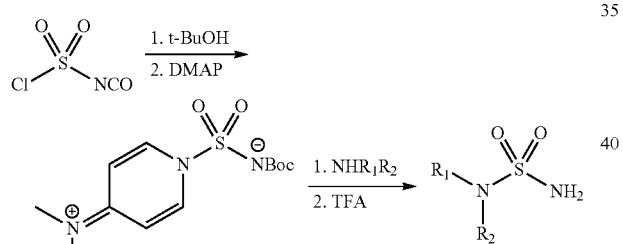
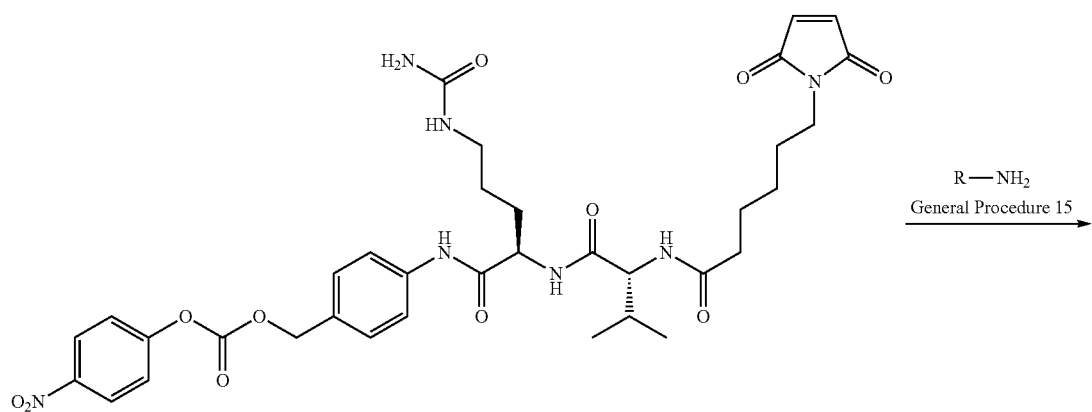

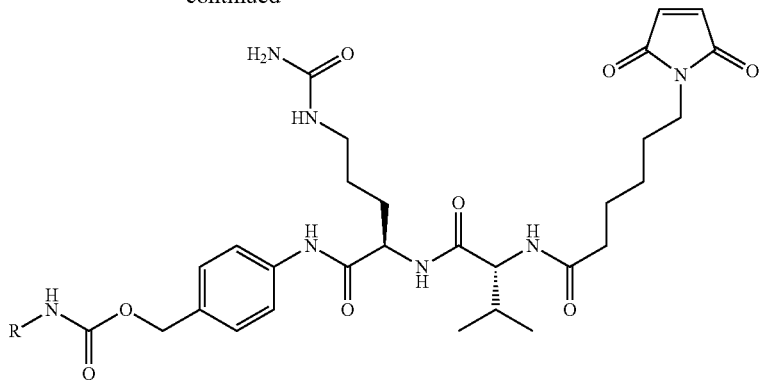

General Procedure 1—Trifluoroacetamide Installation

To a stirred suspension of the amine in 1,4-dioxane was added trifluoroacetic anhydride (1.1 equivalents). The reaction mixture transitioned from a suspension to a solution and back to a suspension again. The progress of the reaction was monitored by TLC and/or HPLC-MS for completion. Once the starting material was fully consumed, the reaction was diluted with hexanes or diethyl ether, filtered on a Buchner funnel and the resulting solids were dried under reduced pressure to give the pure trifluoroacetamide.

General Procedure 2—DCC/DMAP Mediated N-Acyl Sulfonamide Formation

To a stirred solution of the acid in dichloromethane was added a solution of the sulfonamide (1.3 equivalents, in dichloromethane, N,N-dimethylformamide, or a mixture thereof, as necessary). Dicyclohexylcarbodiimide (1.2 equivalents) was added and subsequently N,N-dimethylaminopyridine (1.2 equivalents). Reaction course was monitored by HPLC-MS (typically 16 h) and excess by-products could be precipitated by the addition of diethyl ether. Solids were removed by filtration and washed with 1:1 diethyl ether/dichloromethane. The combined organic layers were concentrated, and the residue was purified by silica gel chromatography or optionally prep-HPLC to give the desired N-acyl sulfonamide.

General Procedure 3—General Saponification

To a solution of the trifluoroacetamide or ester containing construct in 1,4-dioxane or methanol was added lithium hydroxide (10 equivalents) and water (10% v/v). The reaction was allowed to stir at room temperature or optionally heated to 50° C. Reaction course was monitored by HPLC-MS. Upon completion, volatiles were removed under reduced pressure, the aqueous layer was pH adjusted if necessary and washed successively with dichloromethane or ethyl acetate. The organic phases were pooled, dried over $MgSO_4$, filtered and concentrated. The reaction product was either used "as is" or purified by silica gel chromatography as necessary.

General Procedure 4—HATU Mediated Peptide Bond Formation

To a stirred solution of the carboxylic acid in a minimal amount of dichloromethane or N,N-dimethylformamide or mixture thereof, at 0° C. was added HATU (equivalents) and N,N-diisopropylethylamine (4 equivalents). Stirring was continued for a brief induction period (5-20 minutes) at which time the reaction was charged with a solution of the amine in dichloromethane. The reaction was allowed to warm to room temperature and monitored for progress by HPLC-MS. Upon completion, volatiles were removed under reduced pressure and the residual material was purified by silica gel chromatography or reverse phase HPLC to furnish amide in adequate purity.

General Procedure 7—Boc Group Removal

To a solution of the Boc-protected construct in dichloromethane was added 10% v/v trifluoroacetic acid. Reaction course was monitored by HPLC-MS. Upon completion, all volatiles were removed under reduced pressure. The residual material was purified either by reverse phase HPLC, silica gel chromatography or precipitation from a mixture of cold methanol/dichloromethane/diethyl ether.

General Procedure 8—Pd-Catalyzed Suzuki Cross Coupling

A suspension of aryl bromide, aryl (or alkenyl) boronic acid (1.5 eq), $Pd(OAc)_2$ (10 mol %), 2-(di-tert-butylphosphino)biphenyl (20 mol %), and $K_3PO_4$ (3 eq) in THF was stirred under $N_2$ at ambient temperature for 16 h (or 50° C. for 2 h). The resulting brown reaction mixture was dilute with ether and washed with 1M NaOH (3×). The aqueous washes were combined and extracted with ether (2×). The organics were combined, dried over $MgSO_4$, filtered, concentrated in vacuo and purified via silica gel column chromatography (eluted with $MeOH/CH_2Cl_2$ mixtures) to afford the cross-coupled product.

General Procedure 9—Cu-Catalyzed Ullman Cross Coupling (Methoxy Installation)

A mixture of aryl bromide, CuBr (20 mol %), NaOMe (20 eq, 4.9M in MeOH), and EtOAc (1.5 eq) was stirred under $N_2$ at 95° C. for 16 h. The resulting mixture was diluted with $H_2O$ and poured into cold (0° C.) stirring 1M citric acid. After stirring for 10 min, the mixture was extracted with EtOAc (4×). The organics were combined, washed with $H_2O$ (2×) and brine (1×), dried over $MgSO_4$, filtered and concentrated in vacuo. The product was used in the next step without further purification.

General Procedure 10—Vinylogous Amino Ester Synthesis

The procedure for Weinreb amide synthesis, reduction and subsequent olephination thereof as described by Nieman J. A. et al. J. Nat. Prod. 2003, 66, 183-199 was employed to the desired commercially available amino acids with no modifications.

General Procedure 11—Establishment of Boc-t-Leucine-(Me)-Vinylogous Amino Acid The vinylogous amino ester was deprotected and coupled to Boc-t-leucine according to procedures described by Nieman J. A. et al. J. Nat. Prod. 2003, 66, 183-199 with no modifications.

General Procedure 12—Sulfonamide Formation from Alkyl Halide

To a suspension of the desired alkyl halide in 2:1 $H_2O$/EtOH was added sodium sulfite (1.2 equiv). The resulting mixture was heated to reflux for 6-24 h. The reaction was then cooled to room temperature, the solvents were removed at reduced pressure to remove ethanol and the product was precipitated. The sodium alkylsulfonate were filtered, collected and dried in vacuo. These solids were then suspended in dichloromethane and phosphorous pentachloride (2 equiv) was added with stirring. The resulting suspension was heated to reflux for 2 h and allowed to cool to room temperature. The reactions were then cooled to 0° C., and water was added dropwise to consume excess phosphorous pentachloride. The mixture was transferred to a separatory funnel and the organic phase was washed with brine, dried over $MgSO_4$, filtered and concentrated to give the desired sulfonyl chloride. The thusly derived chloride was subsequently dissolved in THF and added dropwise to a stirred aqueous solution of concentrated ammonium hydroxide at 0° C. Upon completion of the addition, the reaction was concentrated under reduced pressure and diluted with water and ethyl acetate. The organic phase was washed with brine, dried over $MgSO_4$, filtered and concentrated to give the desired sulfonamide in sufficient purity for further use.

General Procedure 13—Sulfonamide Formation from Substituted Aryl Compounds

To a stirred mixture of the desired aryl substituted compound in chloroform was added chlorosulfonic acid (4 equiv). The reaction was heated to 70° C. for 1 h and allowed to cool to room temperature. Thionyl chloride (2 equiv) was added and the reaction was again heated to 70° C. for 1 h. The contents of the reaction vessel were concentrated under reduced pressure to give an oil which was subsequently twice dissolved in toluene and concentrated under reduced pressure to remove residual acid. The remaining material was dissolved in THF and added dropwise to a concentrated, stirred solution of ammonium hydroxide at 0° C. Once the addition was complete, the reaction was concentrated under reduced pressure and the residue was partitioned between ethyl acetate and water. The organic phase was washed with brine, dried over $MgSO_4$, filtered and concentrated to give the desired phenylsulfonamide in adequate purity for further use.

General Procedure 14—Sulfamamide Formation

The procedures used to generate the desired sulfamamides were adapted from Winum, J.-Y. et al., Org Lett, 2001, 3(14), 2241-2243

General Procedure 15—Preparation of MC-VC-PA BC-Toxins

The appropriate intermediate amine or aniline was taken up in DMF (~90 mg/mL), and to this was added 1-hydroxybenzotriazole hydrate (0.3 eq), then commercially obtained MC-VC-PABC-PNP (4-((R)-2-((R)-2-(6-(2,5-dioxo-2,5-dihydro-1H-pyrrol-1-yl)hexanamido)-3-methylbutanamido)-5-ureidopentanamido)benzyl 4-nitrophenyl carbonate) (1.3 eq) as described in Firestone, et al. U.S. Pat. No. 6,214,345 was added followed by pyridine (25 eq). The reaction was covered to protect from light and stirred at ambient temperature for 24 to 48 h. The reaction mixture could be purified by concentrating the mixture and performing flash chromatography directly on the crude, or alternatively, it could be diluted with DMSO to an appropriate volume and injected directly onto a preparatory HPLC to give the pure MC-VC-PABC-R construct.

All sulfonamides and sulfamamides or precursors to the materials used in the procedures below were purchased commercially and manipulated, if necessary, such that they were suitable for use. Specifically, General Procedures 1, 12, 13 and 14 were employed to manipulate commercially available starting materials unless otherwise noted below. Sulfamamide analogs of the N-acyl sulfonamide containing compounds disclosed herein may be synthesized by the artisan of reasonable skill based on the teachings herein and knowledge in the art, and are included within the scope of the invention.

Representative Compounds

Example 1

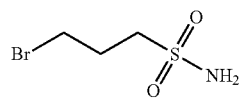

3-bromopropane-1-sulfonamide

To a stirred slurry of potassium bromide (1.904 g) in water (2.8 mL) was added 1,3-propanesultone. The reaction was heated to 60° C. with stirring for 1 h and allowed to cool to room temperature. Ethanol (~45 mL) was added with stirring and a precipitate formed. The suspension was filtered on a Buchner funnel and the solids were collected and dried at high vacuum over night to give potassium 3-bromopropane-1-sulfonate (2.90 g, 12.0 mmol) as a white solid.

The above solid was added to a round bottom flask equipped with a stir bar. Phosphorous pentachloride (3.22 g, 1.3 equiv) was added in a single charge and the flask was gently shaken to mix the solids. A gas was observed to form and the solids became slightly molten. A singular drop of water was added to the mixture and a vigorous evolution of gas was observed, with more significant melting of the reaction mixture. The flask was submerged in an oil bath at 70° C., and the molten mixture manipulated to attempt to make it as uniform as possible. After 10 minutes of heating, the flask was allowed to cool to room temperature and was charged with ice (~60 mL) and diethyl ether (~80 mL) and stirred vigorously. The biphasic mixture was transferred to a separatory funnel, the organic layer washed with brine, then dried over MgSO$_4$, filtered and concentrated to a total volume of ~25 mL. The ethereal layer was added to a 100 mL round bottom flask, a stir bar was added and the flask was cooled to 0° C. in an ice bath. Ammonia (NH$_4$OH, 28% aq, 5 mL) was added with vigorous stirring and an emulsion formed. After the emulsion had subsided, brine (~20 mL) and diethyl ether (~20 mL) were added and the mixture transferred to a separatory funnel. The organic phase was separated, dried over MgSO$_4$ and concentrated to give the title compound as a stiff syrup that solidified on standing (0.782 g).

$^1$H NMR (400 MHz, DMSO-d6) δ (ppm)=2.24 (p, 2H, J=6.5 Hz), 3.12 (t, 2H, J=6.5 Hz), 3.66 (t, 2H, J=6.5 Hz), 6.91 (s, 2H).

Example 2

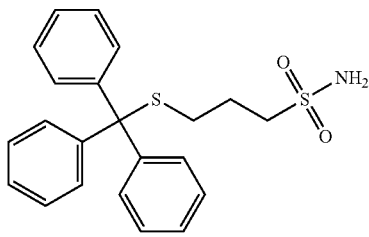 [SMILES: NS(=O)(=O)CCCSC(c1ccccc1)(c1ccccc1)c1ccccc1]

3-(tritylthio)propane-1-sulfonamide

To a stirred solution of triphenylmethanethiol (0.276 g) in N,N-dimethyl formamide at 0° C. was added sodium hydride (0.04 g, 1 equiv). After effervescence had ceased, 3-bromopropance-1-sulfonamide (0.100 g, 0.5 equiv) was added as a solid in a single portion and the reaction was allowed to warm to room temperature. Progress of the reaction was monitored by HPLC-MS and TLC (40% EtOAc in hexanes). After 2 h, the reaction was quenched with water (~0.5 mL) and concentrated on a rotovap at high-vacuum. The resulting oil was partitioned between ethyl acetate and brine, transferred to a separatory funnel and the organic phase was washed with brine, dried over MgSO$_4$, concentrated and purified by flash chromatography (5-50% EtOAc in hexanes) to give the title compound (0.135 g) as a white crystalline solid.

$^1$H NMR (400 MHz, CD3OD) δ (ppm)=1.77-1.85 (m, 2H), 2.35 (t, 2H, J=6.5 Hz), 2.95-2.99 (t, 2H, J=6.5 Hz), 7.22-7.33 (m, 9H), 7.40-7.45 (m, 6H)

Example 3

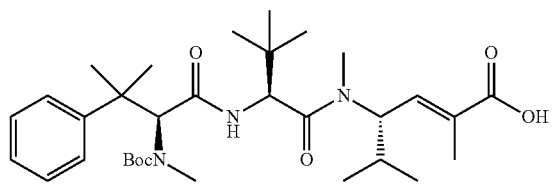 [SMILES: C/C(=C\[C@H](C(C)C)N(C)C(=O)[C@@H](NC(=O)[C@@H](N(C)C(=O)OC(C)(C)C)C(C)(C)c1ccccc1)C(C)(C)C)C(=O)O]

(6S,9S,12S,E)-9-tert-butyl-12-isopopyl-2,2,5,11,14-pentamethyl-4,7,10-trioxo-6-(2-phenylpropan-2-yl)-3-oxa-5,8,11-triazapentadec-13-en-15-oic acid Synthesized as per Nieman J. A. et al. J. Nat. Prod. 2003, 66, 183-199.

Example 4

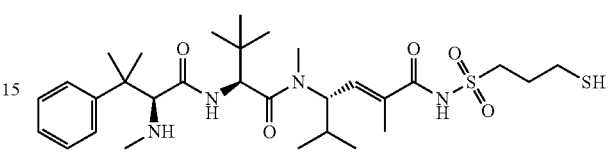

(S,E)-N-(3-mercaptopropylsulfonyl)-2,5-dimethyl-4-((S)—N,3,3-trimethyl-2-((S)-3-methyl-2-(methylamino)-3-phenylbutanamido)butanamido)hex-2-enamide (Compound A)

Example 4 was synthesized from Examples 2 and 3 according to General Procedures 2 and 7 with the inclusion of tri-isoproypsilane (2 equiv) to Procedure 9.

$^1$H NMR (400 MHz, CD3OD) δ (ppm)=0.88 (3H, d, J=6.2 Hz), 0.94 (3H, d, J=6.2 Hz), 1.08 (s, 9H), 1.40 (s, 3H), 1.48 (s, 3H), 1.94 (d, 3H, J=1.29 Hz), 2.03-2.16 (m, 3H), 2.41 (s, 3H), 2.67 (t, 2H, J=9.76 Hz), 3.16 (s, 3H), 3.46-3.50 (m, 2H), 4.08 (br s, 1H), 4.94 (s, 1H), 5.07 (t, 1H, J=10.0 Hz), 6.59 (d, 1H, J=9.5 Hz), 7.32-7.37 (m, 1H), 7.41-7.48 (m, 2H), 7.50-7.57 (m, 2H).

Methods described above were used to generate the following analogous compounds.

Example 5

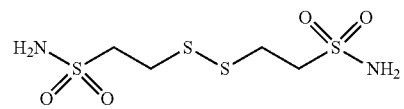 [SMILES: NS(=O)(=O)CCSSCCS(N)(=O)=O]

2,2'-disulfanediyldiethanesulfonamide

Synthesized as described by Lemaire, H, and Rieger, M in J. Org. Chem., 1961, 1330-1331.

Example 6

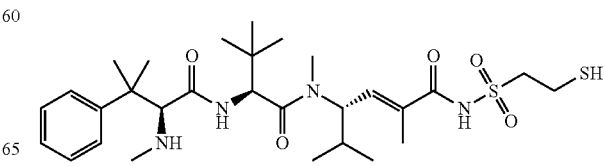

(S,E)-N-(2-mercaptoethylsulfonyl)-2,5-dimethyl-4-((S)—N,3,3-trimethyl-2-((S)-3-methyl-2-(methylamino)-3-phenylbutanamido)butanamido)hex-2-enamide (Compound B)

To a solution of (6S,9S,12S,E)-9-tert-butyl-12-isopropyl-2,2,5,11,14-pentamethyl-4,7,10-trioxo-6-(2-phenylpropan-2-yl)-3-oxa-5,8,11-triazapentadec-13-en-15-oic acid (0.138 g, 2.4 equiv) in dichloromethane (4 mL) was added 2,2'-disulfanediyldiethanesulfonamide (0.028 g), di-isopropyl-carbodiimide (0.044 mL, 2.4 equiv) and N,N-dimethylpyridine (0.034 g, 2.8 equiv). Stirring was continued for 16 h at which point TLC analysis (5% MeOH (with 5% AcOH) in 70/30 $CH_2Cl_2$/Hexanes) indicated complete consumption of the disulfanedisulfonamide. The reaction was diluted with hexanes (~5 mL), filtered to remove solids, concentrated and the resultant oil purified by flash chromatography.

The chromatographically purified materials was then dissolved in dichloromethane (3 mL), a stir bar was added, then trifluoroacetic acid (0.60 mL) and tri-isopropylsilane (0.20 mL). The mixture immediately went yellow, with the colour fading over 5 minutes and conversion of the material to the desired product was monitored by HPLC-MS. Upon complete conversion, the reaction was concentrated to dryness and the residue purified by flash chromatography (0-15% MeOH (containing 5% AcOH) in 80/20 $CH_2Cl_2$/hexanes). HPLC-MS showed this isolate to be a mixture of free thiol and disulfide.

$^1$H NMR (400 MHz, CD3OD) δ (ppm)=0.88 (3H, d, J=6.2 Hz), 0.93 (3H, d, J=6.2 Hz), 1.07 (s, 9H), 1.40 (s, 3H), 1.47 (s, 3H), 1.91-2.05 (m, 5H), 2.32 (s, 3H), 2.67 (t, 2H, J=9.76 Hz), 3.07-3.18 (m, 5H), 3.52-3.59 (m, 2H), 3.85 (s, 1H), HH 4.08 (br s, 1H), 4.93 (s, 1H), 5.09 (t, 1H, J=10.0 Hz), 6.76 (d, 1H, J=9.5 Hz), 7.29-7.35 (m, 1H), 7.39-7.46 (m, 2H), 7.49-7.58 (m, 2H). $C_{29}H_{48}N_4O_5S_2$ calcd. $[M+H]^+$=598.15 amu; found m/z=598.16.

Example 7

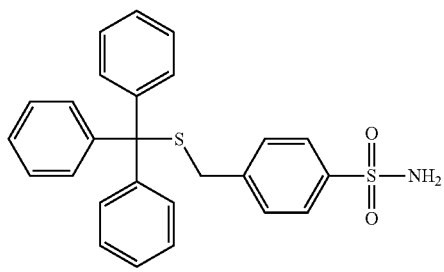 [SMILES: NS(=O)(=O)c1ccc(CSC(c2ccccc2)(c2ccccc2)c2ccccc2)cc1]

4-(tritylthiomethyl)benzenesulfonamide

To a stirred solution of triphenylmethanethiol (0.276 g, 2 equiv) in N,N-dimethylformamide (3 mL) at 0° C. was added sodium hydride (60% w/w dispersion in mineral oil, 0.04 g, 2 equiv). When the effervescence had ceased, 4-(bromomethyl)benzenesulfonamide (0.125 g, 1 equiv) was added in a single portion and the reaction was allowed to warm to room temperature. HPLC-MS at 20 minutes indicated that conversion was complete. The reaction was quenched with acetic acid (~0.2 mL), concentrated to dryness in vacuo and the subsequent residue partitioned between ethyl acetate and brine. The organic layer was separated, dried over $MgSO_4$, filtered, concentrated and purified by flash chromatography (0-50% ethyl acetate in hexanes). Fractions containing the desired material were concentrated to dryness to furnish the desired compound as a colourless solid (0.200 g).

$^1$H NMR (400 MHz, DMSO-d6) δ (ppm)=3.38 (s, 2H), 7.24-7.35 (m, 7H), 7.36-7.44 (m, 12H), 7.67-7.73 (m, 2H)

Example 8

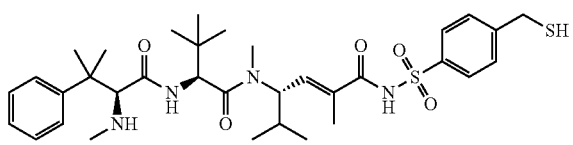 [SMILES: CN[C@H](C(=O)N[C@H](C(=O)N(C)[C@H](/C=C(\C)C(=O)NS(=O)(=O)c1ccc(CS)cc1)C(C)C)C(C)(C)C)C(C)(C)c1ccccc1]

(S,E)-N-(4-(mercaptomethyl)phenylsulfonyl)-2,5-dimethyl-4-((S)—N,3,3-trimethyl-2-((S)-3-methyl-2-(methylamino)-3-phenylbutanamido)butanamido)hex-2-enamide (Compound C)

Title compound prepared from Examples 3 and 7 according to General Procedures 2 and 7

$^1$H NMR (400 MHz, CD3OD) δ (ppm)=0.88 (d, 3H, J=6.2 Hz), 0.91 (d, 3H, J=6.2 Hz), 1.06 (s, 9H), 1.38 (s, 3H), 1.47 (s, 3H), 1.86 (s, 3H), 1.99-2.05 (m, 1H), 2.41 (s, 3H), 2.67 (t, 2H, J=9.76 Hz), 3.14 (s, 3H), 3.80 (s, 2H), HH 4.10 (br s, 1H), 4.93 (s, 1H), 5.00 (t, 1H, J=10.0 Hz), 6.54 (d, 1H, J=9.5 Hz), 7.30-7.51 (m, 5H), 7.52-7.58 (m, 2H), 7.90-7.97 (m, 2H). $C_{34}H_{50}N_4O_5S_2$ calcd. $[M+H]^+$=659.25 amu; found m/z=659.37.

Example 9

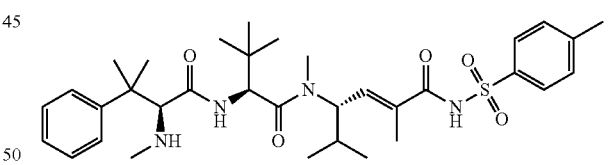

(S,E)-2,5-dimethyl-N-tosyl-4-((S)—N,3,3-trimethyl-2-((S)-3-methyl-2-(methylamino)-3-phenylbutanamido)butanamido)hex-2-enamide (Compound D)

Title compound was prepared from Example 3 and tosylsulfonamide using General Procedures 2 and 7.

$^1$H NMR (400 MHz, CD3OD) δ (ppm)=0.88-0.94 (m, 6H), 1.06 (s, 9H), 1.35 (s, 3H), 1.45 (s, 3H), 1.86 (s, 3H), 2.02-2.11 (m, 1H), 2.44 (s, 3H), 2.51 (s, 3H), 3.17 (s, 3H), HH 4.35 (s, 1H), 4.89-4.99 (m, 2H), 6.48 (d, 1H, J=9.5 Hz), 7.30-7.43 (m, 4H), 7.43-7.50 (m, 2H), 7.51-7.57 (m, 2H). $C_{34}H_{50}N_4O_5S$ calcd. $[M+H]^+$=627.15 amu; found m/z=627.31.

Example 10

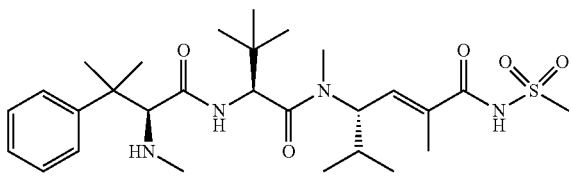 [SMILES: CN[C@H](C(=O)N[C@H](C(=O)N(C)[C@H](/C=C(\C)C(=O)NS(C)(=O)=O)C(C)C)C(C)(C)C)C(C)(C)c1ccccc1]

(S,E)-2,5-dimethyl-N-(methylsulfonyl)-4-((S)—N,3,
3-trimethyl-2-((S)-3-methyl-2-(methylamino)-3-
phenylbutanamido)butanamido)hex-2-enamide
(Compound E)

Title compound was prepared from Example 3 and methanesulfonamide using General Procedures 2 and 7.

$^{1}$H NMR (400 MHz, CD3OD) δ (ppm)=0.87-0.98 (3H (m, 6H), 1.09 (s, 9H), 1.40 (s, 3H), 1.49 (s, 3H), 1.97 (s, 3H), 2.03-2.13 (m, 1H), 2.52 (s, 3H), 2.67 (t, 2H, J=9.76 Hz), 3.18 (s, 3H), 3.31 (s, 3H), 4.38 (s, 1H), 4.94 (d, 1H, J=8.2 Hz), 5.07 (t, 1H, J=10.0 Hz), 6.54 (d, 1H, J=9.5 Hz), 7.30-7.40 (m, 1H), 7.40-7.51 (m, 2H), 7.51-7.59 (m, 2H). $C_{28}H_{46}N_4O_5S$ calcd. $[M+H]^+=551.30$ amu; found m/z=551.34.

Example 11

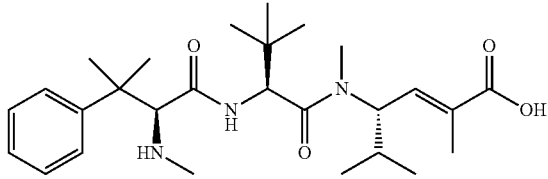 [SMILES: CN[C@H](C(=O)N[C@H](C(=O)N(C)[C@H](/C=C(\C)C(=O)O)C(C)C)C(C)(C)C)C(C)(C)c1ccccc1]

(S,E)-2,5-dimethyl-4-((S)—N,3,3-trimethyl-2-((S)-
3-methyl-2-(methylamino)-3-phenylbutanamido)
butanamido)hex-2-enoic acid (Compound F)

The title compound was synthesized using methods as described by Nieman et al. in J. Nat. Prod. 2003, 66, 183-199.

Example 12

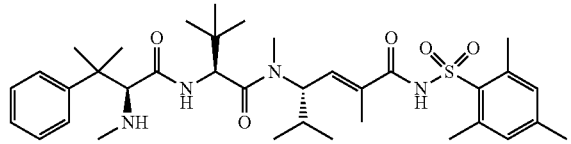

Chemical Formula: $C_{36}H_{54}N_4O_5S$
Exact Mass: 654.38

(S,E)-N-(mesitylsulfonyl)-2,5-dimethyl-4-((S)—N,3,
3-trimethyl-2-((S)-3-methyl-2-(methylamino)-3-
phenylbutanamido)butanamido)hex-2-enamide Title compound was prepared from Example 3 and mesitylsulfonamide using General Procedures 2 and 7.

1H NMR (400 MHz, Methanol-d4) δ 7.60-7.55 (m, 2H), 7.47 (m, 2H), 7.37 (m, 1H), 7.03 (s, 2H), 6.50 (d, J=6 Hz, 1H), 5.06-4.91 (m, 3H), 4.34 (s, 1H), 3.17 (s, 3H), 2.68 (s, 6H), 2.51 (s, 3H), 2.31 (s, 3H), 2.07 (m, 6.6 Hz, 2H), 1.87 (s, 3H), 1.48 (s, 3H), 1.36 (s, 3H), 1.09-1.04 (m, J=16.8 Hz, 10H), 0.92 (t, J=6.3 Hz, 6H).

C36H54N4O5S calcd m/z=654.38 found [M+H]+ =655.03.

Example 13

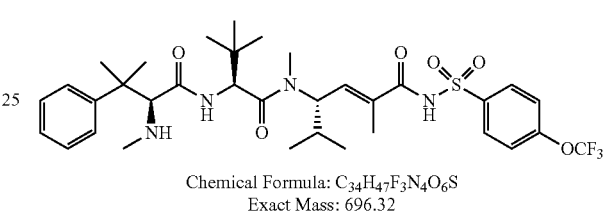

Chemical Formula: $C_{34}H_{47}F_3N_4O_6S$
Exact Mass: 696.32

(S,E)-2,5-dimethyl-N-(4-(trifluoromethoxy)phe-
nylsulfonyl)-4-((S)—N,3,3-trimethyl-2-((S)-3-
methyl-2-(methylamino)-3-phenylbutanamido)bu-
tanamido)hex-2-enamide Title compound was prepared from Example 3 and 4-trifluoromethoxyphenylsulfonamide using General Procedures 2 and 7.

1H NMR (400 MHz, Methanol-d4) δ 8.16 (dd, J=8.7, 1.4 Hz, 1H), 7.69-7.28 (m, 4H), 6.52 (d, J=9.2 Hz, 1H), 5.02-4.95 (m, 1H), 4.92 (s, OH), 4.35 (s, 1H), 3.17 (s, 1H), 2.51 (s, 1H), 2.05 (ddd, J=15.9, 10.9, 3.7 Hz, 1H), 1.87 (s, 1H), 1.47 (s, 1H), 1.36 (s, 1H), 1.07 (s, 4H), 0.91 (t, J=6.1 Hz, 3H).

C34H47F3N4O6S calcd m/z=696.32 found [M+H]+ =697.26.

Example 14

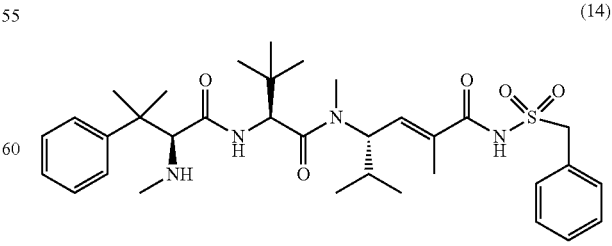

Chemical Formula: $C_{34}H_{50}N_4O_5S$
Exact Mass: 626.35

(S,E)-N-(benzylsulfonyl)-2,5-dimethyl-4-((S)—N,3,3-trimethyl-2-((S)-3-methyl-2-(methylamino)-3-phenylbutanamido)butanamido)hex-2-enamide Title compound was prepared from Example 3 and benzylsulfonamide using General Procedures 2 and 7

1H NMR (400 MHz, Methanol-d4) δ 7.56 (d, J=7.9 Hz, 2H), 7.47 (t, J=7.3 Hz, 2H), 7.38 (brs, 6H), 6.39 (d, J=9.4 Hz, 1H), 5.06 (t, J=10.0 Hz, 1H), 4.93 (s, 1H), 4.75 (s, 2H), 4.36 (s, 1H), 3.13 (s, 3H), 2.51 (s, 3H), 2.06-1.95 (m, 4H), 1.48 (s, 3H), 1.39 (s, 3H), 1.09 (s, 9H), 0.90 (t, J=6.2 Hz, 6H).

C34H47F3N4O6S calcd m/z=626.35 found [M+H]+=626.99.

Example 15

(15)

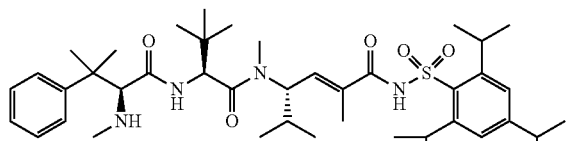

Chemical Formula: C42H66N4O5S
Exact Mass: 738.48

(S,E)-2,5-dimethyl-N-(2,4,6-triisopropylphenylsulfonyl)-4-((S)—N,3,3-trimethyl-2-((S)-3-methyl-2-(methylamino)-3-phenylbutanamido)butanamido)hex-2-enamide Title compound was prepared from Example 3 and 2,4,6-tri-isopropylphenylsulfonamide using General Procedures 2 and 7.

1H NMR (400 MHz, Methanol-d4) δ 7.61-7.53 (m, 2H), 7.47 (t, J=7.8 Hz, 2H), 7.41-7.33 (m, 1H), 7.27 (s, 2H), 6.50 (dd, J=9.6, 1.8 Hz, 1H), 5.05 (t, J=10.0 Hz, 1H), 4.92 (s, 1H), 4.43-4.26 (m, 3H), 3.16 (s, 3H), 2.94 (dd, J=14.3, 7.4 Hz, 1H), 2.51 (s, 3H), 2.07-1.99 (m, 2H), 1.90 (d, J=1.4 Hz, 3H), 1.48 (s, 4H), 1.39 (s, 3H), 1.33-1.22 (m, 18H), 1.11 (s, 2H), 1.06 (s, 9H), 0.91 (t, J=6.0 Hz, 7H).

C42H66N4O5S calcd m/z=738.48 found [M+H]+=738.10.

Example 16

(16)

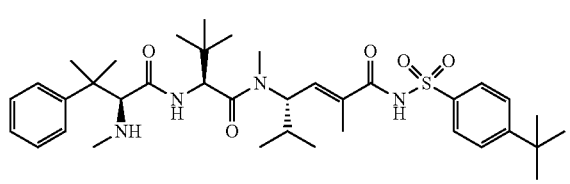

Chemical Formula: C37H56N4O5S
Exact Mass: 668.40

(S,E)-N-(4-tert-butylphenylsulfonyl)-2,5-dimethyl-4-((S)—N,3,3-trimethyl-2-((S)-3-methyl-2-(methylamino)-3-phenylbutanamido)butanamido)hex-2-enamide Title compound was prepared from Example 3 and 4-tert-butylphenylsulfonamide using General Procedures 2 and 7.

1H NMR (400 MHz, Methanol-d4) δ 7.98 (d, J=8.6 Hz, 2H), 7.64 (d, J=8.6 Hz, 2H), 7.55 (d, J=7.9 Hz, 2H), 7.47 (t, J=7.7 Hz, 3H), 7.37 (t, J=7.1 Hz, 1H), 6.48 (dd, J=9.6, 1.8 Hz, 1H), 4.99 (t, J=10.0 Hz, 1H), 4.92 (s, 1H), 4.35 (s, 1H), 3.16 (s, 3H), 2.51 (s, 3H), 1.87 (d, J=1.4 Hz, 3H), 1.47 (s, 3H), 1.38 (s, 10H), 1.06 (s, 9H), 0.91 (t, J=6.2 Hz, 7H).

C42H66N4O5S calcd m/z=668.40 found [M+H]+=669.28.

Example 17

(17)

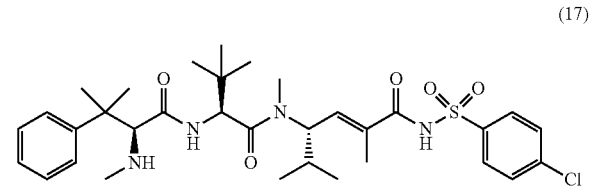

Chemical Formula: C33H47ClN4O5S
Exact Mass: 646.30

(S,E)-N-(4-chlorophenylsulfonyl)-2,5-dimethyl-4-((S)—N,3,3-trimethyl-2-((S)-3-methyl-2-(methylamino)-3-phenylbutanamido)butanamido)hex-2-enamide Title compound was prepared from Example 3 and 4-chlorophenylsulfonamide using General Procedures 2 and 7.

1H NMR (400 MHz, Methanol-d4) δ 8.03 (d, J=8.7 Hz, 2H), 7.60 (d, J=8.7 Hz, 2H), 7.57-7.51 (m, 2H), 7.47 (dd, J=8.6, 6.9 Hz, 2H), 7.42-7.32 (m, 1H), 6.50 (dd, J=9.2, 1.7 Hz, 1H), 4.96 (dd, J=10.9, 9.1 Hz, 2H), 4.92 (s, 1H), 4.35 (s, 1H), 3.17 (s, 3H), 2.51 (s, 3H), 2.14-2.03 (m, 1H), 2.01 (s, 1H), 1.87 (d, J=1.4 Hz, 3H), 1.46 (s, 3H), 1.36 (s, 3H), 1.07 (s, 9H), 0.91 (dd, J=6.5, 4.6 Hz, 7H).

C33H47ClN4O5S calcd m/z=646.30 found [M+H]+=647.20.

Example 18

(18)

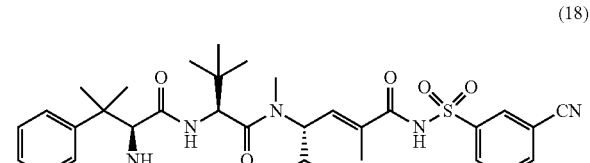

Chemical Formula: C34H47N5O5S
Exact Mass: 637.33

(S,E)-N-(3-cyanophenylsulfonyl)-2,5-dimethyl-4-((S)—N,3,3-trimethyl-2-((S)-3-methyl-2-(methylamino)-3-phenylbutanamido)butanamido)hex-2-enamide Title compound was prepared from Example 3 and 3-cyanophenylsulfonamide using General Procedures 2 and 7.

1H NMR (400 MHz, Methanol-d4) δ 8.38 (s, 1H), 8.31 (dt, J=8.0, 1.5 Hz, 1H), 8.02-7.92 (m, 1H), 7.75 (t, J=7.9 Hz, 1H), 7.53 (d, J=1.2 Hz, 1H), 7.48 (dd, J=8.6, 6.9 Hz, 2H), 7.43-7.33 (m, 1H), 6.55 (dd, J=9.3, 1.7 Hz, 1H), 4.93 (d, J 10=5.4 Hz, 2H), 4.35 (s, 1H), 3.18 (s, 3H), 2.51 (s, 3H), 2.15-1.98 (m, 2H), 1.87 (d, J=1.4 Hz, 3H), 1.45 (s, 3H), 1.32 (s, 3H), 1.07 (s, 9H), 0.92 (dd, J=6.6, 3.9 Hz, 7H).

C34H47N5O5S calcd m/z=637.33 found [M+H]+=638.00.

Example 19

(19)

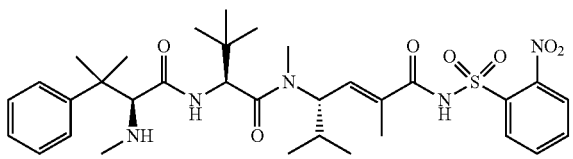

Chemical Formula: C$_{33}$H$_{47}$N$_5$O$_7$S
Exact Mass: 657.32

(S,E)-2,5-dimethyl-N-(2-nitrophenylsulfonyl)-4-((S)—N,3,3-trimethyl-2-((S)-3-methyl-2-(methylamino)-3-phenylbutanamido)butanamido)hex-2-enamide Title compound was prepared from Example 3 and 2-nitrophenylsulfonamide using General Procedures 2 and 7.

1H NMR (400 MHz, Methanol-d4) δ 8.36-8.27 (m, 1H), 7.82 (dd, J=5.9, 3.8 Hz. 3H), 7.61-7.51 (m, 2H), 7.47 (dd, J=8.6, 6.9 Hz, 2H), 7.42-7.31 (m, 1H), 6.63 (dd, J=9.5, 1.7 Hz, 1H), 5.03 (t, J=10.0 Hz, 1H), 4.93 (s, 1H), 4.36 (s, 1H), 3.18 (s, 3H), 2.51 (s, 3H), 2.12-2.01 (m, 1H), 1.88 (d, J=1.4 Hz, 3H), 1.48 (s, 3H), 1.37 (s, 3H), 1.06 (s, 9H), 0.97-0.86 (m, 6H).

C34H47N5O5S calcd m/z=657.32 found [M+H]+=658.21.

Example 20

(20)

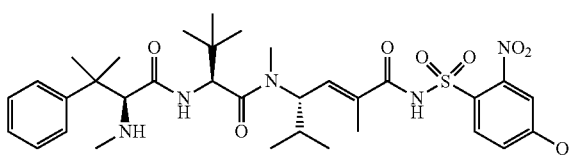

Chemical Formula: C$_{34}$H$_{49}$N$_5$O$_8$S
Exact Mass: 687.33

(S,E)-N-(4-methoxy-2-nitrophenylsulfonyl)-2,5-dimethyl-4-((S)—N,3,3-trimethyl-2-((S)-3-methyl-2-(methylamino)-3-phenylbutanamido)butanamido)hex-2-enamide Title compound Was prepared from Example 3 and 2-nitro-4-methoxyphenylsulfonamide using General Procedures 2 and 7.

1H NMR (400 MHz, Methanol-d4) δ 8.24 (d, J=8.9 Hz, 1H), 7.59-7.51 (m, 2H), 7.47 (t, J=7.6 Hz, 2H), 7.44-7.25 (m, 4H), 6.60 (dd. J=9.2, 1.7 Hz, 1H), 5.03 (t, J=10.0 Hz, 1H), 4.93 (s, 1H), 4.36 (s, 1H), 3.97 (s, 3H), 3.18 (s, 3H), 2.51 (s, 3H), 2.13-2.02 (m, 1H), 1.89 (d, J=1.4 Hz, 3H), 1.48 (s, 3H), 1.38 (s, 3H), 1.11 (s, 2H), 1.06 (s, 9H), 0.99-0.88 (m, 6H).

C34H49N5O8S calcd m/z=687.33 found [M+H]+=689.23.

Example 21

(21)

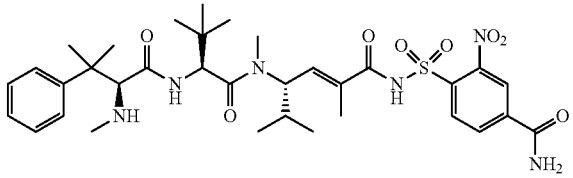

Chemical Formula: C$_{34}$H$_{48}$N$_6$O$_8$S
Exact Mass: 700.33

4-(N—((S,E)-2,5-dimethyl-4-((S)—N,3,3-trimethyl-2-((S)-3-methyl-2-(methylamino)-3-phenylbutanamido)butanamido)hex-2-enoyl)sulfamoyl)-3-nitrobenzamide Title compound was prepared from Example 3 and 3-nitro-4-sulfamoylbenzamide using General Procedures 2 and 7.

1H NMR (400 MHz, Methanol-d4) δ 8.35 (d, J=8.0 Hz, 1H), 8.22 (d, J=8.0 Hz, 2H), 7.59-7.51 (m, 2H), 7.47 (t, J=7.6 Hz. 2H), 7.37 (t, J=7.3 Hz, 1H), 6.70-6.57 (m, 1H), 5.04 (t, J=10.0 Hz, 1H), 4.94 (s, 1H), 4.37 (s, 1H), 3.17 (s, 3H), 2.52 (s, 3H), 2.05 (ddd, J=10.3, 7.4, 5.5 Hz, 1H), 1.87 (d, J=1.4 Hz, 3H), 1.48 (s, 3H), 1.38 (s, 3H), 1.06 (s, 9H), 0.92 (dd, J=14.7, 6.8 Hz, 6H).

C34H48N6O8S calcd m/z=700.33 found [M+H]+=701.28.

Example 22

(22)

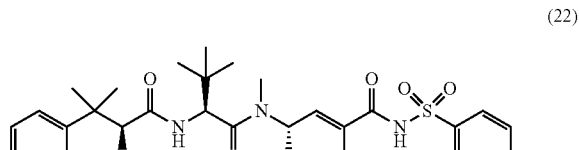

Chemical Formula: C$_{34}$H$_{50}$N$_4$O$_6$S
Exact Mass: 642.35

(S,E)-N-(4-methoxyphenylsulfonyl)-2,5-dimethyl-4-((S)—N,3,3-trimethyl-2-((S)-3-methyl-2-(methylamino)-3-phenylbutanamido)butanamido)hex-2-enamide Title compound was prepared from Example 3 and 4-methoxyphenylsulfonamide using General Procedures 2 and 7.

1H NMR (400 MHz, Methanol-d4) δ 7.97 (d, J=9.0 Hz, 2H), 7.54 (d, J=7.5 Hz, 2H), 7.46 (t, J=7.6 Hz, 2H), 7.36 (t, J=7.2 Hz, 1H), 7.06 (d, J=9.0 Hz, 2H), 6.48 (dd, J=9.3, 1.9 Hz, 1H), 4.97 (t, J=9.9 Hz, 1H), 4.92 (s, 1H), 4.22 (s, 1H), 3.89 (s, 3H), 3.15 (s, 3H), 2.46 (s, 3H), 2.10-1.99 (m, 2H), 1.86 (d, J=1.4 Hz, 3H), 1.46 (s, 3H), 1.36 (s, 3H), 1.06 (s, 9H), 0.94-0.84 (m, 6H).

C34H50N4O6S calcd m/z=642.35 found [M+H]+=643.31.

Example 23

(S,E)-N-(4-aminophenylsulfonyl)-2,5-dimethyl-4-((S)—N,3,3-trimethyl-2-((S)-3-methyl-2-(methylamino)-3-phenylbutanamido)butanamido)hex-2-enamide Title compound was prepared from Example 3 and 2,2,2-trifluoro-N-(4-sulfamoylphenyl)acetamide using General Procedures 2, 3 and 7 ¹H NMR (400 MHz, Methanol-d₄) δ 7.71 (d, J=8.8 Hz, 2H), 7.55 (d, J=7.6 Hz, 2H), 7.47 (d, J=6.9 Hz, 2H), 7.37 (t, J=6.8 Hz, 1H), 6.67 (d, J 8.8 Hz, 2H), 6.44 (dd, J=9.2, 1.6 Hz, 1H), 4.97 (t, J=9.7 Hz, 1H), 4.92 (s, 1H), 4.36 (s, 1H), 3.16 (s, 3H), 2.51 (s, 3H), 2.16-2.00 (m, 1H), 1.87 (d, J=1.4 Hz, 3H), 1.46 (s, 3H), 1.37 (s, 3H), 1.07 (s, 9H), 0.92 (d, J=6.4 Hz, 3H), 0.91 (d, J=6.3 Hz, 3H).

C33H49N5O5S calcd m/z=627.35 found [M+H]+=628.35.

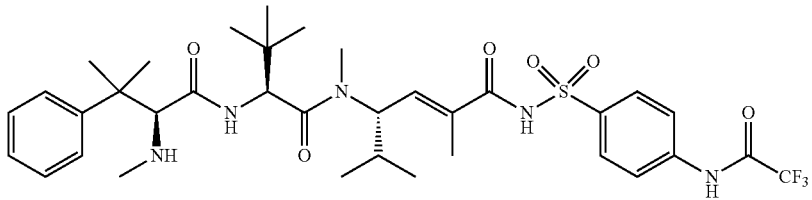

(23)

Chemical Formula: $C_{35}H_{48}F_3N_5O_6S$
Exact Mass: 723.33

(S,E)-2,5-dimethyl-N-(4-(2,2,2-trifluoroacetamido)phenylsulfonyl)-4-((S)—N,3,3-trimethyl-2-((S)-3-methyl-2-(methylamino)-3-phenylbutanamido)butanamido)hex-2-enamide Title compound was prepared from Example 3 and 2,2,2-trifluoro-N-(4-sulfamoylphenyl)acetamide using General Procedures 2 and 7.

1H NMR (400 MHz, Methanol-d4) δ 8.06 (d, J=8.9 Hz, 2H), 7.88 (d, J=8.9 Hz, 2H), 7.52 (d, J=7.1 Hz, 2H), 7.49-7.40 (m, 3H), 7.35 (dd, J=8.1, 6.1 Hz, 1H), 6.47 (dd, J=9.2, 1.8 Hz, 1H), 4.33 (s, 1H), 3.15 (s, 3H), 2.48 (s, 3H), 2.13-1.96 (m, 2H), 1.85 (d, J=1.4 Hz, 3H), 1.43 (s, 3H), 1.33 (s, 3H), 1.04 (s, 9H), 0.89 (dd. J=6.8, 4.7 Hz, 6H).

C35H48F3N5O6S calcd m/z=723.33 found [M+H]+=724.08.

Example 24

(24)

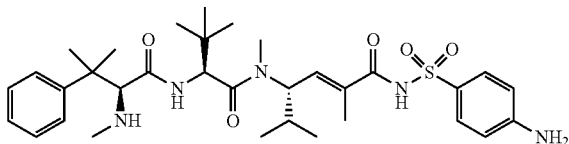

Chemical Formula: $C_{33}H_{49}N_5O_5S$
Exact Mass: 627.35

Example 25

(25)

Chemical Formula: $C_{33}H_{48}N_4O_5S$
Exact Mass: 612.33

(S,E)-2,5-dimethyl-N-(phenylsulfonyl)-4-((S)—N,3,3-trimethyl-2-((S)-3-methyl-2-(methylamino)-3-phenylbutanamido)butanamido)hex-2-enamide Title compound was prepared from Example 3 and phenylsulfonamide using General Procedures 2, and 7.

1H NMR (400 MHz, Methanol-d4) δ 8.06-7.95 (m, 2H), 7.63-7.40 (m, 8H), 7.40-7.30 (m, 1H), 6.53 (dd, J=9.3, 1.6 Hz, 1H), 5.05-4.95 (m, 1H), 4.22 (s, 1H), 3.14 (s, 3H), 2.45 (s, 3H), 2.09-1.95 (m, 1H), 1.85 (d, J=1.4 Hz, 3H), 1.46 (s, 3H), 1.36 (s, 3H), 1.06 (s, 9H), 0.89 (dd, J=11.9, 6.5 Hz, 7H).

C33H48N4O5S calcd m/z=612.33 found [M+H]+=613.06.

Example 26

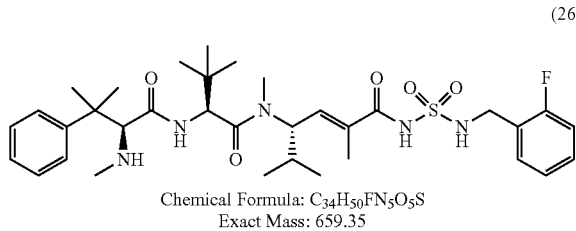

(26)

Chemical Formula: $C_{34}H_{50}FN_5O_5S$
Exact Mass: 659.35

(S,E)-N—(N-(2-fluorobenzyl)sulfamoyl)-2,5-dimethyl-4-((S)—N,3,3-trimethyl-2-((S)-3-methyl-2-(methylamino)-3-phenylbutanamido)butanamido)hex-2-enamide 2-fluorobenzylsulfamamide was prepared from 2-fluorobenzylamine according to General Procedure 14; the title compound was prepared from Example 3 and 2-fluorobenzylsulfamamide using General Procedures 2 and 7.

1H NMR (400 MHz, Methanol-d4) δ 7.63-7.41 (m, 6H), 7.41-7.26 (m, 3H), 7.14 (td, J=7.5, 1.2 Hz, 1H), 7.07 (ddd, J=9.5, 8.2, 1.1 Hz, 1H), 6.37 (dd, J=9.4, 1.7 Hz, 1H), 5.07-4.97 (m, 1H), 4.37 (s, 1H), 4.33 (s, 2H), 3.15 (s, 3H), 2.51 (s, 3H), 2.10-1.97 (m, 1H), 1.83 (d, J=1.4 Hz, 3H), 1.49 (s, 3H), 1.39 (s, 3H), 1.09 (s, 9H), 0.97-0.84 (m, 6H).

C34H50FN5O5S calcd m/z=659.35 found [M+H]+=660.28.

Example 27

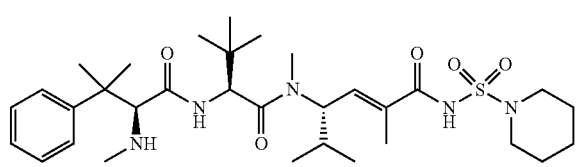

(27)

Chemical Formula: $C_{32}H_{53}N_5O_5S$
Exact Mass: 619.38

(S,E)-2,5-dimethyl-N-(piperidin-1-ylsulfonyl)-4-((S)—N,3,3-trimethyl-2-((S)-3-methyl-2-(methylamino)-3-phenylbutanamido)butanamido)hex-2-enamide Piperidine-1-sulfonamide was synthesized from piperidine according to General Procedure 14; the title compound was prepared from Example 3 and piperidine-1-sulfonamide using General Procedures 2 and 7.

1H NMR (400 MHz, Methanol-d4) δ 7.55 (d, J=1.2 Hz, 1H), 7.47 (t, J=7.6 Hz, 3H), 7.42-7.29 (m, 1H), 6.48 (dd, J=9.7, 1.8 Hz, 1H), 5.05 (t, J=10.0 Hz, 1H), 4.39 (s, 1H), 3.18 (s, 3H), 2.52 (s, 3H), 2.07 (d, J=10.5 Hz, 1H), 1.96 (d, J=1.4 Hz, 3H), 1.61 (ddd, J=20.0, 10.3, 5.4 Hz, 9H), 1.49 (s, 4H), 1.39 (s, 3H), 1.09 (s, 9H), 0.99-0.84 (m, 9H).

C32H53N5O5S calcd m/z=619.38 found [M+H]+=620.38.

Example 28

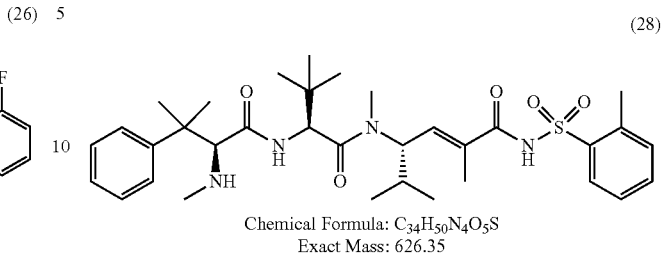

(28)

Chemical Formula: $C_{34}H_{50}N_4O_5S$
Exact Mass: 626.35

(S,E)-2,5-dimethyl-N-(o-tolylsulfonyl)-4-((S)—N,3,3-trimethyl-2-((S)-3-methyl-2-(methylamino)-3-phenylbutanamido)butanamido)hex-2-enamide Title compound was prepared from Example 3 and 2-toluenesulfonamide using General Procedures 2 and 7.

1H NMR (400 MHz, Methanol-d4) δ 8.10 (dd, J=8.0, 1.4 Hz, 1H). 7.60-7.33 (m, 1H), 6.52 (dd, J=9.6, 1.7 Hz, 1H), 5.04-4.90 (m, 2H), 4.35 (s, 1H), 3.18 (s, 3H), 2.67 (s, 3H), 2.51 (s, 3H), 2.15-2.03 (m, 2H), 2.01 (s, 1H), 1.87 (d, J=1.4 Hz, 3H), 1.46 (s, 3H), 1.35 (s, 3H), 1.07 (s, 9H), 0.92 (t, J=6.3 Hz, 6H).

C34H50N4O5S calcd m/z=626.35 found [M+H]+=627.05.

Example 29

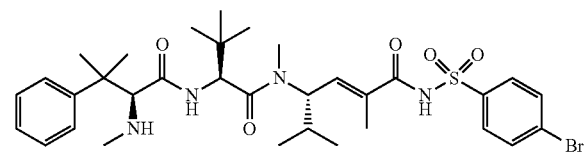

(29)

Chemical Formula: $C_{33}H_{47}BrN_4O_5S$
Exact Mass: 690.25

(S,E)-N-(4-bromophenylsulfonyl)-2,5-dimethyl-4-((S)—N,3,3-trimethyl-2-((S)-3-methyl-2-(methylamino)-3-phenylbutanamido)butanamido)hex-2-enamide Title compound was prepared from Example 3 and 4-bromophenylsulfonamide using General Procedures 2 and 7.

1H NMR (400 MHz, Methanol-d4) δ 7.95 (d, J=8.3 Hz, 2H), 7.76 (d, J=8.0 Hz, 2H), 7.55 (d, J=7.5 Hz, 2H), 7.47 (dd, J=8.6, 6.9 Hz, 2H), 7.41-7.29 (m, 1H), 6.51 (d, J=9.0 Hz, 1H), 4.35 (s, 1H), 3.16 (s, 3H), 2.50 (s, 3H), 2.06 (dt, J=10.7, 6.3 Hz, 1H), 1.87 (s, 3H), 1.46 (s, 3H), 1.36 (s, 3H), 1.07 (s, 9H), 0.91 (dd, J=6.9, 4.9 Hz, 8H).

C33H47BrN4O5S calcd m/z=690.25 found [M+H]+=691.17, 693.18.

Example 30

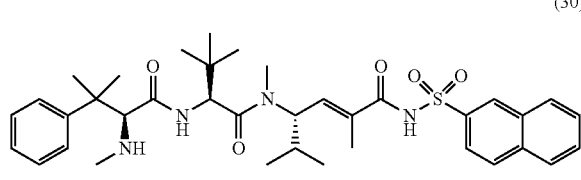

Chemical Formula: C₃₇H₅₀N₄O₅S
Exact Mass: 662.35

(S,E)-2,5-dimethyl-N-(naphthalen-2-ylsulfonyl)-4-((S)—N,3,3-trimethyl-2-((S)-3-methyl-2-(methylamino)-3-phenylbutanamido)butanamido)hex-2-enamide Title compound was prepared from Example 3 and 2-naphthylsulfonamide using General Procedures 2 and 7.

1H NMR (400 MHz, Methanol-d4) δ 8.69-8.62 (m, 1H), 8.47 (d, J=8.2 Hz, 1H), 8.14-7.95 (m, 5H), 7.71 (dddd, J=18.4, 8.2, 6.9, 1.4 Hz, 2H), 7.57-7.50 (m, 2H), 7.46 (dd, J=8.6, 6.9 Hz, 2H), 7.42-7.33 (m, 1H), 6.50 (dd, J=9.3, 1.5 Hz, 1H), 4.92-4.87 (m, 1H), 4.34 (s, 1H), 3.16 (s, 3H), 2.50 (s, 3H), 2.13-1.99 (m, 1H), 1.85 (d, J=1.4 Hz, 3H), 1.44 (s, 3H), 1.34 (s, 3H), 1.04 (s, 9H), 0.90 (dd. J=6.6, 4.0 Hz, 6H).

C37H50N4O5S calcd m/z=662.35 found [M+H]+=663.32.

Example 31

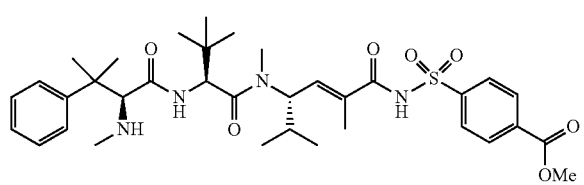

Chemical Formula: C₃₅H₅₀N₄O₇S
Exact Mass: 670.34 methyl 4-(N—((S,E)-2,5-dimethyl-4-((S)—N,3,3-trimethyl-2-((S)-3-methyl-2-(methylamino)-3-phenylbutanamido)butanamido)hex-2-enoyl)sulfamoyl)benzoate Title compound was prepared from Example 3 and 4-carboxymethylphenylsulfonamide using General Procedures 2 and 7.

1H NMR (400 MHz, Methanol-d4) δ 8.24-8.10 (m, 4H), 7.58-7.50 (m, 2H), 7.47 (dd, J=8.6, 6.9 Hz, 2H), 7.41-7.33 (m, 1H), 6.52 (dd, J=9.2, 1.6 Hz, 1H), 4.35 (s, 1H), 3.97 (s, 3H), 3.18 (s, 3H), 2.50 (s, 3H), 2.15-2.00 (m, 1H), 1.86 (d, J=1.4 Hz, 3H), 1.45 (s, 3H), 1.35 (s, 3H), 1.07 (s, 9H), 0.91 (dd, J=6.7, 3.8 Hz, 6H).

C35H50N4O7S calcd m/z=670.34 found [M+H]+=671.10.

Example 32

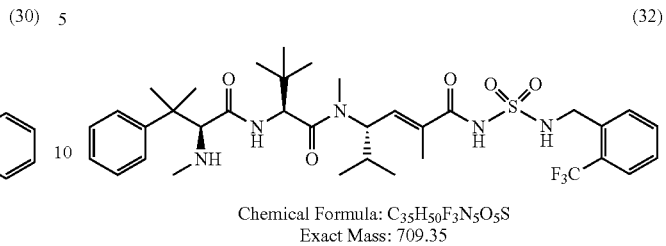

Chemical Formula: C₃₅H₅₀F₃N₅O₅S
Exact Mass: 709.35

(S,E)-2,5-dimethyl-N—(N-(2-(trifluoromethyl)benzyl)sulfamoyl)-4-((S)—N,3,3-trimethyl-2-((S)-3-methyl-2-(methylamino)-3-phenylbutanamido)butanamido)hex-2-enamide Title compound was prepared from Example 3 and 2-trifluoromethylbenzylsulfonamide using General Procedures 2 and 7.

1H NMR (400 MHz, Methanol-d4) δ 7.78 (d, J=7.9 Hz, 1H), 7.74-7.67 (m, 1H), 7.64 (dd, J=8.1, 6.7 Hz, 1H), 7.60-7.52 (m, 2H), 7.48 (dd, J=8.5, 6.8 Hz, 4H), 7.42-7.33 (m, 1H), 6.48-6.40 (m, 1H), 5.11-5.02 (m, 1H), 4.45 (s, 2H), 4.37 (s, 1H), 3.17 (s, 3H), 2.52 (s, 3H), 2.11-1.99 (m, 2H), 1.92 (d, J=1.4 Hz, 3H), 1.49 (s, 3H), 1.40 (s, 3H), 1.09 (s, 9H), 0.92 (dd, J=9.3, 6.7 Hz, 6H).

C35H50F3N5O5S calcd m/z=709.35 found [M+H]+=710.02.

Example 33

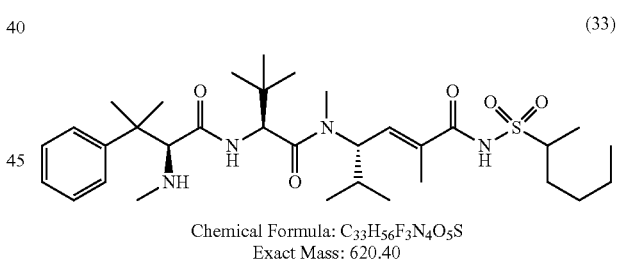

Chemical Formula: C₃₃H₅₆F₃N₄O₅S
Exact Mass: 620.40

(4S,E)-N-(hexan-2-ylsulfonyl)-2,5-dimethyl-4-((S)—N,3,3-trimethyl-2-((S)-3-methyl-2-(methylamino)-3-phenylbutanamido)butanamido)hex-2-enamide Title compound was prepared from Example 3 and hexane-2-sulfonamide using General Procedures 2 and 7.

1H NMR (400 MHz, Methanol-d4) δ 7.56-7.48 (m, 2H), 7.42 (t, J=7.8 Hz, 2H), 7.31 (t, J=7.3 Hz, 1H), 6.58-6.50 (m, 1H), 5.05 (t, J=10.0 Hz, 1H), 4.92 (s, 1H), 3.84 (s, 1H), 3.65 (dt, J=10.8, 4.3 Hz, 1H), 3.14 (s, 3H), 2.32 (s, 3H), 2.09-1.96 (m, 2H), 1.93 (d, J=1.4 Hz, 3H), 1.61-1.27 (m, 3H), 1.06 (s, 9H), 0.98-0.90 (m, 6H), 0.87 (d, J=6.5 Hz, 3H).

C33H56N4O5S calcd m/z=620.40 found [M+H]+=621.55.

Example 34

(34)

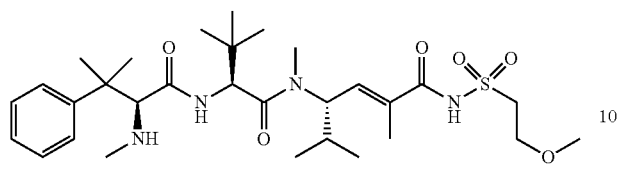

Chemical Formula: $C_{30}H_{50}N_4O_6S$
Exact Mass: 594.35

(S,E)-N-(2-methoxyethylsulfonyl)-2,5-dimethyl-4-((S)—N,3,3-trimethyl-2-((S)-3-methyl-2-(methylamino)-3-phenylbutanamido)butanamido)hex-2-enamide Title compound was prepared from Example 3 and 2-methoxyethanesulfonamide using General Procedures 2 and 7.

1H NMR (400 MHz, Methanol-d4) δ 7.56 (d, J=7.8 Hz, 2H), 7.47 (t, J=7.6 Hz, 2H), 7.37 (t, J=7.3 Hz, 1H), 6.51 (d, J=9.4 Hz, 1H), 5.07 (t, J=10.0 Hz, 1H), 4.95 (s, 1H), 4.33 (s, 1H), 3.82 (t, J=5.8 Hz, 2H), 3.70 (q, J=5.2 Hz, 2H), 3.18 (s, 3H), 2.50 (s, 3H), 2.18-2.00 (m, 1H), 1.95 (d, J=1.4 Hz, 3H), 1.49 (s, 3H), 1.39 (s, 3H), 1.09 (s, 9H), 0.93 (dd, J=14.8, 6.6 Hz, 6H).

C30H50N4O6S calcd m/z=594.35 found [M+H]+=595.44.

Example 35

(35)

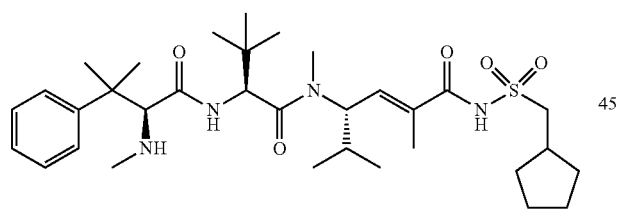

Chemical Formula: $C_{33}H_{54}N_4O_5S$
Exact Mass: 618.38

(S,E)-N-(cyclopentylmethylsulfonyl)-2,5-dimethyl-4-((S)—N,3,3-trimethyl-2-((S)-3-methyl-2-(methylamino)-3-phenylbutanamido)butanamido)hex-2-enamide Title compound was prepared from Example 3 and cyclopentylmethanesulfonamide using General Procedures 2 and 7.

1H NMR (400 MHz, Methanol-d4) δ 7.61-7.52 (m, 2H), 7.48 (dd, J=8.6, 6.9 Hz, 2H), 7.38 (t, J=7.4 Hz, 1H), 6.54 (dd, J=9.4, 1.7 Hz, 1H), 5.06 (t, J=10.0 Hz, 1H), 4.94 (s, 1H), 4.37 (s, 1H), 3.52 (dd, J=7.0, 5.4 Hz, 3H), 3.18 (s, 3H), 2.52 (s, 3H), 2.35 (p, J=8.1 Hz, 1H), 2.16-1.89 (m, 6H), 1.77-1.53 (m, 4H), 1.49 (s, 3H), 1.45-1.26 (m, 5H), 1.09 (s, 9H), 0.93 (dd, J=11.3, 6.7 Hz, 6H).

C33H54N4O5S calcd m/z=618.38 found [M+H]+=619.54.

Example 36

(36)

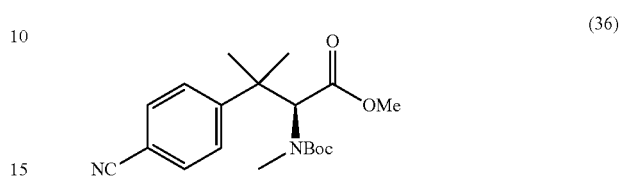

(S)-methyl 2-(tert-butoxycarbonyl(methyl)amino)-3-(4-cyanophenyl)-3-methylbutanoate To a mixture of the methyl ester of Example 38 (0.06 g, 0.15 mmol), tris(dibenzylideneacetone)dipalladium(0) (0.014 g, 0.015 mmol), 1,1'-Bis(diphenylphosphino)ferrocene (0.02 g, 0.25 equiv), magnesium acetate (0.013 g, 0.06 mmol), zinc dust (0.004 g, 0.06 mmol) and zinc cyanide (0.0264 g, 0.225 mmol) under a bath of nitrogen was added N,N-dimethylformamide/water (0.8/0.08 mL). The reaction was sparged with nitrogen gas, then the vial was sealed and immersed in an oil bath at 105° C. The reaction was allowed to stir overnight and allowed to cool to room temperature. HPLC-MS analysis indicated good conversion to the desired product. The reaction was concentrated at reduced pressure, suspended in CH2Cl2 and the resulting suspension purified by silica gel chromatography (15-25% EtOAc in Hexanes) to yield the final compound as a colourless oil (0.036 g, 69%). 1H NMR (400 MHz, Chloroform-d) δ 7.69-7.35 (m, 4H). 5.24 (s, 1H), 3.54 (s, 3H), 2.74 (s, 3H), 1.51 (s, 3H), 1.45-1.25 (m, 12H).

Example 37

(37)

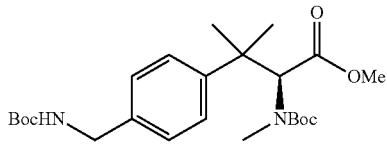

(S)-methyl 2-(tert-butoxycarbonyl(methyl)amino)-3-(4-((tert-butoxycarbonylamino)methyl)phenyl)-3-methylbutanoate To a solution of the benzonitrile (0.300 g, 0.87 mmol) in methanol/acetic acid (10:1, 9 mL) in a shaker vessel was added palladium black. The flask was charged with hydrogen gas at 60 psi and the shaker turned on for 24 h. At that time, the vessel was purged of H2 under reduced pressure. The reaction was diluted with methanol and the suspension filtered through a celite pad. The filtrate was concentrated to a slightly yellow oil and re-dissolved in dichloromethane (5 mL). t-butyl dicarbonate (0.524 g, 2.0 equiv) and triethylamine (0.846 mL, 5 equiv) were added to the solution at 0° C. with stirring. The reaction was allowed to stir for 3 h at which time HPLC-MS indicated complete consumption of the amine. The reaction was concentrated under reduced pressure and purified by silica gel chromatography (diethyl ether in hexanes, 15-30%) to yield the title compound as a colourless oil (0.232 g, 60%).

1H NMR (400 MHz, Chloroform-d) δ 7.38 (dd, J=16.6, 8.0 Hz, 2H), 7.23 (d, J=7.7 Hz, 2H), 5.27 (s, 1H), 4.31 (s, 2H), 3.61 (s, 3H), 2.78 (s, 3H), 1.50-1.61 (m, 6H), 1.47 (d, J=15.2 Hz, 18H).

Example 38

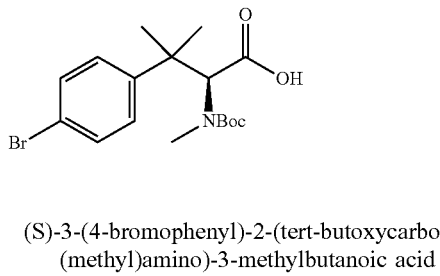

(38)

(S)-3-(4-bromophenyl)-2-(tert-butoxycarbonyl (methyl)amino)-3-methylbutanoic acid To a stirred solution of (S)-methyl 3-(4-bromophenyl)-2-(tert-butoxycarbonyl(methyl)amino)-3-methylbutanoate (0.710 g, 1.77 mmol) in 1,4 dioxane (4 mL) was added water (1 mL) (2 mL) and lithium hydroxide monohydrate (0.367 g, 8.9 mmol). The reaction was heated to 50° C., and monitored by HPLC for completion. The reaction was cooled to room temperature, acidified to pH 3 with 1M citric acid and concentrated to near dryness under reduced pressure. The residue was taken up in ~20 mL ethyl acetate, washed with brine, dried over MgSO₄, filtered and concentrated to give analytically pure material that was used without further manipulation.

1H NMR (400 MHz, Chloroform-d) δ 7.44 (d, J=8.3 Hz, 2H), 7.33 (d, J=8.3 Hz, 2H), 5.18 (s, 1H), 2.71 (s, 3H), 1.60-1.42 (m, 15H).

Example 39

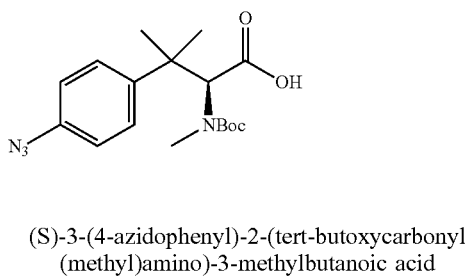

(39)

(S)-3-(4-azidophenyl)-2-(tert-butoxycarbonyl (methyl)amino)-3-methylbutanoic acid To an open pressure tube containing a magnetic stir bar was added Example 38 (0.690 g, 1.8 mmol), copper(I) iodide (0.034 g, 0.18 mmol), sodium azide (0.350 g, 5.4 mmol), N1,N2-dimethylethane-1,2-diamine (0.029 mL, 0.27 mmol), sodium ascorbate (0.036 g, 0.18 mmol), sodium hydroxide (0.072 g, 1.8 mmol), ethanol (6 mL) and water (1 mL). The suspension was sparged with nitrogen gas, the vessel was sealed and immersed in an oil bath at 105° C. with vigorous stirring. The course of reaction was monitored by HPLC-MS over the course of 24 h at which time little starting material remained. The reaction was diluted with ethyl acetate (~20 mL) and washed with brined. The aqueous layer was extracted 2× with ~20 mL ethyl acetate. The organic layers were combined, dried over MgSO₄, filtered and concentrated under reduced pressure. The residue was purified by silica gel chromatography (20-65% EtOAc (containing 2% v/v AcOH) in hexanes) to give the title compound as a colourless oil (0.475 g, 75%).

1H NMR (400 MHz, Chloroform-d) δ 7.44 (d, J=8.6 Hz, 2H), 6.99 (dd, J=9.0, 3.4 Hz, 2H), 5.24 (s, 1H), 2.71 (s, 3H), 1.63-1.38 (m, 18H).

Example 40

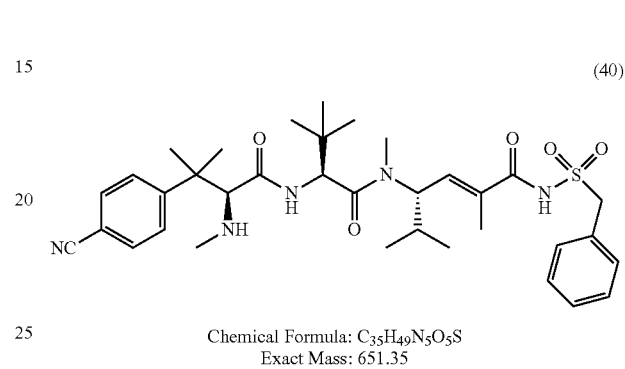

(40)

Chemical Formula: $C_{35}H_{49}N_5O_5S$
Exact Mass: 651.35

(S,E)-N-(benzylsulfonyl)-4-((S)-2-((S)-3-(4-cyanophenyl)-3-methyl-2-(methylamino)butanamido)-N,3,3-trimethylbutanamido)-2,5-dimethylhex-2-enamide Title compound was prepared from Example 36 and (S,E)-4-((S)-2-amino-N,3,3-trimethylbutanamido)-N-(benzylsulfonyl)-2,5-dimethylhex-2-enamide using General Procedures 3, 4 and 7.

$^1$H NMR (400 MHz, Methanol-d₄) δ 7.83 (d, J=8.2 Hz, 2H), 7.73 (d, J=8.4 Hz, 2H), 7.38 (d, J=2.6 Hz, 5H), 6.39 (dd, J=9.2, 1.8 Hz, 1H), 5.04 (t, J=10.1 Hz, 1H), 4.91 (s, 1H), 4.75 (s, 2H), 4.34 (s, 1H), 3.12 (s, 3H), 2.54 (s, 3H), 2.05-1.97 (m, 2H), 1.95 (d, J=1.5 Hz, 3H), 1.52 (s, 3H), 1.41 (s, 3H), 1.09 (s, 9H), 0.91 (dd, J=11.2, 4.8 Hz, 6H).

$C_{35}H_{49}N_5O_5S$ calcd m/z=651.35 found [M+H]⁺=652.4.

Example 41

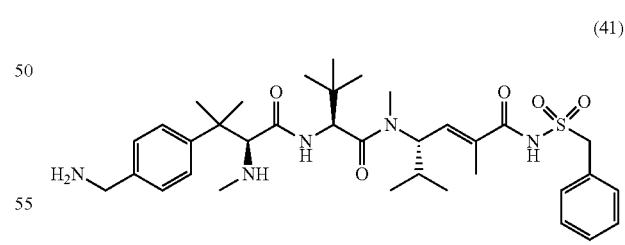

(41)

(S,E)-4-((S)-2-((S)-3-(4-(aminomethyl)phenyl)-3-methyl-2-(methylamino)butanamido)-N,3,3-trimethylbutanamido)-N-(benzylsulfonyl)-2,5-dimethylhex-2-enamide Title compound was prepared from Example 37 and (S,E)-4-((S)-2-amino-N,3,3-trimethylbutanamido)-N-(benzylsulfonyl)-2,5-dimethylhex-2-enamide using General Procedures 3, 4 and 7.

1H NMR (400 MHz, Methanol-d4) δ 7.63 (t, J=8.8 Hz, 2H), 7.54 (d, J=8.3 Hz, 2H), 7.49-7.43 (m, 3H), 7.39 (m, 2H), 6.39 (d, J=9.4 Hz, 1H), 5.05-4.97 (m, 1H), 4.75 (s, 2H), 4.35 (s, 3H), 4.16 (s, 2H), 3.14 (s, 3H), 2.54 (s, 3H), 2.03 (m, 1H), 1.95 (s, 3H), 1.51 (s, 3H), 1.39 (s, 3H), 1.31 (s, 3H), 1.09 (s, 9H), 0.98-0.81 (m, 6H).

Example 42

(42)

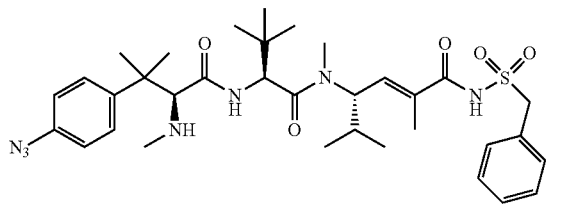

Chemical Formula: $C_{34}H_{49}N_7O_5S$
Exact Mass: 667.35

(S,E)-4-((S)-2-((S)-3-(4-azidophenyl)-3-methyl-2-(methylamino)butanamido)-N,3,3-trimethylbutanamido)-N-(benzylsulfonyl)-2,5-dimethylhex-2-enamide Title compound was prepared from Example 39 and (S,E)-4-((S)-2-amino-N,3,3-trimethylbutanamido)-N-(benzylsulfonyl)-2,5-dimethylhex-2-enamide using General Procedures 4 and 7.

$C_{34}H_{49}N_7O_5S$ calcd m/z=667.35 amu; found [M+H]+=668.4.

Example 43

(43)

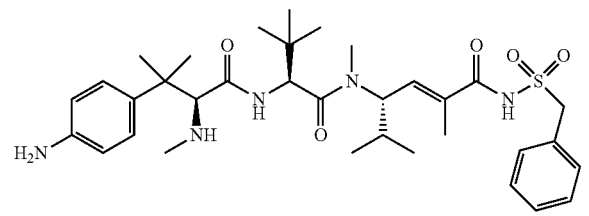

Chemical Formula: $C_{34}H_{51}N_5O_5S$
Exact Mass: 641.36

(S,E)-4-((S)-2-((S)-3-(4-aminophenyl)-3-methyl-2-(methylamino)butanamido)-N,3,3-trimethylbutanamido)-N-(benzylsulfonyl)-2,5-dimethylhex-2-enamide To a stirred solution of Boc protected Example 42 (0.035 g, 0.046 mmol) in ethanol (1.6 mL) and water (0.5 mL) was added zinc dust (0.015 g, 0.23 mmol) and ammonium chloride (0.025 g, 0.46 mmol). After 1 h HPLC-MS indicated complete consumption of the starting material. The reaction was quenched with ammonium hydroxide (~0.1 mL) and diluted with ethyl acetate (5 mL). The reaction was filtered, the solids washed with ethyl acetate (5 mL) and the biphasic filtrate transferred to a separatory funnel. The aqueous phase was washed twice with ethyl acetate (5 mL) and the organic phases were combined, washed with brine, dried over MgSO4, filtered and concentrated. The reaction product was purified by silica gel chromatography (5-15% MeOH in CH2Cl2) to afford the Boc protected intermediate as a colourless glass (0.027 g, 66%). The intermediate was deprotected according to General Procedure 7 to give the title compound.

$C_{34}H_{51}N_5O_5S$ calcd m/z=641.36 amu; found [M+H]+=642.4.

Example 44

(44)

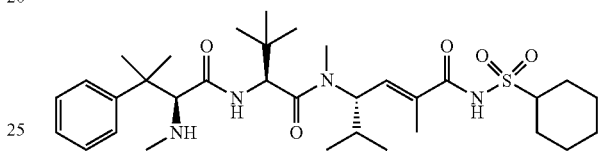

Chemical Formula: $C_{33}H_{54}N_4O_5S$
Exact Mass: 618.38

(S,E)-N-(cyclohexylsulfonyl)-2,5-dimethyl-4-((S)—N,3,3-trimethyl-2-((S)-3-methyl-2-(methylamino)-3-phenylbutanamido)butanamido)hex-2-enamide Title compound was prepared from Example 3 and cyclohexylsulfonamide using General Procedures 2 and 7.

1H NMR (400 MHz, Methanol-d4) δ 7.61-7.52 (m, 2H), 7.47 (dd, J=8.6, 6.9 Hz, 2H), 7.36 (t, J=7.5 Hz, 1H), 6.61-6.50 (m, 1H), 5.11-4.99 (m, 1H), 4.94 (s, 1H), 4.28 (s, 1H), 3.59-3.51 (m, 1H), 3.18 (s, 3H), 2.48 (s, 3H), 2.20-2.00 (m, 4H), 1.97-1.87 (m, 6H), 1.78-1.69 (m, 1H), 1.60 (td, J=14.2, 10.9 Hz, 2H), 1.48 (s, 3H), 1.44-1.23 (m, 6H), 1.09 (s, 9H), 0.93 (dd, J=13.7, 6.6 Hz, 7H).

C33H54N4O5S calcd m/z=618.38 found [M+H]+=619.47.

Example 45

(45)

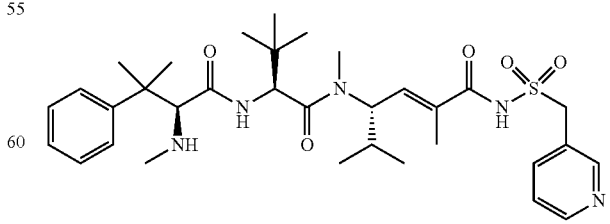

Chemical Formula: $C_{33}H_{49}N_5O_5S$
Exact Mass: 627.35

(S,E)-2,5-dimethyl-N-(pyridin-3-ylmethylsulfonyl)-4-((S)—N,3,3-trimethyl-2-((S)-3-methyl-2-(methylamino)-3-phenylbutanamido)butanamido)hex-2-enamide Title compound was prepared from Example 3 and pyridin-3-ylmethanesulfonamide using General Procedures 2 and 7.

1H NMR (400 MHz, Methanol-d4) δ 8.55 (d, J=1.7 Hz, 1H), 8.48 (dd, J=5.0, 1.6 Hz, 1H), 7.89 (d, J=8.0 Hz, OH), 7.55 (d, J=7.6 Hz, 2H), 7.50-7.39 (m, 2H), 7.35 (s, 1H), 6.52 (dd, J=9.6, 2.0 Hz, 1H), 5.05 (s, OH), 4.94 (s, 1H), 4.64 (s, 2H), 4.19 (s, 1H), 3.11 (s, 3H), 2.45 (s, 3H), 1.91 (d, J=1.5 Hz, 3H), 1.48 (s, 3H), 1.39 (s, 3H), 1.07 (s, 8H), 0.89 (dd, J=15.1, 6.5 Hz, 6H).

C33H54N4O5S calcd m/z=627.35 found [M+H]+=628.35.

Example 46

(S,E)-2,5-dimethyl-N-(3-(2,2,2-trifluoroacetamido)phenylsulfonyl)-4-((S)—N,3,3-trimethyl-2-((S)-3-methyl-2-(methylamino)-3-phenylbutanamido)butanamido)hex-2-enamide Title compound was prepared from Example 3 and 2,2,2-trifluoro-N-(3-sulfamoylphenyl)acetamide using General Procedures 2 and 7.

$^1$H NMR (400 MHz, Methanol-d$_4$) δ 8.49 (p, J=2.2 Hz, 1H), 7.90 (dtd, J=6.0, 4.8, 2.9 Hz, 2H), 7.64-7.56 (m, 1H), 7.53 (tt, J=5.4, 4.3, 1.8 Hz, 2H), 7.51-7.42 (m, 2H), 7.41-7.28 (m, 1H), 6.56-6.38 (m, 1H), 4.97 (s, 1H), 4.90 (d, J=3.3 Hz, 1H), 4.35 (s, 1H), 3.16 (d, J=15.5 Hz, 3H), 2.49 (d, J=14.2 Hz, 3H), 2.14-2.01 (m, 1H), 1.89-1.83 (m, 3H), 1.57-1.28 (m, 6H), 1.14-0.94 (m, 9H), 0.95-0.85 (m, 6H).

$^{13}$C NMR (101 MHz, Methanol-d$_4$) δ 172.26, 168.81, 167.10, 167.00, 144.95, 141.82, 138.82, 138.47, 135.31, 130.71, 130.38, 128.91, 127.36, 126.65, 126.32, 121.39, 71.20, 66.92, 57.87, 57.78, 42.05, 35.83, 34.15, 32.66, 30.84, 29.79, 26.95, 21.39, 19.84, 19.82, 15.45, 14.03.

$^{19}$F NMR (377 MHz, Methanol-d$_4$) δ -76.96, -77.07. C$_{35}$H$_{48}$F$_3$N$_5$O$_6$S calcd m/z=723.33 amu; found [M+H]$^+$=724.30, [M+Na]$^+$=746.30.

(46)

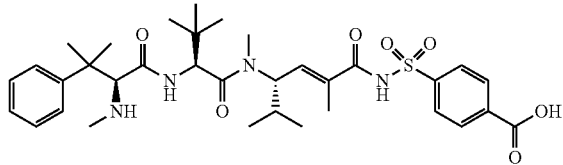

4-(N—((S,E)-2,5-dimethyl-4-((S)—N,3,3-trimethyl-2-((S)-3-methyl-2-(methylamino)-3-phenylbutanamido)butanamido)hex-2-enoyl)sulfamoyl)benzoic acid Title compound was prepared from Example 3 and methyl 4-sulfamoylbenzoate using General Procedures 2, 3 and 7.

1H NMR (400 MHz, Methanol-d4) δ 8.25-8.07 (m, 4H), 7.54 (d, J=7.8 Hz, 2H), 7.47 (t, J=7.6 Hz, 2H), 7.37 (t, J=7.3 Hz, 1H), 6.55 (d, J=9.3 Hz, 1H), 4.98 (t, J=9.9 Hz, 1H), 4.92 (s, 1H), 4.36 (s, 1H), 3.16 (s, 3H), 2.51 (s, 3H), 2.06 (q, J=9.0, 7.7 Hz, 1H), 1.88 (s, 3H), 1.46 (s, 3H), 1.36 (s, 3H), 1.06 (s, 9H), 0.91 (t, J=6.0 Hz, 6H)

Example 47

Example 48

(48)

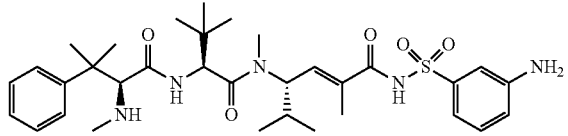

Chemical Formula: C$_{33}$H$_{49}$N$_5$O$_5$S
Exact Mass: 627.35

(47)

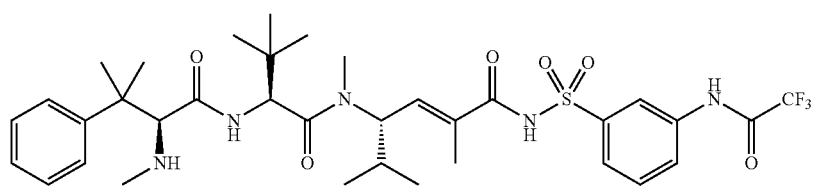

Chemical Formula: C$_{35}$H$_{48}$F$_3$N$_5$O$_6$S
Exact Mass: 723.33
Molecular Weight: 723.85

(S,E)-N-(3-aminophenylsulfonyl)-2,5-dimethyl-4-((S)—N,3,3-trimethyl-2-((S)-3-methyl-2-(methylamino)-3-phenylbutanamido)butanamido)hex-2-enamide Title compound was prepared from Example 3 and 2,2,2-trifluoro-N-(3-sulfamoylphenyl)acetamide using General Procedures 2, 3 and 7.

$^1$H NMR (400 MHz, Methanol-$d_4$) δ 7.55 (d, J=7.5 Hz, 2H), 7.51-7.45 (m, 2H), 7.43-7.20 (m, 4H), 6.97 (d, J=8.1 Hz, 1H), 6.48 (d, J=9.4 Hz, 1H), 5.02-4.89 (m, 2H), 4.36 (s, 1H), 3.17 (s, 3H), 2.50 (s, 3H), 2.14-2.00 (m, 1H), 1.88 (d, J=1.4 Hz, 3H), 1.46 (s, 3H), 1.35 (s, 3H), 1.07 (s, 9H), 0.92 (d, J=6.3 Hz, 3H), 0.90 (s, 3H).

$C_{33}H_{49}N_5O_5S$ calcd. m/z=627.35 found [M+H]$^+$=628.36.

Example 49

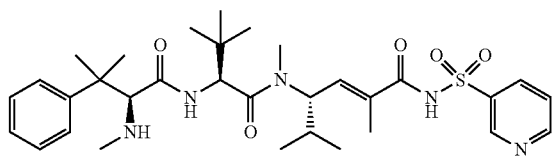

(49)

Chemical Formula: $C_{32}H_{47}N_5O_5S$
Exact Mass: 613.33

(S,E)-2,5-dimethyl-N-(pyridin-3-ylsulfonyl)-4-((S)—N,3,3-trimethyl-2-((S)-3-methyl-2-(methylamino)-3-phenylbutanamido)butanamido)hex-2-enamide Title compound was prepared from Example 3 and pyridine-3-sulfonamide using General Procedures 2, and 7.

$^1$H NMR (400 MHz, Methanol-$d_4$) δ 9.18 (s, 1H), 8.80 (s, 1H), 8.46 (dt, J=8.2, 1.8 Hz, 1H), 7.65 (dd, J=8.1, 4.9 Hz, 1H), 7.54 (d, J=7.3 Hz, 2H), 7.47 (t, J=7.8 Hz, 2H), 7.37 (t, J=7.3 Hz, 1H), 6.54 (d, J=9.3 Hz, 1H), 5.01-4.88 (m, 2H), 4.36 (s, 1H), 3.18 (s, 3H), 2.51 (s, 3H), 2.15-2.01 (m, 1H), 1.86 (d, J=1.4 Hz, 3H), 1.46 (s, 3H), 1.33 (s, 3H), 1.07 (s, 9H), 0.92 (d, J=3.3 Hz, 3H), 0.91 (d, J=3.5 Hz, 3H).

$C_{32}H_{47}N_5O_5S$ calcd. m/z=613.33 found [M+H]$^+$=614.23.

Example 50

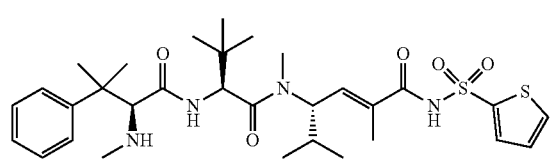

(50)

Chemical Formula: $C_{31}H_{46}N_4O_5S_2$
Exact Mass: 618.29

(S,E)-2,5-dimethyl-N-(thiophen-2-ylsulfonyl)-4-((S)—N,3,3-trimethyl-2-((S)-3-methyl-2-(methylamino)-3-phenylbutanamido)butanamido)hex-2-enamide Title compound was prepared from Example 3 and thiophene-2-sulfonamide using General Procedures 2, and 7.

$^1$H NMR (400 MHz, Methanol-$d_4$) δ 7.93-7.82 (m, 2H), 7.55 (d, J=8.3 Hz, 1H), 7.48 (t, J=7.8 Hz, 2H), 7.37 (t, J=7.2 Hz, 1H), 7.15 (dd, J=5.0, 3.8 Hz, 1H), 6.51 (d, J=9.1 Hz, 1H), 5.02-4.93 (m, 2H), 4.36 (s, 1H), 3.18 (s, 3H), 2.51 (s, 3H), 2.15-2.01 (m, 1H), 1.89 (d, J=1.4 Hz, 3H), 1.46 (s, 3H), 1.34 (s, 3H), 1.08 (s, 9H), 0.93 (d, J=4.8 Hz, 3H), 0.91 (d, J=4.7 Hz, 3H).

$C_{31}H_{46}N_4O_5S_2$ calcd. m/z=618.29 found [M+H]$^+$=619.24.

Example 51

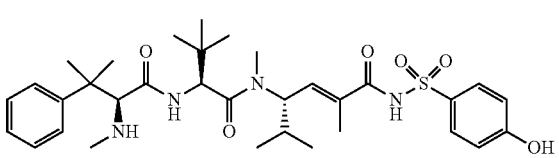

(51)

Chemical Formula: $C_{33}H_{48}N_4O_6S$
Exact Mass: 628.33

(S,E)-N-(4-hydroxyphenylsulfonyl)-2,5-dimethyl-4-((S)—N,3,3-trimethyl-2-((S)-3-methyl-2-(methylamino)-3-phenylbutanamido)butanamido)hex-2-enamide Title compound was prepared from Example 3 and 4-(tert-butyldimethylsilyloxy)benzenesulfonamide using General Procedures 2, and 7.

$^1$H NMR (400 MHz, Methanol-$d_4$) δ 7.89 (d, J=8.8 Hz, 2H), 7.55 (d, J=7.0 Hz, 1H), 7.47 (t, J=7.6 Hz, 2H), 7.37 (t, J=7.3 Hz, 1H), 6.91 (d, J=8.9 Hz, 2H), 6.46 (d, J=9.2 Hz, 1H), 4.97 (d, J=10.2 Hz, 1H), 4.92 (s, 1H), 4.33 (s, 1H), 3.16 (s, 3H), 2.50 (s, 3H), 2.11-2.00 (m, 1H), 1.87 (d, J=1.4 Hz, 3H), 1.46 (s, 3H), 1.36 (s, 3H), 1.07 (s, 9H), 0.92 (d, J=6.5 Hz, 4H), 0.89 (d, J=6.7 Hz, 3H).

$C_{33}H_{48}N_4O_6S$ calcd. m/z=628.33 found [M+H]$^+$=629.38.

Example 52

(52)

[Structure: TrtS-CH2-C6H4-CN]

4-(tritylthiomethyl)benzonitrile

Tritylmercaptan (1.48 g, 5.36 mmol, 1.05 eq) in THF (5 mL) was added dropwise to a stirred suspension of sodium hydride (60% dispersion in mineral oil, 214 mg, 5.36 mmol, 1.05 eq) in THF (5 mL) under $N_2$ at 0° C. After 15 min, 4-(bromomethyl)benzonitrile (1.00 g, 5.10 mmol, 1.0 eq) in THF (5 mL) was added and the reaction was allowed to come to rt. After 1 h, TLC indicated complete conversion of starting material. The reaction was quenched by adding saturated ammonium chloride, then some $dH_2O$. The mixture was extracted three times with ether, washed with saturated brine, dried over sodium sulfate, and concentrated to a viscous yellow oil. Purification by flash chromatography gave the title compound (1.76 g, 88%) as a light white powder.

$^1$H NMR (400 MHz, Chloroform-d) δ 7.52 (d, J=8.2 Hz, 2H), 7.47 (d, J=7.1 Hz, 6H), 7.33 (t, J=7.5 Hz, 6H), 7.26 (t, J=7.2 Hz, 3H), 7.19 (d, J=8.2 Hz, 2H), 3.40 (s, 2H). m/z calcd. for $C_{27}H_{21}NS$=391.14. Found $[M+Na]^+$=414.13. $R_f$=0.32 (10% EtOAc/Hex).

Example 53

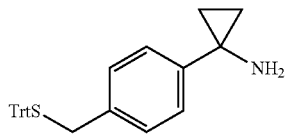

(53)

1-(4-(tritylthiomethyl)phenyl)cyclopropanamine 4-(tritylthiomethyl)benzonitrile (1.47 g, 3.75 mmol, 1.0 eq) was taken up in 40 mL THF, under $N_2$ atmosphere, then cooled to −78° C. To this solution was added Ti(O-iPr)$_4$ (1.21 mL, 4.13 mmol, 1.1 eq), then ethylmagnesium bromide (3 M, 2.75 mL, 8.26 mmol, 2.2 eq) was added dropwise over 5 min. The dry-ice bath was removed, allowing the solution to reach rt. After 45 min at rt, BF$_3$·Et$_2$O (0.93 mL, 7.51 mmol, 2.0 eq) was added to the now very dark reaction mixture. After stirring for an additional 2.5 h, the reaction was quenched with 5 mL of 2 M HCL, followed by pH adjustment to strong base with about 15 mL 2 M NaOH. Some water was added to the mixture, then it was extracted three times with 75 mL EtOAc, washed once with $dH_2O$, once with saturated brine, dried over sodium sulfate, and concentrated to a clear oil. The material was purified by flash chromatography to afford the title compound (680 mg, 36%) as a clear oil.

$^1$H NMR (400 MHz, Chloroform-d) δ 7.49 (d, J=7.8 Hz, 6H), 7.33 (t, J=7.7 Hz, 6H), 7.26 (t, J=7.2 Hz, 3H), 7.20 (d, J=8.2 Hz, 2H), 7.11 (d, J=8.2 Hz, 2H), 3.32 (s, 2H), 1.06 (dd, J=7.9, 5.0 Hz, 2H), 0.95 (dd, J=7.9, 4.7 Hz, 2H). m/z calcd. for $C_{29}H_{27}NS$=421.19. Found $[M+H]^+$=422.19. $R_f$=0.21 (50% EtOAc/Hex).

Example 54

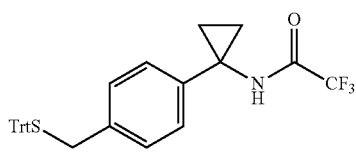

(54)

2,2,2-trifluoro-N-(1-(4-(tritylthiomethyl)phenyl)cyclopropyl)acetamide

To a stirred solution of 1-(4-(tritylthiomethyl)phenyl)cyclopropanamine (680 mg, 1.61 mmol, 1.0 eq) in $CH_2Cl_2$ was added trifluoroacetic anhydride (0.448 mL, 3.22 mmol, 2.0 eq) and triethylamine (0.45 mL, 3.22 mmol, 2.0 eq). After two hours, TLC and HPLC indicated complete conversion of starting material. The reaction was quenched by the addition of 3 mL NaHCO$_3$, then some $dH_2O$ was added, and the mixture was extracted three times with $CH_2Cl_2$. The combined organics were washed with saturated brine, dried over sodium sulfate, and concentrated to a yellow foam, giving the title compound (715 mg, 86%) in sufficient purity to move to the next step.

$^1$H NMR (400 MHz, Chloroform-d) δ 7.48 (d, J=7.7 Hz, 6H), 7.32 (t, J=7.6 Hz, 6H), 7.25 (t, J=7.2 Hz, 3H), 7.19 (d, J=8.2 Hz, 2H), 7.10 (d, J=8.3 Hz, 2H), 6.83 (s, 1H), 3.31 (s, 2H), 1.40-1.24 (m, 4H). m/z calcd. for $C_{31}H_{26}F_3NOS$=517.17. Found $[M+Na]^+$=540.25. $R_f$=0.71 (50% EtOAc/Hex).

Example 55

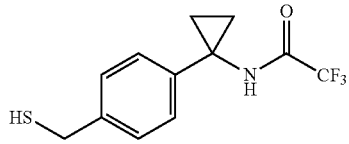

(55)

2,2,2-trifluoro-N-(1-(4-(mercaptomethyl)phenyl)cyclopropyl)acetamide 2,2,2-trifluoro-N-(1-(4-(tritylthiomethyl)phenyl)cyclopropyl)acetamide (715 mg, 1.38 mmol, 1.0 eq) in 5 mL $CH_2Cl_2$ was treated with 2.5 mL TFA. After 1 min, TIPSH (0.42 mL, 2.1 mmol, 1.5 eq) was added, causing the yellow color to fade. After 30 min, TLC indicated the reaction to be complete. The mixture was concentrated, then co-evaporated once with $CH_2Cl_2$ and twice with toluene. The residue was purified by flash chromatography to afford the title compound (261 mg, 69%) as a white solid. $^1$H NMR (400 MHz, Chloroform-d) δ 7.35-7.23 (m, 4H), 6.87 (s, 1H), 3.74 (d, J=7.6 Hz, 2H), 1.77 (t, J=7.6 Hz, 1H), 1.36 (s, 4H). $R_f$=0.47 (20% EtOAc/Hex).

Example 56

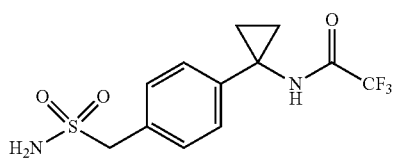

(56)

2,2,2-trifluoro-N-(1-(4-(sulfamoylmethyl)phenyl)cyclopropyl)acetamide

To a stirred solution of 2,2,2-trifluoro-N-(1-(4-(mercaptomethyl)phenyl)cyclopropyl)acetamide (220 mg, 0.799 mmol, 1.0 eq) in acetonitrile were added dH$_2$O (0.029 mL, 1.6 mmol, 2.0 eq), tetrabutylammonium chloride (110 mg, 0.40 mmol, 0.5 eq), then N-chlomsuccinimide (320 mg, 2.40 mmol, 3.0 eq). After 20 minutes, no starting material was visible by TLC. After 90 min, concentrated NH$_4$OH (0.18 mL, 3.2 mmol, 4.0 eq) was added. After 10 minutes, 1 mL of NH$_4$Cl was added, and the mixture was extracted three times with EtOAc. The combined organics were washed twice with dH$_2$O, once with saturated brine, dried over sodium sulfate, and concentrated to a clear oil. The residue was purified by flash chromatography to afford the title compound (192 mg, 74%) as a white solid.

$^1$H NMR (400 MHz, DMSO-d$_6$) δ 10.21 (s, 1H), 7.31 (d, J=8.2 Hz, 2H), 7.16 (d, J=8.3 Hz, 2H), 6.85 (s, 2H), 4.23 (s, 2H), 1.27 (dt, J=6.1, 2.3 Hz, 4H). R$_f$=0.26 (50% EtOAc/Hex).

Example 57

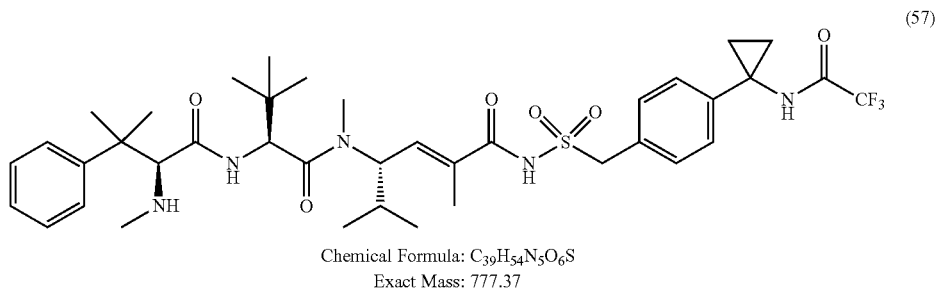 [SMILES: CN[C@H](C(=O)N[C@H](C(=O)N(C)[C@H](/C=C(\C)C(=O)NS(=O)(=O)Cc1ccc(C2(NC(=O)C(F)(F)F)CC2)cc1)C(C)C)C(C)(C)C)C(C)(C)c1ccccc1]

Chemical Formula: C$_{39}$H$_{54}$N$_5$O$_6$S
Exact Mass: 777.37

(S,E)-2,5-dimethyl-N-(4-(1-(2,2,2-trifluoroacet-amido)cyclopropyl)benzylsulfonyl)-4-((S)—N,3,3-trimethyl-2-((S)-3-methyl-2-(methylamino)-3-phenylbutanamido)butanamido)hex-2-enamide Title compound was prepared from Example 3 and Example 56 using General Procedures 2, and 7.

$^1$H NMR (400 MHz, Methanol-d$_4$) δ 7.56 (d, J=8.4 Hz, 2H), 7.48 (t, J=7.7 Hz, 2H), 7.37 (t, J=7.4 Hz, 1H), 7.32 (d, J=8.5 Hz, 2H), 7.28 (d, J=8.5 Hz, 2H), 6.37 (d, J=9.6 Hz, 1H), 5.07 (t, J=10.0 Hz, 1H), 4.94 (s, 1H), 4.72 (s, 2H), 4.37 (s, 1H), 3.13 (s, 3H), 2.52 (s, 3H), 2.08-1.96 (m, 1H), 1.96 (d, J=1.5 Hz, 3H), 1.49 (s, 3H), 1.40 (s, 3H), 1.35-1.27 (m, 4H), 1.10 (s, 9H), 0.92 (d, J=7.1 Hz, 3H), 0.89 (d, J=6.8 Hz, 3H).

$^{13}$C NMR (101 MHz, MeOD) δ 170.93, 168.81, 165.64, 143.58, 142.24, 136.87, 134.19, 130.64, 129.00, 127.63, 127.53, 125.95, 125.61, 69.90, 57.10, 57.02, 56.39, 40.73, 34.55, 34.25, 32.80, 30.60, 29.33, 28.39, 25.57, 20.11, 18.38, 18.34, 16.21, 16.15, 14.04, 12.85.

C$_{39}$H$_{54}$F$_3$N$_5$O$_6$S calcd. m/z=777.37 found [M+H]$^+$=778.55.

Example 58

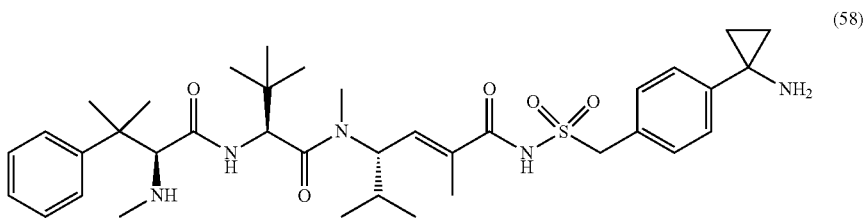

Chemical Formula: C₃₇H₅₅N₅O₅S
Exact Mass: 681.39

(S,E)-N-(4-(1-aminocyclopropyl)benzylsulfonyl)-2,5-dimethyl-4-((S)—N,3,3-trimethyl-2-((S)-3-methyl-2-(methylamino)-3-phenylbutanamido)butanamido)hex-2-enamide Title compound was prepared from Example 3 and Example 56 using General Procedures 2, 3 and 7.

$^1$H NMR (400 MHz, Methanol-$d_4$) δ 7.56 (d, J=8.7 Hz, 2H), 7.51 (s, 4H), 7.47 (t, J=7.6 Hz, 2H), 7.37 (t, J=7.3 Hz, 1H), 6.49 (d, J=9.5 Hz, 1H), 5.07 (t, J=10.0 Hz, 1H), 4.94 (s, 1H), 4.81 (d, J=14.0 Hz, 1H), 4.77 (d, J=13.8 Hz, 1H), 4.39 (s, 1H), 3.16 (s, 3H), 2.52 (s, 3H), 2.11-1.99 (m, 1H), 1.97 (d, J=1.5 Hz, 3H), 1.49 (s, 8H), 1.45-1.41 (m, 2H), 1.40 (s, 3H), 1.34-1.26 (m, 2H), 1.10 (s, 9H), 0.93 (d, J=6.2 Hz, 3H), 0.90 (d, J=6.3 Hz, 3H).

$^{13}$C NMR (101 MHz, MeOD) δ 170.94, 169.00, 165.69, 143.57, 137.54, 137.12, 134.38, 131.43, 129.66, 128.98, 127.51, 125.98, 69.85, 65.51, 57.68, 57.15, 56.39, 40.72, 36.16, 34.51, 32.80, 30.68, 29.42, 28.40, 25.61, 20.14, 18.42, 18.39, 14.05, 12.86, 11.80.

$C_{17}H_{55}N_5O_5S$ calcd. m/z=681.39 found [M+H]⁺=682.49.

Example 59

(59)

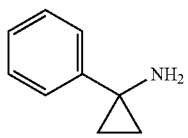

1-phenylcyclopropanamine

The title compound was prepared as described in Bertus, P., Szymoniak, J. *J. Org. Chem.*, 2003, 68, 7133-7136 from benzonitrile (1.0 mL, 9.7 mmol) to give 270 mg (21%).

$^1$H NMR (400 MHz, Chloroform-d) δ 7.44-7.28 (m, 4H), 7.27-7.15 (m, 1H), 1.18-1.06 (m, 2H), 1.07-0.95 (m, 2H). $R_f$=0.28 (5% (5% NH₄OH/MeOH)/CH₂Cl₂).

Example 60

(60)

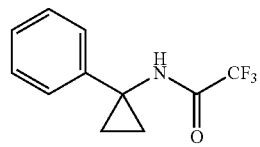

2,2,2-trifluoro-N-(1-phenylcyclopropyl)acetamide

To a stirred solution of 1-phenylcyclopropanamine (270 mg, 2.03 mmol, 1.0 eq) in dioxane (5 mL), was added trifluoroacetic anhydride (0.310 mL, 2.23 mmol, 1.1 eq). After 5 min, TLC indicated complete conversion of starting material. The mixture was concentrated, then coevaporated once with CH₂Cl₂ and once with toluene to yield the title compound (453 mg, 97%) as a flaky white powder.

$^1$H NMR (400 MHz, Chloroform-d) δ 7.47-7.15 (m, 5H), 6.88 (s, 1H), 1.65 (s, 4H). m/z calcd. for $C_{11}H_{10}F_3NO$=229.07. Found [M+H]⁺=230.14. $R_f$=0.82 (5% (5% NH₄OH/MeOH)/CH₂Cl₂)

Example 61

(61)

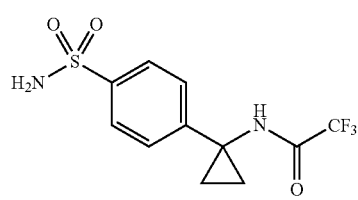

2,2,2-trifluoro-N-(1-(4-sulfamoylphenyl)cyclopropyl)acetamide

To stirred chlorosulfonic acid (0.78 mL, 11.8 mmol, 6.0 eq) at 0° C., was added solid 2,2,2-trifluoro-N-(1-phenylcyclopropyl)acetamide (450 mg, 1.96 mmol, 1.0 eq) portionwise, keeping the temperature low. After complete addition, the mixture was heated to 50° C. After 10 minutes, gas evolution ceased, and the reaction was allowed to cool. The mixture was added slowly to a beaker of ice, being mindful of splattering. The solid that was left in the ice was filtered off. This solid was dried in vacuo and then taken up in THF (4 mL). Concentrated NH₄OH (0.44 mL, 7.85 mmol, 4.0 eq) was added, turning the solution green-black. After 2 min, TLC indicated complete consumption of the sulfonylchloride intermediate. HCl was added until the color faded, then the mixture was extracted three times with EtOAc, washed once with saturated NaHCO₃, once with saturated brine, dried over sodium sulfate, and concentrated to a flaky solid. The crude material was purified by flash chromatography to yield the title compound (235 mg, 39%) as a white solid.

¹H NMR (400 MHz, DMSO-$d_6$) δ 10.28 (s, 1H), 7.76 (d, J=8.5 Hz, 2H), 7.32 (d, J=8.1 Hz, 2H), 7.31 (s, 2H), 1.42-1.35 (m, 2H), 1.35-1.27 (m, 2H). m/z calcd. for $C_{11}H_{11}F_3N_2O_3S$=308.04. Found [M+H]⁺=309.07. $R_f$=0.27 (50% EtOAc/Hex).

Example 62

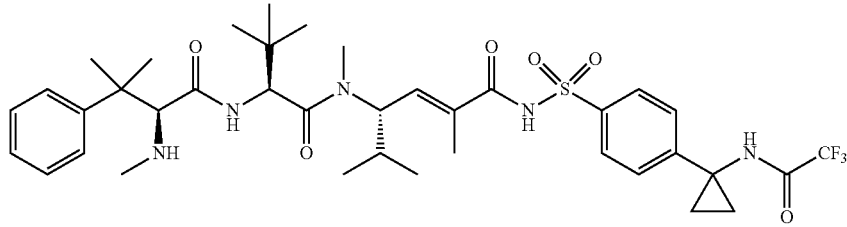

(62)

Chemical Formula: $C_{38}H_{52}F_3N_5O_6S$
Exact Mass: 763.36

(S,E)-2,5-dimethyl-N-(4-(1-(2,2,2-trifluoroacetamido)cyclopropyl) phenylsulfonyl)-4-((S)—N,3,3-trimethyl-2-((S)-3-methyl-2-(methylamino)-3-phenylbutanamido)butanamido)hex-2-enamide Title compound was prepared from Example 3 and Example 61 using General Procedures 2 and 7.

¹H NMR (400 MHz, Methanol-$d_4$) δ 8.00 (d, J=8.6 Hz, 2H), 7.55 (d, J=7.6 Hz, 2H), 7.48 (t, J=7.7 Hz, 2H), 7.48-7.33 (m, 4H), 6.47 (dd. J=9.4, 1.6 Hz, 1H), 5.00 (t, J=10.0 Hz, H), 4.92 (s, 1H), 4.35 (s, 1H), 3.15 (s, 3H), 2.51 (s, 3H), 2.11-2.00 (m, 1H), 1.86 (d, J=1.4 Hz, 3H), 1.47 (d, J=6.2 Hz, 3H), 1.45 (s, 2H), 1.43 (s, 2H), 1.38 (s, 3H), 1.06 (s, 9H), 0.91 (d, J=6.1 Hz, 3H), 0.89 (d, J=6.2 Hz, 3H).

$C_{37}H_{50}F_3N_5O_6S$ calcd. m/z=763.36 found [M+H]⁺=764.45.

Example 63

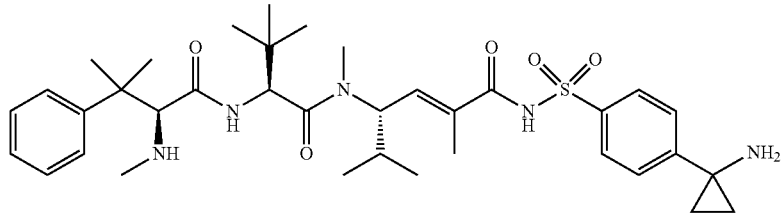

(63)

Chemical Formula: $C_{36}H_{53}N_5O_5S$
Exact Mass: 667.38

(S,E)-N-(4-(1-aminocyclopropyl)phenylsulfonyl)-2,5-dimethyl-4-((S)—N,3,3-trimethyl-2-((S)-3-methyl-2-(methylamino)-3-phenylbutanamido) butanamido) hex-2-enamide Title compound was prepared from Example 3 and 2,2,2-trifluoro-N-(1-(4-sulfamoylphenyl)cyclopropyl)acetamide using General Procedures 2, 3 and 7.

$^1$H NMR (400 MHz, Methanol-d$_4$) δ 8.13 (d, J=8.5 Hz, 2H), 7.66 (d, J=8.6 Hz, 2H), 7.55 (d, J=7.2 Hz, 2H), 7.47 (t, J=7.6 Hz, 2H), 7.37 (t, J=7.2 Hz, 1H), 6.50 (dd, J=9.4, 1.7 Hz, 1H), 5.02 (t, J=10.0 Hz, 1H), 4.93 (d, J=4.9 Hz, 1H), 4.38 (s, 1H), 3.16 (s, 3H), 2.51 (s, 3H), 2.12-1.99 (m, 1H), 1.84 (d, J=1.4 Hz, 3H), 1.51-1.46 (m, 5H), 1.46-1.42 (m, 2H), 1.38 (s, 3H), 1.07 (s, 9H), 0.91 (dd, J=6.7, 1.7 Hz, 6H).

$C_{36}H_{53}N_5O_5S$ calcd. m/z=667.38 found [M+H]$^+$=668.40.

Example 64

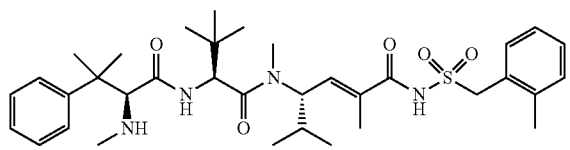

Chemical Formula: $C_{35}H_{52}N_4O_5S$
Exact Mass: 640.37

(S,E)-2,5-dimethyl-N-(2-methylbenzylsulfonyl)-4-((S)—N,3,3-trimethyl-2-((S)-3-methyl-2-(methylamino)-3-phenylbutanamido)butanamido)hex-2-enamide Title compound was prepared from Example 3 and 2-methylbenzylsulfonamide using General Procedures 2 and 7.

$^1$H NMR (400 MHz, Methanol-d$_4$) δ 7.61-7.52 (m, 2H), 7.48 (t, J=7.6 Hz, 2H), 7.37 (t, J=7.3 Hz, 1H), 7.30-7.23 (m, 3H), 7.22-7.14 (m, 1H), 6.48 (dd, J=9.3, 1.7 Hz, 1H), 5.08 (t, J=10.0 Hz, 1H), 4.94 (s, 1H), 4.81 (s, 2H), 4.34 (s, 1H), 3.15 (s, 3H), 2.51 (s, 3H), 2.48 (s, 3H), 2.08-2.00 (m, 1H), 1.98 (d, J=1.1 Hz, 3H), 1.49 (s, 3H), 1.40 (s, 3H), 1.10 (s, 9H), 0.93 (d, J=6.6 Hz, 3H), 0.91 (d, J=6.6 Hz, 3H).

$C_5H_{52}N_4O_5S$ calcd. m/z=640.37 found [M+H]$^+$=641.41.

Example 65

(S,E)-2,5-dimethyl-N-(4-nitrobenzylsulfonyl)-4-((S)—N,3,3-trimethyl-2-((S)-3-methyl-2-(methylamino)-3-phenylbutanamido)butanamido)hex-2-enamide Title compound was prepared from Example 3 and 4-nitrobenzylsulfonamide using General Procedures 2 and 7.

$^1$H NMR (400 MHz, Methanol-d$_4$) δ 8.18 (d, J=8.7 Hz, 2H), 7.64 (d, J=8.7 Hz, 2H), 7.52 (d, J=7.5 Hz, 2H), 7.42 (t, J=7.7 Hz, 2H), 7.31 (t, J=7.3 Hz, 1H), 6.55 (d, J=9.4 Hz, 1H), 5.04 (t, J=10.0 Hz, 1H), 4.92 (s, 1H), 4.63 (s, 2H), 3.08 (s, 3H), 2.32 (s, 3H), 1.95 (dt, J=11.4, 6.6 Hz, 4H), 1.89 (d, J=1.4 Hz, 3H), 1.46 (s, 3H), 1.38 (s, 3H), 1.05 (s, 9H), 0.89 (d, J=6.5 Hz, 3H), 0.85 (d, J=6.5 Hz, 3H).

$C_{34}H_{49}N_5O_7S$ calcd. m/z=671.34 found [M+H]$^+$=672.36.

Example 66

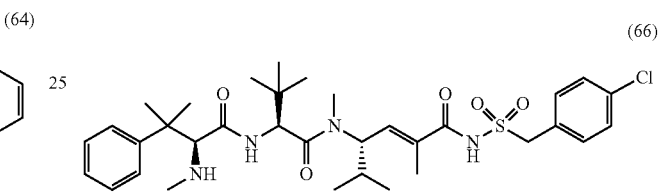

Chemical Formula: $C_{34}H_{49}ClN_4O_5S$
Exact Mass: 660.31

(S,E)-N-(4-chlorobenzylsulfonyl)-2,5-dimethyl-4-((S)—N,3,3-trimethyl-2-((S)-3-methyl-2-(methylamino)-3-phenylbutanamido)butanamido)hex-2-enamide Title compound was prepared from Example 3 and 4-chlorobenzylsulfonamide using General Procedures 2 and 7.

$^1$H NMR (400 MHz, Methanol-d$_4$) δ 7.56 (d, J=7.9 Hz, 2H), 7.48 (t, J=7.6 Hz, 2H), 7.44-7.34 (m, 5H), 6.39 (d, J=9.5 Hz, 1H), 5.06 (t, J=10.0 Hz, 1H), 4.94 (s, 1H), 4.75 (s, 2H), 4.35 (s, 1H), 3.13 (s, 3H), 2.51 (s, 3H), 2.06-1.95 (m, 1H), 1.95 (d, J=1.4 Hz, 3H), 1.49 (s, 3H), 1.39 (s, 3H), 1.09 (s, 9H), 0.91 (d, J=6.1 Hz, 3H), 0.89 (d, J=5.9 Hz, 3H).

$C_{34}H_{49}ClN_4O_5S$ calcd. m/z=660.31 found [M+H]$^+$=661.32.

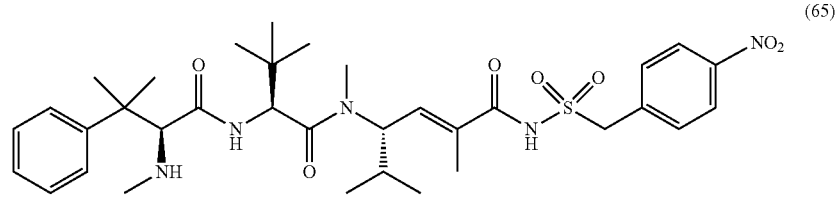 [SMILES: CN[C@H](C(=O)N[C@H](C(=O)N(C)[C@H](/C=C(\C)C(=O)NS(=O)(=O)Cc1ccc(N)cc1)C(C)C)C(C)(C)C)C(C)(C)c1ccccc1]

Chemical Formula: $C_{34}H_{49}N_5O_7S$
Exact Mass: 671.34

Example 67

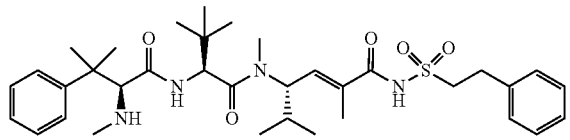

Chemical Formula: C₃₅H₅₂N₄O₅S
Exact Mass: 640.37

(S,E)-2,5-dimethyl-N-(phenethylsulfonyl)-4-((S)—N,3,3-trimethyl-2-((S)-3-methyl-2-(methylamino)-3-phenylbutanamido)butanamido)hex-2-enamide Title compound was prepared from Example 3 and homobenzylsulfonamide using General Procedures 2 and 7.

¹H NMR (400 MHz, Methanol-d₄) δ 7.56 (d, J=7.6 Hz, 2H), 7.48 (t, J=7.5 Hz, 2H), 7.38 (t, J=7.4 Hz, 1H), 7.34-7.28 (m, 2H), 7.28-7.20 (m, 3H), 6.47 (dd, J=9.2, 1.7 Hz, 1H), 5.03 (t, J=10.0 Hz, 1H), 4.94 (s, 1H), 4.36 (d, J=2.3 Hz, 2H), 3.78 (td, J=7.5, 4.1 Hz, 2H), 3.17 (s, 3H), 3.12 (t, J=7.8 Hz, 2H), 2.51 (s, 3H), 2.14-2.01 (m, 1H), 1.89 (d, J=1.4 Hz, 3H), 1.49 (s, 3H), 1.39 (s, 3H), 1.09 (s, 9H), 0.94 (d, J=6.6 Hz, 3H), 0.91 (d, J=6.6 Hz, 3H).

C₃₅H₅₂N₄O₅S calcd. m/z=640.37 found [M+H]⁺=641.36.

Example 68

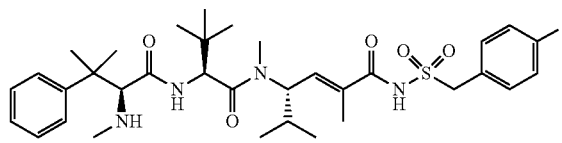

Chemical Formula: C₃₄H₄₉BrN₄O₅S
Exact Mass: 704.26

(S,E)-N-(4-bromobenzylsulfonyl)-2,5-dimethyl-4-((S)—N,3,3-trimethyl-2-((S)-3-methyl-2-(methylamino)-3-phenylbutanamido)butanamido)hex-2-enamide Title compound was prepared from Example 3 and 4-bromobenzylsulfonamide using General Procedures 2 and 7.

¹H NMR (400 MHz, Methanol-d₄) δ 7.60-7.51 (m, 4H), 7.48 (t, J=7.7 Hz, 2H), 7.39 (s, 1H), 7.31 (d, J=8.3 Hz, 2H), 6.38 (d, J=9.3 Hz, 1H), 5.06 (t, J=10.0 Hz, 1H), 4.93 (s, 1H), 4.74 (s, 2H), 4.36 (s, 1H), 3.13 (s, 3H), 2.52 (s, 3H), 2.03-1.98 (m, 1H), 1.95 (d, J=1.4 Hz, 3H), 1.49 (s, 3H), 1.39 (s, 3H), 1.09 (s, 9H), 0.91 (d, J=6.1 Hz, 3H), 0.89 (d, J=6.3 Hz, 3H)

C₃₄H₄₉BrN₄O₅S calcd. m/z=704.26 found [M+H]⁺=705.23.

Example 69

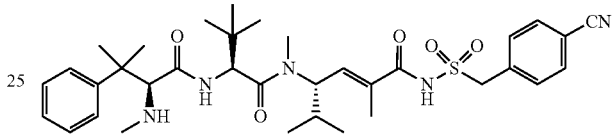

Chemical Formula: C₃₅H₄₉N₅O₅S
Exact Mass: 651.35

(S,E)-N-(4-cyanobenzylsulfonyl)-2,5-dimethyl-4-((S)—N,3,3-trimethyl-2-((S)-3-methyl-2-(methylamino)-3-phenylbutanamido)butanamido)hex-2-enamide Title compound was prepared from Example 3 and 4-cyanobenzylsulfonamide using General Procedures 2 and 7.

¹H NMR (400 MHz, Methanol-d₄) δ 7.77 (d, J=8.3 Hz, 2H), 7.64-7.53 (m, 4H), 7.48 (t, J=7.7 Hz, 2H), 7.38 (t, J=7.3 Hz, 1H), 6.41 (dd, J=9.3, 1.7 Hz, 1H), 5.05 (t, J=10.0 Hz, H), 4.94 (s, 1H), 4.87 (s, 2H), 4.36 (s, 1H), 3.14 (s, 3H), 2.52 (s, 3H), 2.06-1.98 (m, 1H), 1.95 (d, J=1.4 Hz, 3H), 1.49 (s, 3H), 1.39 (s, 3H), 1.09 (s, 9H), 0.91 (d, J=4.0 Hz, 3H), 0.90 (d, J=4.0 Hz, 3H).

C₃₅H₄₉N₅O₅S calcd. m/z=651.35 found [M+H]⁺=652.38.

Example 70

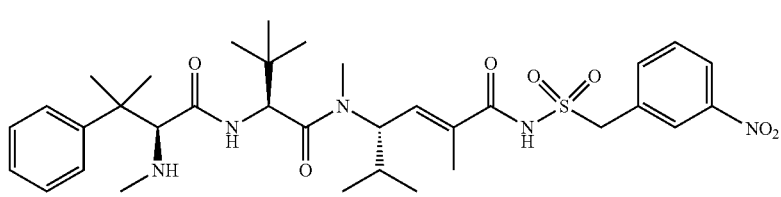

Chemical Formula: C₃₄H₄₉N₅O₇S
Exact Mass: 671.34

(S,E)-2,5-dimethyl-N-(3-nitrobenzylsulfonyl)-4-((S)—N,3,3-trimethyl-2-((S)-3-methyl-2-(methylamino)-3-phenylbutanamido)butanamido)hex-2-enamide Title compound was prepared from Example 3 and 3-nitrobenzylsulfonamide using General Procedures 2 and 7.

$^1$H NMR (400 MHz, Methanol-$d_4$) δ 8.29 (d, J=8.0 Hz, 1H), 8.26 (s, 1H), 7.83 (d, J=7.8 Hz, 1H), 7.67 (t, J=8.0 Hz, 1H), 7.56 (d, J=7.2 Hz, 2H), 7.48 (t, J=7.7 Hz, 2H), 7.38 (t, J=7.3 Hz, 1H), 6.43 (dd, J=9.4, 1.7 Hz, 1H), 5.05 (t, J=10.0 Hz, 1H), 4.93 (s, 2H), 4.93 (s, 1H), 4.36 (s, 1H), 3.13 (s, 3H), 2.52 (s, 3H), 2.08-1.98 (m, 1H), 1.96 (d, J=1.4 Hz, 3H), 1.48 (s, 3H), 1.39 (s, 3H), 1.07 (s, 9H), 0.89 (d, J=6.6 Hz, 3H), 0.88 (d, J=6.6 Hz, 3H).

$C_{34}H_{49}NSO_7S$ calcd. m/z=671.34 found [M+H]$^+$=672.39.

Example 71

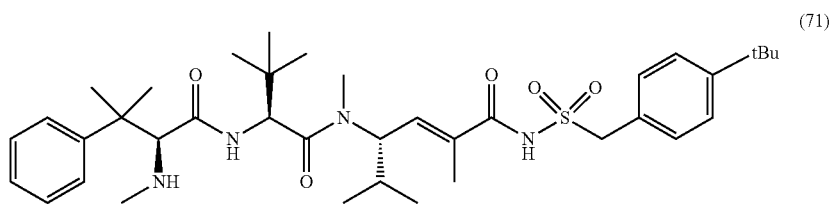

Chemical Formula: $C_{38}H_{58}N_4O_5S$
Exact Mass: 682.41

(S,E)-N-(4-tert-butylbenzylsulfonyl)-2,5-dimethyl-4-((S)—N,3,3-trimethyl-2-((S)-3-methyl-2-(methylamino)-3-phenylbutanamido)butanamido)hex-2-enamide Title compound was prepared from Example 3 and 4-t-butylbenzylsulfonamide using General Procedures 2 and 7.

$^1$H NMR (400 MHz, Methanol-$d_4$) δ 7.56 (d, J=7.6 Hz, 2H), 7.48 (t, J=7.7 Hz, 2H), 7.43 (d, J=8.2 Hz, 2H), 7.38 (t, J=7.3 Hz, 1H), 7.30 (d, J=8.2 Hz, 2H), 6.39 (dd, J=9.4, 1.6 Hz, 1H), 5.07 (t, J=10.0 Hz, 1H), 4.93 (s, 1H), 4.72 (s, 2H), 4.37 (s, 1H), 3.13 (s, 3H), 2.52 (s, 3H), 2.06-1.98 (m, 1H), 1.96 (d, J=1.4 Hz, 3H), 1.49 (s, 3H), 1.39 (s, 3H), 1.33 (s, 9H), 1.10 (s, 9H), 0.92 (d, J=6.6 Hz, 3H), 0.89 (d, J=6.5 Hz, 3H).

$C_{38}H_{58}N_4O_5S$ calcd. m/z=682.41 found [M+H]$^+$=683.47.

Example 72

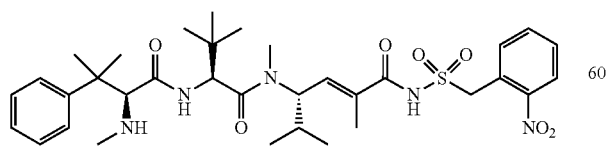

Chemical Formula: $C_{34}H_{49}N_5O_7S$
Exact Mass: 671.34

(S,E)-2,5-dimethyl-N-(2-nitrobenzylsulfonyl)-4-((S)—N,3,3-trimethyl-2-((S)-3-methyl-2-(methylamino)-3-phenylbutanamido)butanamido)hex-2-enamide Title compound was prepared from Example 3 and 2-nitrobenzylsulfonamide using General Procedures 2 and 7.

$^1$H NMR (400 MHz, Methanol-d$_4$) δ 8.03 (dd. J=8.0, 1.4 Hz, 1H), 7.72 (td, J=7.5, 1.5 Hz, 1H), 7.65 (td, J=7.7, 1.6 Hz, 1H), 7.60 (dd, J=7.6, 1.6 Hz, 1H), 7.56 (d, J=7.2 Hz, 2H), 7.48 (t, J=7.7 Hz, 2H), 7.38 (t, J=7.3 Hz, 1H), 6.43 (dd, J=9.4, 1.6 Hz, 1H), 5.31 (d, J=14.2 Hz, 1H), 5.26 (d, J=15.3 Hz, 1H), 5.06 (t, =10.0 Hz, 1H), 4.94 (s, 1H), 4.37 (s, 1H), 3.15 (s, 3H), 2.52 (s, 3H), 2.08-1.98 (m, 1H), 1.96 (d, J=1.4 Hz, 3H), 1.49 (s, 3H), 1.39 (s, 3H), 1.10 (s, 9H), 0.92 (d, J=6.6 Hz, 3H), 0.90 (d, J=6.6 Hz, 3H).

$C_{34}H_{49}N_5O_7S$ calcd. m/z=671.34 found [M+H]$^+$=672.39.

Example 73

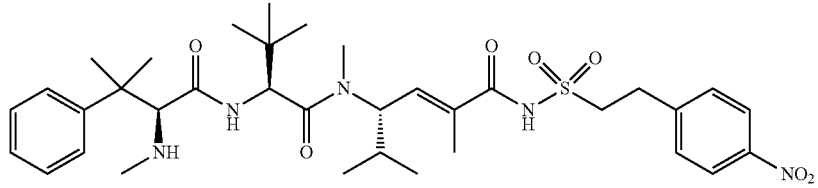

(73)

Chemical Formula: $C_{35}H_{51}N_5O_7S$
Exact Mass: 685.35

(S,E)-2,5-dimethyl-N-(4-nitrophenethylsulfonyl)-4-((S)—N,3,3-trimethyl-2-((S)-3-methyl-2-(methylamino)-3-phenylbutanamido)butanamido)hex-2-enamide Title compound was prepared from Example 3 and 4-nitro-homobenzylsulfonamide using General Procedures 2 and 7.

1H NMR (400 MHz, Methanol-d4) δ 8.19 (d, J=8.7 Hz, 2H), 7.58-7.51 (m, 4H), 7.47 (t, J=7.6 Hz, 2H), 7.37 (t, J=7.3 Hz, 1H), 6.47 (dd, J=9.5, 1.7 Hz, 1H), 5.00 (t, J=10.0 Hz, 1H), 4.93 (s, 1H), 4.36 (s, 1H), 3.91 (dd, J=14.9, 8.5 Hz, 1H), 3.84 (dd, J=12.9, 8.5 Hz, 1H), 3.28 (t, J=7.5 Hz, 2H), 3.16 (s, 3H), 2.51 (s, 3H), 2.12-1.98 (m, 1H), 1.87 (d, J=1.4 Hz, 3H), 1.48 (s, 3H), 1.39 (s, 3H), 1.08 (s, 9H), 0.91 (d, J=6.6 Hz, 3H), 0.91 (d, J=6.6 Hz, 3H).

$C_{35}H_{51}N_5O_7S$ calcd. m/z=685.35 found [M+H]$^+$=686.38.

Example 74

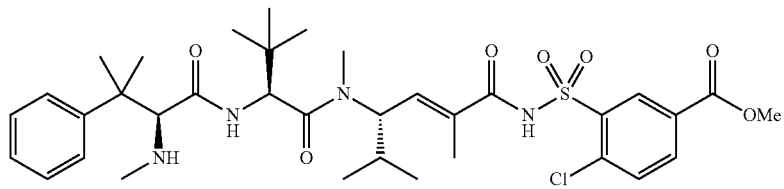

(74)

Chemical Formula: $C_{35}H_{49}ClN_4O_7S$
Exact Mass: 704.30
Molecular Weight: 705.30 methyl 4-chloro-3-(N—((S,E)-2,5-dimethyl-4-((S)—N,3,3-trimethyl-2-((S)-3-methyl-2-(methylamino)-3-phenylbutanamido)butanamido)hex-2-enoyl)sulfamoyl)benzoate Title compound was prepared from Example 3 and methyl 4-chloro-3-sulfamoylbenzoate using General Procedures 2 and 7.

$^1$H NMR (400 MHz, Methanol-d$_4$) δ 8.80 (d, J=2.1 Hz, 1H), 8.20 (dd, J=8.3, 2.1 Hz, 1H), 7.71 (d, J=8.3 Hz, 1H), 7.59-7.52 (m, 2H), 7.47 (t, J=7.7 Hz, 2H), 7.40-7.32 (m, 1H), 6.63-6.56 (m, 1H), 5.02 (t, J=10.0 Hz, 1H), 4.37 (s, 1H), 3.98 (s, 3H), 3.18 (s, 3H), 2.51 (s, 3H), 2.13-2.00 (m, 1H), 1.86 (d, J=1.4 Hz, 3H), 1.47 (s, 3H), 1.37 (s, 3H), 1.06 (s, 9H), 0.96-0.87 (m, 6H).

$^{13}$C NMR (101 MHz, Methanol-d$_4$) δ 170.87, 165.65, 164.87, 143.61, 137.01, 136.04, 134.29, 133.23, 131.81, 129.16, 128.98, 128.88, 127.50, 125.98, 69.81, 65.53, 57.39, 56.35, 56.15, 55.37, 51.86, 40.70, 34.51, 32.77, 30.80, 29.39, 28.44, 26.18, 25.56, 20.06, 18.40, 14.06, 12.74.

C$_{35}$H$_{49}$ClN$_4$O$_7$S calcd m/z=704.30 amu; found [M+H]$^+$=705.25, [M+Na]$^+$=727.25.

Example 75

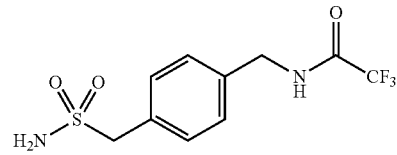

2,2,2-trifluoro-N-(4-(sulfamoylmethyl)benzyl)acetamide

The title compound was synthesized from commercially available (4-(aminomethyl)phenyl)methanesulfonamide and TFAA using General Procedure 1.

$^1$H NMR (400 MHz, Acetone-d$_6$) δ 9.05 (s, 1H), 7.48-7.40 (m, 2H), 7.40-7.32 (m 2H), 6.17 (s, 1H), 4.56 (d, J=6.1 Hz, 2H), 4.35 (s, 2H)

Example 76

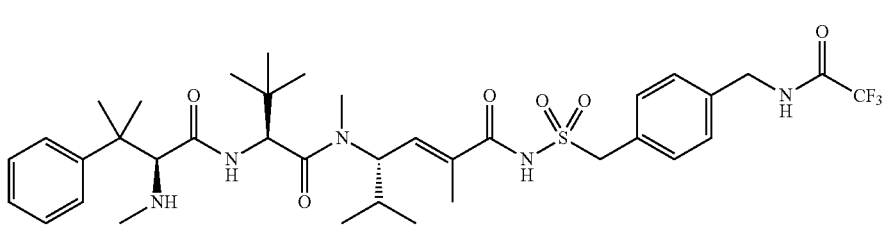

Chemical Formula: C$_{37}$H$_{52}$F$_3$N$_5$O$_6$S
Exact Mass: 751.36
Molecular Weight: 751.90

(S,E)-2,5-dimethyl-N-(4-((2,2,2-trifluoroacetamido)methyl) benzylsulfonyl)-4-((S)—N,3,3-trimethyl-2-((S)-3-methyl-2-(methylamino)-3-phenylbutanamido)butanamido)hex-2-enamide Title compound was prepared from Example 3 and Example 75 using General Procedures 2 and 7.

$^1$H NMR (400 MHz, Methanol-d$_4$) δ 7.57-7.49 (m, 2H), 7.45 (t, J=7.5 Hz, 2H), 7.33 (p, J=8.8, 7.9 Hz, 5H), 6.37 (d, J=9.7 Hz, 1H), 5.09-5.00 (m, 1H), 4.69 (s, 2H), 4.44 (s, 2H), 4.30 (s, 1H), 3.10 (s, 3H), 2.45 (d, J=17.5 Hz, 3H), 2.02-1.87 (m, 4H), 1.46 (s, 3H), 1.37 (s, 3H), 1.07 (s, 9H), 0.95-0.81 (m, 6H).

$^{19}$F NMR (377 MHz, Methanol-d$_4$) δ -76.94, -77.24.

C$_{37}$H$_{52}$F$_3$N$_5$O$_6$S calcd m/z=751.36 amu; found [M+H]$^+$=752.46, [M+Na]$^+$=774.38.

Example 77

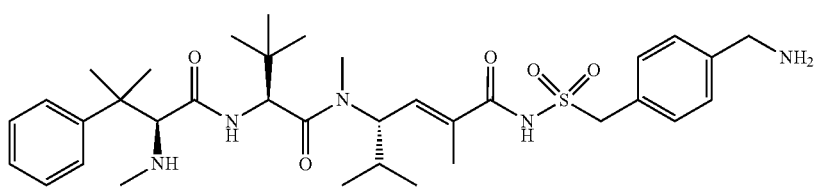

(S,E)-N-(4-(aminomethyl)benzylsulfonyl)-2,5-dimethyl-4-((S)—N,3,3-trimethyl-2-((S)-3-methyl-2-(methylamino)-3-phenylbutanamido)butanamido)hex-2-enamide Prepared from Example 3 and Example 75 using General Procedures 2, 3 and 7

$^1$H NMR (400 MHz, Methanol-$d_4$) δ 7.60-7.54 (m, 2H), 7.54-7.50 (m, 4H), 7.47 (d, J=8.1 Hz, 2H), 7.37 (t, J=7.4 Hz, 1H), 6.49 (dd, J=9.5, 1.5 Hz, 1H), 5.07 (t, J=10.0 Hz, 1H), 4.94 (s, 1H), 4.83 (d, J=14.3 Hz, 1H), 4.79 (d, J=13.9 Hz, 1H), 4.38 (s, 1H), 4.16 (s, 2H), 3.16 (s, 3H), 2.52 (s, 3H), 2.10-2.00 (m, 1H), 1.97 (d, J=1.4 Hz, 3H), 1.49 (s, 3H), 1.40 (s, 3H), 1.10 (s, 9H), 0.93 (d, J=6.9 Hz, 3H), 0.91 (d, J=7.0 Hz, 3H).

$C_{35}H_{53}N_5O_5S$ calcd. m/z=655.4; found [M+H]$^+$=656.3. [M+2H]$^+$=328.8.

Example 78

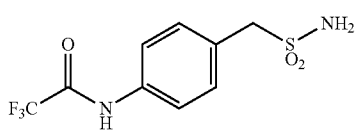

(78)

2,2,2-trifluoro-N-(4-(sulfamoylmethyl)phenyl)acetamide

The title compound was synthesized from commercially available (4-aminophenyl)methanesulfonamide and TFAA using General Procedure 1.

$^1$H NMR (400 MHz, DMSO-$d_6$) δ 11.31 (s, 1H), 7.79-7.51 (m, 2H), 7.51-7.23 (m, 2H), 6.85 (s, 2H), 4.27 (s, 2H).

Example 79

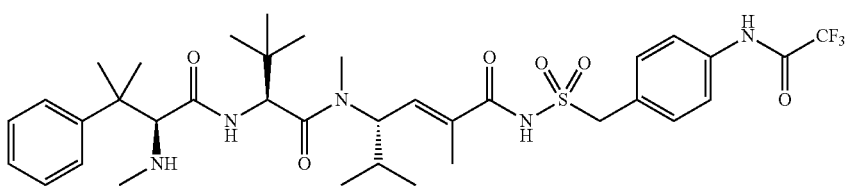

(79)

Chemical Formula: $C_{36}H_{50}F_3N_5O_6S$
Exact Mass: 737.34
Molecular Weight: 737.87

(S,E)-2,5-dimethyl-N-(4-(2,2,2-trifluoroacetamido)benzylsulfonyl)-4-((S)—N,3,3-trimethyl-2-((S)-3-methyl-2-(methylamino)-3-phenylbutanamido)butanamido)hex-2-enamide Title compound was prepared from Example 3 and Example 78 using General Procedures 2 and 7.

$^1$H NMR (400 MHz, Methanol-$d_4$) δ 7.68 (d, J=8.6 Hz, 2H), 7.54 (d, J=7.1 Hz, 2H), 7.45 (t, J=7.6 Hz, 2H), 7.37 (dd, J=10.6, 5.0 Hz, 3H), 6.34 (d, 1=9.4 Hz, 1H), 5.04 (t, J=10.1 Hz, 2H), 4.74 (s, 2H), 4.35 (s, 1H), 3.10 (s, 3H), 2.49 (s, 3H), 2.02-1.94 (m, 1H), 1.93 (d, J=1.4 Hz, 3H), 1.46 (s, 3H), 1.37 (s, 3H), 1.06 (s, 9H), 0.88 (d, J=6.3 Hz, 3H), 0.86 (s, 3H).

$^{19}$F NMR (377 MHz, Methanol-$d_4$) δ −76.97, −77.05.

$C_{36}H_{50}F_3N_5O_6S$ calcd m/z=737.34 amu; found [M+H]$^+$=738.38, [M+Na]$^+$=760.35.

Example 80

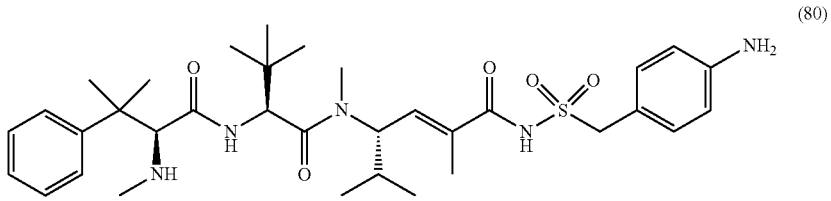

(S,E)-N-(4-aminobenzylsulfonyl)-2,5-dimethyl-4-((S)—N,3,3-trimethyl-2-((S)-3-methyl-2-(methyl-amino)-3-phenylbutanamido)butanamido)hex-2-enamide Title compound was prepared from Example 3 and Example 78 using General Procedures 2, 3 and 7

$^1$H NMR (400 MHz, Methanol-$d_4$) δ 7.56 (d, J=7.6 Hz, 2H), 7.48 (t, J=7.7 Hz, 2H), 7.37 (t, J=7.3 Hz, 1H), 7.20 (d, J=8.5 Hz, 2H), 6.87 (d, J=8.5 Hz, 2H), 6.39 (d, J=9.4 Hz, 1H), 5.07 (t, J=10.0 Hz, 1H), 4.95 (s, 1H), 4.64 (s, 2H), 4.38 (s, 1H), 3.14 (s, 3H), 2.52 (s, 3H), 2.07-1.98 (m, 1H), 1.96 (d, J=1.4 Hz, 3H), 1.49 (s, 3H), 1.39 (s, 3H), 1.10 (s, 9H), 0.92 (d, J=6.7 Hz, 3H), 0.90 (d, J=6.4 Hz, 3H).

$C_{34}H_{51}N_5O_5S$ calcd. m/z=641.4; found [M+H]$^+$=642.3.

Example 81

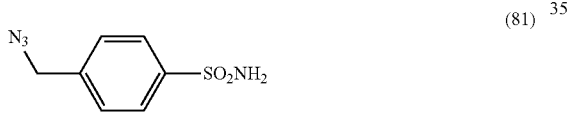

4-(azidomethyl)benzenesulfonamide

To a stirred solution of 4-(bromomethyl)benzenesulfonamide (0.50 g) in N,N-dimethylformamide (1 mL) was added sodium azide (0.20 g). The suspension was heated to 50° C. for 3 hours at which points the solvent was removed under reduced pressure. The residue was partitioned between ethyl acetate and water. The organic phase was washed with brine, dried over magnesium sulfate, filtered and concentrated to dryness to give the title compound as a syrup that solidified on standing.

$^1$H NMR (400 MHz, Chloroform-d) δ 8.06-7.91 (m, 2H), 7.58-7.44 (m, 2H), 4.96 (s, 2H), 4.48 (s, 2H).

Example 82

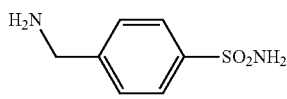

4-(aminomethyl)benzenesulfonamide

To a solution of 4-(azidomethyl)benzenesulfonamide (0.354 g) in methanol (10 mL) in a round bottom flask equipped with a magnetic stirrer was added 10% Pd/C (~0.05 g). The flask was evacuated of gases at reduced pressure and charged with hydrogen. This evacuation and charge was repeated three times at which point the suspension was left to stir overnight. At 16 h, TLC analysis indicated complete consumption of the starting material. The reaction was diluted with methanol (40 mL), celite was added and the mixture was filtered through a fritted glass funnel. The resulting solution was concentrated to dryness. $^1$H NMR suggested that the material was sufficiently clean at this stage for further use without purification.

$^1$H NMR (400 MHz, DMSO-$d_6$) δ 7.77 (m, 2H), 7.53 (m, 2H), 5.76 (s, 2H), 3.76 (d, J=11.9 Hz, 2H).

Example 83

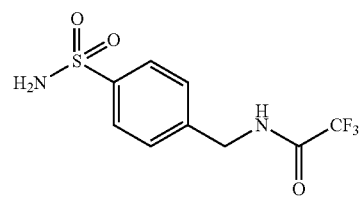

2,2,2-trifluoro-N-(4-sulfamoylbenzyl)acetamide

The title compound was synthesized by reaction of 4-(aminomethyl)benzenesulfonamide with TFAA according to General Procedure 1, with a $^1$H NMR spectrum that was complicated by rotamers.

$^1$H NMR (400 MHz, DMSO-$d_6$) δ 7.91-7.75 (m, 2H), 7.55-7.31 (m, 4H), 4.72 (m, 2H), 4.47 (d, J=6.0 Hz, 1H), 3.18 (s, 2H).

Example 84

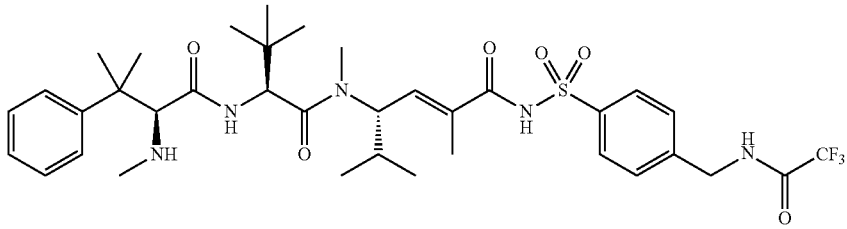

(84)

Chemical Formula: $C_{36}H_{50}F_3N_5O_6S$
Exact Mass: 737.34
Molecular Weight: 737.87

(S,E)-2,5-dimethyl-N-(4-((2,2,2-trifluoroacetamido)methyl) phenylsulfonyl)-4-((S)—N,3,3-trimethyl-2-((S)-3-methyl-2-(methylamino)-3-phenylbutanamido)butanamido)hex-2-enamide Title compound was prepared from Example 3 and Example 83 using General Procedures 2 and 7.

$^1$H NMR (400 MHz, Methanol-$d_4$) δ 8.02 (d, J=8.5 Hz, 2H), 7.58-7.42 (m, 7H), 7.35 (t, J=7.3 Hz, 1H), 6.46 (d, J=8.5 Hz, 1H), 4.97 (d, J=10.4 Hz, 1H), 4.54 (s, 2H), 4.33 (s, 1H), 3.14 (s, 3H), 2.48 (s, 3H), 2.11-1.97 (m, 1H), 1.83 (d, J=1.4 Hz, 3H), 1.53 (s, 1H), 1.44 (s, 3H), 1.34 (s, 3H), 1.04 (s, 9H), 0.89 (d, J=3.9 Hz, 3H), 0.88 (d, J=4.1 Hz, 3H).

$^{19}$F NMR (377 MHz, Methanol-$d_4$) δ −76.94, −77.26.

$C_{36}H_{50}F_3N_5O_6S$ calcd m/z=737.34 amu; found [M+H]$^+$=738.39, [M+Na]$^+$=760.41.

Example 85

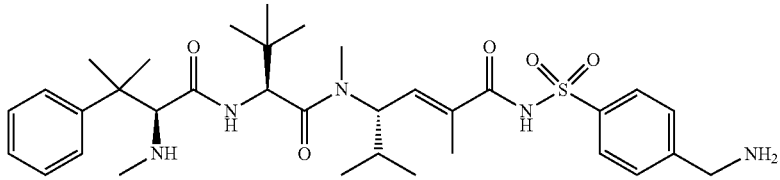

(85)

Chemical Formula: $C_{34}H_{51}N_5O_5S$
Exact Mass: 641.36

(S,E)-N-(4-(aminomethyl)phenylsulfonyl)-2,5-dimethyl-4-((S)—N,3,3-trimethyl-2-((S)-3-methyl-2-(methylamino)-3-phenylbutanamido)butanamido)hex-2-enamide Prepared from Example 3 and Example 83 using General Procedures 2, 3 and 7

$^1$H NMR (400 MHz, Methanol-$d_4$) δ 8.13 (d, J=8.3 Hz, 2H), 7.68 (d, J=8.3 Hz, 2H), 7.55 (d, J=7.6 Hz, 2H), 7.47 (t, J=7.7 Hz, 2H), 7.37 (t, J=7.3 Hz, 1H), 6.51 (dd, J=9.2, 1.8 Hz, 1H), 5.01 (t, J=10.0 Hz, 1H), 4.37 (s, 1H), 4.24 (s, 2H), 3.17 (s, 3H), 2.51 (s, 3H), 2.13-1.97 (m, 1H), 1.84 (d, J=1.4 Hz, 3H), 1.47 (s, 3H), 1.37 (s, 3H), 1.07 (s, 9H), 0.91 (dd, J=6.7, 2.0 Hz, 7H).

$C_{34}H_{51}N_5OS$ calcd m/z=641.36 amu; found [M+H]$^+$=642.4.

Example 86

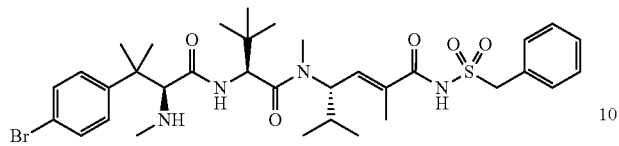

(86)

Chemical Formula: C$_{34}$H$_{49}$BrN$_4$O$_5$S
Exact Mass: 704.26
Molecular Weight: 705.75

(S,E)-N-(benzylsulfonyl)-4-((S)-2-((S)-3-(4-bromophenyl)-3-methyl-2-(methylamino)butanamido)-N,3,3-trimethylbutanamido)-2,5-dimethylhex-2-enamide Title compound was prepared from Example 38 and (S,E)-4-((S)-2-amino-N,3,3-trimethylbutanamido)-N-(benzylsulfonyl)-2,5-dimethylhex-2-enamide using General Procedures 4 and 7.

$^1$H NMR (400 MHz, Methanol-d$_4$) δ 7.62 (t, J=9.2 Hz, 2H), 7.50-7.43 (m, 2H), 7.38 (d, J=2.2 Hz, 5H), 6.38 (dd, J=9.5, 1.8 Hz, 1H), 5.05 (t, J=10.0 Hz, 1H), 4.92 (s, 1H), 4.75 (d, J=2.2 Hz, 2H), 4.30 (s, 1H), 3.12 (s, 3H), 2.53 (s, 3H), 2.06-1.97 (m, 1H), 1.95 (d, J=1.5 Hz, 3H), 1.47 (s, 3H), 1.39 (s, 3H), 1.09 (s, 9H), 0.94-0.86 (m, 6H).

C$_{34}$H$_{49}$BrN$_4$O$_5$S calcd m/z=704.26 amu; found [M+H]$^+$=705.29, [M+Na]$^+$=727.36.

Example 87

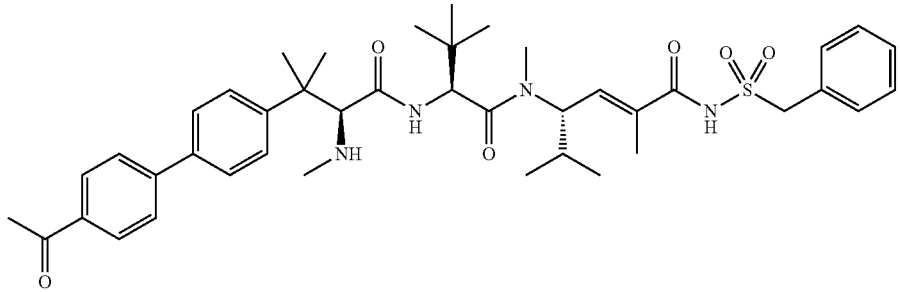

(87)

Chemical Formula: C$_{42}$H$_{56}$N$_4$O$_6$S
Exact Mass: 744.39
Molecular Weight: 744.98

(S,E)-4-((S)-2-((S)-3-(4'-acetylbiphenyl-4-yl)-3-methyl-2-(methylamino)butanamido)-N,3,3-trimethylbutanamido)-N-(benzylsulfonyl)-2,5-dimethylhex-2-enamide Title compound was prepared according to General Procedure 8 from Boc protected Example 86 and 4-acetylphenylboronic acid.

$^1$H NMR (400 MHz, Methanol-d$_4$) δ 8.15-8.08 (m, 2H), 7.86-7.76 (m, 4H), 7.66 (dd, J=14.7, 8.4 Hz, 2H), 7.38 (d, J=4.9 Hz, 5H), 6.39 (d, J=9.3 Hz, 1H), 5.05 (t, J=10.1 Hz, 1H), 4.94 (s, 1H), 4.75 (d, J=4.1 Hz, 2H), 4.37 (d, J=16.1 Hz, 1H), 3.13 (d, J=3.4 Hz, 3H), 2.67 (s, 3H), 2.53 (d, J=11.6 Hz, 3H), 2.01 (s, 1H), 1.96 (d, J=1.5 Hz, 3H), 1.54 (d, J=3.7 Hz, 3H), 1.44 (s, 3H), 1.09 (d, J=2.7 Hz, 9H), 0.96-0.83 (m, 6H).

C$_{42}$H$_{56}$N$_4$O$_6$S calcd m/z=744.39 amu; found [M+H]$^+$=745.42, [M+Na]$^+$=767.36.

Example 88

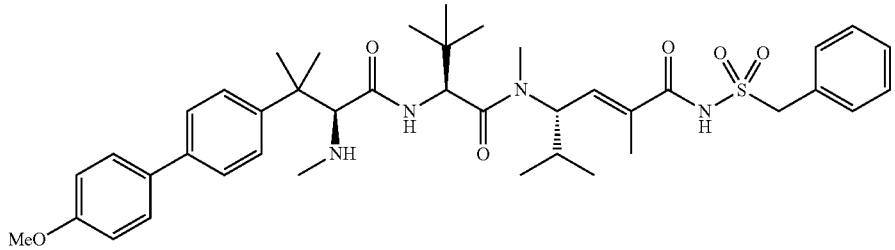

(88)

Chemical Formula: $C_{41}H_{56}N_4O_6S$
Exact Mass: 732.39
Molecular Weight: 732.97

(S,E)-N-(benzylsulfonyl)-4-((S)-2-((S)-3-(4'-methoxybiphenyl-4-yl)-3-methyl-2-(methylamino)butanamido)-N,3,3-trimethylbutanamido)-2,5-dimethylhex-2-enamide Title compound was prepared according to General Procedure 8 from Boc protected Example 86 and 4-methoxyphenylboronic acid.

$^1$H NMR (400 MHz, Methanol-$d_4$) δ 7.74-7.53 (m, 6H), 7.38 (d, J=4.7 Hz, 5H), 7.08-6.99 (m, 2H), 6.43-6.35 (m, 1H), 5.06 (s, 1H), 4.94 (s, 1H), 4.75 (d, J=4.1 Hz, 2H), 4.38 (s, 1H), 3.86 (s, 3H), 3.13 (s, 3H), 2.54 (s, 3H), 1.99 (d, J=11.0 Hz, 1H), 1.96 (d, J=1.5 Hz, 3H), 1.51 (s, 3H), 1.43 (s, 3H), 1.09 (s, 9H), 0.96-0.85 (m, J=6.0, 5.1 Hz, 6H).

$C_{41}H_{56}N_4O_FS$ calcd m/z=732.39 amu; found [M+H]$^+$=733.41, [M+Na]$^+$=755.40.

Example 89

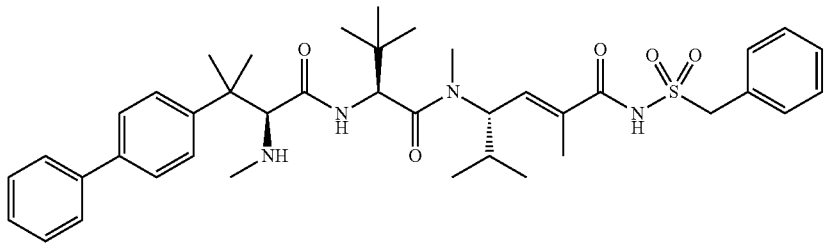

(89)

Chemical Formula: $C_{40}H_{54}N_4O_5S$
Exact Mass: 702.38
Molecular Weight: 702.95

(S,E)-N-(benzylsulfonyl)-4-((S)-2-((S)-3-(biphenyl-4-yl)-3-methyl-2-(methylamino)butanamido)-N,3,3-trimethylbutanamido)-2,5-dimethylhex-2-enamide Title compound was prepared according to General Procedure 8 from Boc protected Example 86 and phenylboronic acid.

$^1$H NMR (400 MHz, Methanol-$d_4$) δ 7.86-7.51 (m, 6H), 7.48 (t, J=7.6 Hz, 2H), 7.43-7.33 (m, 6H), 6.39 (d, J=9.5 Hz, 1H), 5.06 (t, J=10.1 Hz, 1H), 4.94 (s, 1H), 4.75 (d, J=3.3 Hz, 2H), 4.37 (d, J=14.4 Hz, 1H), 3.13 (d, J=3.7 Hz, 3H), 2.55 (d, J=4.5 Hz, 3H), 2.06-1.97 (m, 1H), 1.96 (d, J=1.5 Hz, 3H), 1.52 (s, 3H), 1.44 (d, J=4.5 Hz, 3H), 1.09 (d, J=5.6 Hz, 9H), 0.96-0.83 (m, 6H).

$C_{40}H_{54}N_4O_5S$ calcd m/z=702.38 amu; found [M+H]$^+$=703.40, [M+Na]$^+$=725.45.

Example 90

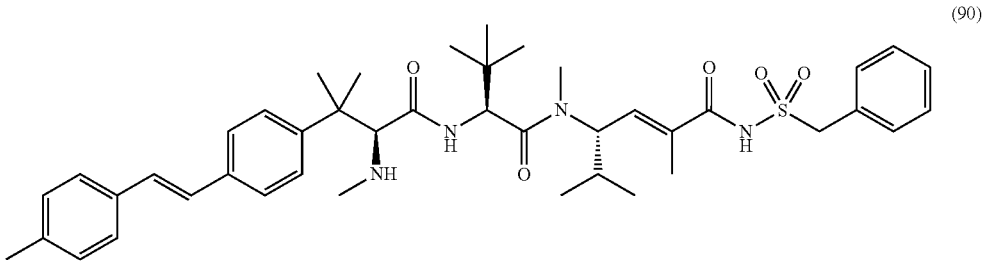

Chemical Formula: C₄₃H₅₈N₄O₅S
Exact Mass: 742.41
Molecular Weight: 743.01

(S,E)-N-(benzylsulfonyl)-2,5-dimethyl-4-((S)—N,3,
3-trimethyl-2-((S)-3-methyl-2-(methylamino)-3-(4-
(4-methylstyryl)phenyl)butanamido)butanamido)
hex-2-enamide Title compound was prepared according to General Procedure 8 from Boc protected Example 86 and (E)-4-methylstyrylboronic acid.
$^1$H NMR (400 MHz, Methanol-d$_4$) δ 7.65 (d, J=8.2 Hz, 2H), 7.54 (d, J=8.2 Hz, 2H), 7.47 (d, J=7.8 Hz, 2H), 7.38 (s, 5H), 7.26-7.11 (m, 4H), 6.39 (d, J=9.3 Hz, 1H), 5.06 (t, J=10.0 Hz, 1H), 4.97-4.91 (m, 1H), 4.76 (s, 2H), 4.36 (s, 1H), 3.12 (d, J=8.9 Hz, 3H), 2.54 (s, 3H), 2.37 (s, 3H), 2.05-1.97 (m, 1H), 1.97-1.93 (m, 3H), 1.49 (s, 3H), 1.41 (s, 3H), 1.09 (d, J=3.5 Hz, 9H), 0.91 (tq, J=10.8, 4.9 Hz, 6H).
C₄₃H₅₈N₄O₅S calcd m/z=742.41 amu; found [M+H]⁺=743.44, [M+Na]⁺=765.41.

Example 91

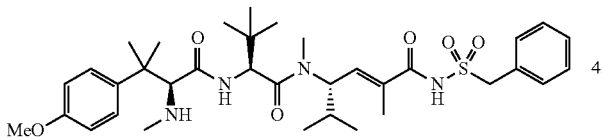

Chemical Formula: C₃₅H₅₂N₄O₆S
Exact Mass: 656.36
Molecular Weight: 656.88

(S,E)-N-(benzylsulfonyl)-4-((S)-2-((S)-3-(4-
methoxyphenyl)-3-methyl-2-(methylamino)butana-
mido)-N,3,3-trimethylbutanamido)-2,5-dimethylhex-
2-enamide Title compound was prepared according to General Procedure 9 from Boc protected Example 86.
Major Diastereomer:
$^1$H NMR (400 MHz, Methanol-d$_4$) δ 7.44 (dd, J=12.9, 8.6 Hz, 2H), 7.40-7.34 (m, 5H), 7.00 (t, J=8.4 Hz, 2H), 6.38 (d, J=9.2 Hz, 1H), 5.05 (t, J=9.9 Hz, 1H), 4.93 (s, 1H), 4.75 (d, J=1.8 Hz, 2H), 4.29 (s, 1H), 3.84 (s, 3H), 3.12 (s, 3H), 2.51 (s, 3H), 2.04-1.98 (m, 1H), 1.95 (d, J=1.4 Hz, 3H), 1.45 (s, 3H), 1.37 (s, 3H), 1.09 (s, 9H), 0.92-0.86 (m, 6H).

Minor Diastereomer:
$^1$H NMR (400 MHz, Methanol-d$_4$) δ 7.44 (dd, J=12.9, 8.6 Hz, 2H), 7.40-7.34 (m, 5H), 7.00 (t, J=8.4 Hz, 2H), 6.38 (d, J=9.2 Hz, 1H), 4.99 (t, J=10.1 Hz, 1H), 4.93 (s, 1H), 4.75 (d, J=1.8 Hz, 2H), 4.26 (s, 1H), 3.82 (s, 3H), 3.11 (s, 3H), 2.47 (s, 3H), 2.04-1.98 (m, 1H), 1.92 (d, J=1.4 Hz, 3H), 1.53 (s, 3H), 1.48 (s, 3H), 0.94 (s, 9H), 0.92-0.86 (m, 6H).
C₃₅H₅₂N₄O₆S calcd m/z=656.36 amu; found [M+H]⁺=657.35, [M+Na]⁺=679.25.

Example 92

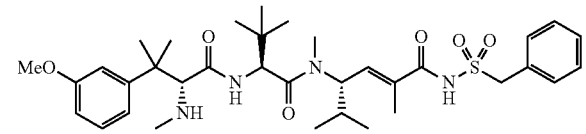

Chemical Formula: C₃₅H₅₂N₄O₆S
Exact Mass: 656.36
Molecular Weight: 656.88

(S,E)-N-(benzylsulfonyl)-4-((S)-2-((R)-3-(3-
methoxyphenyl)-3-methyl-2-(methylamino)butana-
mido)-N,3,3-trimethylbutanamido)-2,5-dimethylhex-
2-enamide Title compound was prepared according to General Procedure 9 from Boc protected (S,E)-N-(benzylsulfonyl)-4-((S)-2-((S)-3-(3-bromophenyl)-3-methyl-2-(methylamino)butanamido)-N,3,3-trimethylbutanamido)-2,5-dimethylhex-2-enamide. The two diastereomeric products resulted from diastereomerically impure starting material and were separable by prep-scale HPLC.
Major Diastereomer:
$^1$H NMR (400 MHz, Methanol-d$_4$) δ 7.51-7.32 (m, 6H), 7.14-7.07 (m, 1H), 7.06 (t, J=2.2 Hz, 1H), 6.98-6.90 (m, 1H), 6.38 (dd, J=9.6, 1.7 Hz, 1H), 4.99 (t, J=10.3 Hz, 1H), 4.93 (s, 1H), 4.75 (d, J=1.8 Hz, 2H), 4.32 (s, 1H), 3.85 (s, 3H), 3.11 (s, 3H), 2.47 (s, 3H), 2.04-1.96 (m, 1H), 1.93 (d, J=1.4 Hz, 3H), 1.54 (s, 3H), 1.47 (s, 3H), 0.96 (s, 9H), 0.89 (dd, J=6.6, 3.4 Hz, 6H).
Minor diastereomer: refer to Example 93 (immediately following) for $^1$H NMR spectral data
C₃₅H₅₂N₄O₆S calcd m/z=656.36 amu; found [M+H]⁺=657.36, [M+Na]⁺=679.29.

Example 93

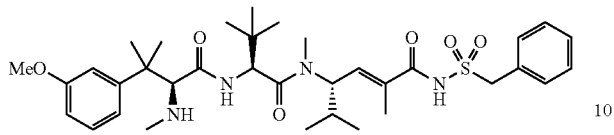

(93)

Chemical Formula: $C_{35}H_{52}N_4O_6S$
Exact Mass: 656.36
Molecular Weight: 656.88

(S,E)-N-(benzylsulfonyl)-4-((S)-2-((S)-3-(3-methoxyphenyl)-3-methyl-2-(methylamino)butanamido)-N,3,3-trimethylbutanamido)-2,5-dimethylhex-2-enamide Title compound was prepared according to Example 92. The two diastereomeric products resulted from diastereomerically impure starting material and were separable by prep-scale HPLC.

$^1$H NMR (400 MHz, Methanol-d$_4$) δ 7.39 (d, J=5.5 Hz, 6H), 7.11 (dd, J=4.9, 2.8 Hz, 3H), 6.38 (d, J=9.4 Hz, 1H), 5.06 (d, J=9.5 Hz, 1H), 4.93 (s, 1H), 4.76 (s, 2H), 4.35 (s, 1H), 3.86 (s, 3H), 3.13 (s, 3H), 2.52 (s, 3H), 2.05-1.97 (m, 1H), 1.95 (d, J=1.6 Hz, 3H), 1.46 (s, 3H), 1.38 (s, 3H), 1.09 (s, 9H), 0.90 (t, J=6.6 Hz, 6H).

$C_{35}H_{52}N_4O_6S$ calcd m/z=656.36 amu; found [M+H]$^+$=657.36, [M+Na]$^+$=679.32.

Example 94

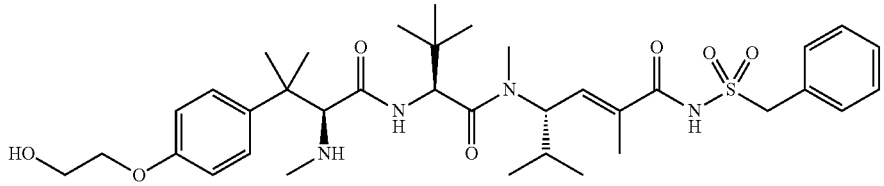

(94)

Chemical Formula: $C_{36}H_{54}N_4O_7S$
Exact Mass: 686.37
Molecular Weight: 686.90

(S,E)-N-(benzylsulfonyl)-4-((S)-2-((S)-3-(4-(2-hydroxyethoxy)phenyl)-3-methyl-2-(methylamino)butanamido)-N,3,3-trimethylbutanamido)-2,5-dimethylhex-2-enamide Title compound was prepared as follows: a mixture of Boc protected Example 86, CuI (10 mol %), 3,4,7,8-tetramethyl-1,10-phenanthroline (20 mol %), Cs$_2$CO$_3$ (2.5 eq), and ethylene glycol (90 eq) was stirred under N$_2$ at 130° C. for 20 h. The resulting mixture was diluted with H$_2$O, carefully acidified with 1 M citric acid and extracted with CH$_2$Cl$_2$ (5×). The organics were combined, washed with brine (1×), dried over MgSO$_4$, filtered, concentrated in vacuo and purified via silica gel column chromatography (eluted with AcOH/EtOAc/hexanes mixtures) to afford the cross-coupled product which was subsequently deprotected and purified according to General Procedure 7.

$^1$H NMR (400 MHz, Methanol-d$_4$) δ 7.46 (d, J=8.8 Hz, 2H), 7.38 (d, J=2.5 Hz, 5H), 7.05 (d, J=8.4 Hz, 2H), 6.38 (d, J=9.5 Hz, 1H), 5.05 (t, J=10.1 Hz, 1H), 4.93 (s, 1H), 4.76 (s, 2H), 4.28 (d, J=11.0 Hz, 1H), 4.13-4.04 (m, 2H), 3.90 (t, J=4.6 Hz, 2H), 3.12 (d, J=6.2 Hz, 3H), 2.50 (d, J=16.9 Hz, 3H), 2.05-1.97 (m, 1H), 1.94 (d, J=11.0 Hz, 3H), 1.56-1.34 (m, 6H), 1.09 (s, 9H), 0.90 (t, J=6.4 Hz, 6H).

$C_{36}H_{54}N_4O_7S$ calcd m/z=686.37 amu; found [M+H]$^+$=687.42, [M+Na]$^+$=709.37.

Example 95

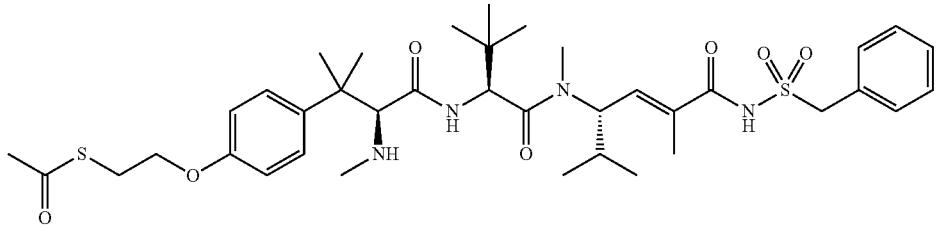

(95)

Chemical Formula: $C_{38}H_{56}N_4O_7S_2$
Exact Mass: 744.36
Molecular Weight: 745.00

S-2-(4-((S)-4-((S)-1-(((S,E)-2,5-dimethyl-6-oxo-6-(benzylsulfonamido)hex-4-en-3-yl)(methyl)amino)-3,3-dimethyl-1-oxobutan-2-ylamino)-2-methyl-3-(methylamino)-4-oxobutan-2-yl)phenoxy)ethyl ethanethioate Title compound was prepared as follows: Tributylphosphine (6 eq) was added to a cold (0° C.) stirring solution of di-tert-butyl azodicarboxylate (6 eq) in THF. After 0.5 h, a solution of the Boc protected Example 94 (1 eq) in THF was added, followed by a solution of AcSH (4.5 eq) in THF. The pale yellow mixture was stirred at 0° C. for 1 h then at ambient temperature for 23 h. The resulting mixture was concentrated in vacuo, dissolved in EtOAc and successively washed with 1M HCl (2×), sat'd NH$_4$Cl (1×) and brine (1×). The organics were dried over MgSO$_4$, filtered, concentrated in vacuo and purified via silica gel column chromatography (eluted with AcOH/EtOAc/hexanes mixtures) to afford the Boc-protected thioacetate product (HPLC/MS—[M+Na]$^+$=867.47).

The thioacetate was dissolved in CH$_2$Cl$_2$ and treated with TFA. After stirring for 1 h, the reaction mixture was concentrated in vacuo. The yellow/brown residue was dissolved in minimal amount of CH$_2$Cl$_2$, cooled to 0° C., and treated with ether to precipitate out the desired aminothioacetate as an off-white solid in 10% yield over two synthetic steps.

$^1$H NMR (400 MHz, Methanol-d$_4$) δ 7.46 (d, J=8.7 Hz, 2H), 7.38 (d, J=2.4 Hz, 5H), 7.03 (d, J=8.6 Hz, 2H), 6.38 (d, J=9.5 Hz, 1H), 5.05 (t, J=10.0 Hz, 1H), 4.93 (s, 1H), 4.75 (s, 2H), 4.27 (d, J=11.4 Hz, 1H), 4.14 (t, J=6.6 Hz, 2H), 3.28 (t, J=6.6 Hz, 2H), 3.11 (d, J=6.6 Hz, 3H), 2.49 (d, J=15.5 Hz, 3H), 2.38 (s, 3H), 2.05-1.97 (m, 1H), 1.95 (s, 3H), 1.45 (s, 3H), 1.37 (s, 3H), 1.08 (s, 9H), 0.96-0.85 (m, 6H).

$C_{38}H_{56}N_4O_7S_2$ calcd m/z=744.36 amu; found [M+H]$^+$=745.39, [M+Na]$^+$=777.32.

Example 96

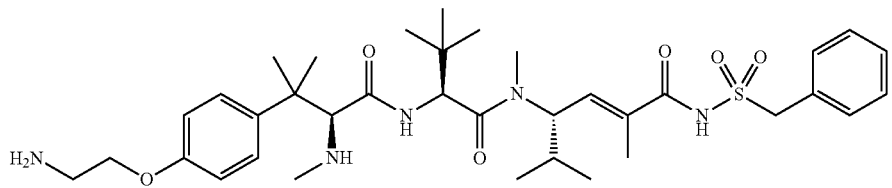

(96)

Chemical Formula: $C_{36}H_{55}N_5O_6S$
Exact Mass: 685.39
Molecular Weight: 685.92

(S,E)-4-((S)-2-((S)-3-(4-(2-aminoethoxy)phenyl)-3-methyl-2-(methylamino)butanamido)-N,3,3-trimethylbutanamido)-N-(benzylsulfonyl)-2,5-dimethylhex-2-enamide Title compound was prepared as follows: Et$_3$N (4 eq) was added to a cold (0° C.) stirring solution of MsCl (3.7 eq) in CH$_2$Cl$_2$. After 2 min, a solution of the Boc protected Example 94 in CH$_2$Cl$_2$ was added. The pale yellow mixture was stirred cold for 5 min and then at ambient temperature for 72 h. The resulting mixture was dilute with EtOAc and successively washed with 1M citric acid (1×), 1M NaHCO$_3$ (0×) and brine (1×). The organics were dried over MgSO$_4$, filtered and concentrated in vacuo to afford the mesylated-alcohol (HPLC/MS—[M+Na]$^+$=887.42) which was used in the next step without further purification.

The mesylate was dissolved in DMF and treated with NaN$_3$ (7 eq). The resulting suspension was stirred at ambient temperature for 18 h and then at 60° C. for 5 h. The reaction mix was diluted with H$_2$O, acidified with 1M HCl and extracted with CH$_2$Cl$_2$ (4×). The combined organics were dried over MgSO$_4$, filtered and concentrated in vacuo to afford the azido product (HPLC/MS—[M+Na]+=834.44) which was used in the next step without further purification.

The azide was dissolved in THF/H$_2$O (10:1) and treated with tributylphosphine (3.5 eq). The mixture was stirred at ambient temperature for 21 h and then concentrated in vacuo. The resulting residue was dissolved in EtOAc and successively washed with 1M HCl (3×), 1M NaHCO$_3$ (3×), H$_2$O (2×) and brine (2×). The organics were dried over MgSO$_4$, filtered, concentrated in vacuo and purified via silica gel column chromatography (eluted with MeOH/CH$_2$Cl$_2$ mixtures) to afford the primary amine as a white solid (HPLC/MS—[M+H]$^+$=786.45).

The amine was dissolved in CH$_2$Cl$_2$ and treated with TFA. After stirring for 1 h, the reaction mixture was concentrated in vacuo. The off-white solid residue was dissolved in minimal amount of MeOH, cooled to 0° C., and treated with ether to precipitate out the desired diamine product as an off-white solid in 6% yield over four synthetic steps.

$^1$H NMR (400 MHz, Methanol-d$_4$) δ 7.50 (d, J=8.6 Hz, 2H), 7.37 (s, 5H), 7.09 (d, J=8.6 Hz, 2H), 6.41 (d, J=9.4 Hz, 1H), 5.02 (t, J=10.0 Hz, 1H), 4.91 (s, 1H), 4.70 (s, 2H), 4.27 (t, J=5.0 Hz, 2H), 3.40 (t, J=5.0 Hz. 2H), 3.37 (s, 1H), 3.12 (s, 3H), 2.47 (s, 3H), 2.06-1.95 (m, 1H), 1.94 (d, J=1.4 Hz, 3H), 1.45 (s, 3H), 1.37 (s, 3H), 1.08 (s, 9H), 0.89 (dd, J=9.7, 6.6 Hz, 6H).

C$_{38}$H$_{55}$N$_5$O$_6$S calcd m/z=685.39 amu; found [M+H]$^+$=686.32, [M+Na]$^+$=708.27, [(M+2H)/$^{2+}$]=343.77.

Example 97

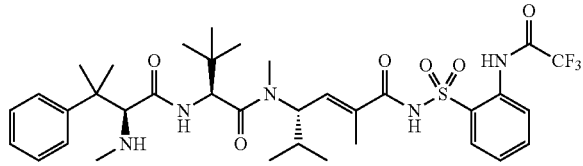

(97)

Chemical Formula: C$_{35}$H$_{48}$F$_3$N$_5$O$_6$S
Exact Mass: 723.33
Molecular Weight: 723.85

(S,E)-2,5-dimethyl-N-(2-(2,2,2-trifluoroacetamido)phenylsulfonyl)-4-((S)—N,3,3-trimethyl-2-((S)-3-methyl-2-(methylamino)-3-phenylbutanamido)butanamido)hex-2-enamide Title compound was prepared from Example 3 an 2,2,2-trifluoro-N-(2-sulfamoylphenyl)acetamide according to General Procedures 2, and 7.

$^1$H NMR (400 MHz, Methanol-d$_4$) δ 8.27 (d, J=8.4 Hz, 1H), 8.05 (d, J=7.8 Hz, 1H), 7.67 (t, J=7.9 Hz, 1H), 7.54 (d, J=8.1 Hz, 2H), 7.48 (t, J=7.7 Hz, 2H), 7.40 (dt, J=13.3, 7.4 Hz, 2H), 6.57 (d, J=9.2 Hz, 1H), 4.92 (s, 2H), 4.34 (s, 1H), 3.17 (s, 3H), 2.50 (s, 3H), 2.06 (m, 1H), 1.87 (d, J=1.3 Hz, 3H), 1.45 (s, 3H), 1.33 (s, 3H), 1.07 (s, 9H), 0.91 (dd, J=6.6, 3.5 Hz, 6H).

$^{19}$F NMR (377 MHz, Methanol-d$_4$) δ −76.96, −77.73.

C$_{35}$H$_{48}$F$_3$N$_5$O$_6$S calcd m/z=723.33 amu; found [M+H]$^+$=723.34, [M+Na]$^+$=746.23.

Example 98

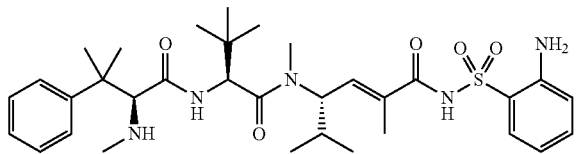

(98)

Chemical Formula: C$_{33}$H$_{49}$N$_5$O$_5$S
Exact Mass: 627.35
Molecular Weight: 627.84

(S,E)-N-(2-aminophenylsulfonyl)-2,5-dimethyl-4-((S)—N,3,3-trimethyl-2-((S)-3-methyl-2-(methylamino)-3-phenylbutanamido)butanamido)hex-2-enamide Title compound was prepared from Example 3 an 2,2,2-trifluoro-N-(2-sulfamoylphenyl)acetamide according to General Procedures 2, 3 and 7.

$^1$H NMR (400 MHz, Methanol-d$_4$) δ 7.75 (dd, J=8.2, 1.5 Hz, 1H), 7.55 (d, J=7.8 Hz, 2H), 7.48 (t, J=7.7 Hz, 2H), 7.38 (t, J=7.4 Hz, 1H), 7.33-7.27 (m, 1H), 6.81 (d, J=8.2 Hz, 1H), 6.69 (t, J=7.5 Hz, 1H), 6.49 (dd, J=9.1, 1.5 Hz, 1H), 4.97 (t, J=10.1 Hz, 1H), 4.92 (s, 1H), 4.35 (s, 1H), 3.17 (s, 3H), 2.51 (s, 3H), 2.07 (m, 1H), 1.88 (d, J=1.4 Hz, 3H), 1.46 (s, 3H), 1.36 (s, 3H), 1.06 (s, 9H), 0.92 (t, J=6.8 Hz, 6H).

C$_{33}$H$_{49}$N$_5$O$_5$S calcd m/z=627.35 amu; found [M+H]$^+$=628.36, [M+Na]$^+$=650.37, [(M+2H)/2]$^{2+}$=314.76.

Example 99

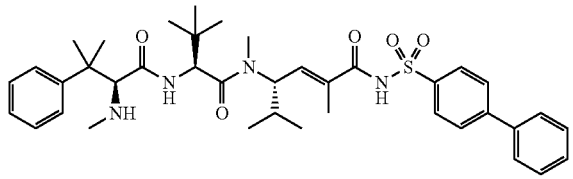

Chemical Formula: C$_{39}$H$_{52}$N$_4$O$_5$S
Exact Mass: 688.37
Molecular Weight: 688.92

(S,E)-N-(biphenyl-4-ylsulfonyl)-2,5-dimethyl-4-((S)—N,3,3-trimethyl-2-((S)-3-methyl-2-(methylamino)-3-phenylbutanamido)butanamido)hex-2-enamide Title compound was prepared using from Boc protected Example 56 with phenylboronic acid according to General Procedures 8 and 7.

$^1$H NMR (400 MHz, Methanol-d$_4$) δ 8.12 (d, J=8.3 Hz, 2H), 7.83 (d, J=8.4 Hz, 2H), 7.71 (d, J=7.7 Hz, 2H), 7.52 (dd, J=11.6, 7.6 Hz, 4H), 7.45 (t, J=7.3 Hz, 3H), 7.36 (t, J=7.2 Hz, 1H), 6.52 (d, J=9.4 Hz, 1H), 4.96 (t, J=9.5 Hz, 1H), 4.92 (s, 1H), 4.33 (s, 1H), 3.18 (s, 3H), 2.50 (s, 3H), 2.14-2.03 (m, 1H), 1.88 (s, 3H), 1.45 (s, 3H), 1.35 (s, 3H), 1.07 (s, 9H), 0.92 (t, J=6.9 Hz, 6H).

C$_{39}$H$_{52}$N$_4$O$_5$S calcd m/z=688.37 amu; found [M+H]$^+$=689.10, [M+Na]$^+$=711.32.

Example 100

(S,E)-N-(4'-aminobiphenyl-4-ylsulfonyl)-2,5-dimethyl-4-((S)—N,3,3-trimethyl-2-((S)-3-methyl-2-(methylamino)-3-phenylbutanamido)butanamido)hex-2-enamide Title compound was prepared from Boc protected Example 68 with 4-(tert-butoxycarbonylamino)phenylboronic acid according to General Procedures 8 and 7

$^1$H NMR (400 MHz, Methanol-d$_4$) δ 8.05 (d, J=8.6 Hz, 2H), 7.75 (d, J=8.6 Hz, 2H), 7.59-7.51 (m, 4H), 7.45 (t, J=7.7 Hz, 2H), 7.36 (t, J=7.3 Hz, 1H), 6.91 (d, J=8.3 Hz, 2H), 6.50 (d, J=9.1 Hz, 1H), 4.98-4.92 (m, 1H), 4.91 (s, 1H), 4.34 (s, 1H), 3.18 (s, 3H), 2.50 (s, 3H), 2.13-2.03 (m, 1H), 1.88 (d, J=1.4 Hz, 3H), 1.45 (s, 3H), 1.35 (s, 3H), 1.06 (s, 9H), 0.92 (t, J=6.2 Hz, 6H).

C$_{39}$H$_{53}$N$_5$O$_5$S calcd m/z=703.38 amu; found [M+H]$^+$=704.26, [M+Na]$^+$=726.41, [(M+2H)/2]$^{24}$=352.77.

Example 101

(S,E)-N-(4-fluorobenzylsulfonyl)-2,5-dimethyl-4-((S)—N,3,3-trimethyl-2-((S)-3-methyl-2-(methylamino)-3-phenylbutanamido)butanamido)hex-2-enamide Title compound was prepared from Example 3 and 4-fluorobenzylsulfonamide according to General Procedures 2 and 7.

1H NMR (400 MHz, Methanol-d4) δ 7.60-7.52 (m, 2H), 7.48 (t, J=7.7 Hz, 2H), 7.44-7.34 (m, 3H), 7.18-7.05 (m, 2H), 6.41 (dd, J=9.5, 1.7 Hz, 1H), 5.06 (t, J=10.0 Hz, 1H),

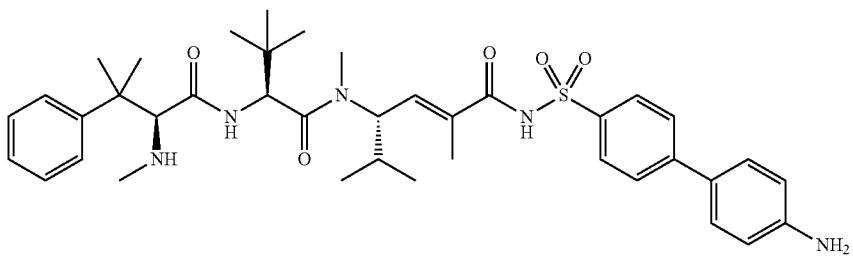

Chemical Formula: C$_{39}$H$_{53}$N$_5$O$_5$S
Exact Mass: 703.38
Molecular Weight: 703.93

4.94 (s, 1H), 4.74 (s, 2H), 4.35 (s, 1H), 3.13 (s, 3H), 2.51 (s, 3H), 2.07-1.97 (m, 1H), 1.95 (d, J=1.4 Hz, 3H), 1.48 (s, 3H), 1.39 (s, 3H), 1.09 (s, 9H), 0.90 (t, J=6.3 Hz, 6H).

C$_{34}$H$_{49}$FN$_4$O$_5$S calcd m/z=644.34 found [M+H]$^+$=645.32.

Example 102

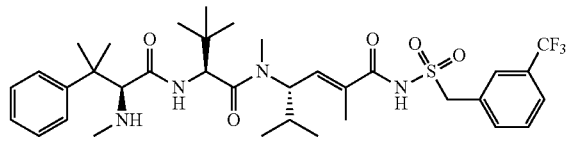

(102)

(S,E)-2,5-dimethyl-N-(3-(trifluoromethyl)benzylsulfonyl)-4-((S)—N,3,3-trimethyl-2-((S)-3-methyl-2-(methylamino)-3-phenylbutanamido)butanamido)hex-2-enamide Title compound was prepared from Example 3 and 3-trifluorobenzylsulfonamide according to General Procedures 2 and 7.

1H NMR (400 MHz, Methanol-d4) δ 7.74-7.64 (m, 3H), 7.61 (d, J=7.7 Hz, 1H), 7.60-7.54 (m, 2H), 7.48 (t, J=7.7 Hz, 2H), 7.38 (t, J=7.3 Hz, 1H), 6.42 (dd, J=9.4, 1.7 Hz, 1H), 5.06 (t, J=10.0 Hz, 1H), 4.93 (s, 1H), 4.36 (s, 1H), 3.13 (s, 3H), 2.51 (s, 3H), 2.07-1.97 (m, 1H), 1.95 (d, J=1.4 Hz, 3H), 1.48 (s, 3H), 1.39 (s, 3H), 1.08 (s, 9H), 0.89 (d, J=6.5 Hz, 6H).

C$_{35}$H$_{49}$F$_3$N$_4$O$_5$S calcd m/z=694.34 found [M+H]$^+$=695.38.

Example 103

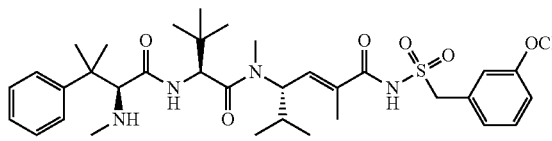

(103)

(S,E)-2,5-dimethyl-N-(3-(trifluoromethoxy)benzylsulfonyl)-4-((S)—N,3,3-trimethyl-2-((S)-3-methyl-2-(methylamino)-3-phenylbutanamido)butanamido)hex-2-enamide Title compound was prepared from Example 3 and 3-trifluoromethoxybenzylsulfonamide according to General Procedures 2, and 7.

1H NMR (400 MHz, Methanol-d4) δ 7.56 (d, J=7.8 Hz, 2H), 7.48 (t, J=7.9 Hz, 3H), 7.43-7.36 (m, 2H), 7.32 (d, J=9.3 Hz, 2H), 6.43 (dd, J=9.4, 1.7 Hz, 1H), 5.06 (t, J=10.0 Hz, 1H), 4.93 (s, 1H), 4.82 (s, 2H), 4.35 (s, 1H), 3.13 (s, 3H), 2.51 (s, 3H), 2.07-1.97 (m, 1H), 1.95 (d, J=1.4 Hz, 3H), 1.48 (s, 3H), 1.39 (s, 3H), 1.08 (s, 9H), 0.90 (dd. J=6.6, 4.3 Hz, 6H).

C$_{35}$H$_{49}$F N$_4$O$_6$S calcd m/z=710.33 found [M+H]$^+$=711.38.

Example 104

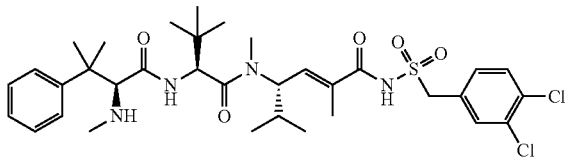

(104)

(S,E)-N-(3,4-dichlorobenzylsulfonyl)-2,5-dimethyl-4-((S)—N,3,3-trimethyl-2-((S)-3-methyl-2-(methylamino)-3-phenylbutanamido)butanamido)hex-2-enamide Title compound was prepared from Example 3 and 3,4-dichlorobenzylsulfonamide according to General Procedures 2, and 7.

1H NMR (400 MHz, Methanol-d4) δ 7.56 (td, J=5.2, 4.5, 1.9 Hz, 4H), 7.48 (t, J=7.7 Hz, 2H), 7.38 (t, J=7.3 Hz, 1H), 7.33 (dd, J=8.4, 2.1 Hz, 1H), 6.41 (dd, J=9.5, 1.8 Hz, 1H), 5.06 (t, J=10.0 Hz, 1H), 4.93 (s, 1H), 4.77 (s, 2H), 4.36 (s, 1H), 3.14 (s, 3H), 2.52 (s, 3H), 2.07-1.97 (m, 1H), 1.95 (d, J=1.4 Hz, 3H), 1.49 (s, 3H), 1.39 (s, 3H), 1.08 (s, 9H), 0.90 (dd, J=6.6, 4.9 Hz, 6H).

C$_{34}$H$_{48}$Cl$_2$N$_4$O$_5$S calcd m/z=694.27 found [M+H]$^+$=695.32.

Example 105

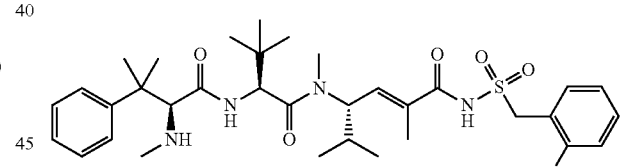

(105)

(S,E)-N-(2-cyanobenzylsulfonyl)-2,5-dimethyl-4-((S)—N,3,3-trimethyl-2-((S)-3-methyl-2-(methylamino)-3-phenylbutanamido)butanamido)hex-2-enamide Title compound was prepared from Example 3 and 2-cyanobenzylsulfonamide according to General Procedures 2, and 7.

$^1$H NMR (400 MHz, Methanol-d$_4$) δ 7.81 (dd, J=7.7, 1.3 Hz, 1H), 7.72 (td, J=7.7, 1.3 Hz, 1H), 7.66 (d, J=7.7 Hz, 1H), 7.62-7.59 (m, 1H), 7.58-7.53 (m, 2H), 7.48 (t, J=7.7 Hz, 2H), 7.38 (t, J=7.3 Hz, 1H), 6.50 (d, J=9.4 Hz, 1H), 5.08 (dd, J=10.6, 9.3 Hz, 1H), 4.99 (s, 2H), 4.95 (s, 1H), 4.36 (s, 1H), 3.16 (s, 3H), 2.52 (s, 3H), 2.09-1.99 (m, 1H), 1.98 (d, J=1.4 Hz, 3H), 1.49 (s, 3H), 1.39 (s, 3H), 1.10 (s, 9H), 0.94 (d, J=6.6 Hz, 3H), 0.91 (d, J=6.6 Hz, 3H).

C$_{35}$H$_{49}$N$_5$O$_5$S calcd m/z=651.35 found [M+H]$^+$=652.38.

Example 106

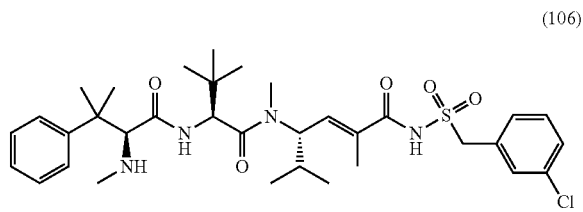 [SMILES: CN[C@H](C(=O)N[C@H](C(=O)N(C)[C@H](/C=C(\C)C(=O)NS(=O)(=O)Cc1cccc(Cl)c1)C(C)C)C(C)(C)C)C(C)(C)c1ccccc1]

(106)

(S,E)-N-(3-chlorobenzylsulfonyl)-2,5-dimethyl-4-((S)—N,3,3-trimethyl-2-((S)-3-methyl-2-(methylamino)-3-phenylbutanamido)butanamido)hex-2-enamide Title compound was prepared from Example 3 and 3-chlorobenzylsulfonamide according to General Procedures 2, and 7.

1H NMR (400 MHz, Methanol-d4) δ 7.58-7.53 (m, 2H), 7.48 (t, 0.1=7.6 Hz, 2H), 7.43-7.34 (m, 4H), 7.32 (d, J=7.5 Hz, 1H), 6.42 (d, J=9.5 Hz, 1H), 5.06 (t, J=10.0 Hz, 1H), 4.94 (s, 1H), 4.74 (s, 2H), 4.33 (s, 1H), 3.13 (s, 3H), 2.50 (s, 3H), 2.07-1.97 (m, 1H), 1.95 (d, J=1.4 Hz, 3H), 1.48 (s, 3H), 1.39 (s, 3H), 1.08 (s, 9H), 0.90 (t, J=7.2 Hz, 6H).

$C_{34}H_{49}ClN_4O_5S$ calcd m/z=660.31 found $[M+H]^+$=661.32.

Example 107

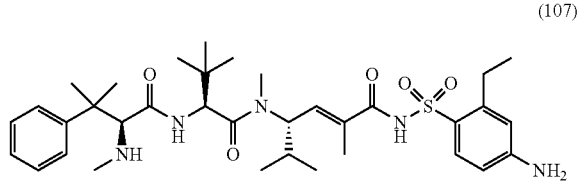 [SMILES: CCc1cc(N)ccc1S(=O)(=O)NC(=O)/C(C)=C/[C@H](C(C)C)N(C)C(=O)[C@@H](NC(=O)[C@@H](NC)C(C)(C)c1ccccc1)C(C)(C)C]

(107)

(S,E)-N-(4-amino-2-ethylphenylsulfonyl)-2,5-dimethyl-4-((S)—N,3,3-trimethyl-2-((S)-3-methyl-2-(methylamino)-3-phenylbutanamido)butanamido)hex-2-enamide Title compound was prepared from Example 3 and 2-ethylbenzylsulfonamide according to General Procedures 2, and 7.

$^1$H NMR (400 MHz, Methanol-d$_4$) δ 7.79 (d, J=8.7 Hz, 1H), 7.55 (d, J=7.9 Hz, 2H), 7.48 (t, J=7.6 Hz, 2H), 7.37 (t, J=7.4 Hz, 1H), 6.57 (d, J=2.3 Hz, 1H), 6.54 (dd, J=8.8, 2.4 Hz, 1H), 6.46 (d, J=9.4 Hz, 1H), 5.01 (t, J=10.0 Hz, 1H), 4.92 (s, 1H), 4.34 (s, 1H), 3.16 (s, 3H), 2.99-2.90 (m, 2H), 2.50 (s, 3H), 2.11-2.00 (m, 1H), 1.87 (d, J=1.4 Hz, 3H), 1.47 (s, 3H), 1.38 (s, 3H), 1.22 (t, J=7.5 Hz, 3H), 1.06 (s, 9H), 0.91 (dd, J=6.6 Hz, 6H).

$C_{35}H_{53}N_5O_5S$ calcd m/z=655.38 found $[M+H]^+$=656.4.

Example 108

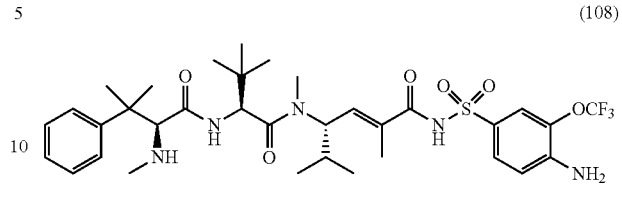

(108)

(S,E)-N-(4-amino-3-(trifluoromethoxy)phenylsulfonyl)-2,5-dimethyl-4-((S)—N,3,3-trimethyl-2-((S)-3-methyl-2-(methylamino)-3-phenylbutanamido)butanamido)hex-2-enamide Title compound was prepared from Example 3 and 2,2,2-trifluoro-N-(4-sulfamoyl-2-(trifluoromethoxy)phenyl)acetanide according to General Procedures 2, 3 and 7.

$^1$H NMR (400 MHz, Methanol-d$_4$) δ 7.81-7.75 (m, 1H), 7.71 (dd, J=8.7, 2.1 Hz, 1H), 7.55 (d, J=7.9 Hz, 2H), 7.47 (t, J=7.6 Hz, 2H), 7.37 (t, J=7.1 Hz, 1H), 6.89 (d, J=8.7 Hz, 1H), 6.51-6.42 (m, 1H), 4.98 (t, J=10.0 Hz, 1H), 4.92 (t, J=4.1 Hz, 1H), 4.37 (s, 1H), 3.16 (s, 3H), 2.51 (s, 3H), 2.12-2.01 (m, 1H), 1.88 (d, J=1.4 Hz, 3H), 1.47 (s, 3H), 1.37 (s, 3H), 1.07 (s, 9H), 0.92 (dd, J=6.6 Hz, 6H).

$C_{34}H_{48}F_3N_5O_6S$ calcd m/z=711.33 found $[M+H]^+$=712.4.

Example 109

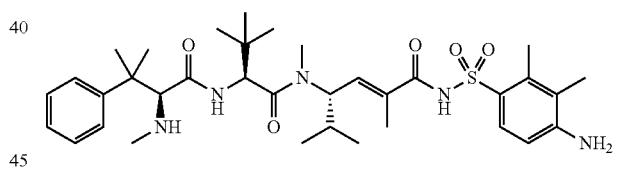

(109)

(S,E)-N-(4-amino-2,3-dimethylphenylsulfonyl)-2,5-dimethyl-4-((S)—N,3,3-trimethyl-2-((S)-3-methyl-2-(methylamino)-3-phenylbutanamido)butanamido)hex-2-enamide Title compound was prepared from Example 3 and 2,2,2-trifluoro-N-(4-sulfamoyl-2,3-dimethylphenyl)acetamide according to General Procedures 2, 3 and 7.

$^1$H NMR (400 MHz, Methanol-d$_4$) δ 7.75 (d, J=8.8 Hz, 1H), 7.55 (d, J=7.9 Hz, 2H), 7.47 (t, J=7.7 Hz, 2H), 7.37 (t, J=6.9 Hz, 1H), 6.63 (d, J=8.8 Hz, 1H), 6.46 (d, J=9.7 Hz, 1H), 5.00 (t, J=10.0 Hz, 1H), 4.93 (s, 1H), 4.32 (s, 1H), 3.17 (s, 3H), 2.54 (s, 3H), 2.49 (s, 3H), 2.09 (s, 3H), 2.08-2.02 (m, 1H), 1.87 (d, J=1.4 Hz, 3H), 1.47 (s, 3H), 1.37 (s, 3H), 1.07 (s, 9H), 0.92 (dd, J=6.8, 6.5 Hz, 6H).

$C_5H_{53}N_5O_5S$ calcd m/z=655.38 found $[M+H]^+$=656.4.

Example 110

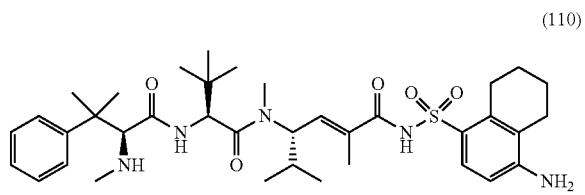 [SMILES: CN[C@H](C(=O)N[C@H](C(=O)N(C)[C@H](/C=C(\C)C(=O)NS(=O)(=O)c1ccc(N)c2c1CCCC2)C(C)C)C(C)(C)C)C(C)(C)c1ccccc1]
(110)

(S,E)-N-(4-amino-5,6,7,8-tetrahydronaphthalen-1-ylsulfonyl)-2,5-dimethyl-4-((S)—N,3,3-trimethyl-2-((S)-3-methyl-2-(methylamino)-3-phenylbutanamido)butanamido)hex-2-enamide Title compound was prepared from Example 3 and 2,2,2-trifluoro-N-(4-sulfamoyl-5,6,7,8-tetrahydronaphthalen-1-yl)acetamide according to General Procedures 2, 3 and 7.

$^1$H NMR (400 MHz, Methanol-d$_4$) δ 7.74 (d, J=8.7 Hz, 1H), 7.55 (d, J 25=7.9 Hz, 2H), 7.48 (t, J=7.6 Hz, 2H), 7.38 (t, J=7.2 Hz, 1H), 6.60 (d, J=8.7 Hz, 1H), 6.46 (d, J=9.2 Hz, 1H), 5.00 (t, J=10.0 Hz, 1H), 4.95-4.91 (m, 1H), 4.36 (s, 1H), 3.17 (s, 3H), 3.10-3.05 (m, 2H), 2.51 (s, 3H), 2.46 (t, J=6.5 Hz, 2H), 2.10-2.02 (m, 1H), 1.88 (s, 3H), 1.87-1.75 (m, 4H), 1.47 (s, 3H), 1.38 (s, 3H), 1.07 (s, 9H), 0.92 (dd, J=7.1 Hz, 6H).

C$_{37}$H$_{55}$N$_5$O$_5$S calcd m/z=681.39 found [M+H]$^+$=682.4.

Example 111

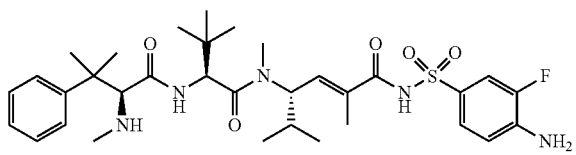
(111)

(S,E)-N-(4-amino-3-methylphenylsulfonyl)-2,5-dimethyl-4-((S)—N,3,3-trimethyl-2-((S)-3-methyl-2-(methylamino)-3-phenylbutanamido)butanamido)hex-2-enamide Title compound was prepared from Example 3 and 2,2,2-trifluoro-N-(2-methyl-4-sulfamoylphenyl)acetamide according to General Procedures 2, 3 and 7.

$^1$H NMR (400 MHz, Methanol-d$_4$) δ 7.64 (s, 1H), 7.61 (dd, J=8.5, 2.3 Hz, 1H), 7.57-7.51 (m, 2H), 7.48 (t, J=7.7 Hz, 2H), 7.41-7.35 (m, 1H), 6.71 (d, J=8.5 Hz, 1H), 6.43 (dd, J=9.3, 1.6 Hz, 1H), 4.96 (t, J=10.0 Hz, 1H), 4.92 (s, 1H), 4.35 (s, 1H), 3.16 (s, 3H), 2.51 (s, 3H), 2.17 (s, 3H), 2.10-2.01 (m, 1H), 1.87 (d, J=1.4 Hz, 3H), 1.46 (s, 3H), 1.36 (s, 3H), 1.07 (s, 9H), 0.91 (dd, J=6.3 Hz, 6H).

C$_{34}$H$_{51}$N$_5$O$_5$S calcd in/z=641.36 found [M+H]$^+$=642.4.

Example 112

(112)

(S,E)-N-(4-amino-3-fluorophenylsulfonyl)-2,5-dimethyl-4-((S)—N,3,3-trimethyl-2-((S)-3-methyl-2-(methylamino)-3-phenylbutanamido)butanamido)hex-2-enamide Title compound was prepared from Example 3 and 2,2,2-trifluoro-N-(2-fluoro-4-sulfamoylphenyl)acetamide according to General Procedures 2, 3 and 7.

$^1$H NMR (400 MHz, Methanol-d$_4$) δ 7.62-7.55 (m, 3H), 7.54 (s, 1H), 7.48 (t, J=7.7 Hz, 2H), 7.37 (t, J=7.3 Hz, 1H), 6.85 (t, J=8.6 Hz, 1H), 6.45 (d, J=9.3 Hz, 1H), 4.98 (t, J=9.9 Hz, 1H), 4.92 (s, 1H), 4.34 (s, 1H), 3.16 (s, 3H), 2.50 (s, 3H), 2.12-2.00 (m, 1H), 1.88 (d, J=1.4 Hz, 3H), 1.46 (s, 3H), 1.37 (s, 3H), 1.07 (s, 9H), 0.91 (dd, J=6.8 Hz, 6H).

C$_{13}$H$_{48}$FN$_5$O$_5$S calcd m/z=645.34 found [M+H]$^+$=646.4.

Example 113

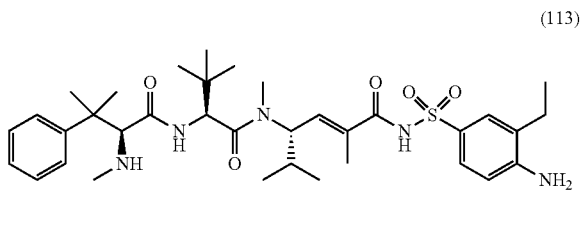 [SMILES: CCc1cc(S(=O)(=O)NC(=O)/C(C)=C/[C@H](C(C)C)N(C)C(=O)[C@@H](NC(=O)[C@@H](NC)C(C)(C)c2ccccc2)C(C)(C)C)ccc1N]
(113)

(S,E)-N-(4-amino-3-ethylphenylsulfonyl)-2,5-dimethyl-4-((S)—N,3,3-trimethyl-2-((S)-3-methyl-2-(methylamino)-3-phenylbutanamido)butanamido)hex-2-enamide Title compound was prepared from Example 3 and 2,2,2-trifluoro-N-(2-ethyl-4-sulfamoylphenyl)acetamide according to General Procedures 2, 3 and 7.

$^1$H NMR (400 MHz, Methanol-d$_4$) δ 7.66 (d, J=2.3 Hz, 1H), 7.61 (dd, J=8.6, 2.3 Hz, 1H), 7.55 (d, J=7.6 Hz, 2H), 7.48 (t, J=7.7 Hz, 2H), 7.37 (t, J=7.3 Hz, 1H), 6.71 (d, J=8.5 Hz, 1H), 6.43 (dd, J=9.3, 1.7 Hz, 1H), 4.96 (t, J=9.9 Hz, 1H), 4.92 (s, 1H), 4.35 (s, 1H), 3.16 (s, 3H), 2.54 (dd, J=7.4, 2.2 Hz, 2H), 2.51 (s, 3H), 2.12-1.99 (m, 1H), 1.87 (d, J=1.4 Hz, 3H), 1.46 (s, 3H), 1.36 (s, 3H), 1.27 (t, J=7.5 Hz, 3H), 1.07 (s, 9H), 0.91 (dd, J=6.4 Hz, 6H)

C$_{35}$H$_{53}$N$_5$O$_5$S calcd m/z=655.38 found [M+H]$^+$=656.5.

Example 114

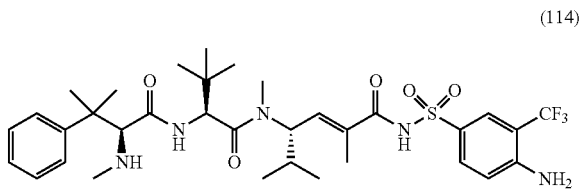 [SMILES: CN[C@H](C(=O)N[C@H](C(=O)N(C)[C@H](/C=C(\C)C(=O)NS(=O)(=O)c1ccc(N)c(C(F)(F)F)c1)C(C)C)C(C)(C)C)C(C)(C)c1ccccc1]

(114)

(S,E)-N-(4-amino-3-(trifluoromethyl)phenylsulfonyl)-2,5-dimethyl-4-((S)—N,3,3-trimethyl-2-((S)-3-methyl-2-(methylamino)-3-phenylbutanamido)butanamido)hex-2-enamide Title compound was prepared from Example 3 and 2,2,2-trifluoro-N-(2-trifluoromethyl-4-sulfamoylphenyl)acetamide according to General Procedures 2, 3 and 7.

$^1$H NMR (400 MHz, Methanol-$d_4$) δ 8.04 (s, 1H), 7.87 (d, J=8.8 Hz, 1H), 7.55 (d, J=7.6 Hz, 2H), 7.48 (t, J=7.3 Hz, 2H), 7.36 (dd, J=14.5, 7.4 Hz, 1H), 6.89 (d, J=8.9 Hz, 1H), 6.47 (d, J=9.3 Hz, 1H), 4.99 (t, J=10.2 Hz, 1H), 4.92 (s, 1H), 4.33 (s, 1H), 3.16 (s, 3H), 2.50 (s, 3H), 2.11-2.00 (m, 1H), 1.88 (s, 3H), 1.47 (s, 3H), 1.37 (s, 3H), 1.07 (s, 9H), 0.91 (dd, J=7.0 Hz, 6H).

$C_{34}H_{48}F_3N_5O_5S$ calcd m/z=695.33 found [M+H]$^+$=696.4.

Example 115

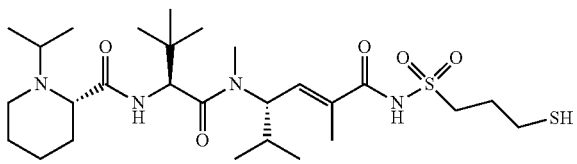

(115)

(S)-1-isopropyl-N—((S)-1-(((S,E)-6-(3-mercaptopropylsulfonamido)-2,5-dimethyl-6-oxohex-4-en-3-yl)(methyl)amino)-3,3-dimethyl-1-oxobutan-2-yl)piperidine-2-carboxamide To a solution of (S,E)-ethyl 4-((S)-2-(tert-butoxycarbonylamino)-N,3,3-trimethylbutanamido)-2,5-dimethylhex-2-enoate (0.373 g, 0.905 mmol) in $CH_2Cl_2$ (5 mL) was added trifluoroacetic acid (2 mL). The reaction was monitored by HPLC and upon complete conversion of the starting material concentrated under reduced pressure. N-isopropyl-pipecolic acid (0.200 g, 1.3 equiv) was dissolved in $CH_2Cl_2$ (5 mL) and stirred at 0° C., to which was added HBTU (0.450 g, 1.3 equiv) and N,N-di-isopropylethylamine (0.400 uL, 2.5 equiv). After 10 minutes, the above deprotected dipeptide was added as a solution in $CH_2Cl_2$ (~1 mL). The reaction was monitored by HPLC for complete consumption of the dipeptide at which time the entire reaction was concentrated under reduced pressure. The crude reaction mixture was dissolved in $CH_2Cl_2$ and purified by silica gel chromatography (1-20% MeOH (5% $NH_4OH$) in $CH_2Cl_2$).

The resulting ester was saponified with LiOH in 1,4-dioxane. The resulting carboxylic acid (0.128 g, 0.29 mmol) was dissolved in $CH_2Cl_2$ (5 mL) and to the stirred solution was added dicyclohexylcarbodiimide (0.084 g, 1.4 equiv), N,N-dimethylaminopyridine (0.05 g, 1.4 equiv) and 3-(tritylthio)propane-1-sulfonamide (0.174 g, 1.5 equiv). The resulting mixture was stirred overnight and monitored for reaction progress by HPLC-MS. When the reaction was complete, the mixture was concentrated under reduced pressure and the residue was purified by silica gel chromatography (5-30% MeOH in $CH_2Cl_2$) to give the S-trityl derivative of the parent compound as a colourless oil (0.056 g).

$^1$H NMR (400 MHz, Methanol-$d_4$) δ 7.44-7.35 (m, 6H), 7.36-7.15 (m, 9H), 6.56 (dd, J=9.1, 1.7 Hz, 1H), 5.03 (dd, J=10.6, 9.3 Hz, 1H), 4.73 (s, 1H), 4.05 (dd, J=11.5, 3.3 Hz, 1H), 3.51-3.37 (m, 2H), 3.25-3.15 (m, 2H), 3.09 (s, 3H), 2.92 (td, J=12.5, 2.9 Hz, 1H), 2.31 (t, J=7.2 Hz, 2H), 2.18-1.70 (m, 15H), 1.61 (ddt, J=12.8, 8.4, 4.9 Hz, 1H), 1.28 (dd, J=30.1, 6.7 Hz, 7H), 1.04 (s, 9H), 0.88 (dd, J=37.3, 6.5 Hz, 6H).

Finally, the trityl protected thiol was dissolved in $CH_2Cl_2$ (3 mL) and trifluoroacetic acid was added (0.6 mL) with triisopropyl silane (0.1 mL). The reaction was monitored by HPLC-MS and upon completion, was concentrated to dryness under reduced pressure. The residue was taken up in $CH_2Cl_2$ (~0.8 mL) with a couple of drops of ethanol and cooled to 0° C. in an ice bath. Cold diethyl ether (~3 mL) was added with vigorous stirring to generate a white precipitate which was collected by filtration on a Buchner funnel at dried under high vacuum to yield the parent compound as an amorphous white solid.

$^1$H NMR (400 MHz, Methanol-$d_4$) δ 6.52 (d, J=9.0 Hz, 1H), 5.06 (dd. J=10.7, 8.8 Hz, 1H), 4.73 (s, 1H), 4.16-4.04 (m, 1H), 3.69-3.56 (m, 2H), 3.48 (dd, J=13.3, 7.2 Hz, 2H), 3.15 (s, 3H), 3.03-2.94 (m, 1H), 2.68 (t, J=6.9 Hz, 1H), 2.24-1.77 (m, 11H), 1.61 (s, 1H), 1.31 (dd, J=27.2, 6.7 Hz, 6H), 1.06 (s, 9H), 0.91 (dd, J=34.1, 6.6 Hz, 6H).

Example 116

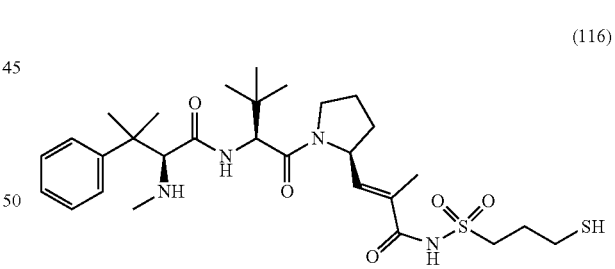

(116)

Chemical Formula: $C_{29}H_{46}N_4O_5S_2$
Exact Mass: 594.29

S)—N—((S)-1-((S)-2-((E)-3-(3-mercaptopropylsulfonamido)-2-methyl-3-oxoprop-1-enyl)pyrrolidin-1-yl)-3,3-dimethyl-1-oxobutan-2-yl)-3-methyl-2-(methylamino)-3-phenylbutanamide The title compound was synthesized from Boc-proline and Example 2 according to General Procedures 10, 11, 2, 3, 7 and others from Nieman J. A. et al. J. Nat. Prod. 2003, 66, 183-199. The compound was isolated as two diastereoisomers in an approximately 1:1 ratio.

¹H NMR (400 MHz, Methanol-d₄) δ 7.57-7.12 (m, 5H), 6.39 (dd, J=9.4, 1.6 Hz, 0.5H), 6.31 (dd, J=8.2, 1.5 Hz, 0.5H), 4.72 (q, J=7.5 Hz, 0.5H), 4.66-4.56 (m, 0.5H), 4.40 (s, 0.5H), 4.28 (d, J=11.9 Hz, 1H), 3.81 (m, 0.5H), 3.76-3.56 (m, 3H), 2.77-2.64 (m, 2H), 2.59 (m, 3H), 2.39-2.22 (m, 1H), 2.18-1.72 (m, 7H), 1.61-1.33 (m, 6H), 1.15-0.85 (m, 11H).

$C_{29}H_{46}N_4O_5S_2$ calcd m/z=594.35 found [M+H]⁺=595.3.

Example 117

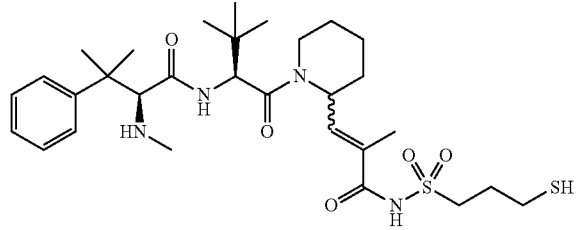

(117)

S)—N—((S)-1-(2-(3-(3-mercaptopropylsulfonamido)-2-methyl-3-oxoprop-1-enyl)piperidin-1-yl)-3,3-dimethyl-1-oxobutan-2-yl)-3-methyl-2-(methylamino)-3-phenylbutanamide The title compound was synthesized from Boc-homoproline and Example 2 according to General Procedures 10, 11, 2, 3, 7 and others from Nieman J. A. et al. J. Nat. Prod. 2003, 66, 183-199. The compound was isolated as two diastereoisomers in an approximately 2:3 ratio.

¹H NMR (600 MHz, Methanol-d₄) δ 7.55 (d, J=7.8 Hz, 1H), 7.46 (m, 3H), 7.38 (m, 1H), 6.81 (d, J=8.3 Hz, 0.6H), 6.79 (d, J=7.8 Hz, 0.4H), 5.66 (m, 0.6H), 5.12 (m, 0.4H), 5.05 (s, 0.6H), 4.86 (s, 0.4H), 4.42 (d, J=14.9 Hz, 0.4H), 4.35 (s, 0.6H), 4.26 (s, 0.4H), 4.12 (d, J=13.8 Hz, 0.6H), 3.64 (d, J=7.6 Hz, 1H), 3.63 (d, J=7.4 Hz, 1H), 3.39 (m, 0.6H), 2.94 (td, J=13.8, 2.6 Hz, 0.4H), 2.68 (t, J=6.7 Hz, 2H), 2.56 (m, 3H), 2.10 (m, 3.5H), 1.97 (s, 1.5H), 1.90-1.70 (m, 7H), 1.65-1.29 (m, 6H), 1.07 (s, 3.5H), 1.04 (s, 4.5H) ppm.

$C_{30}H_{47}N_4O_5S_2$ calcd. m/z=608.31; found [M+H]⁺=609.32.

Example 118

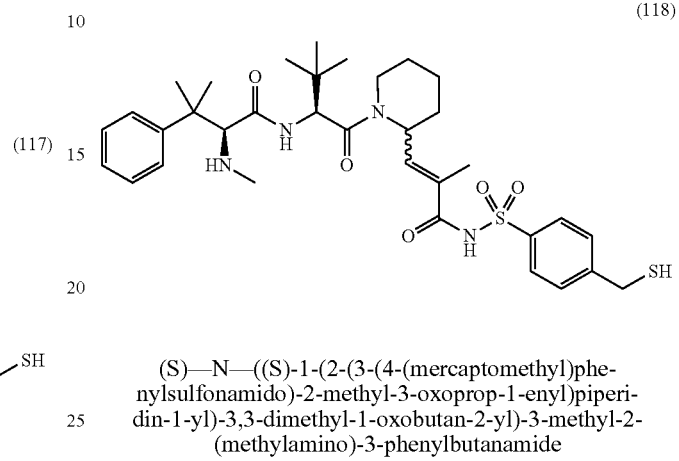

(118)

(S)—N—((S)-1-(2-(3-(4-(mercaptomethyl)phenylsulfonamido)-2-methyl-3-oxoprop-1-enyl)piperidin-1-yl)-3,3-dimethyl-1-oxobutan-2-yl)-3-methyl-2-(methylamino)-3-phenylbutanamide The title compound was synthesized from Boc-homoproline and Example 7 according to General Procedures 10, 11, 2, 3, 7 and others from Nieman J. A. et al. J. Nat. Prod. 2003, 66, 183-199. The compound was isolated as two diastereoisomers in an approximately 2:3 ratio.

¹H NMR (600 MHz, Methanol-d₄) δ 8.02 (d, J=8.4 Hz, 0.8H), 8.00 (d, J=8.5 Hz, 1.2H), 7.58 (d, J=8.5 Hz, 1H), 7.54 (d, J=8.5 Hz, 2H), 7.45 (t, J=8.2 Hz, 2H), 7.40 (d, J=7.2 Hz, 0.6H), 7.36 (m, 1H), 7.31 (t, J=7.1 Hz, 0.4H), 6.74 (d, J=8.2 Hz, 1H), 5.59 (m, 0.6H), 5.06 (m, 0.4H), 5.02 (s, 0.6H), 4.84 (s, 0.4H), 4.39 (d, J=12.5 Hz, 0.4H), 4.34 (s, 0.6H), 4.20 (s, 0.4H), 4.08 (d, J=12.0 Hz, 0.6H), 3.83 (s, 1.2H), 3.73 (s, 0.8H), 3.35 (m, 0.6H), 2.93 (td, J=13.6, 3.0 Hz, 0.4H), 2.55 (m, 3H), 2.00 (s, 1H), 1.90-1.51 (m, 7H), 1.51-1.30 (m, 4H), 1.30 (s, 1H), 1.15 (s, 1H), 1.04 (s, 3.5H), 1.01 (s, 4.5H) ppm.

$C_{14}H_{47}N_4O_5S_2$ calcd. m/z=656.31; found [M+H]⁺=657.30.

Example 119

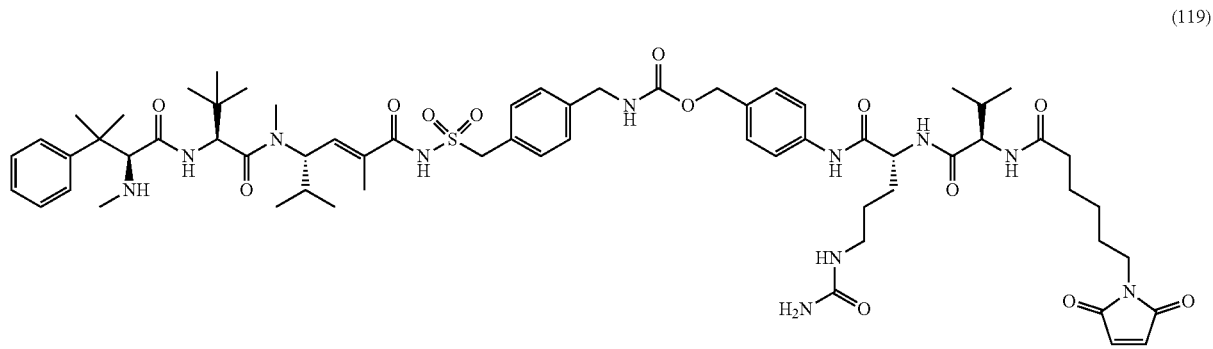 [SMILES: CN[C@H](C(=O)N[C@H](C(=O)N(C)[C@H](/C=C(\C)C(=O)NS(=O)(=O)Cc1ccc(CNC(=O)OCc2ccc(NC(=O)[C@@H](CCCNC(N)=O)NC(=O)[C@H](NC(=O)CCCCCN3C(=O)C=CC3=O)C(C)C)cc2)cc1)C(C)C)C(C)(C)C)C(C)(C)c1ccccc1]

(119)

MC-VC-PABC-77

The title compound was prepared by application of general procedures 15 and 7 from Boc protected Example 77.

$^1$H NMR (400 MHz, Methanol-$d_4$) δ 7.58 (d, J=8.2 Hz, 2H), 7.49 (d, J=7.5 Hz, 2H), 7.38 (t, J=7.7 Hz, 2H), 7.36-7.24 (m, 6H), 7.22 (d, J=7.8 Hz, 2H), 6.81 (s, 2H), 6.57 (d, J=9.1 Hz, 1H), 5.08 (s, 2H), 5.04 (t, J=10.0 Hz, 1H), 4.91 (s, 1H), 4.53 (dd, J=9.0, 5.1 Hz, 1H), 4.40 (s, 2H), 4.28 (s, 2H), 4.19 (d, J=7.4 Hz, 1H), 3.49 (t, J=7.1 Hz, 2H), 3.26-3.11 (m, 2H), 3.07-2.93 (m, 3H), 2.30 (t, J=7.4 Hz, 2H), 2.18 (s, 3H), 2.15-2.05 (m, 1H), 1.99-1.91 (m, 1H), 1.89 (s, 3H), 1.83-1.72 (m, 1H), 1.72-1.53 (m, 7H), 1.44 (s, 3H), 1.37 (s, 3H), 1.35-1.27 (m, 2H), 1.03 (s, 9H), 1.00 (d, J=6.8 Hz, 3H), 0.99 (d, J=6.7 Hz, 3H), 0.88 (d, J=6.5 Hz, 3H), 0.82 (d, J=6.6 Hz, 3H).

$C_{64}H_{91}N_{11}O_{13}S$ calcd. m/z=1253.7; found [M+H]$^+$=1254.8.

Example 120

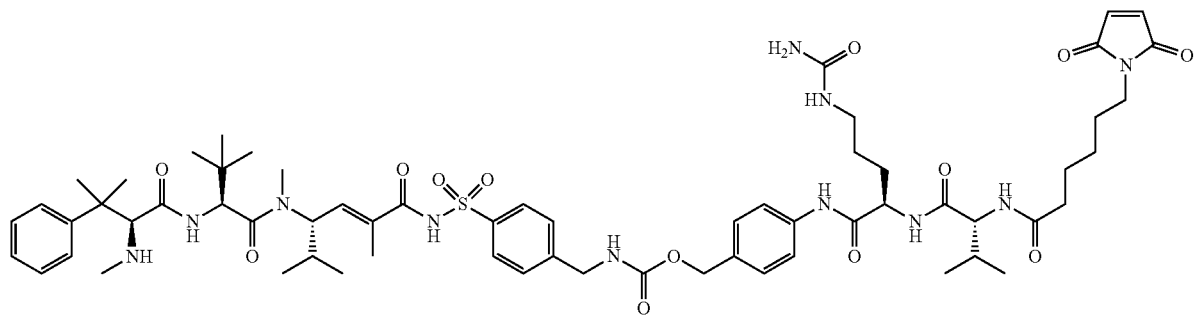

(120)

4-((R)-2-((R)-2-(6-(2,5-dioxo-2,5-dihydro-1H-pyrrol-1-yl)hexanamido)-3-methylbutanamido)-5-ureidopentanamido)benzyl 4-(N—((S,E)-2,5-dimethyl-4-((S)—N,3,3-trimethyl-2-((S)-3-methyl-2-(methylamino)-3-phenylbutanamido)butanamido)hex-2-enoyl)sulfamoyl)benzylcarbamate

MC-VC-PABC-85

The title compound was prepared by application of general procedures 15 and 7 to Boc protected Example 85.

$C_{63}H_{89}N_{11}O_{13}S$ calcd. m/z=1239.6; found [M+H]$^+$=1240.9.

Example 121

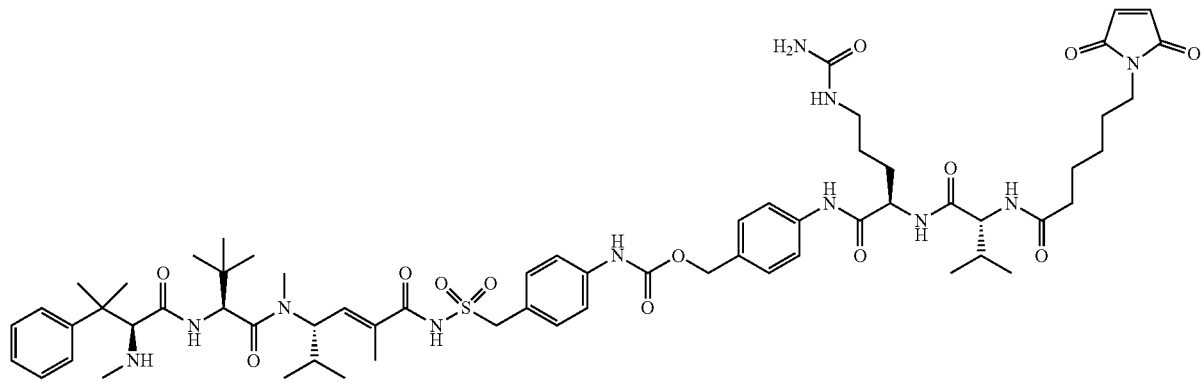

(121)

MC-VC-PABC-80

The title compound was prepared by application of general procedures 15 and 7 to Boc protected Example 80.

$C_{63}H_{89}N_{11}O_{13}S$ calcd. m/z=1239.6; found $[M+H]^+$=1240.9.

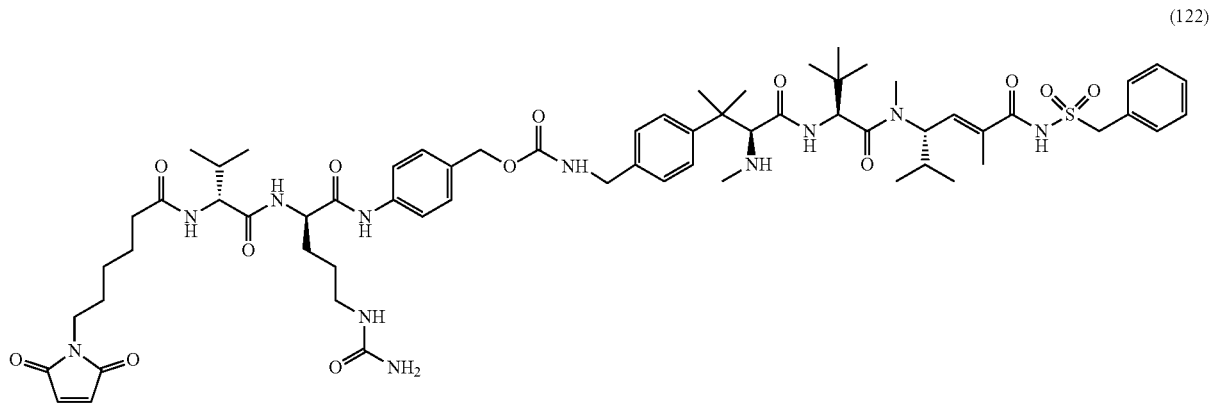 [SMILES: CN[C@H](C(=O)N[C@H](C(=O)N(C)[C@H](/C=C(\C)C(=O)NS(=O)(=O)Cc1ccccc1)C(C)C)C(C)(C)C)C(C)(C)c1ccc(CNC(=O)OCc2ccc(NC(=O)[C@@H](CCCNC(N)=O)NC(=O)[C@H](NC(=O)CCCCCN3C(=O)C=CC3=O)C(C)C)cc2)cc1]

(122)

MC-VC-PA BC-41

The title compound was prepared by application of General Procedure to Example 41.

$C_{64}H_{91}N_{11}O_{13}S$ calcd. m/z=12-53.65; found $[M+H]^+$=1254.75, $[M+2H]^{2+}$=628.20.

Example 123

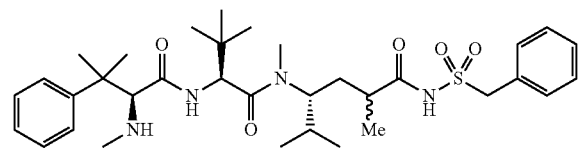

(123)

Chemical Formula: $C_{34}H_{52}N_4O_5S$
Exact Mass: 628.37
Molecular Weight: 628.87

Example 122

(R)—N-(benzylsulfonyl)-2,5-dimethyl-4-((S)—N,3,3-trimethyl-2-((S)-3-methyl-2-(methylamino)-3-phenylbutanamido)butanamido)hexanamide A suspension of the Example 14 and 10% palladium on carbon (25 mol % Pd) in glacial acetic acid was stirred under a $H_2$ atmosphere (1 atm) at ambient temperature. After 142 h, the reaction suspension was passed through a bed of celite, rinsed with MeOH (5×) and concentrated in vacuo. The residual light brown crude film was dissolved and purified on the preparative HPLC (30-70% MeCN/$H_2O$ with 0.1% TFA) and lyophilized to afford one diastereomer of the reduced product as a pale yellow solid in 15% yield $^1$H NMR (400 MHz, Methanol-$d_4$) δ 7.55 (d, J=7.2 Hz, 2H), 7.46 (t, J=7.8 Hz, 2H), 7.43-7.31 (m, 6H), 5.01 (s, 1H), 4.79 (d, J=14.1 Hz, 1H), 4.65 (d, J=14.1 Hz, 1H), 4.35 (s, 1H), 4.24 (s, 1H), 3.07 (s, 3H), 2.52 (s, 3H), 2.27 (m, J=10.3, 7.0, 3.2 Hz, 1H), 2.14 (ddd, J=13.5, 10.6, 2.7 Hz, 2H), 1.78 (d, J=8.6 Hz, 1H), 1.47 (s, 3H), 1.34 (s, 3H), 1.15 (d, J=6.9 Hz, 3H), 1.14 (s, 9H), 1.04 (d, J=6.6 Hz, 3H), 0.82 (d, J=6.6 Hz, 3H).

$C_{14}H_{52}N_4O_5S$ calcd m/z=628.37 amu; found $[M+H]^+$=629.6, $[M+Na]^+$ =651.6.

General Synthetic Schemes for (T)-(L)-(D) Using LC-SPDP and SMCC Linkers

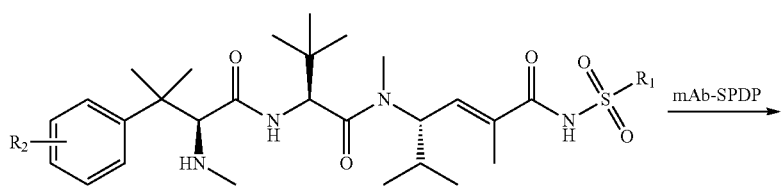

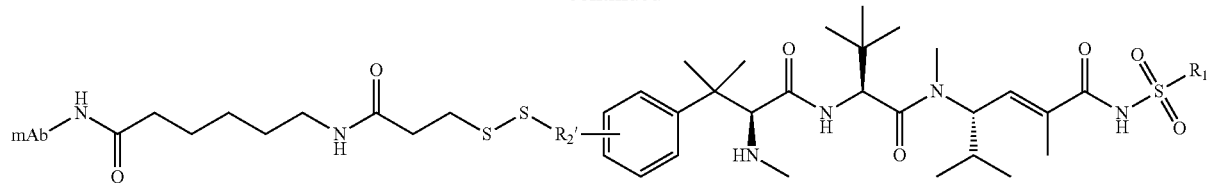
mAb-SPDP-S-R$_2$'-peptide-NHSO$_2$R$_1$
Composition produced using the SPDP linkage method described below. Note R$_2$' is distinct from R$_2$, as R$_2$ includes R$_2$'—S.
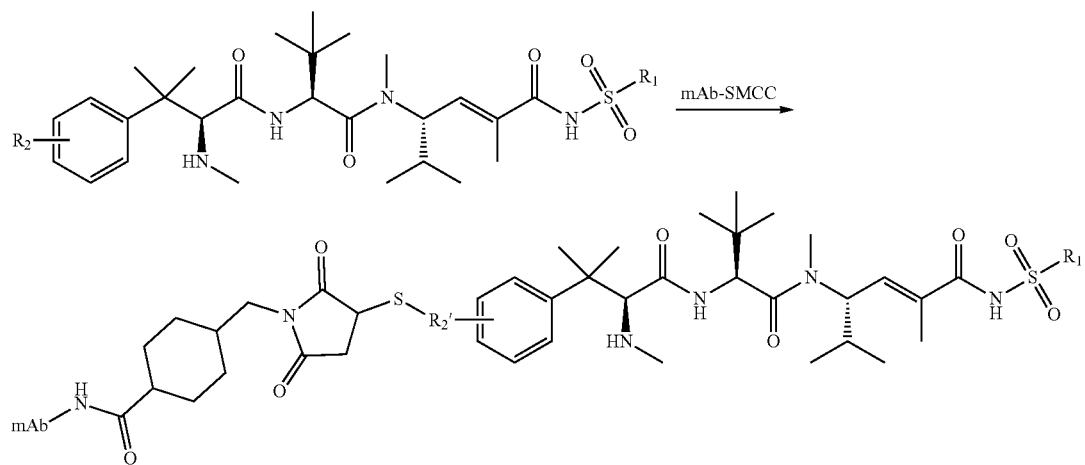
mAb-SMCC-S-R$_2$'-peptide-NHSO$_2$R,
Composition produced using the SMCC linkage method described below. Note R$_2$' is distinct from R$_2$, as R$_2$ includes R$_2$'—S.
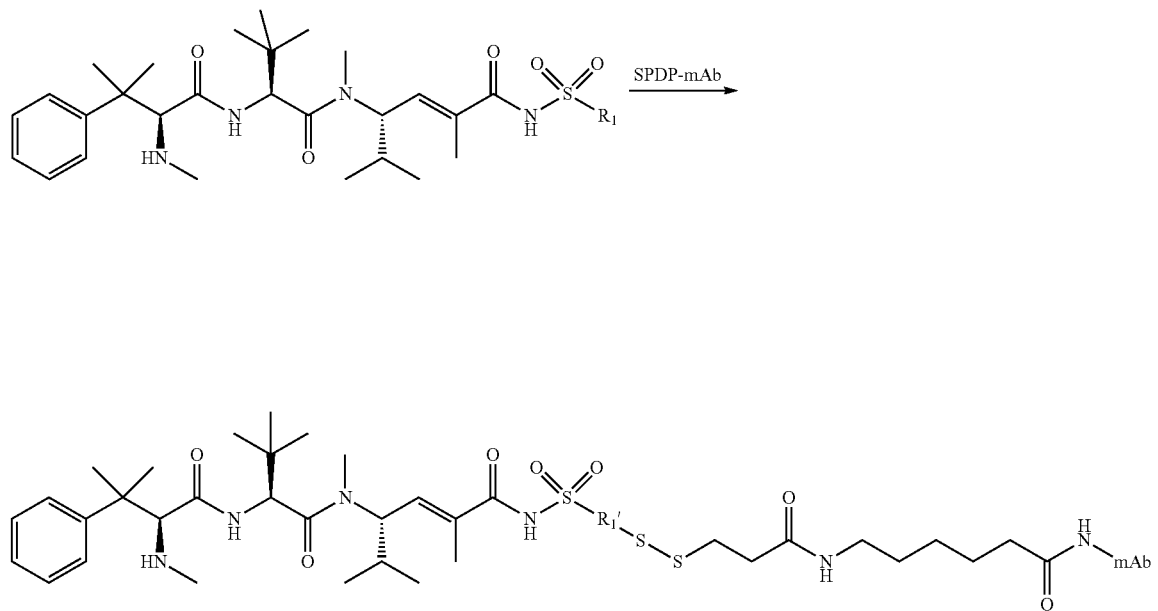

peptide-NHSO$_2$R$_1$'—S-SPDP

Composition produced using the SPDP linkage method described below. Note R$_1$' is distinct from R$_1$, as R$_1$ includes R$_1$'—S.

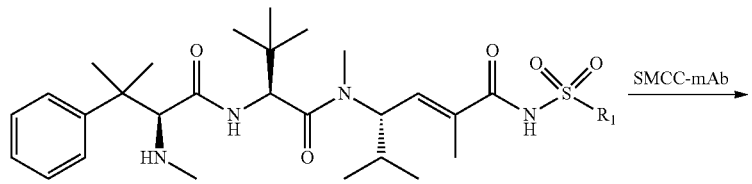

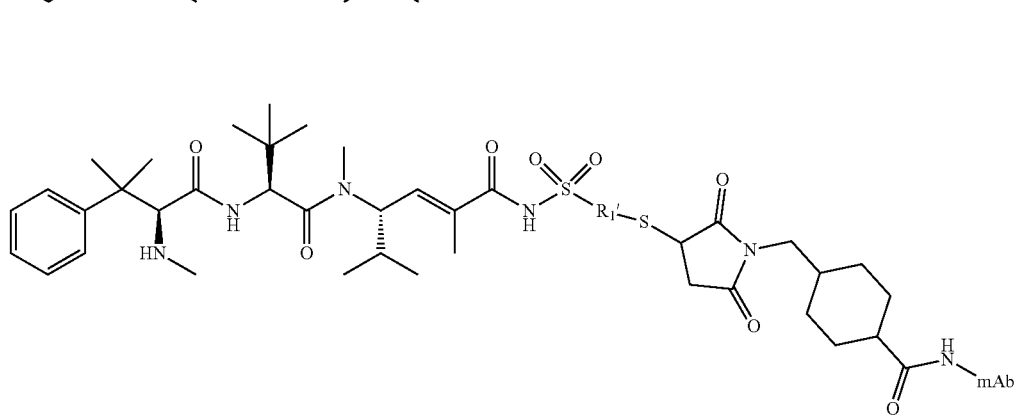

peptide-NHSO$_2$R$_1$'—S-SMCC

Composition produced using the SMCC linkage method described below. Note R$_1$' is distinct from R$_1$, as R$_1$ includes R$_1$'—S.

Example 124

(124)

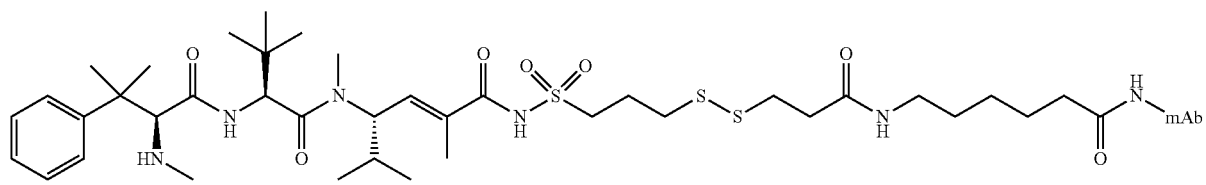

(Compound A—SPDP-mAb) produced using the Compound A synthesis method, above, and the SPDP linkage method described below.

Example 125

(125)

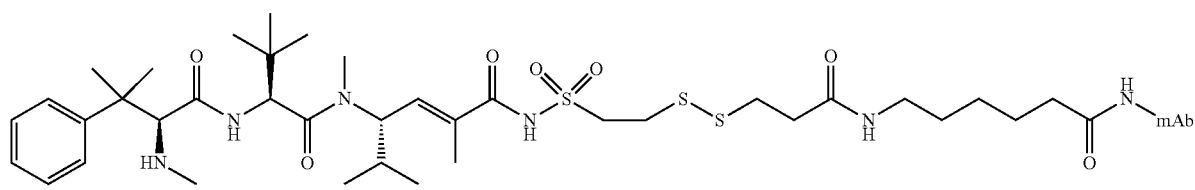

(Compound B—SPDP-mAb) produced using the Compound B synthesis method, above, and the SPDP linkage method described below.

Example 126

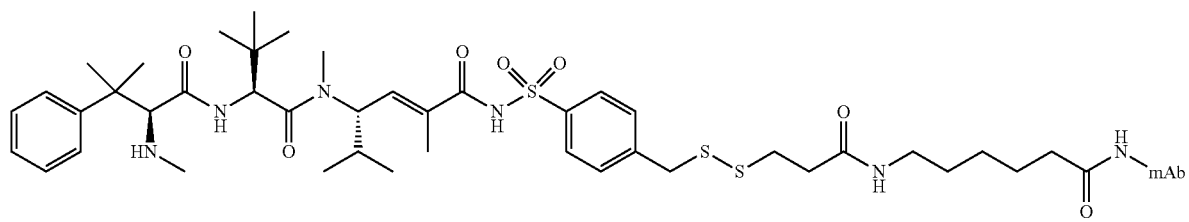

(126)

(Compound C—SPDP-mAb) produced using the Compound C synthesis method, above, and the SPDP linkage method described below.

Example 127

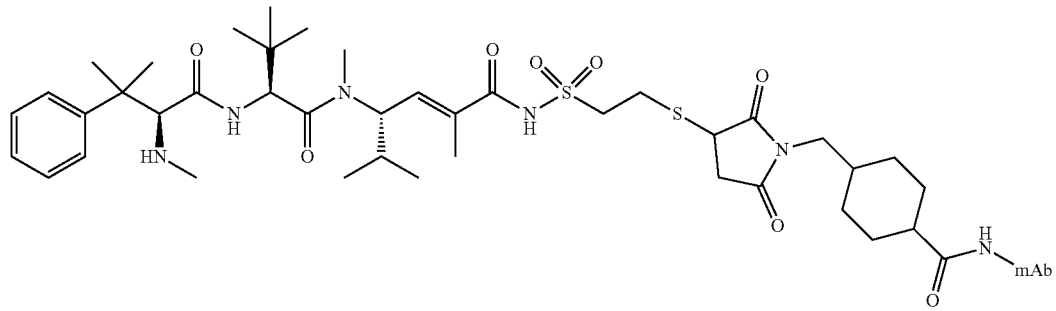

(127)

(Compound B—SMCC-mAb) produced using the Compound B synthesis method, above, and the SMCC linkage method described below.

Example 128

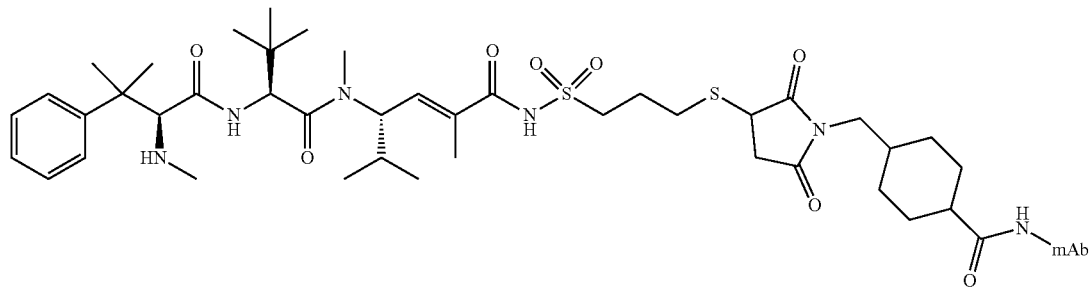

(128)

(Compound A—SMCC-mAb) produced using the Compound A synthesis method, above, and the SMCC linkage method described below.

Example 129

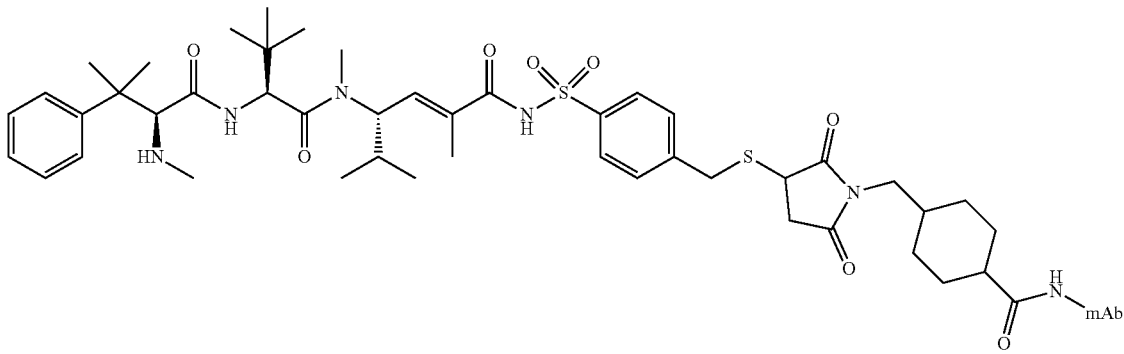

(Compound C—SMCC-mAb) produced using the Compound C synthesis method, above, and the SMCC linkage method described below.

Example 130

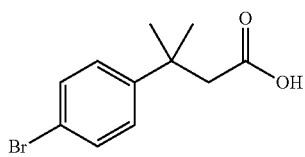

3-methyl-3-(4-bromophenyl)-butanoic acid

To a vigorously stirred solution of bromobenzene (4.70 g, 30.0 mmol) and 3,3-dimethylacrylic acid (1.00 g, 10.0 mmol) in 20 mL $CH_2Cl_2$ cooled to −10° C. in an $NH_4Cl_{(aq)}$/ice bath, solid $AlCl_3$ was added portion-wise, keeping the internal temperature below −5° C. The solution turned yellow, then brown after addition. After one hour, analysis by LC and TLC indicated complete consumption of the limiting reagent. The reaction was then quenched by the addition of 1 M citric acid, causing the brown color to fade to yellow. The resulting sloppy suspension was extracted four times with 20 mL $Et_2O$, the combined organics washed with $NaCl_{(sat)}$, dried over $Na_2SO_{4(s)}$ and concentrated in vacuo with heating to 45° C. to remove solvent and residual bromobenzene. The resulting oil solidified slowly. Recrystallization of the crude solid in hexanes afforded the title compound (1.29 g, 50%) as clusters of white prisms.

$^1$H NMR (400 MHz, Chloroform-d) δ (ppm) 7.42 (d, J=8.6 Hz, 2H), 7.23 (d, J=8.6 Hz, 2H), 2.63 (s, 2H), 1.43 (s, 6H). $C_{11}H_{13}BrO_2$ calcd. $[M+H]^+$=257.02 amu; found m/z=257.03. $R_f$=0.21 (20% (2% AcOH/EtOAc)/Hex).

Example 131

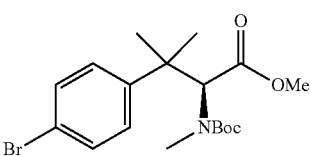

3-methyl-3-(3-bromophenyl)-butanoic acid

The title compound was prepared in the same manner as 3-methyl-3-phenylbutanoic acid in Nieman J. A., et al. *J. Nat. Prod.* 2003, 66, 183-199, using bromobenzene in place of benzene as the solvent, and substituting the acid-base workup with a simple extraction of the reaction mixture from 1 M citric acid and three successive recrystallizations from hexanes. From a crude product enriched in the desired meta isomer as a 2:1 mixture, the title compound could be obtained as white stubby needles in greater than 95% purity.

$^1$H NMR (400 MHz, Chloroform-d) δ (ppm) 7.49 (t, J=1.9 Hz, 1H), 7.34 (ddd, J=7.9, 1.9, 1.0 Hz, 1H), 7.29 (ddd, J=7.9, 1.9, 1.0 Hz, 1H), 7.18 (t, J=7.9 Hz, 1H), 2.64 (s, 2H), 1.44 (s, 6H). $C_{11}H_{13}BrO_2$ calcd. $[M+H]^+$=257.02 amu; found m/z=257.01. $R_f$=0.21 (20% (2% AcOH/EtOAc)/Hex).

Example 132

(S)-methyl 3-(4-bromophenyl)-2-(tert-butoxycarbonyl(methyl)amino)-3-methylbutanoate The title compound was synthesized from Example 130 according to the sequence of procedures described by Nienian et al. for the synthesis of (S)-methyl 2-(tert-butoxycarbonyl(methyl)amino)-3-methyl-3-phenylbutanoate.

Example 133

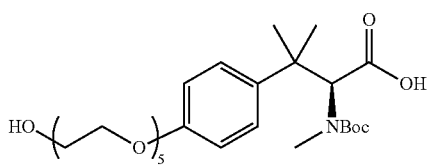

(133)

(S)-2-((tert-butoxycarbonyl)(methyl)amino)-3-(4-((14-hydroxy-3,6,9,12-tetraoxatetradecyl)oxy)phenyl)-3-methylbutanoic acid To a stirred solution of Example 68 (157 mg, 0.405 mmol) in pentacthylene glycol (1.5 mL) were added $CsCO_3$ (330 mg, 1.01 mmol), 3,4,7,8-tetramethyl-1,10-phenanthroline (57 mg, 0.24 mmol), and CuI (23 mg, 0.12 mmol). Nitrogen was blown into the flask, then it was sealed and heated to 130° C., the solution quickly turning red to brown to black. After 40 h, the reaction looked to be nearly complete by HPLC analysis. Thus, the mixture was allowed to cool to ambient temperature, diluted with $H_2O$, and transferred to a larger Erlenmeyer with a stir bar. This mixture was carefully acidified to pH~3 with 1 M citric acid, paying attention not to allow the foamy mixture to spill over. The mixture was then extracted five times with $CH_2Cl_2$, the combined organic extracts washed with $NaCl_{(sat)}$, dried over $Na_2SO_{4(s)}$, and concentrated in vacuo to yield about 300 mg of crude oil. Purification by flash chromatography (1-10% MeOH/(2% AcOH/EtOAc)) yielded the title compound (66 mg, 30%) as a clear film which existed as a set of N-Boc rotamers an an approximate 2:1 ratio.

$^1$H NMR (400 MHz, Chloroform-d) δ (ppm) 7.35 (d, J=7.8 Hz, 1.3H), 7.30 (d, J=7.6 Hz, 0.7H), 6.87 (d, J=7.1 Hz, 2H), 5.07 (s, 0.7H), 4.93 (s, 0.3H), 4.14 (m, 2H), 3.86 (m, 2H), 3.70 (m, 16H), 2.83 (s, 1H), 2.72 (s, 2H), 1.54 (s, 3H), 1.49 (s, 3H), 1.45 (s, 9H). $C_{27}H_{45}NO_{10}$ calcd. [M+H]$^+$=544.31 amu; found m/z=544.36. $R_f$=0.36 (5% MeOH/(2% AcOH/EtOAc)).

Example 134

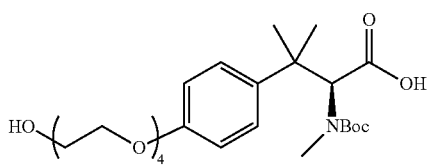

(134)

(S)-2-((tert-butoxycarbonyl)(methyl)amino)-3-(4-(2-(2-(2-(2-hydroxyethoxy)ethoxy)ethoxy)ethoxy)phenyl)-3-methylbutanoic acid The title compound was prepared according to the above method from Example 68 (132 mg, 0.341 mmol), $CsCO_3$ (278 mg, 0.853 mmol), 3,4,7,8-tetramethyl-1,10-phenanthroline (24 mg, 0.10 mmol), and CuI (10 mg, 0.051 mmol). Flash chromatography (1-10% MeOH/(2% AcOH/EtOAc)) gave the title compound (66 mg, 38%) as a clear oil in an approximate 2:1 ratio of N-Boc rotamers.

$^1$H NMR (400 MHz, Chloroform-d) δ (ppm) 7.34 (d, J=8.4 Hz, 1.3H), 7.29 (d, J=8.1 Hz, 0.7H), 6.85 (d, J=8.4 Hz, 2H), 5.05 (s, 0.7H), 4.91 (s, 0.3H), 4.13 (t, J=4.6 Hz, 2H), 3.87-3.79 (m, 2H), 3.76-3.60 (m, 10H), 3.59 (t, J=4.1 Hz, 2H), 2.80 (s, 1H), 2.69 (s, 2H), 1.53 (s, 3H), 1.48 (s, 3H), 1.44 (s, 9H). $C_{25}H_{41}NO_9$ calcd. [M+H]$^+$=500.29 amu; found m/z=500.36. $R_f$=0.46 (5% MeOH/(2% AcOH/EtOAc)).

Example 135

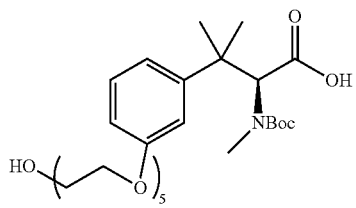

(135)

(S)-3-(3-((14-hydroxy-3,6,9,12-tetraoxatetradecyl)oxy)phenyl)-3-methyl-2-(methylamino)butanoic acid The precursor to the title compound, (S)-3-(3-bromophenyl)-2-((tert-butoxycarbonyl)(methyl)amino)-3-methylbutanoic acid, was prepared from Example 131 by following the procedures in Neiman et al.

Thus, following the procedures above, from (S)-3-(3-bromophenyl)-2-((tert-butoxycarbonyl)(methyl)amino)-3-methylbutanoic acid (166 mg, 0.43 mmol), $CsCO_3$ (330 mg, 1.01 mmol), 3,4,7,8-tetramethyl-1,10-phenanthroline (31 mg, 0.13 mmol), and CuI (12.3, 0.060 mmol) in 1.5 mL pentaethylene glycol heated to 130° C. for two days, the title compound (73 mg, 31%) was obtained as a clear oil after flash chromatography (1-10% MeOH/(2% AcOH/EtOAc)) in an approximate 2:1 ratio of N-Boc rotamers.

$^1$H NMR (400 MHz, Chloroform-d) δ (ppm) 7.17 (t, J=7.8 Hz, 1H), 7.14-7.07 (m, 1H), 7.07-6.93 (m, 2H), 6.74 (d, J=8.0 Hz, 1H), 5.11 (s, 0.7H), 4.93 (s, 0.3H), 4.25-4.03 (m, 2H), 3.91-3.77 (m, 2H), 3.78-3.66 (m, 2H), 3.69-3.43 (s, 14H), 2.72 (s, 1H), 2.65 (s, 1H), 1.51 (s, 3H), 1.49 (s, 3H), 1.45 (s, 9H). $C_{27}H_{45}NO_{10}$ calcd. [M+H]$^+$=544.31 amu; found m/z=544.34.

Example 136

(136)

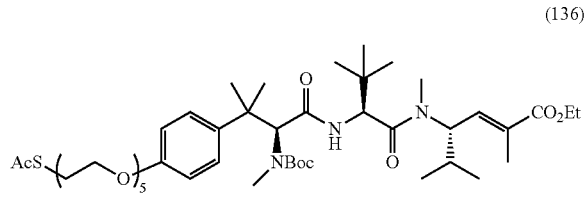

(6S,9S,12S,E)-ethyl 9-(tert-butyl)-12-isopropyl-2,2,5,11,14-pentamethyl-4,7,10-trioxo-6-(2-(4-((16-oxo-3,6,9,12-tetraoxa-15-thiaheptadecyl)oxy)phenyl)propan-2-yl)-3-oxa-5,8,11-triazapentadec-13-en-15-oate (S)-2-((tert-butoxycarbonyl)(methyl)amino)-3-(4-((14-hydroxy-3,6,9,12-tetraoxatetradecyl)oxy)phenyl)-3-methylbutanoic acid (65 mg, 0.120 mmol) was coupled to (S,E)-ethyl 4-((S)-2-amino-N,3,3-trimethylbutanamido)-2,5-dimethylhex-2-enoate with HATU and DIPEA following the same stoichiometry and procedure as described in the general coupling procedures in Nieman et al. to give an intermediate free alcohol after purification by flash chromatography (1-10% MeOH/(2% AcOH/EtOAc)). Next, to triphenylphosphine (40 mg, 0.15 mmol) in 0.75 mL THF under $N_2$ at 0° C., di-tert-butylazodicarboxylate (35 mg, 0.15 mmol) was added in one portion. After 35 minutes, a white precipitate crashed out and the reaction became difficult to stir. To this suspension, a solution of the intermediate alcohol (42 mg, 0.050 mmol) in 0.75 mL THF was added diluting the precipitate enough to restore stirring. Five minutes later, thioacetic acid (5.7 mg, 0.075 mmol) in 0.05 mL THF was added causing all yellow color to fade from the mixture. After 30 min, the reaction was allowed to warm to ambient temperature. The precipitate disappeared after another 15 min, and analysis by TLC and LCMS showed nearly complete conversion. After another 40 minutes, the reaction mixture was concentrated in vacuo, then subjected directly to flash chromatography (40-100% EtOAc/Hex then to 10% MeOH/EtOAc) to yield the title compound (26 mg, 57%) as a clear film.

$^1$H NMR (400 MHz, Chloroform-d) δ (ppm) 7.43 (d, J=8.4 Hz, 1.3H), 7.31 (d, J=8.3 Hz, 0.7H), 6.97-6.72 (m, 2H), 6.62 (dd, J=9.3, 1.6 Hz, 1H), 6.14 (d, J=9.6 Hz, 1H), 5.22 (s, 0.7H), 5.12-4.99 (m, 1H), 4.84 (s, 0.3H), 4.69 (d, J=9.3 Hz, 0.3H), 4.60 (d, J=8.9 Hz, 0.7H), 4.19 (q, J=7.2 Hz, 2H), 4.09 (td, J=4.6, 2.3 Hz, 2H), 3.84 (t, J=4.9 Hz, 2H), 3.77-3.70 (m, 2H), 3.70-3.61 (m, 10H), 3.59 (t, J=6.4 Hz, 2H), 3.07 (t, J=6.4 Hz, 2H), 2.97-2.91 (m, 3H), 2.84 (s, 3H), 2.32 (s, 3H), 1.87 (s, 3H), 1.49 (s, 3H), 1.43 (s, 9H), 1.35 (s, 3H), 1.30 (t, J=7.1 Hz, 3H), 0.87 (d, J=6.6 Hz, 3H), 0.80 (d, J=16.6 Hz, 3H), 0.77 (s, 9H). $C_{46}H_{77}N_3O_{12}S$ calcd. [M+H]$^+$=896.53 amu; found m/z=896.77. $R_f$=0.56 (80% EtOAc/Hex).

Example 137

(137)

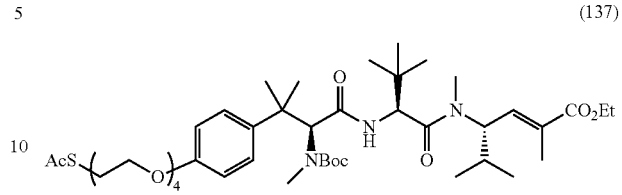

(6S,9S,12S,E)-ethyl 9-(tert-butyl)-12-isopropyl-2,2,5,11,14-pentamethyl-4,7,10-trioxo-6-(2-(4-((13-oxo-3,6,9-trioxa-12-thiatetradecyl)oxy)phenyl)propan-2-yl)-3-oxa-5,8,11-triazapentadec-13-en-15-oate The title compound was prepared from (S)-2-((tert-butoxycarbonyl)(methyl)amino)-3-(4-(2-(2-(2-(2-hydroxyethoxy)ethoxy)ethoxy) ethoxy)phenyl)-3-methylbutanoic acid (66 mg, 0.065 mmol) following the same procedure described above to give 32 mg (57%) as a clear film after flash chromatography (20-100% EtOAc/Hex)

$^1$H NMR (400 MHz, Chloroform-d) δ (ppm) 7.44 (d, J=8.5 Hz, 1.3H), 7.32 (d, J=8.5 Hz, 0.7H), 6.95-6.77 (m, 2H), 6.62 (dd, J=9.2, 1.7 Hz, 1H), 6.09 (d, J=9.1 Hz, 1H), 5.24 (s, 0.7H), 5.13-4.95 (m, 1H), 4.84 (s, 0.3H), 4.69 (d, J=9.6 Hz, 0.3H), 4.60 (d, J=9.0 Hz, 0.7H), 4.19 (q, J=7.1 Hz, 2H), 4.09 (td, J=4.7, 2.4 Hz, 2H), 3.84 (t, J=4.9 Hz, 2H), 3.72 (dd, J=5.7, 3.2 Hz, 2H), 3.70-3.65 (m, 2H), 3.66-3.62 (m, 4H), 3.60 (t, J=6.5 Hz, 2H), 3.09 (t, J=6.5 Hz, 2H), 2.96-2.88 (m, 3H), 2.84 (s, 3H), 2.33 (s, 3H), 1.88 (d, J=3.5 Hz, 3H), 1.49 (s, 2H), 1.43 (d, J=5.5 Hz, 11H), 1.35 (s, 2H), 1.30 (t, J=7.1 Hz, 2H), 0.87 (d, J=6.6 Hz, 3H), 0.80 (d, J=15.9 Hz, 3H), 0.76 (s, 9H). $C_{44}H_{73}N_3O_{11}S$ calcd. [M+H]$^+$=852.51 amu; found m/z=852.79. $R_f$=0.60 (60% EtOAc/Hex).

Example 138

(138)

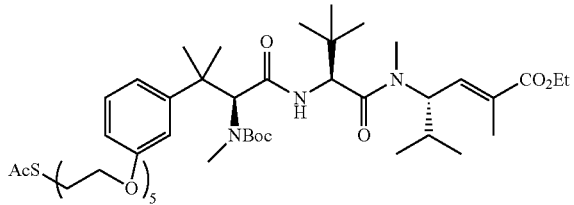

(6S,9S,12S,E)-ethyl 9-(tert-butyl)-12-isopropyl-2,2,5,11,14-pentamethyl-4,7,10-trioxo-6-(2-(3-((16-oxo-3,6,9-trioxa-12-thiatetradecyl)oxy)phenyl)propan-2-yl)-3-oxa-5,8,11-triazapentadec-13-en-15-oate The title compound was prepared from (S)-3-(3-((14-hydroxy-3,6,9,12-tetraoxatetradecyl)oxy)phenyl)-3-methyl-2-(methylamino)butanoic acid (73 mg, 0.080 mmol) following the same procedure described above to give 66 mg (47%) as a clear film after flash chromatography (20-100% EtOAc/Hex).

¹H NMR (400 MHz, Chloroform-d) δ (ppm) 7.25-6.92 (m, 3H), 6.78-6.70 (m, 1H), 6.62 (d, J=8.9 Hz, 1H), 6.12 (d, J=8.9 Hz, 1H), 5.26 (s, 0.7H), 5.12-4.99 (m, 1H), 4.89 (s, 0.3H), 4.74-4.56 (m, 1H), 4.19 (q, J=7.2 Hz, 1H), 4.16-4.03 (m, 2H), 3.84 (td, J=5.0, 3.2 Hz, 2H), 3.77-3.61 (m, 14H), 3.60 (t, J=6.4 Hz, 2H), 3.09 (t, J=6.5 Hz, 2H), 2.97-2.75 (m, 6H), 2.33 (s, 3H), 1.91-1.83 (m, 3H), 1.52-1.35 (m, 16H), 1.26 (t, J=7.1 Hz, 3H), 0.87 (d, J=6.0 Hz, 3H), 0.81 (d, J=12.9 Hz, 3H), 0.77 (s, 9H). $C_{46}H_{77}N_3O_{12}S$ calcd. $[M+H]^+$=896.53 amu; found m/z=896.68. $R_f$=0.61 (75% EtOAc/Hex).

Example 139

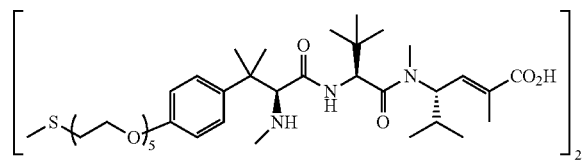

(S,E)-4-((S)-2-((S)-3-(4-((14-mercapto-3,6,9,12-tetraoxatetradecyl)oxy)phenyl)-3-methyl-2-(methylamino)butanamido)-N,3,3-trimethylbutanamido)-2,5-dimethylhex-2-enoic acid disulfide The title compound was prepared by saponification, then TFA promoted Boc removal, according to the exact methods described in Nieman et al. from (6S,9S,12S,E)-ethyl 9-(tert-butyl)-12-isopropyl-2,2,5,11,14-pentamethyl-4,7,10-trioxo-6-(2-(4-((16-oxo-3,6,9,12-tetraoxa-15-thiaheptadecyl)oxy)phenyl)propan-2-yl)-3-oxa-5,8,11-triazapentadec-13-en-15-oate (26 mg, 0.029 mmol) to afford the title compound (16 mg, 90%) as a clear glass after complete removal of excess TFA.

¹H NMR (400 MHz, Methanol-d₄) δ (ppm) 8.43 (d, J=8.1 Hz, 1H), 7.47 (d, J=8.5 Hz, 2H), 7.08-6.94 (m, 2H), 6.80 (dq, J=9.9, 1.5 Hz, 1H), 5.08 (t, J=10.1 Hz, 1H), 4.94 (d, J=8.1 Hz, 1H), 4.32 (s, 1H), 4.21-4.12 (m, 2H), 3.93-3.81 (m, 3H), 3.76 (t, J=6.4 Hz, 2H), 3.76-3.72 (m, 2H), 3.72-3.62 (m, 10H), 3.17 (s, 3H), 2.92 (t, J=6.4 Hz, 2H), 2.61-2.47 (m, 3H), 2.14-2.00 (m, 1H), 1.94 (d, J=1.5 Hz, 3H), 1.46 (s, 3H), 1.40 (d, J=7.7 Hz, 3H), 1.09 (s, 9H), 0.94 (d, J=5.0 Hz, 3H), 0.92 (d, J=4.8 Hz, 3H). $C_{74}H_{124}N_6O_{18}S_2$ calcd. $[M+H]^+$=1449.85 amu; found m/z=1450.49.

Example 140

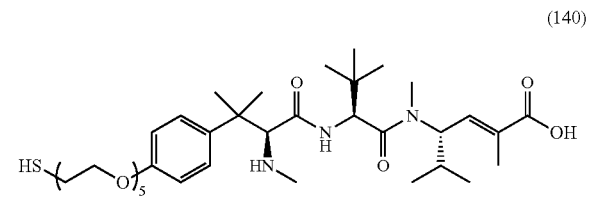

Compound of Example 139 is reduced according to the methods below to produce the subject compound.

Example 141

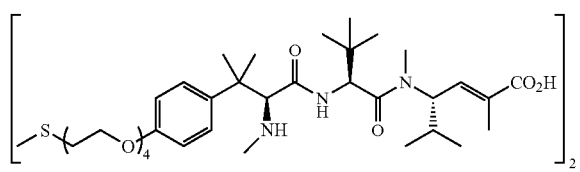

(S,E)-4-((S)-2-((S)-3-(4-(2-(2-(2-(2-mercaptoethoxy)ethoxy)ethoxy)phenyl)-3-methyl-2-(methylamino)butanamido)-N,3,3-trimethylbutanamido)-2,5-dimethylhex-2-enoic acid disulfide The title compound was prepared by saponification, then TFA promoted Boc removal, according to the exact methods described in Nieman et al. from (6S,9S,12S,E)-ethyl 9-(tert-butyl)-12-isopropyl-2,2,5,11,14-pentamethyl-4,7,10-trioxo-6-(2-(4-((13-oxo-3,6,9-trioxa-12-thiatetradecyl)oxy)phenyl)propan-2-yl)-3-oxa-5,8,11-triazapentadec-13-en-15-oate (32 mg, 0.037 mmol) to afford the title compound (29 mg, 86%) as a clear glass after complete removal of excess TFA.

¹H NMR (400 MHz, Methanol-d₄) δ (ppm) 8.39 (d, J=8.2 Hz, 1H), 7.44 (d, J=8.9 Hz, 2H), 7.01 (d, J=8.5 Hz, 2H), 6.77 (d, J=7.9 Hz, 1H), 5.05 (t, J=10.1 Hz, 1H), 4.92 (d, J=8.3 Hz, 1H), 4.28 (s, 1H), 4.15 (dd, J=5.8, 3.4 Hz, 2H), 3.89-3.80 (m, 2H), 3.73 (t, J=6.4 Hz, 2H), 3.72-3.69 (m, 2H), 3.69-3.60 (m, 6H), 3.14 (s, 3H), 2.89 (t, J=6.4 Hz, 2H), 2.50 (s, 3H), 2.11-1.97 (m, 1H), 1.91 (d, J=1.4 Hz, 3H), 1.43 (s, 3H), 1.36 (s, 3H), 1.06 (s, 9H), 0.92-0.87 (m, 6H). $C_{70}H_{118}N_6O_{16}S_2$ calcd. $[M+H]^+$=1361.80 amu; found m/z=1362.26.

Example 142

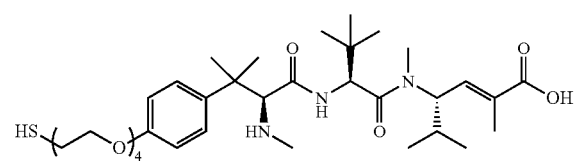

Compound of Example 141 is reduced according to the methods below to produce the subject compound.

Example 143

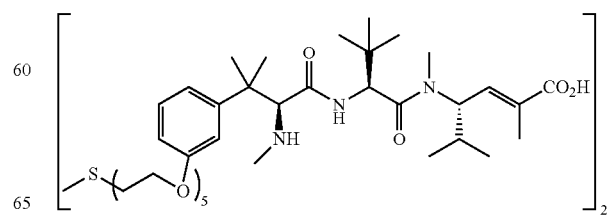

(S,E)-4-((S)-2-((S)-3-(3-((14-mercapto-3,6,9,12-tetraoxatetradecyl)oxy)phenyl)-3-methyl-2-(methylamino)butanamido)-N,3,3-trimethylbutanamido)-2,5-dimethylhex-2-enoic acid The title compound was prepared by saponification, then TFA promoted Boc removal, according to the exact methods described in Nieman et al. from (6S,9S,12S,E)-ethyl 9-(tert-butyl)-12-isopropyl-2,2,5,11,14-pentamethyl-4,7,10-trioxo-6-(2-(3-((16-oxo-3,6,9,12-tetraoxa-15-thiaheptadecyl)oxy)phenyl)propan-2-yl)-3-oxa-5,8,11-triazapentadec-13-en-15-oate (56 mg, 0.029 mmol) to afford the title compound (43 mg, 82%) as an off-white foam after complete removal of excess TFA.

$^1$H NMR (400 MHz, Methanol-$d_4$) δ (ppm) 8.48 (d, J=8.3 Hz, 1H), 7.47-7.29 (m, 1H), 7.21-7.04 (m, 1H), 6.95 (t, J=9.4 Hz, 1H), 6.80 (d, J=9.7 Hz, H), 5.08 (t, J=10.1 Hz, 1H), 4.97-4.94 (m, 1H), 4.38 (s, 1H), 4.24-4.13 (m, 2H), 3.95-3.82 (m, 2H), 3.80-3.58 (m, 14H), 3.17 (s, 3H), 2.92 (t, J=6.4 Hz, 2H), 2.53 (s, 3H), 2.11-2.03 (m, 1H), 1.94 (d, J=1.4 Hz, 3H), 1.47 (s, 3H), 1.40 (s, 3H), 1.09 (s, 9H), 0.93 (dt, J=11.2, 3.4 Hz, 15H). $C_{74}H_{124}N_6O_{18}S_2$ calcd. [M+H]$^+$=1449.85 amu; found m/z=1450.06.

Example 144

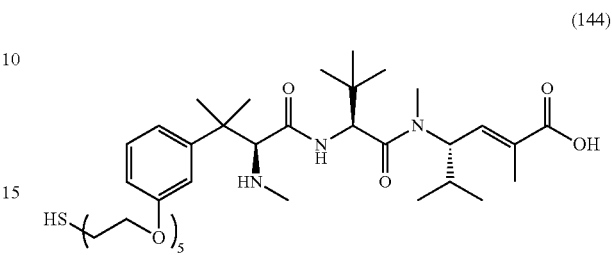

(144)

Compound of Example 143 is reduced according to the methods below to produce the subject compound.

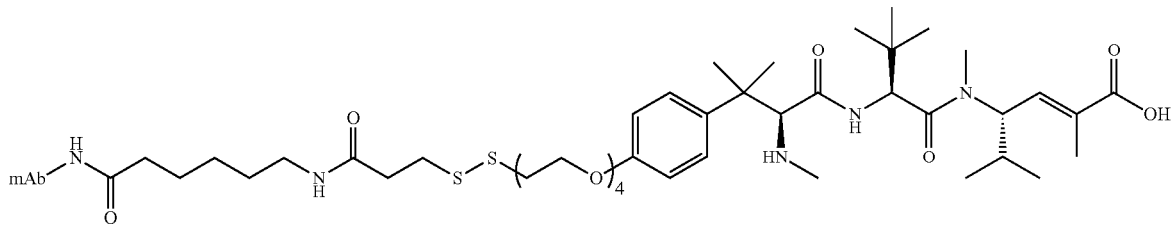

(145)

(mAb-SPDP—Compound 142) produced using the Compound 142 synthesis method, above, and the SPDP linkage method described below.

Example 146

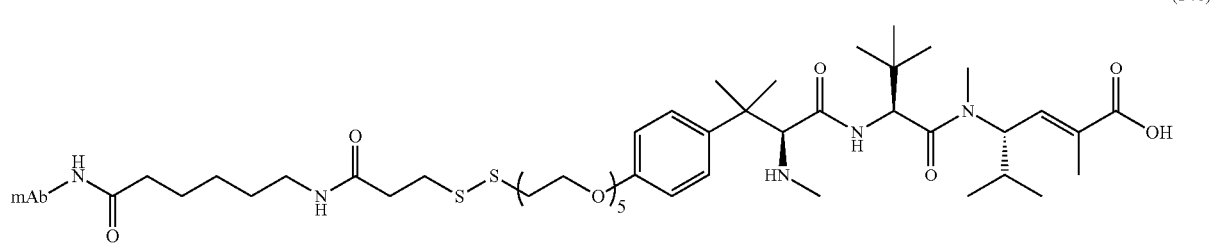
(146)

(mAb-SPDP—Compound 140) produced using the Compound 140 synthesis method, above, and the SPDP linkage method described below.

Example 147

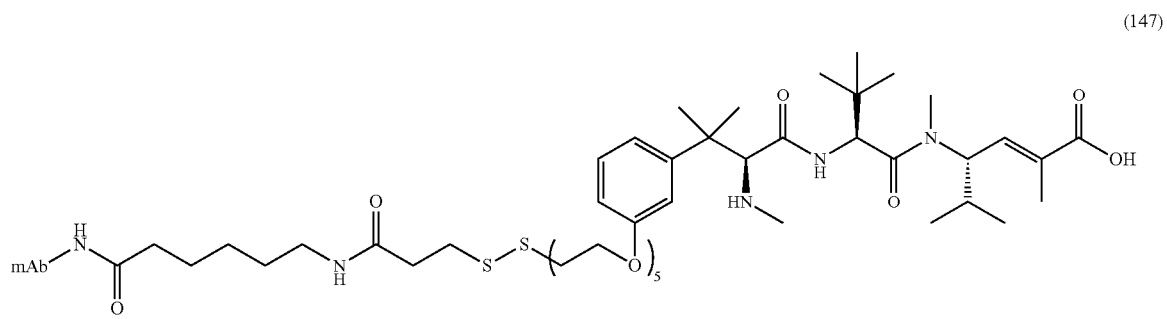
(147)

(mAb-SPDP—Compound 144) produced using the Compound 144 synthesis method, above, and the SPDP linkage method described below.

Example 148

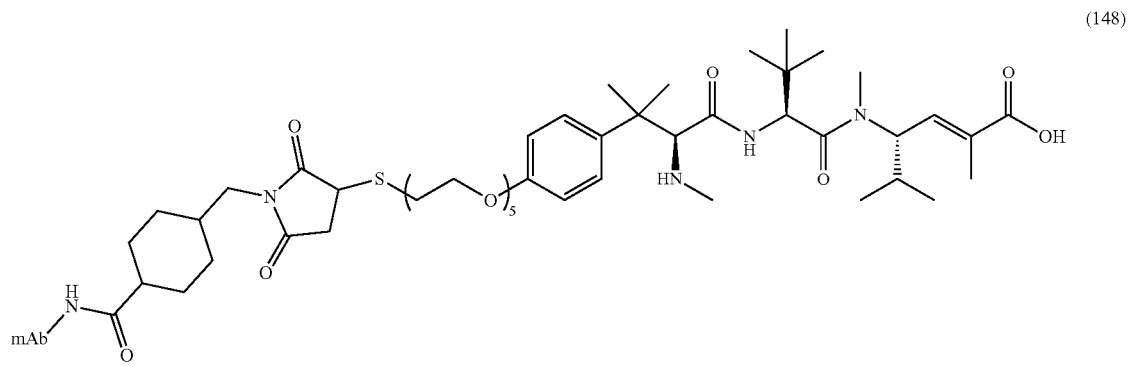
(148)

(mAb-SMCC-Compound 140) produced using the Compound 140 synthesis method, above, and the SMCC linkage method described below.

Example 149

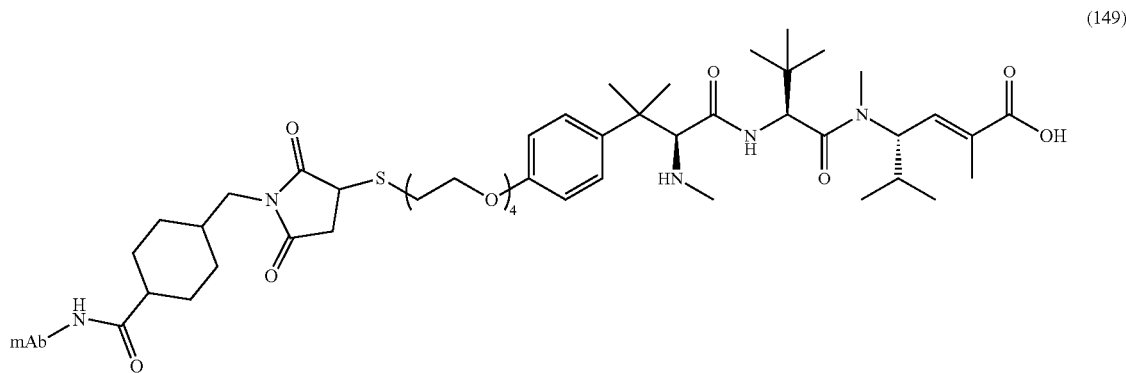

(149)

(mAb-SMCC-Compound 142) produced using the Compound 142 synthesis method, above, and the SMCC linkage method described below.

Example 150

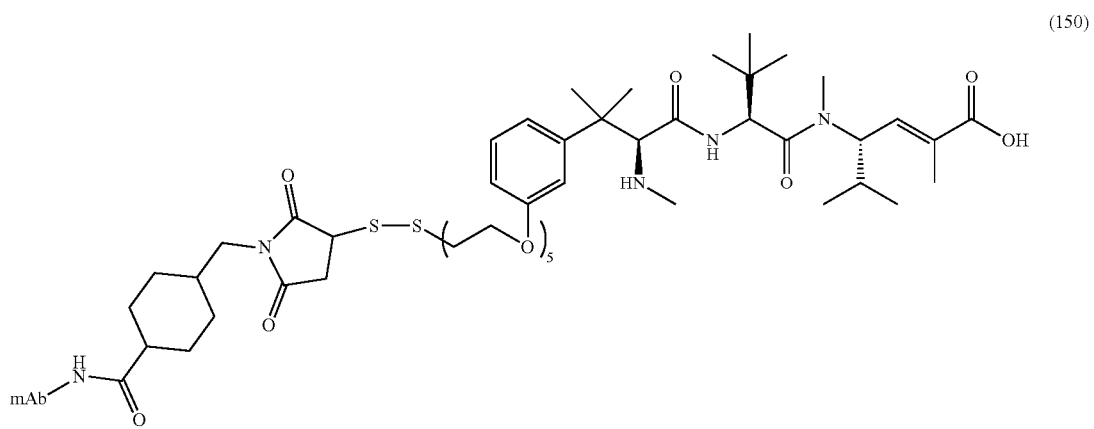

(150)

(mAb-SMCC-Compound 144) produced using the Compound 144 synthesis method, above, and the SMCC linkage method described below.

Other Examples

Example 151

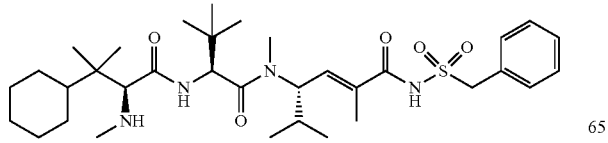

(151)

(S,E)-N-(benzylsulfonyl)-4-((S)-2-((S)-3-cyclo-hexyl-3-methyl-2-(methylamino)butanamido)-N,3,3-trimethylbutanamido)-2,5-dimethylhex-2-enamide The title compound was synthesized from (S)-2-(tert-butoxycarbonyl(methyl)amino)-3-cyclohexyl-3-methylbutanoic acid as prepared by Zask et al., J. Med. Chem. 2004, 47, (19), 4774-4786 and (S,E)-4-((S)-2-amino-N,3,3-trimethylbutanamido)-N-(benzylsulfonyl)-2,5-dimethylhex-2-enamide, prepared using General Procedures 10, 11, 3 and 2 by application of General Procedures 4 and 7.

$^1$H NMR (400 MHz, Methanol-$d_4$) δ 7.38 (s, 5H), 6.37 (dd, J=9.4, 1.7 Hz, 1H), 5.01 (t, J=10.0 Hz, 1H), 4.91 (s, 1H), 4.75 (s, 2H), 4.01 (s, 1H), 3.10 (s, 3H), 2.66 (s, 3H), 2.05-1.91 (m, 4H), 1.91-1.67 (m, 6H), 1.45-1.28 (m, 3H), 1.29-1.01 (m, 17H), 0.95-0.75 (m, 9H).

C34H56N4O5S calcd m/z=632.40 found [M+H]$^+$=633.35.

Example 152

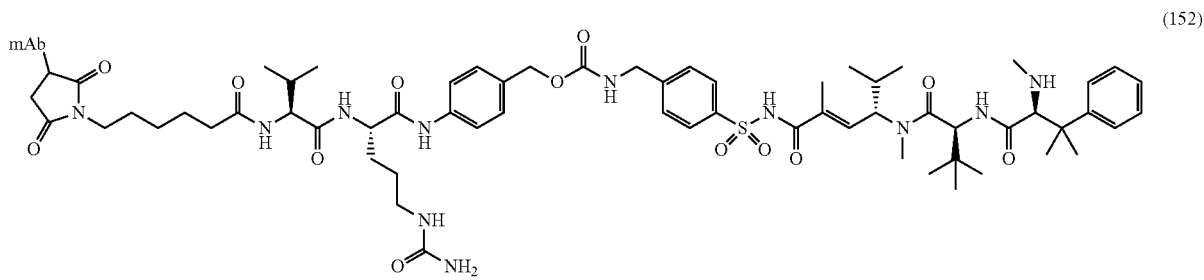

(152)

(mAb-MCvcPABC—Compound 85) produced using Example compound 120, above, and the general MCvcPABC conjugation method described below.

Example 153

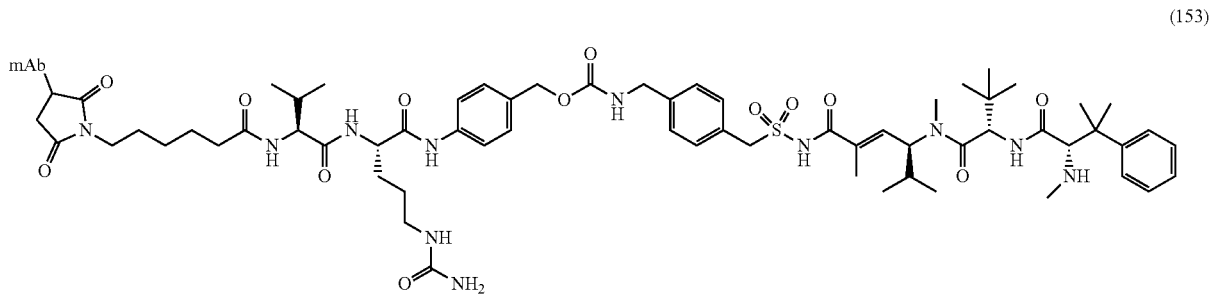

(153)

(mAb-MCvcPABC—Compound 77) produced using Example compound 119, above, and the general MCvcPABC conjugation method described below.

Example 154

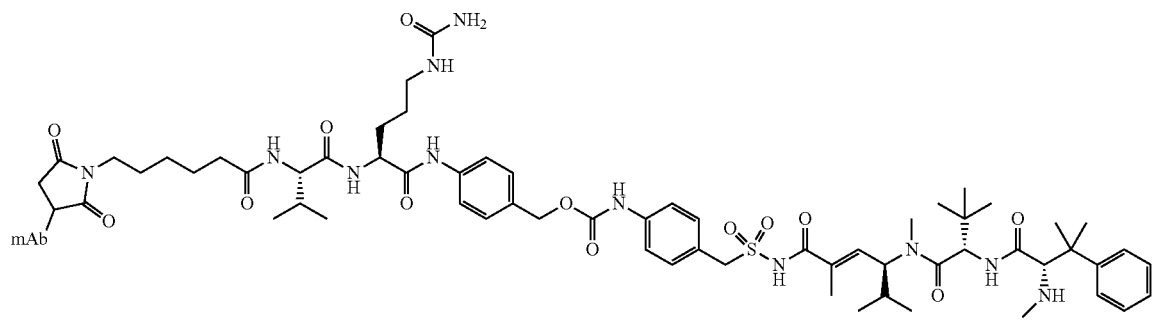

(154)

(mAb-MCvcPABC—Compound 80) produced using Example compound 121, above, and the MCvcPABC conjugation method described below.

Example 155

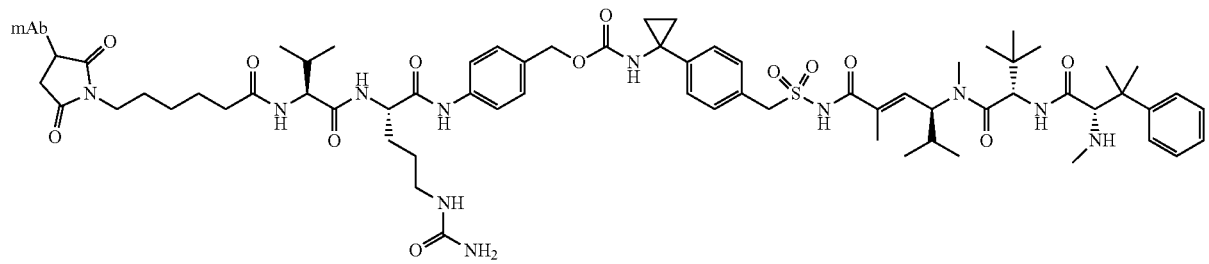

(155)

(mAb-MCvcPABC—Compound 58) produced using Example compound 158 (MCvcPABC58), below, and the MCvcPABC conjugation method described below.

Example 156

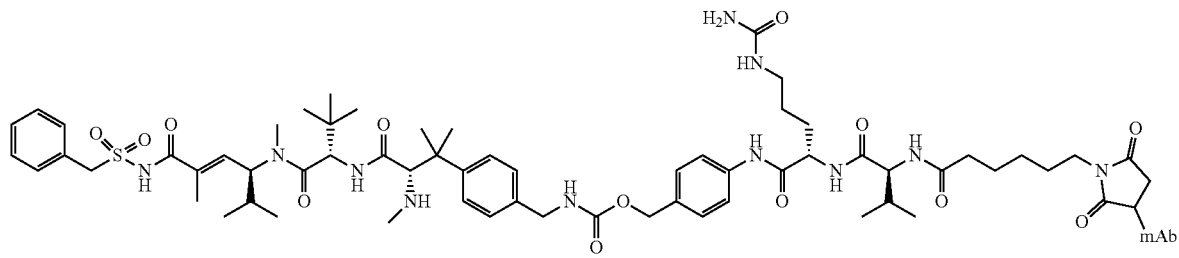

(156)

(mAb-MCvcPABC—Compound 41) produced using Example compound 122, above, and the MCvcPABC conjugation method described below.

Example 157

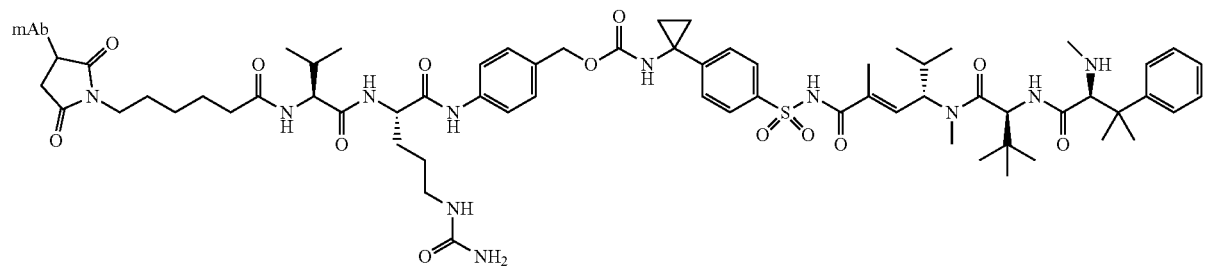

(157)

(mAb-MCvcPABC—Compound 63) produced using Example compound 159 (MCvcPABC830), below, and the MCvcPABC conjugation method described below.

Example 158

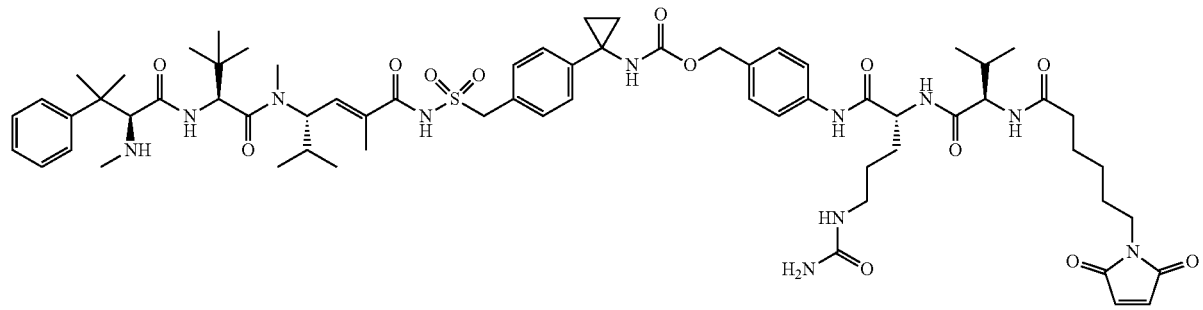

(158)

The title compound was prepared by application of General Procedure 15 and 7 to Boc protected Example 58.

$^1$H NMR (400 MHz, Methanol-d$_4$) δ 7.60 (d, J=8.1 Hz, 2H), 7.56 (d, J=7.8 Hz, 2H), 7.47 (t, J=7.6 Hz, 2H), 7.37 (t, J=7.3 Hz, 1H), 7.33 (d, J=8.2 Hz, 2H), 7.26 (d, J=8.0 Hz, 2H), 7.22 (d, J=7.9 Hz, 2H), 6.81 (s, 2H), 6.37 (d, J=9.3 Hz, 1H), 5.13-5.01 (m, 3H), 4.96 (s, 1H), 4.70 (s, 2H), 4.56-4.51 (m, 1H), 4.38 (s, 1H), 4.23-4.16 (m, 1H), 3.50 (t, J=7.1 Hz, 2H), 3.27-3.19 (m, 1H), 3.18-3.04 (m, 4H), 2.52 (s, 3H), 2.30 (t, J=7.4 Hz, 2H), 2.15-2.05 (m, 1H), 1.96 (s, 3H), 1.98-1.88 (m, 1H), 1.83-1.73 (m, 1H), 1.64 (dq, J=23.1, 7.3 Hz, 7H), 1.48 (s, 3H), 1.39 (s, 3H), 1.37-1.30 (m, 2H), 1.27 (s, 2H), 1.21 (s, 2H), 1.08 (s, 9H), 1.00 (d, J=6.7 Hz, 3H), 0.99 (d, J=6.8 Hz, 3H), 0.91 (d, J=6.6 Hz, 3H), 0.88 (d, J=6.5 Hz, 3H).

$C_{66}H_{93}N_{11}O_{13}S$ calcd. m/z=1279.7 found $[M+H]^+$=1281.0.

Example 159

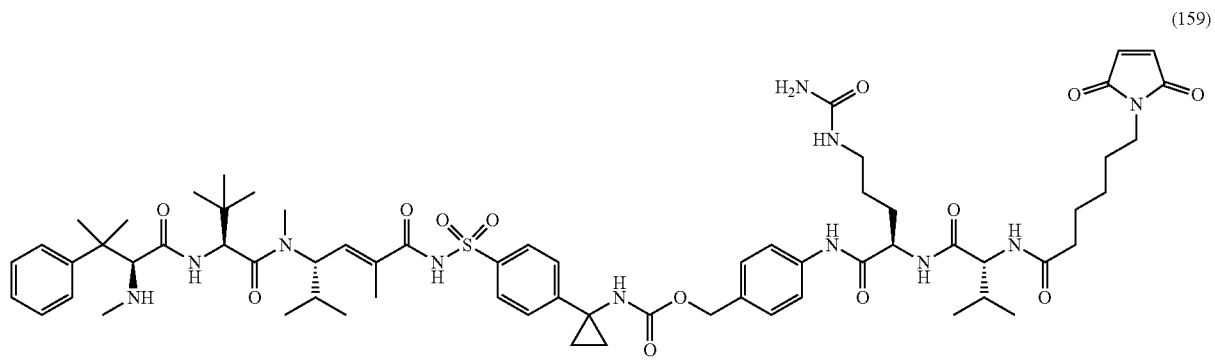 [SMILES: CN[C@H](C(=O)N[C@H](C(=O)N(C)[C@H](/C=C(\C)C(=O)NS(=O)(=O)c1ccc(C2(NC(=O)OCc3ccc(NC(=O)[C@@H](CCCNC(N)=O)NC(=O)[C@H](NC(=O)CCCCCN4C(=O)C=CC4=O)C(C)C)cc3)CC2)cc1)C(C)C)C(C)(C)C)C(C)(C)c1ccccc1]

(159)

The title compound was prepared by application of General Procedures 15 and 7 to Boc protected Example 63.

$C_{65}H_{91}N_{11}O_{13}S$ calcd. m/z=1265.7 found [M+H]⁺=1266.7

It is understood to those skilled in the art that it may be possible to carry out the chemical conversions shown in the schemes above with modifications of one or more parameters. As examples, alternate non-nucleophilic solvents may be suitable for the chemistry, such as THF, DMF, Toluene etc. Reaction temperatures may be varied. Alternate reagents may be suitable to act as dehydrating or acid-activating agents which are normally used in amide formation reactions, such as pentafluorophenyl esters, NHS esters, EDAC, HBTU, HOBT etc.

Other Representative Compounds

The following representative compounds may be prepared according to the foregoing procedures. As recognized by the artisan of reasonable skill, the following compounds are synthetically accessible using the disclosure of WO 2004/026293 to achieve the precursor reactant and applying General Procedures with the appropriate sulfonamide.

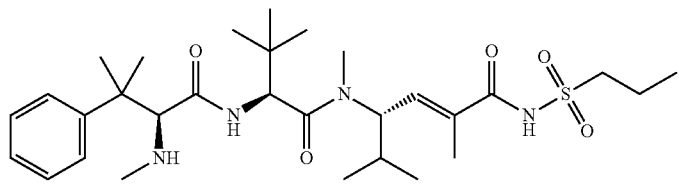

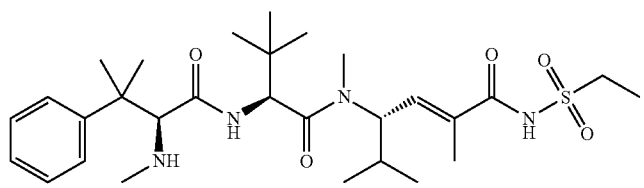

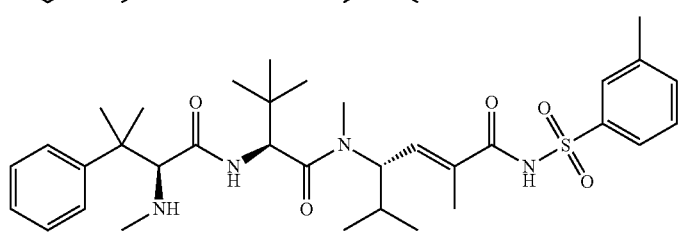

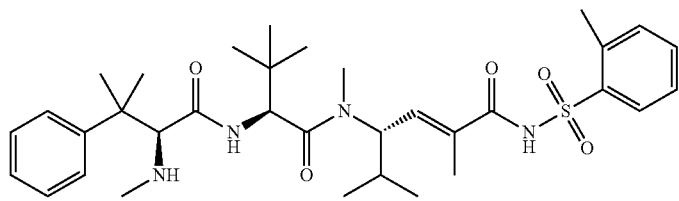

-continued
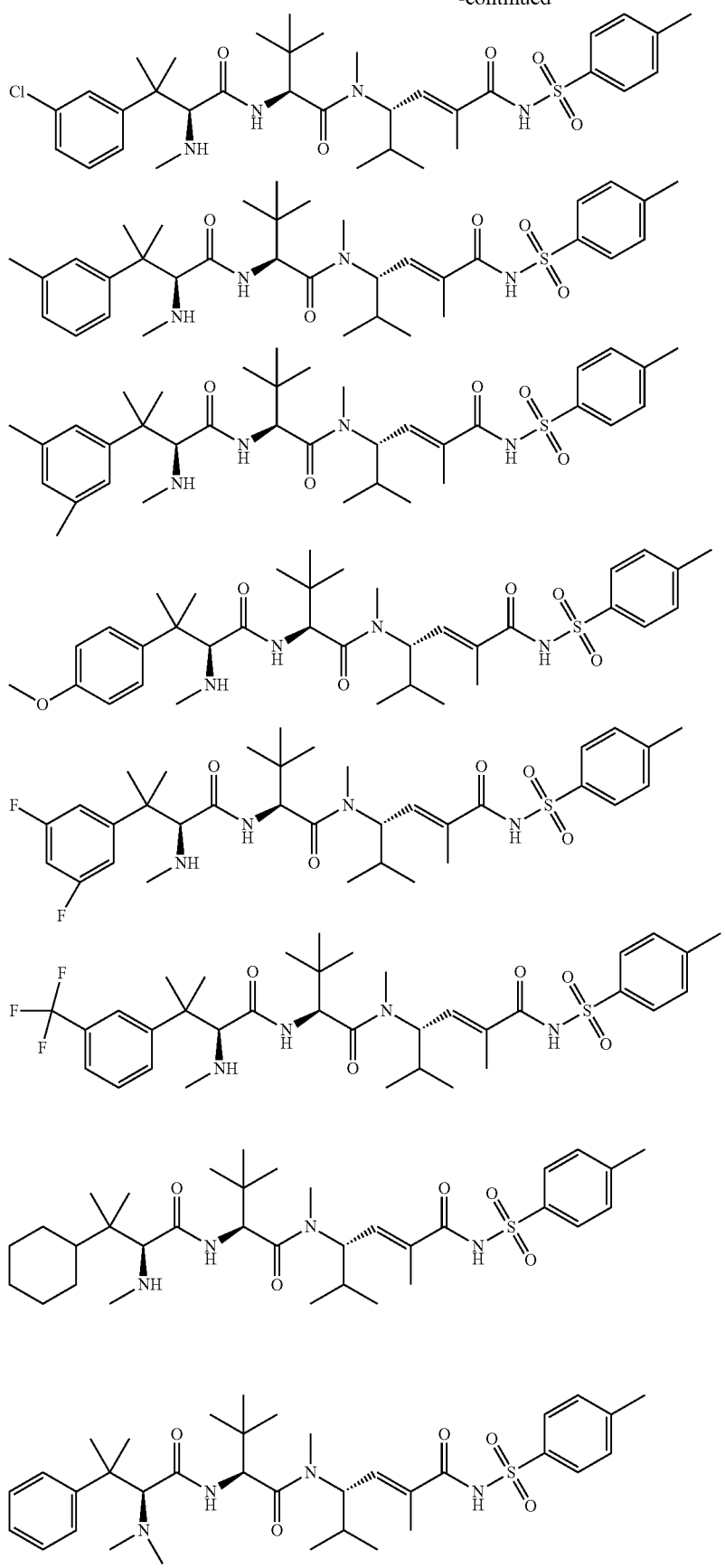

-continued
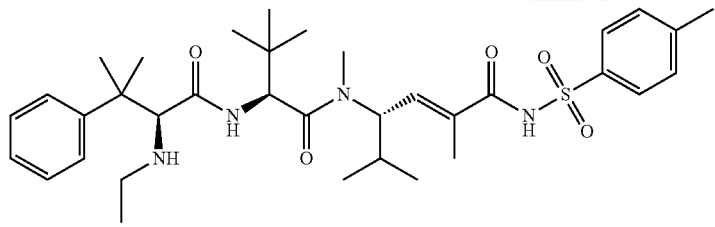
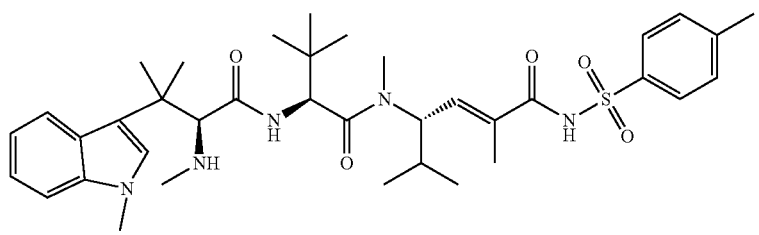
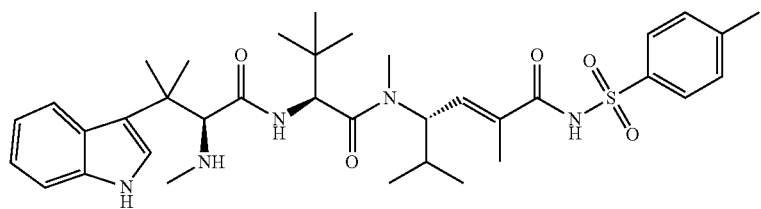
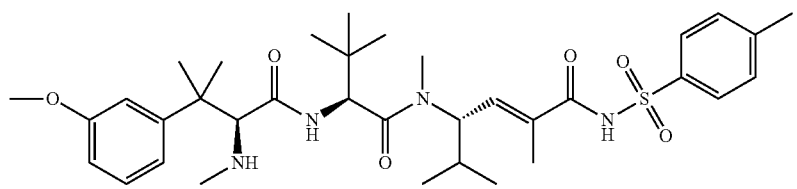
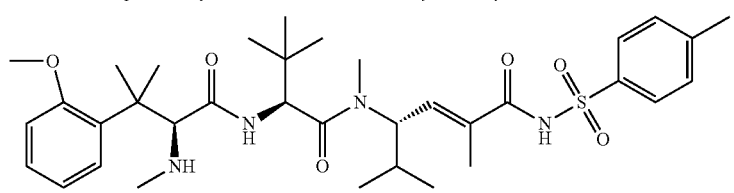
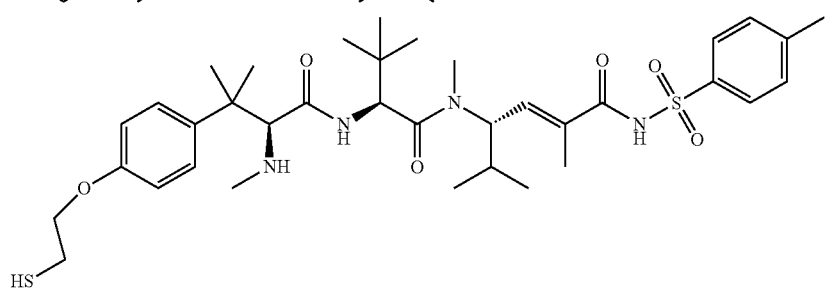
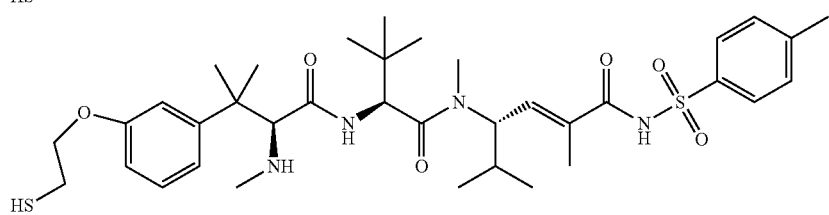

-continued
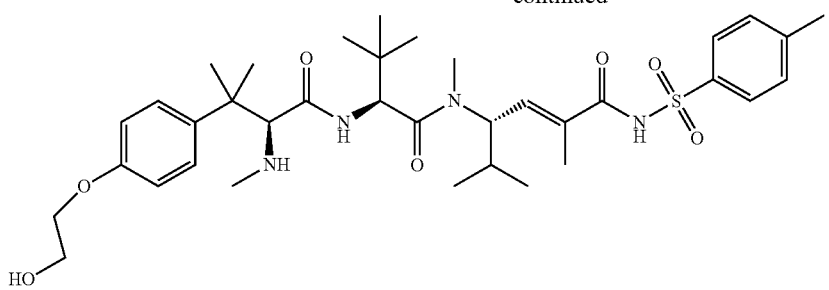
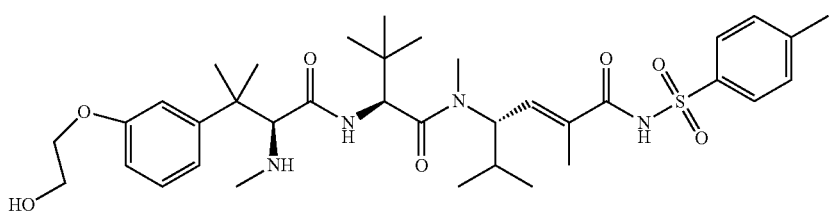
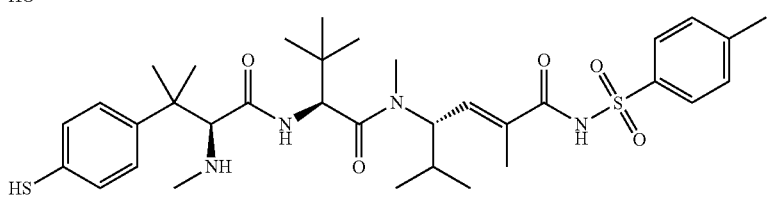
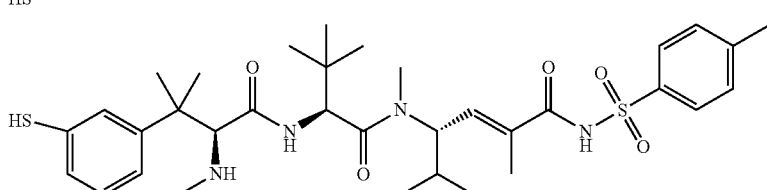
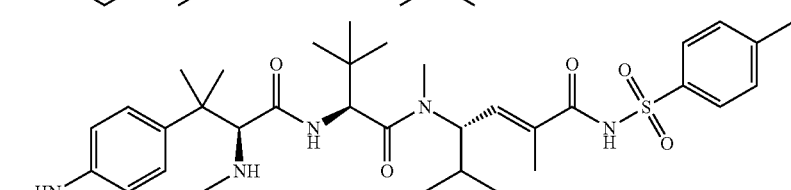
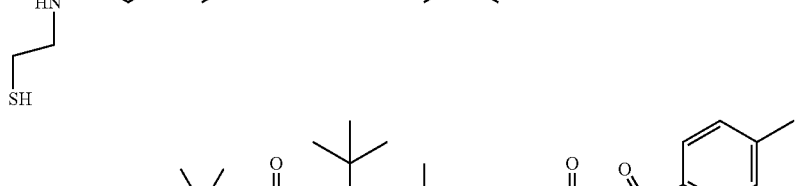
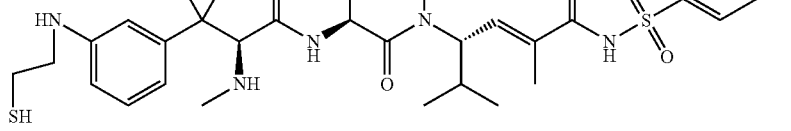
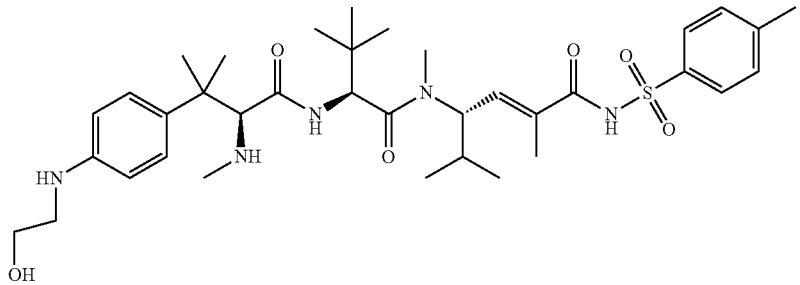

-continued
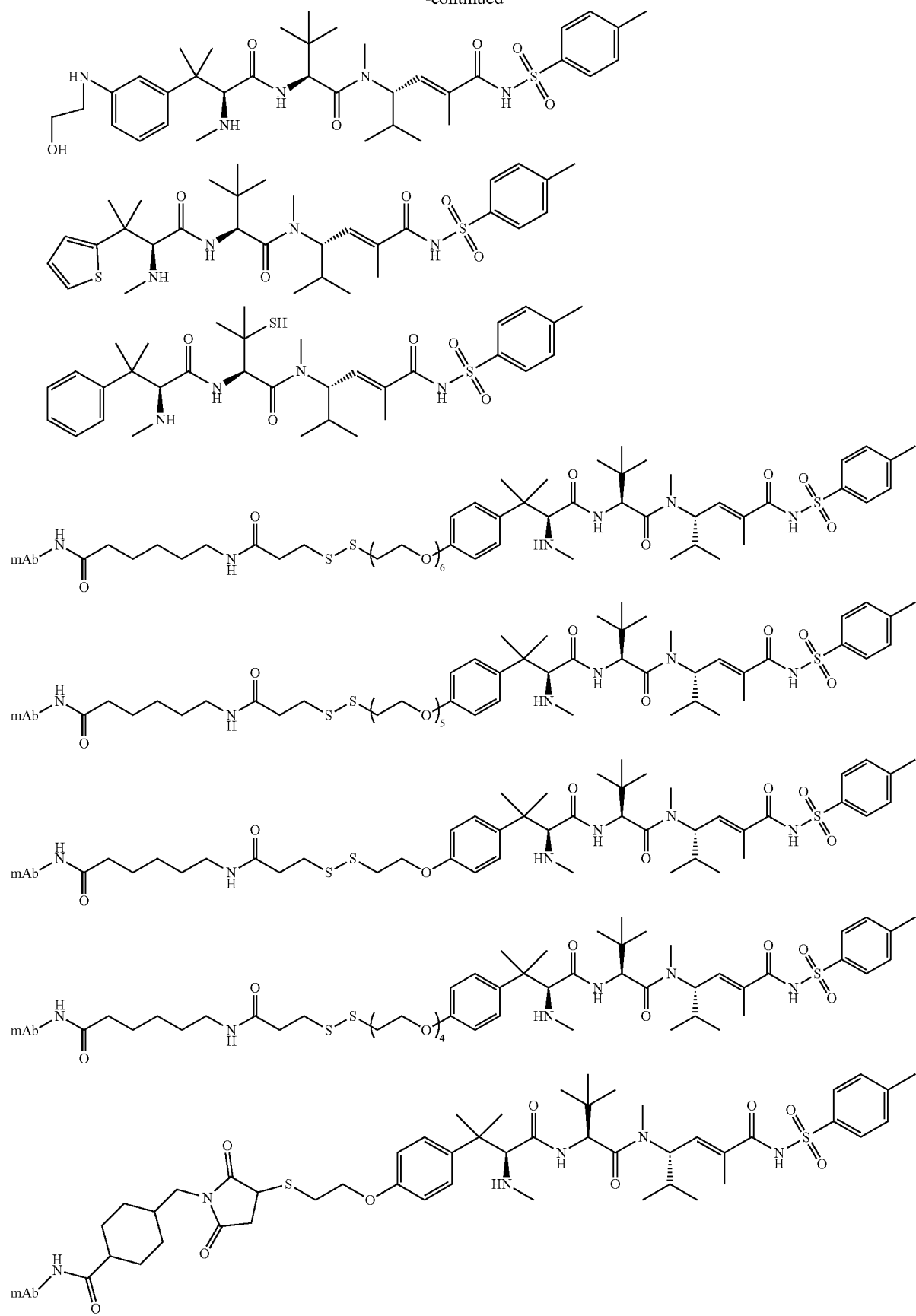

-continued

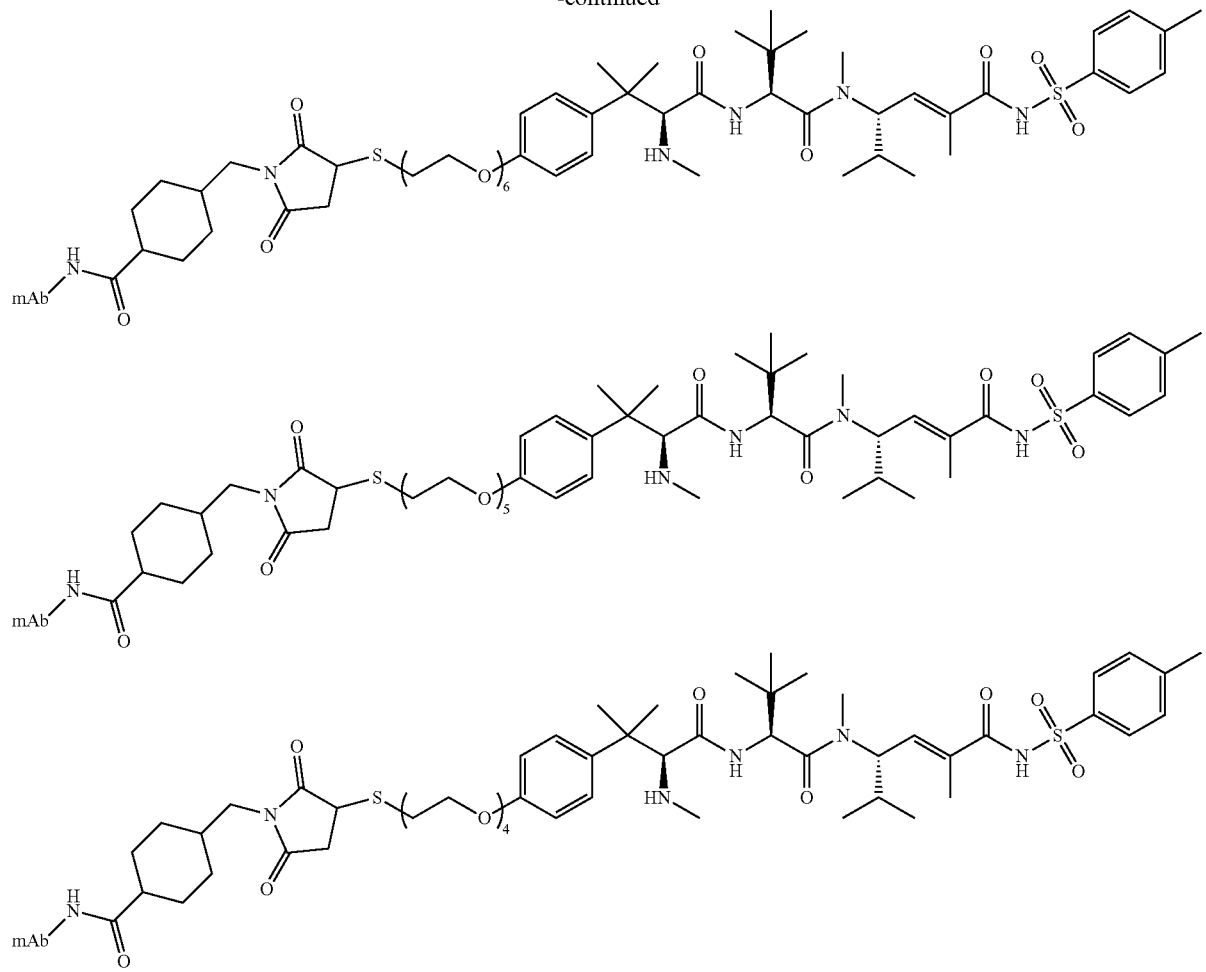

Example 1

Biological Assays

Tables 1-8 summarize the cytotoxic activity of the subject compounds on cell lines. FIG. 1 summarizes the data for compounds A, B, C, D, and E when tested using the Human mammary carcinoma cell line HCC1954 or Human T-cell leukemia cell line Jurkat. FIGS. 2-6 show the cytotoxicity data plots for individual compounds A-E, Tables 2-6 summarize the results of additional cytotoxicity assays.

Cell lines used: Human T-cell leukemia cell line Jurkat (ATCC: TIB-152); HCC1954 (ATCC: CRL. 2338); Human Pancreatic cells AsPC-1 (ATCC: CRL-1682), BxPC-3 (ATCC: CRL.1687), HPAF-II (ATCC: CRL.1997), MiaPaCa2 (ATCC: CRL.1420), PANC-1 (ATCC: CRL.1469), Capan-1 (ATCC: HTB-79), Capan-2 (ATCC: HTB-80) and the Human gastric carcinoma cell line NCI-N87 (ATCC: CRL. 5822); AML-193 (ATCC: CRL.9589), CCRF-CEM (ATCC: CCL-119), DU145 (ATCC: HTB-81), PC-3 (ATCC: CRL.1435), A-431 (ATCC: CRL.1555), HT-29 (ATCC: HTB-38), A-172 (ATCC: CRL.1620), NCI-H358 (ATCC: CRL.5807), A549 (ATCC: CCL-185), Colo-205 (ATCC: CCL-222), MDA-MB-231 (ATCC: HTB-26), OVCAR-3 (ATCC: HTB-161), OV-90 (ATCC: CRL.11732), OE19 (Sigma: 96071721), RT 112/84 (Sigma: 85061106).

On the day prior to adding compounds, HCC1954 AsPC-1, BxPC-3, HPAF-II, MiaPaCa2, PANC-1, Capan-1, Capan-2 and NCI-N87 cells were added to opaque-walled 96-well tissue culture-treated microtiter plates using complete growth medium at a density of 2500 cells/100 microlitre (uL) of medium. These adherant cell lines cells were incubated for one night at 37° C./5% $CO_2$ to allow the cells to attach to the microtiter plate surface. On the day that compounds were added, Jurkat cells are added to separate 96-well microtiter plates at 2500 cells/100 uL using the same growth medium as HCC1954. Compound were first serially diluted using dimethyl sulfoxide, and then the prepared dilutions are added to complete growth medium at five-times the final concentration—compounds were then titrated 1:3, eight steps. A control with no compound (growth medium alone) was included on each microtiter plate in sextuplicate. The prepared compounds titrations were added (twenty-five uL/well) in triplicate. The cells and compound titrations were incubated at 37° C./5% $CO_2$ for three nights. After the incubation, cell viability is measured using CellTiter-Glo® reagent by adding thirty uL of prepared CellTiter-Glo® to each assay well. The assay is incubated for at least twenty minutes in the dark prior to measuring emitted luminescence using a microplate luminometer (500 ms integration time). The collected relative luminescence units (RLU) are converted to % cytotoxicity using the Growth medium alone control mentioned above (% Cytotoxicity=1−[Well RLU/average medium alone control RLU]).

GraphPad Prism was used for generation of EC$_{50}$ values using three parameter non-linear regression curve fitting.

TABLE 1

Cytotoxicity of Compounds

| COMPOUND | HCC1954 cells (HER2+) | | Jurkat cells (HER2−) | |
|---|---|---|---|---|
| | EC$_{50}$ (nM) | EC$_{50}$ bounds (nM) | EC$_{50}$ (nM) | EC$_{50}$ bounds (nM) |
| A | 0.86 | 0.3765 to 1.966 | 0.78 | 0.5970 to 1.013 |
| B | 8.1 | 4.778 to 13.56 | 10.5 | 6.221 to 17.70 |
| C | 0.67 | 0.3738 to 1.186 | 0.57 | 0.4088 to 0.8085 |
| D | 0.061 | 0.04550 to 0.08050 | 0.043 | 0.03127 to 0.05921 |
| E | 0.79 | 0.5418 to 1.140 | 1.67 | 1.223 to 2.268 |

TABLE 2

Cytotoxicity of Compounds

| | HCC1954 | | | Jurkat | | |
|---|---|---|---|---|---|---|
| | EC$_{50}$ (nM) | EC$_{50}$ bounds (nM) | R square | EC$_{50}$ (nM) | EC$_{50}$ bounds (nM) | R square |
| A | 3 | 1.582 to 5.228 | 0.9158 | 5 | 3.127 to 6.641 | 0.9647 |
| B | 13 | 10.50 to 16.27 | 0.9878 | 59 | 33.41 to 104.5 | 0.9257 |
| C | 1.3 | 0.7970 to 1.977 | 0.9493 | 1.9 | 1.248 to 2.896 | 0.9562 |
| D | 0.06 | 0.04550 to 0.08050 | 0.9656 | 0.04 | 0.03127 to 0.05921 | 0.9497 |
| E | 0.79 | 0.5418 to 1.140 | 0.9314 | 1.67 | 1.223 to 2.268 | 0.9518 |

TABLE 3

Cytotoxicity of Compounds on Jurkat Cells

| Compound | EC$_{50}$ (nM) |
|---|---|
| A | 4.5 |
| B | 59 |
| 115 | 36 |
| C | 1.9 |
| 118 | 13 |
| D | 0.033 |
| E | 1.67 |
| 12 | 0.030 |
| 13 | 0.038 |
| 14 | 0.007 |
| 14 | 0.015 |
| 15 | 7.604 |
| 16 | 0.041 |
| 17 | 0.325 |
| 18 | 1.358 |
| 19 | 0.152 |
| 22 | 0.021 |
| 47 | 0.261 |
| 24 | 0.070 |
| 48 | 0.208 |
| 23 | 0.031 |
| 28 | 0.021 |
| 29 | 0.121 |
| 30 | 0.109 |
| 31 | 0.094 |
| 74 | 0.087 |
| 25 | 0.050 |
| 26 | 0.105 |
| 49 | 2.5 |
| 50 | 0.171 |
| 27 | 0.157 |
| 32 | 0.265 |
| 76 | 0.328 |
| 79 | 0.386 |
| 84 | 1.393 |
| 80 | 0.389 |
| 51 | 0.247 |
| 57 | 0.566 |
| 58 | 0.816 |
| 34 | 0.200 |
| 97 | 1.616 |
| 44 | 0.114 |
| 45 | 0.869 |
| 42 | 0.165 |

TABLE 4

Cytotoxicity of Compounds on HCC-1954 Cells

| Compound | EC$_{50}$ (nM) |
|---|---|
| A | 2.1 |
| B | 13 |
| 115 | 172 |
| C | 1.3 |
| D | 0.06 |
| E | 0.79 |
| 79 | 0.241 |
| 80 | 0.207 |

TABLE 5

Cytotoxicity (EC$_{50}$) of Compounds on Various Tumour Cell Lines (nM)

| Compound | NCI-N87 | AsPC-1 | BxPC-3 | HPAF-II | MiaPaCa2 | PANC-1 | Capan-1 | Capan-2 |
|---|---|---|---|---|---|---|---|---|
| D | 0.272 | 0.1704 | 0.06635 | 0.177 | 0.136 | 0.806 | — | — |
| 14 | 0.175 | 0.206 | 0.0458 | 0.172 | 0.204 | 1.356 | 2.081 | 1.103 |
| 24 | — | 0.5857 | 0.2704 | 0.396 | 0.566 | 2.181 | — | — |
| 23 | 0.402 | — | — | — | — | — | — | — |
| 77 | — | 15.53 | 36.5 | 17.240 | 94.290 | 97.190 | | |
| 63 | — | 0.9697 | 0.6973 | 0.826 | 1.018 | 3.997 | — | — |

TABLE 6

Compound Cytotoxicity on Jurkat

| Compound | EC$_{50}$ (nM) |
|---|---|
| 108 | 0.017 |
| 110 | 0.031 |
| 107 | 0.043 |
| 114 | 0.056 |
| 112 | 0.064 |
| 98 | 0.077 |
| 109 | 0.087 |
| 91 | 0.109 |
| 64 | 0.138 |
| 66 | 0.145 |
| 93 | 0.196 |
| 103 | 0.209 |
| 104 | 0.272 |
| 95 | 0.288 |
| 102 | 0.289 |
| 97 | 0.307 |
| 68 | 0.337 |
| 45 | 0.373 |
| 92 | 0.485 |
| 72 | 0.531 |
| 67 | 0.562 |
| 33 | 0.636 |
| 88 | 0.641 |
| 105 | 0.731 |
| 105 | 0.753 |
| 35 | 0.832 |
| 70 | 0.856 |
| 71 | 1.021 |
| 62 | 1.195 |
| 44 | 1.479 |
| 13 | 1.515 |
| 69 | 1.564 |
| 94 | 1.673 |
| 73 | 2.684 |
| 96 | 10.260 |
| 111 | ~0.1178 |
| 91 | 0.109 |
| 93 | 0.196 |
| 95 | 0.288 |
| 97 | 0.307 |
| 92 | 0.485 |
| 88 | 0.641 |
| 62 | 1.195 |
| 94 | 1.673 |
| 96 | 10.260 |
| 64 | 0.138 |
| 66 | 0.145 |
| 103 | 0.209 |
| 104 | 0.272 |
| 102 | 0.289 |
| 68 | 0.337 |
| 72 | 0.531 |
| 105 | 0.731 |
| 105 | 0.753 |
| 70 | 0.856 |
| 71 | 1.021 |
| 69 | 1.564 |
| 46 | — |
| 108 | 0.017 |

TABLE 6-continued

Compound Cytotoxicity on Jurkat

| Compound | EC$_{50}$ (nM) |
|---|---|
| 110 | 0.031 |
| 107 | 0.043 |
| 114 | 0.056 |
| 112 | 0.064 |
| 98 | 0.077 |
| 109 | 0.087 |
| 111 | 0.12 |
| 97 | 0.307 |
| 45 | 0.373 |
| 44 | 1.479 |
| 67 | 0.562 |
| 33 | 0.636 |
| 35 | 0.832 |
| 72 | 2.684 |

TABLE 7

Cytotoxicity on Jurkat

| Compound | EC$_{50}$ (nM) |
|---|---|
| 107 | 0.043 |
| 108 | 0.017 |
| 109 | 0.087 |
| 110 | 0.031 |
| 111 | 0.12 |
| 112 | 0.064 |
| 114 | 0.056 |

TABLE 8

Cytotoxicity on Various Cell Lines

| Tumour Cell Line | Compound-14 (EC$_{50}$) (nM) |
|---|---|
| AML-193 | 0.191 |
| CCRF-CEM | 0.130 |
| DU145 | 0.649 |
| PC-3 | 0.455 |
| A-431 | 0.191 |
| HT-29 | 0.167 |
| HCC-1954 | 0.131 |
| A-172 | 0.598 |
| NCI-N87 | 0.325 |
| Jurkat | 0.068 |
| BxPC-3 | 0.196 |
| NCI-H358 | 0.311 |
| Mia PaCa-2 | 0.332 |
| A549 | 0.860 |
| Colo-205 | ~0.3168 |
| PANC-1 | 0.759 |
| MDA-MB-231 | 1.242 |
| AsPC-1 | 0.334 |
| HPAF-II | ~0.3850 |
| OVCAR-3 | 0.090 |

TABLE 8-continued

Cytotoxicity on Various Cell Lines

| Tumour Cell Line | Compound-14 (EC$_{50}$) (nM) |
|---|---|
| OV-90 | 0.515 |
| OE19 | 0.210 |
| RT112/84 | 0.178 |

Example 2: Exemplary Antibody-Drug Conjugates

Antibody-Drug Conjugates—Exemplary Linkers

As recognized by the artisan of reasonable skill, the particular linker used for conjugate formation will depend upon the reactive group of the reactant compound being used for bond formation. As an example, and within the scope of the present invention, compounds having thiol moiety may be used for conjugate formation. In some of the present examples, the commercially available cleavable linker sulfosuccinimidyl 6-[3'(2-pyridyldithio)-propionamido] hexanoate (sulfo-LC-SPDP: Thermo Pierce Cat #21650) and Non-cleavable linker succinimidyl 4-[N-maleimidomethyl]cyclohexane-1-carboxylate (SMCC: Thermo Pierce Cat #22360) were utilized for antibody-drug conjugation reactions. The coupling procedure is performed in two major steps: 1) incorporation of the linkers onto the antibody via reaction with antibody primary amine groups (Lysine residues) and the N-hydroxysuccinimide (NHS) ester moiety of the linkers, and 2) reaction of the incorporated maleimide group (SMCC) or 2-pyridyldithio group (LC-SPDP) with thiol-containing compounds.

Activation of Antibody with Cleavable (LC-SPDP) or Non-Cleavable (SMCC) Linkers

Antibody (Herceptin) was diluted into either Potassium Phosphate pH 8 (sulfo-LC-SPDP) or D-PBS (Invitrogen) pH 7.4 (SMCC) to 5 mg/mL. To the diluted antibody, freshly dissolved linker was added—using ultra-pure water for sulfo-LC-SPDP or anhydrous N,N-Dimethylacetamide (DMA) for SMCC. 10-14 fold molar-excesses of SMCC: antibody or sulfo-LC-SPDP:antibody result in incorporation of 5-7 linkers/antibody. The linker-antibody "activation" reaction was incubated at 28° C. for 2 hours. Following the incubation, the un-reacted linker was removed from each antibody sample using 40 kda Zeba Size-exclusion chromatography/desalting columns (Thermo Pierce Cat #87771, or 87772 depending on the scale). During the same chromatography step the buffer was exchanged in preparation for the next reaction; either Phosphate Buffer/EDTA pH 6.5 (LC-SPDP), or Citrate buffer/EDTA pH 5 (SMCC). The purified preparations were then assayed for total protein content versus an antibody standard curve using the microplate adapted BCA assay (Thermo Pierce Cat #23225). To estimate the extent of linker incorporation a small scale reaction with excess (~10-fold compared to protein concentration) Cysteine was performed. Following a 10 minute incubation the un-reacted Cysteine was detected using 5,5-Dithio-bis-(2-nitrobenzoic acid) (Ellman's reagent, Thermo Pierce Cat #22582). By interpolating the concentration from a Cysteine standard curve the linker concentration was determined by subtracting the determined value from the known concentration of Cysteine used.

Reaction of Thiol-Containing Compounds to Linker-Activated Antibody

In the second step of the coupling reaction, the activated-antibody was utilized by first diluting the preparation to 2 mg/mL using either Phosphate Buffer/EDTA pH 6.5 (LC-SPDP), or Citrate buffer/EDTA pH 5 (SMCC). Prior to use, the thiol containing n-acyl sulfonamide compounds or maytansinoid DM1 were reduced using TCEP-agarose beads to ensure the thiol group was available to react to the incorporated linkers. In brief, compounds were diluted to 5 mM using Phosphate Buffer/EDTA pH 6.5. In instances where aqueous solubility was an issue, a small volume of 37% HCl (1:300) was added and this was sufficient to solubilize the compounds at 5 mM. TCEP-agarose beads (Thermo Pierce Cat #77712), were equilibrated with Phosphate Buffer/EDTA/10% DMA prior to use. The compound dilutions were rotated with TCEP-agarose beads for at least 0.5 hours, or up to 3 hours. The reduced compounds were collected by centrifugation over a filter which excluded the TCEP-agarose. The extent of reduction and thiol concentration was measured using Ellman's reagent (compared to a Cysteine standard curve). The reduced thiol-containing compounds were then added to the activated antibody samples at a molar excess of ~2-fold compared to the previously determined linker concentrations. In order to monitor the coupling reaction effectiveness an "overnight" conjugation control was prepared by diluting each compound into Phosphate Buffer/EDTA pH 6.5 or Citrate buffer/EDTA pH 5 at the same dilution factor that was used in the conjugation reaction. The remaining compound stocks were frozen at −80° C. The reactions and overnight controls were incubated at ambient temperature overnight. The next morning the frozen compound stocks were thawed and another control was prepared for each compound exactly like the "overnight" control—this is the "fresh" control. A small volume of each conjugation reaction was compared to the overnight and fresh compound controls using Ellman's reagent. Non-reacted compound was purified away from the ADCs using 40 kda Zeba Size-exclusion/desalting columns; during the same step the buffer was exchanged to D-PBS pH7.4 (Invitrogen).

The purified ADCs were then analysed for: total protein content (BCA assay, Pierce microBCA protocol), relative affinity for antigen binding (equilibrium native binding), and selective cytotoxic killing of HER2-positive cells (HCC1954) compared HER2-negative cells (Jurkat).

Cytotoxicity Assay

Figure 7:
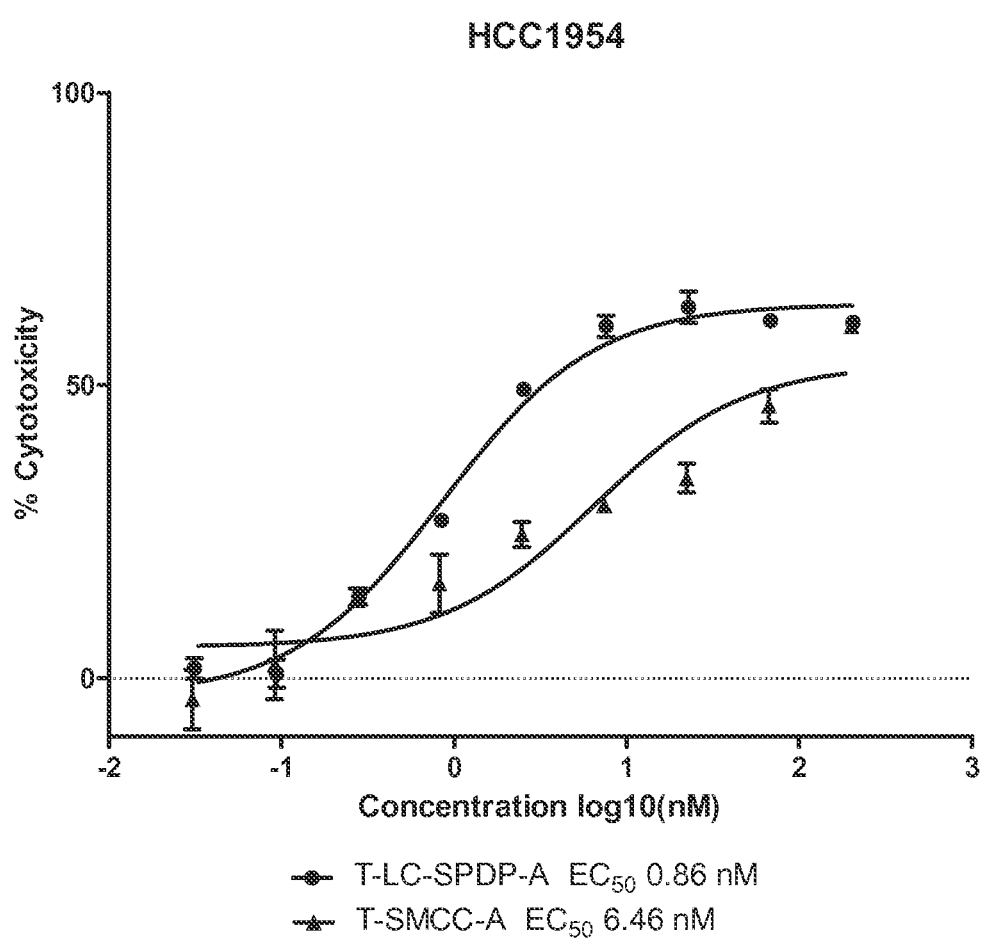
FIG. 7 shows a cell kill curve on HCC 1954 cells in vitro with the antibody-drug conjugates: T-LC-SPDP-A (Trastuzumab, LC-SPDP linker, Compound A) and T-SMCC-A (Trastuzumab, SMCC linker, Compound A). $EC_{50}$ values are shown in the figure.
Figure 8:
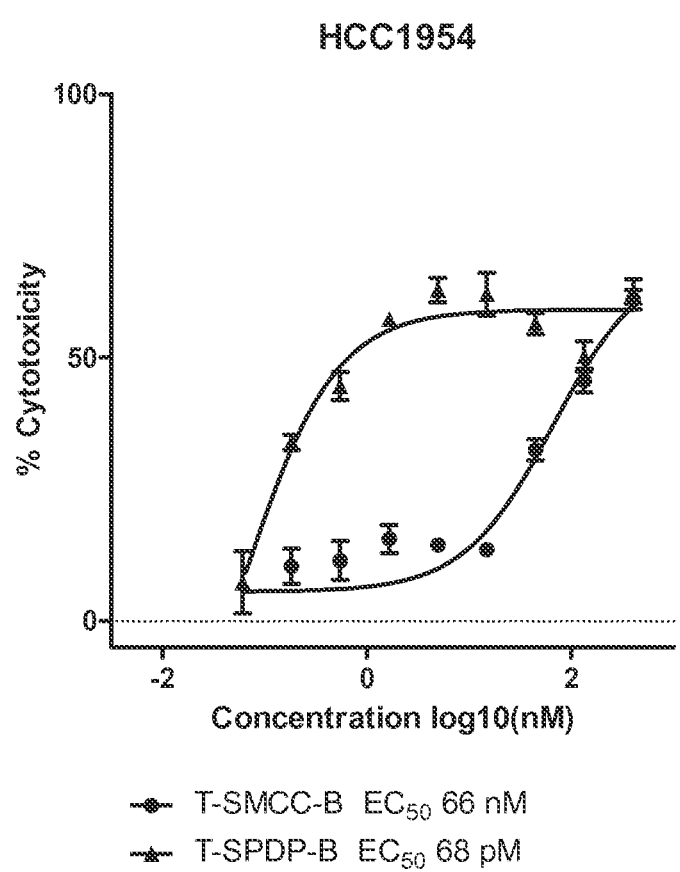
FIG. 8 shows a cell kill curve on HCC 1954 cells in vitro with the antibody-drug conjugates: T-SPDP-B (Trastuzumab, LC-SPDP linker, Compound B) and T-SMCC-A (Trastuzumab, SMCC linker, Compound B). $EC_{50}$ values are shown in the figure.
Figure 9:
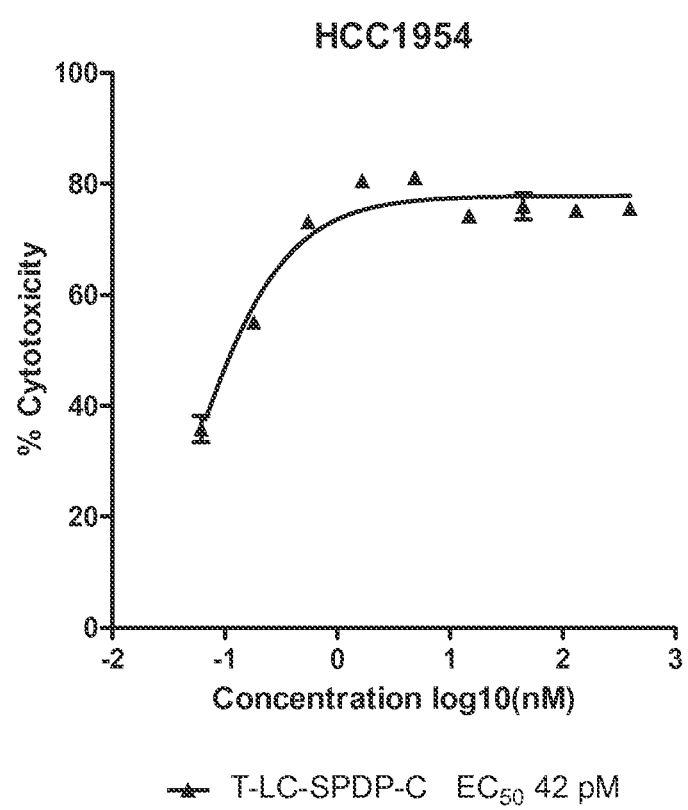
FIG. 9 shows a cell kill curve on HCC 1954 cells in vitro with the antibody-drug conjugate: T-LC-SPDP-C (Trastuzumab, LC-SPDP linker, Compound C). $EC_{50}$ value is shown in the figure.
Figure 10:
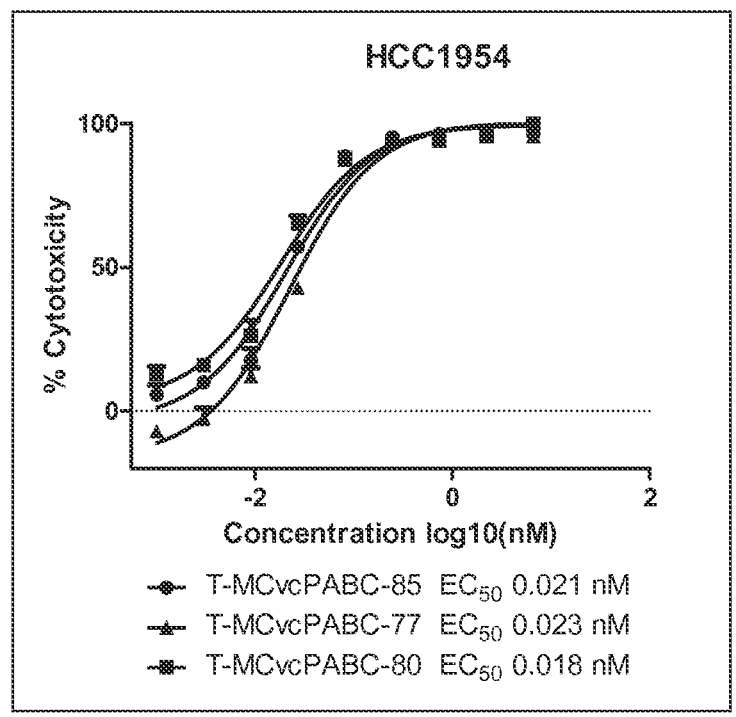
FIG. 10 shows a cell kill curve on HCC 1954 cells in vitro with the antibody-drug conjugates: T-MCvcPABC-85 (Trastuzumab, MCvc PABC linker, Compound 85), T-MCvcPABC-77 (Trastuzumab, MCvc PABC linker, Compound 77) and T-MCvcPABC-80 (Trastuzumab, MCvc PABC linker, Compound 80). $EC_{50}$ values are shown in the figure.
Figure 11:
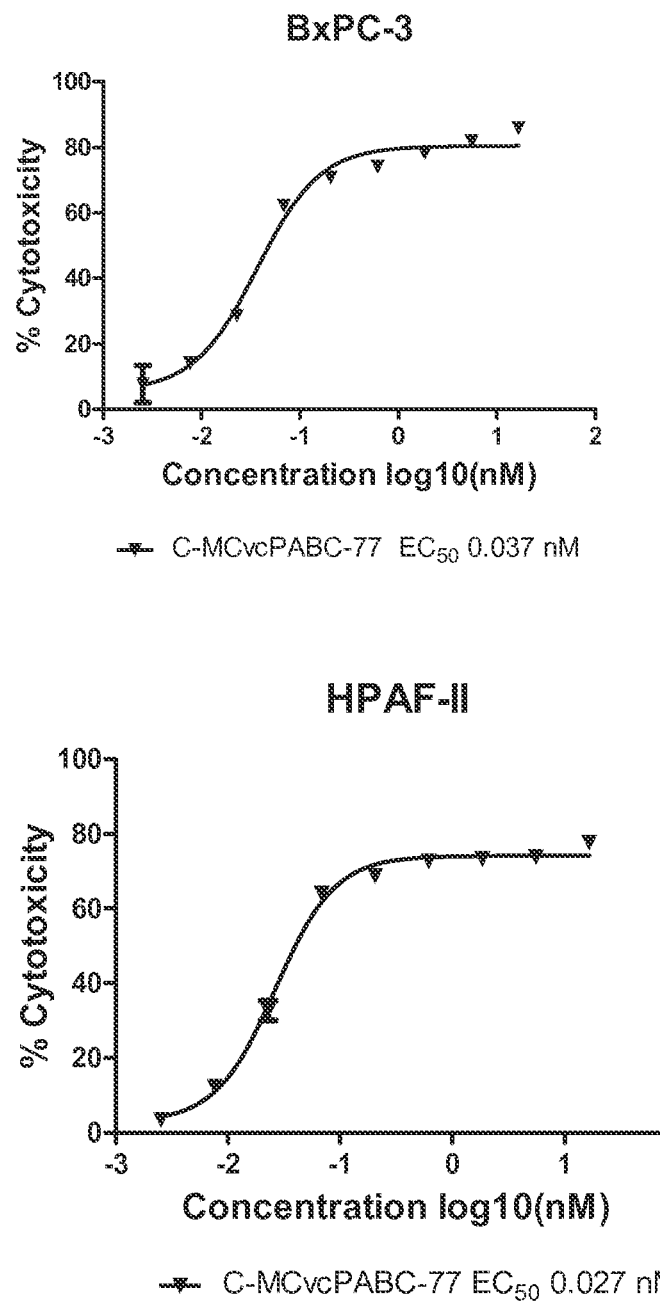
FIG. 11 shows a cell kill curve on BxPC-3 cells in vitro with the antibody-drug conjugate C-MCvcPABC-77, (Cetuximab, MCvc PABC linker, Compound 77), and a cell kill curve on HPAF-II cells in vitro with the antibody-drug conjugate C-MCvcPABC-77, (Cetuximab, MCvc PABC linker, Compound 77). $EC_{50}$ values are shown in the figure.
Figure 12:
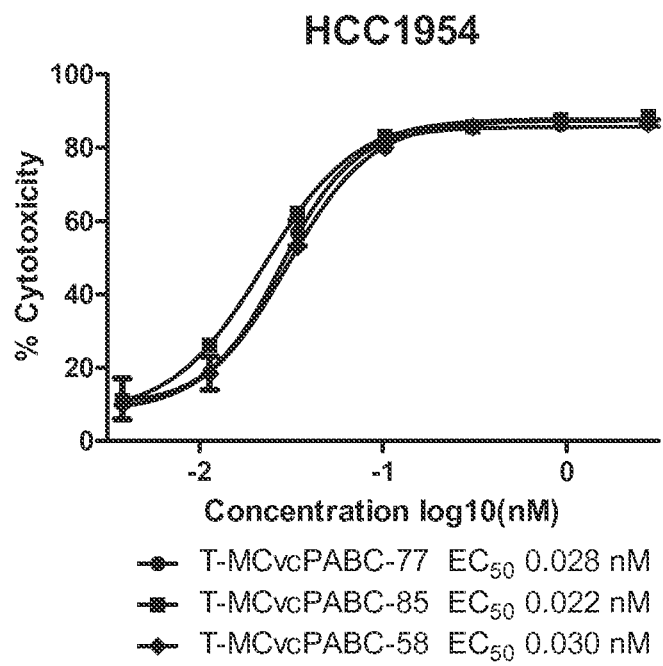
FIG. 12 shows a cell kill curve on HCC1954 cells in vitro with the antibody-drug conjugates: T-MCvcPABC-77, (Trastuzumab, MCvc PABC linker, Compound 77), T-MCvcPABC-85, (Trastuzumab, MCvc PABC linker, Compound 85), T-MCvcPABC-58, (Trastuzumab, MCvc PABC linker, Compound 58), and T-MCvcPABC-63, (Trastuzumab, MCvc PABC linker, Compound 63). $EC_{50}$ values are shown in the figure.
Figure 12:
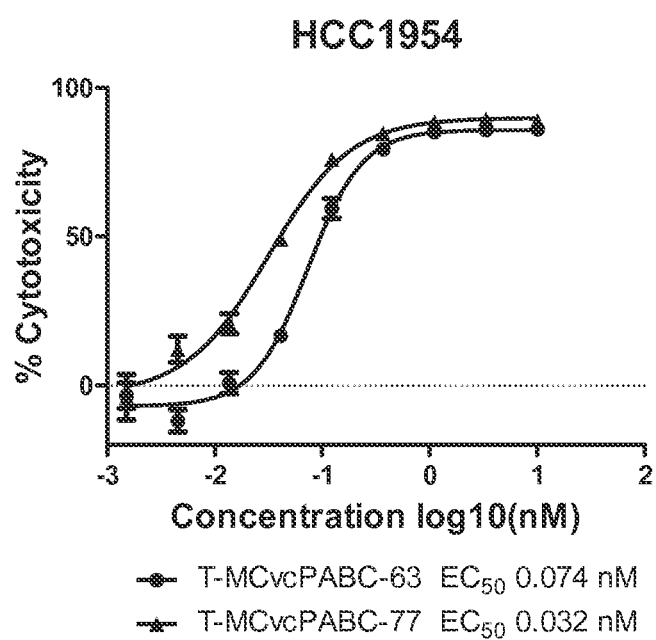
Figure 13:
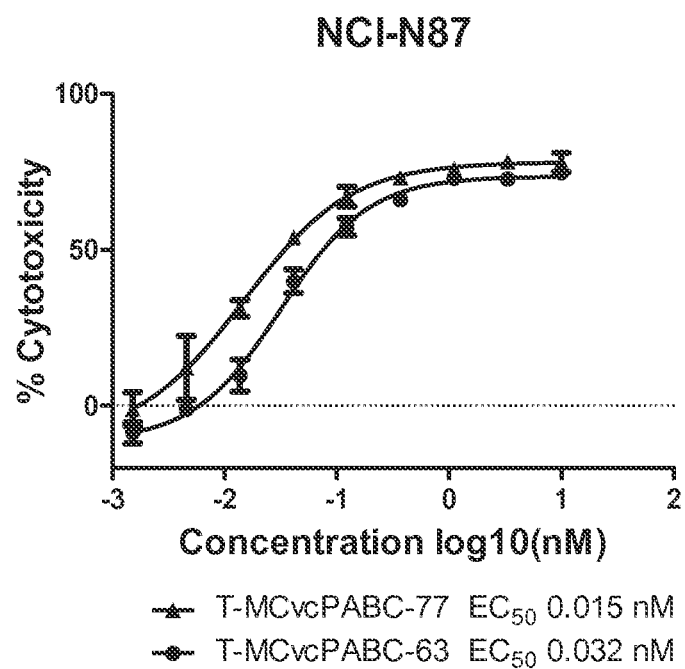
FIG. 13 shows a cell kill curve on NCI-N87 cells in vitro with the antibody-drug conjugates: T-MCvcPABC-77, (Trastuzumab, MCvc PABC linker, Compound 77), T-MCvcPABC-63, (Trastuzumab, MCvc PABC linker, Compound 63), T-MCvcPABC-85, (Trastuzumab, MCvc PABC linker, Compound 85), T-MCvcPABC-77, (Trastuzumab, MCvc PABC linker, Compound 77), and T-MCvcPABC-80, (Trastuzumab, MCvc PABC linker, Compound 80). $EC_{50}$ values are shown in the figure.
Figure 13:
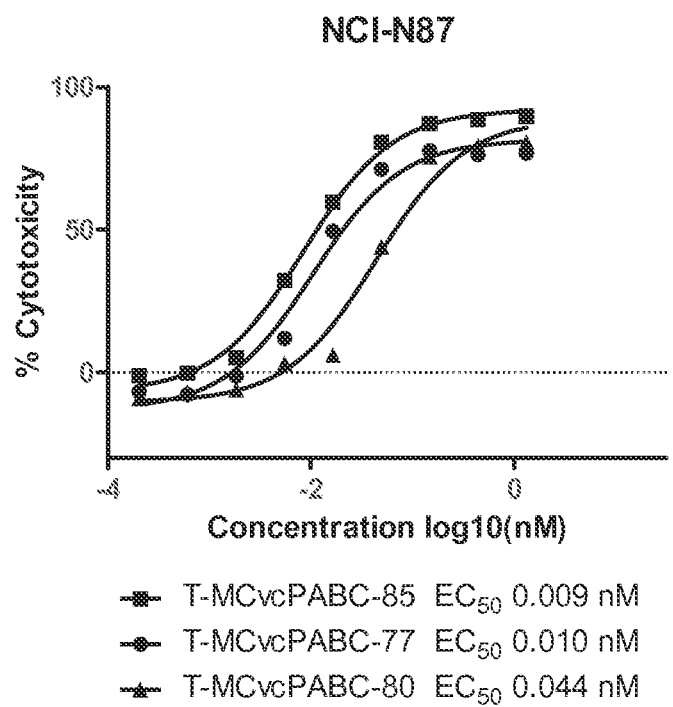

Tables 9 and 10 summarize the cytotoxic activity of ADCs comprising compounds A, B, or C when tested using the Human mammary carcinoma cell line HCC1954 or Human T-cell leukemia cell line Jurkat. FIGS. 7-9 show cytotoxicity data plots for individual compositions as indicated.

On the day prior to adding test articles, HCC1954 cells were added to opaque-walled 96-well tissue culture-treated microtiter plates using complete growth medium at a density of 2500 cells/100 microlitre (uL) of medium. The HCC1954 cells were incubated for one night at 37° C./5% CO$_2$ to allow the cells to attach to the microtiter plate surface. On the day that test articles were added, Jurkat cells are added to separate 96-well microtiter plates at 2500 cells/100 uL using the same growth medium as HCC1954. To compare the ADC killing to that obtained from the free-compounds, the n-acyl sulfonamide compounds were first serially diluted using dimethyl sulfoxide or DMA, and then the prepared dilutions are added to complete growth medium at five-times the final concentration—compounds were then titrated 1:3, eight steps. To test the ADCs, they were diluted directly in growth medium at five-times the final concentration—ADCs were then titrated 1:3, eight steps. A control with no test article present (growth medium alone) was included on each microtiter plate in sextuplicate. The prepared compound/

ADC titrations were added (twenty-five uL/well) in triplicate to both the HCC1954 cells and Jurkat cells. The cells and titrations were incubated at 37° C./5% $CO_2$ for three nights. After the incubation, cell viability was measured using CellTiter-Glo) reagent by adding thirty uL of prepared CellTiter-Glo® to each assay well. The assay was incubated for at least twenty minutes in the dark prior to measuring emitted luminescence using a microplate luminometer (500 ms integration time). The collected relative luminescence units (RLU) were converted to % cytotoxicity using the Growth medium alone control mentioned above (% Cytotoxicity=1−[Well RLU/average medium alone control RLU]).

The data indicate that the subject compounds are active cytotoxins on both cell lines used. The LC-SPDP-linked compound conjugates demonstrated potent killing of HER2-positive HCC1954 cells. Jurkat cell killing was observed at high-doses of ADC due to the presence of β-mercaptoethanol in cell culture medium, which resulted in the release of free compound (data not shown).

TABLE 9

Cytotoxicity - Coupling #1

| | | HCC1954 | | Jurkat | |
|---|---|---|---|---|---|
| | | Best-fit $EC_{50}$ (nM) | Bounds $EC_{50}$ (nM) | Best-fit $EC_{50}$ (nM) | Bounds $EC_{50}$ (nM) |
| SMCC-linked | Herceptin-SMCC-Compound A | 6.5 | 2.740 to 15.22 | 332 | 134.6 to 819.0 |
| | Herceptin-SMCC-Compound B | 66 | 26.48 to 165.1 | 83 | 48.29 to 144.0 |
| | Herceptin-SMCC-Compound C | 6 | 2.966 to 12.79 | 12 | 6.594 to 20.26 |
| LC-SPDP-linked | Herceptin-LC-SPDP-Compound A | 0.86 | 0.6660 to 1.121 | 21 | 13.74 to 32.68 |
| | Herceptin-LC-SPDP-Compound B | 0.068 | 0.02234 to 0.2093 | 11 | 7.028 to 15.91 |
| | Herceptin-LC-SPDP-Compound C | 0.070 | 0.02590 to 0.1914 | 2 | 1.521 to 3.613 |
| Free Compounds | Compound A | 2.1 | 1.352 to 3.280 | 1.1 | 0.7580 to 1.473 |
| | Compound B | 8.1 | 4.778 to 13.56 | 10 | 6.221 to 17.70 |
| | Compound C | — | — | — | — |

TABLE 10

Cytotoxicity - Coupling #2

| | | HCC1954 | | Jurkat | |
|---|---|---|---|---|---|
| | | Best-fit $EC_{50}$ (nM) | Bounds $EC_{50}$ (nM) | Best-fit $EC_{50}$ (nM) | Bounds $EC_{50}$ (nM) |
| SMCC-linked | Herceptin-SMCC-Compound A | 15 | 8.266 to 27.50 | 50 | 28.62 to 87.34 |
| | Herceptin-SMCC-Compound B | | | not done | |
| | Herceptin-SMCC-Compound C | | | | |
| LC-SPDP-linked | Herceptin-LC-SPDP-Compound A | 0.061 | 0.01410 to 0.2672 | 8.7 | 5.852 to 12.96 |
| | Herceptin-LC-SPDP-Compound B | 0.22 | 0.1381 to 0.3441 | 14 | 9.469 to 21.41 |
| | Herceptin-LC-SPDP-Compound C | 0.042 | 0.01371 to 0.1275 | 1.6 | 1.160 to 2.110 |
| Free Compounds | Compound A | 0.86 | 0.3765 to 1.966 | 0.78 | 0.5970 to 1.013 |
| | Compound B | 9.2 | 5.300 to 15.98 | 36 | 20.52 to 64.36 |
| | Compound C | 0.67 | 0.3738 to 1.186 | 0.57 | 0.4088 to 0.8085 |

Analysis of Antibody-Drug Conjugate (ADC) by EsiToF Mass Spectrometry.

Electrospray ionization time of flight (EsiToF) mass spectrometer instrument -QStar XL Hybrid quadrupole-TOF LC/MSMS-(AB Sciex) was used to determine molecular weight of the ADC's and to evaluate the drug-to-antibody ratio (DAR). The EsiToF MS instrument was equipped with electrospray ionization turbo spray source. Data acquisition was performed in the positive ion mode, and the sample's total ion current was acquired over the mass range 2000 m/z to 4000 m/z using Analyst QS 1.1 software. The ion source was operated with an ion spray needle voltage of 5.2 KV, and a nebulization (Gas 1) at 25 (arbitrary units), curtain gas of 30 (arbitrary units), declustering potential of 150 V and at temperature of 150° C. The. The ADC test sample solutions was introduced at 5 uL/min into the ion source by direct infusion via a fused silica capillary with the help of syringe and syringe pump.

Preparation of the ADC Sample for ESI-ToF MS Analysis

All ADC sample were deglycosylated using EndoS(Ig-GZERO)™ endoglycosidase and buffer exchanged with water prior to EsiToF-MS analysis. Briefly, the original ADC sample was run through a 100K MWCO Amicon concentrator for buffer exchange in sodium phosphate buffer. The buffer exchanged sample was then treated with IgGZERO (1 unit/1 ug of antibody) in sodium phosphate cleavage buffer, containing 150 mM NaCl, and incubated for 30 minutes at 37° C. The resulting deglycosylated ADC was again buffer exchanged with water using a 100K MWCO Amicon concentrator, and diluted with 0.1% formic acid in acetonitrile/water(50/50 v/v %) to a concentration of 3.0 μg/μL prior to analysis.

Analyses indicated that antibody was loaded with a DAR range of between 4-7 (data not shown).

Example 3: Exemplary Antibody-Drug Conjugates

Preparation of Antibody-Drug Conjugates from MCvcPABC-Toxins, General Methods:

To a solution of antibody (1-10 mg/mL) in 25 mM sodium borate, 25 mM sodium chloride, 1 mM DTPA (pH 8.0) was added TCEP from a freshly prepared stock (1-10 mM) in the same buffer (2.0-3.0 molar equivalents). The solution was mixed thoroughly and incubated at 37° C. for two hours before cooling on ice. In some instances the reduced antibody solution was further diluted with either ice-cold phosphate buffered saline containing 1 mM DTPA (final protein concentration 2.0 mg/mL) or ice-cold 25 mM sodium borate, 25 mM sodium chloride, 1 mM DTPA (pH 8.0), to obtain a solution with a final protein concentration of between 1 and 4 mg/mL. To the reduced protein solution stored on ice was added the maleimide functionalized toxin (10-12 molar equivalents) from a 10 mM dmso stock solution. The conjugation reaction was immediately mixed thoroughly by inversion and conjugation was allowed to proceed on ice for a period of approximately 1 hour before purification by passage over Zeba Spin Desalting Columns (40 KDa MWCO; Peirce) pre-equilibrated with phosphate buffered saline or 10 mM sodium citrate, 150 mM sodium chloride, pH 5.5.

The eluate was pooled, filter sterilized (Steriflip, Millipore), and stored at 4° C. The purified ADCs were analyzed for total protein content (bicinchonic acid assay, Pierce microBCA protocol, catalogue #23225). The ADC product was characterized by reducing and non-reducing PAGE, HPLC-HIC, SEC, and RP-UPLC-MS. The average DAR and drug distribution were derived from interpretation of HIC and LC-MS data with reference to non-reducing PAGE. Average DAR estimates were normally in the range of 3.5-4.5. Relative affinity of ADCs for antigen binding (equilibrium native binding) was performed as described (above/below). The selective cytotoxicity of the antibody drug conjugates was assessed by testing for killing of both antigen positive and antigen negative cell lines.

Assay of Selective In Vitro Cytotoxicity of Antigen-Positive Cells by Antibody Drug Conjugates:

Selective killing of an antigen positive cell line (including HCC1954, NCI-N87, HPAF-II and BxPC-3 cell lines) over antigen-negative Jurkat cells was demonstrated for each conjugate prepared. Cytotoxicity of example ADCs on several antigen positive cell lines is summarized in the identified Figures and Tables 9-13. In addition, the conjugates indicated by (*) in Table 11 were tested and showed potent cell kill activity against a human breast cancer cell line (data not shown). Briefly, cells were obtained from the ATCC and cultured as described in the product sheet provided. Cells were seeded at 25000 cells/mL (2500 cells/well) in Costar 3904 black walled, flat bottomed 96-well plates. Adherent cell lines cells were incubated for one night at 37° C. in a 5% $CO_2$ atmosphere to allow the cells to attach to the microtitre plate surface, while suspension (Jurkat) cells were plated immediately before use. ADCs were diluted directly in the appropriate cell growth medium at five-times the desired final concentration. These ADCs were then titrated, normally 1:3, over eight steps. A control with no test article present (growth medium alone) was included on each microtiter plate in sextuplicate. The prepared ADC titrations were added (25 uL/well) in triplicate to each cell line assayed. The cells and titrations were incubated at 37° C./5% $CO_2$ for three nights (Jurkat) and five nights (all other cell lines). After the incubation, cell viability was measured using CellTiter-Glo® reagent by adding thirty uL of prepared CellTiter-Glo® to each assay well. The mixtures were incubated for at least twenty minutes in the dark prior to measuring emitted luminescence using a microplate luminometer (500 ms integration time). The collected relative luminescence units (RLU) were converted to % cytotoxicity using the growth medium alone control mentioned above (% Cytotoxicity=1−[Well RLU/average medium alone control RLU]). Data (% Cytotoxicity vs. Concentration of ADC (log 10 (nM)) were plotted and were analyzed by non-linear regression methods using GraphPad Prism software v. 5.02 to obtain $EC_{50}$ estimates.

Estimation of Drug to Antibody Ratio (DAR):

The average degree of conjugation of toxin-linker to antibody was assessed by hydrophobic interaction chromatography and high performance liquid chromatography-mass spectrometry. These techniques are described in Antibody Drug Conjugates, Methods in Molecular Biology vol. 1045, 2013. pp 275-284. L. Ducry, Ed., and Asish B. Chakraborty, Scott J. Berger and John C. Gebler, Characterization of an IgG1 Monoclonal Antibody and related Sub-structures by LC/ESI-TOF/MS: Application note, Waters Corporation. March 2007. 720002107EN.

Method 1. Hydrophobic Interaction Chromatography

Antibody drug conjugates were subjected to hydrophobic interaction chromatography (HIC) on a TSKgel Butyl-NPR column (Tosoh Bioscience; 4.6 mm×35 mm i.d.; 2.5 um particle size) connected to an Agilent 1100 series HPLC. Samples were injected (5 uL) at or above 4 mg/mL. Where necessary, ADCs were concentrated prior to injection using PALL Nanosep Omega centrifugal concentration devices (part #OD010C34). A linear gradient elution was employed starting at 95% mobile phase A/5% mobile phase B, transitioning to 5% mobile phase A/95% mobile phase B over a period of 12 minutes (mobile phase A: 1.5M ammonium sulfate+25 mM sodium phosphate at pH 6.95 and mobile phase B: 25% isopropanol, 75% 25 mM sodium phosphate at pH 6.95). Injection of unmodified antibody provided a means of identifying the peak with DAR=0. Antibodies were detected on the basis of absorbance at 280 nm.

Method 2. Ultra Performance Liquid Chromatography-Mass Spectrometry for DAR Estimation Reversed phase ultra performance liquid-chromatography tandem ESI-QToF-mass spectrometry (UPLC-ESI-QToF-MS) was used to characterize antibody drug conjugates for extent of drug conjugation following reduction with dithiothreitol. The characterization was performed using Acquity-UPLC (H-class) Bio coupled to a Quatro-Premier QToF mass spectrometer with an electrospray ion source (WATERS Corporation). UPLC analysis of the reduced ADC sample was performed at 70° C. with a PolymerX 5u PR-1 100A, 50×2.0 mm column (Phenomenex, Inc.) and with a mobile phase composed of Solvent A: Acetonitrile/Water/Trifluoroacetic acid/Formic acid (10/90/0.1/0.1, v/v %), and Solvent B: Acetonitrile/Formic acid (100/0.1, % v/v). Components of the reduced ADC sample were eluted with a linear gradient starting at Solvent A/Solvent B (80/20 v/v and a flow rate of 0.3 ml/min to Solvent A/Solvent B (40/60, v/v %) over 25 min, and then to Solvent A/Solvent B(10/90, v/v %) over 2 minutes before equilibrating back to initial conditions. The total run time was 30 minutes. The ESI-Tof MS total ion current (TIC) data was acquired over 500-4500 m/z range using MassLynx data acquisition software (Waters Corporation). Sample component mass data was acquired in the positive ion V-mode, and the ESI source was operated at source temperature: 150° C., desolvation temperature: 350° C., desolvation gas: 800 L/hr, sample cone voltage: 60 V, capillary voltage: 3.0 kV, desolvation gas: nitrogen, and collision gas: argon. The summed TIC mass spectra for each peak was deconvoluted by the MaxEnt1 algorithm to generate the neutral mass data of the peak component.

Preparation of Reduced ADC Samples for UPLC/ESI-ToF MS Analysis

Reduction of the disulfide bonds in the antibody of the ADC (~1 μg/μL solution) to generate the light and heavy chains was performed using 20 mM DTT at 60° C. for 20 minutes. An injection volume of 5-10 μL of the reduced ADC sample was employed for UPLC/ESI-ToF-MS analysis.

Exemplary ADC (PABC) for Illustration Purposes:

TABLE 11

| ADC | ADC Cytotoxicity (EC$_{50}$, nM) | | |
| --- | --- | --- | --- |
| | JIMT-1 | NCI-N87 | HCC1954 |
| *T-VC-PABC-85 | — | — | 0.021 |
| *T-VC-PABC-77 | 0.046 | 0.002 | 0.069 |
| *T-VC-PABC-77 | — | — | 0.023 |
| C-VC-PABC-77 | — | — | — |
| *T-VC-PABC-80 | — | — | 0.018 |
| *T-VC-PABC-58 | — | — | 0.030 |
| *T-VC-PABC-63 | — | — | — |

TABLE 12

| ADC | ADC Cytotoxicity (EC$_{50}$, nM) | | | | | |
| --- | --- | --- | --- | --- | --- | --- |
| | AsPC-1 | BxPC-3 | HPAF II | PANC-1 | OE19 | A549 |
| T-VC-PABC-77 | | | | | 0.01047 | |
| Cetuximab-VC-PABC-77 | 0.00401 | 0.03673 | 0.02637 | 0.1441 | | 0.09405 |

TABLE 13

| ADC | ADC Cytotoxicity (EC$_{50}$, nM) | |
| --- | --- | --- |
| | CAPAN-1 | CAPAN-2 |
| T-VC-PABC-77 | 2.035 | — |
| C-VC-PABC-77 | — | 0.115 |

Example 4: Efficacy Study of Toxins in PC-3 Tumour-Bearing Mice

Figure 14:
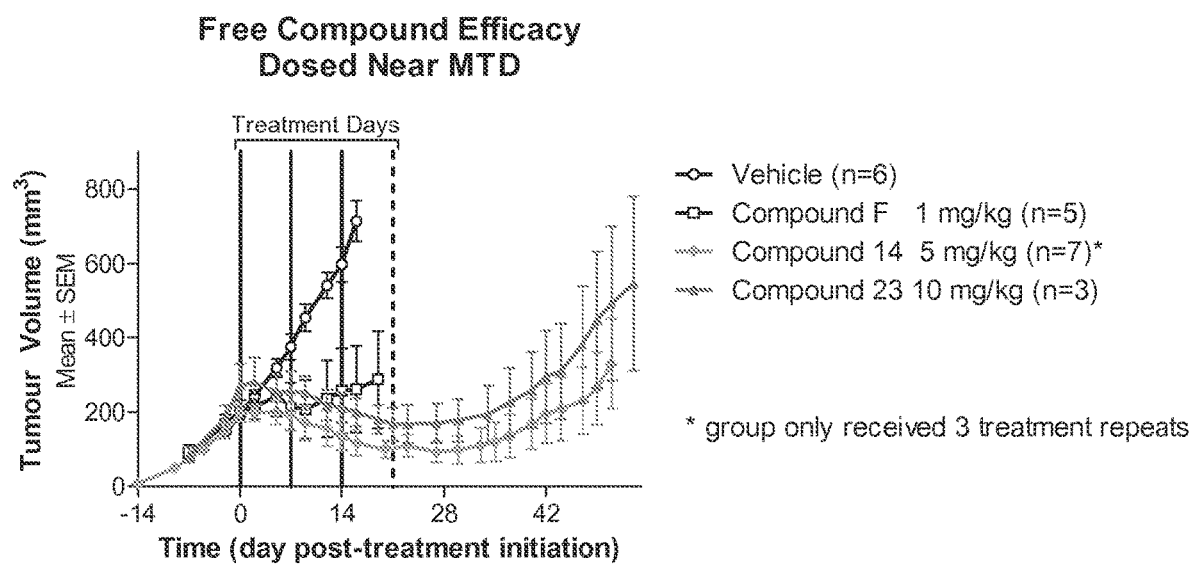
FIG. 14 shows the in vivo results of administration of Compound F, Compound 14, or Compound 23 on tumour volume in female athymic nude mice with established tumours.

Test articles were administered IV. Dosage was as indicated in FIG. 14, each being dosed near maximum tolerated dosage. One injection of test article was delivered every seven days for four repeats/injections (compound D) or one injection every seven days for three repeats/injections (compound 23). Vehicle: 6.3% Trehalose, 0.05% Tween20, 20 mM Citrate Buffer, pH5.0, 4° C.

Procedure Overview

Thirty six (66) female athymic nude mice, purchased from Harlan Laboratories at 7-8 weeks of age, were inoculated subcutaneously in the back with 5×10$^6$ PC-3 tumour cells on experimental day 0. Tumours were measured every

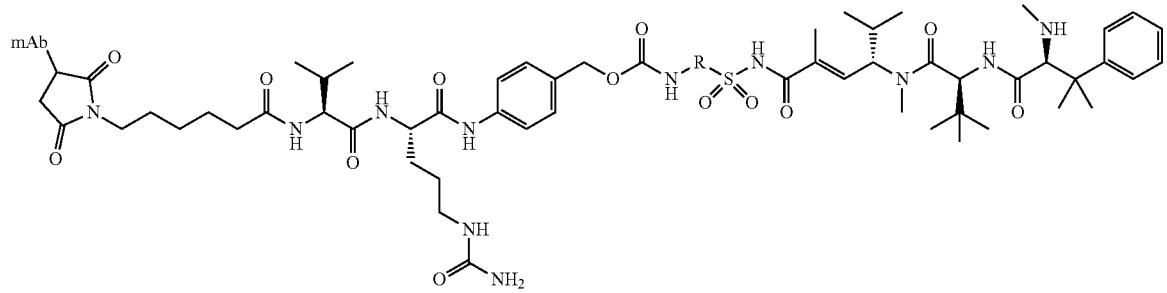

Note that T=Trastuzumab, which is used interchangeably with "Herceptin" herein; VC=valine-citruline; C=Cetuximab (Erbitux)

Monday, Wednesday, and Friday. Once tumors reach 150-200 mm$^3$ in size (experimental day 27 to 34), animals were assigned to one of 4 treatment groups by counterbalancing the average tumor size across groups. Animals were treated with their respective compound as indicated, and tumour measures continued every Monday, Wednesday, and Friday. Data shows animal results to experimental day 54 or until tumours reached 800 mm$^3$ in size.

PC-3 Cells

Cell Preparation-Tissue Culture:

The PC-3 human prostate adenocarcinoma cell line was obtained from ATCC (Cat #CRL-1435) in 2002.

Cells were started from a frozen vial of lab stock which were frozen down from ATCC original vial, tested for *mycoplasma* negative and kept in lab liquid nitrogen tanks. Cell cultures with passage #3 to #10 and a confluence of 80-90% were harvested for in vivo studies. Cells were grown in Ham's F12 medium supplemented with 2 mM L-glutamine and 10% FBS at 37° C. in 5% $CO_2$ environment. Cells were sub-cultured once a week with split ratio 1:3 to 1:6 and expanded. The medium was renewed once a week.

Cell Preparation—Harvesting for Implantation

Cells were rinsed briefly one time with 2 mL of fresh Trypsin/EDTA solution (0.25% trypsin with EDTA 4Na), then the extra trypsin/EDTA was aspirated. Then 1.5 mL of Trypsin/EDTA was added, the flask was laid horizontally to ensure the cells were covered by trypsin/EDTA. The cells were then incubated at 37° C. for a few minutes. The cells were observed under an inverted microscope to ensure the cell layer was dispersed, then fresh medium was added, and 50 µL of cell suspension was sampled and mixed with trypan blue (1:1) and the cells were counted and cell viability assessed using the Cellometer Auto T4. The cells were centrifuged at 1,000 rpm for 7 min and the supernatant aspirated. The cells were then re-suspend in growth medium to the appropriate concentration for inoculation. Injection volume was 100 µL per animal.

Tumour Cell Implantation—SC Back

On Day 0, $5.0 \times 10^6$ tumour cells was implanted subcutaneously into the back of mice in a volume of 100 µL using a 27/28-gauge needle under Isoflurane anesthesia.

Animal Housing

Animals were housed in ventilated cages, 2 to 5 animals per cage, in a 12-hour light/dark cycle. Animals received sterile food and water ad libitum and housing and use of animals was performed in accordance with Canadian Council on Animal Care guidelines. Animals were handled aseptically, and cages changed once every 10-14 days.

Data Collection (Tumour Size)

Mice were monitored every Monday, Wednesday and Friday for tumour development. Dimensions of established tumours was measured with calipers. Tumour volumes were calculated according to the equation $L \times W^2/2$ with the length (mm) being the longer axis of the tumour. Animals were also weighed at the time of tumour measurement. Tumours were allowed to grow to a maximum of 800 mm$^3$.

Institutional Animal Care Committee

The methodology used was reviewed and approved by the University of British Columbia Animal Care Committee (ACC) prior to conducting the studies to ensure studies were planned in accordance with the Canadian Council on Animal Care guidelines. During the study the care, housing and use of animals was performed in accordance with the Canadian Council on Animal Care guidelines.

Analysis Methods

Tumour Volume X Experimental Day Growth Curves

Tumour volumes of each group across the treatment days were plotted. Growth curves were cutoff for each group at the time point when the first animal reached the tumour-size experimental endpoint (800 mm3), or at the last day of the study. Any animal that was withdrawn from the study prior to the group growth curve cutoff was removed entirely from the study.

Animal Exclusions

Any animal with ulcerating tumours, necessitating euthanasia of the animal, with tumour volume of 700 mm$^3$ or smaller were removed from the study and did not contribute to the data analysis (except for Days to Recurrence if the final tumour volume was >2.0 fold higher than on the treatment day).

Figure 15:
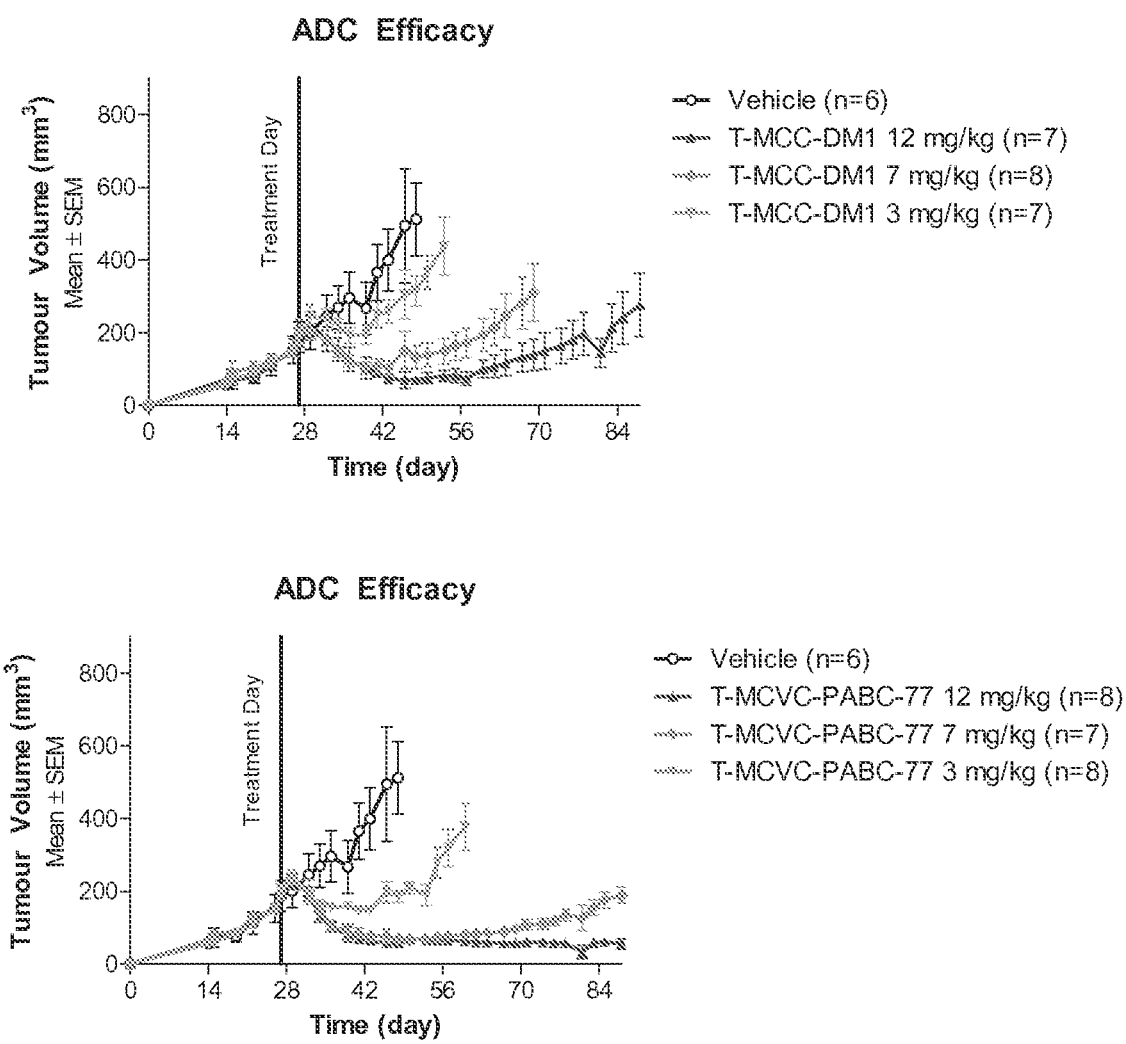
FIG. 15 shows the in vivo results of administration of antibody-drug conjugate T-MCC-DM1 (Trastuzumab, MCC linker, maytansinoid DM1) at varied dosages as indicated, or T-MCvcPABC-77 at varied dosages as indicated, on tumour volume in female NOD/SCID Gamma mice with established tumours.

Example 5: Efficacy Dose Range Finding of Antibody Drug Conjugates in the NCI-N87 Tumour Model Using NOD SCID Gamma Mice Test articles were administered IV, one treatment only. "T" refers to Trastuzumab. Dosage was as indicated in FIG. 15. Vehicle: 20 mM Sodium Citrate, 6.3% Trehalose, 0.02% Tween-20, pH 5, 4° C.

Procedure Overview

Seventy six (76) female NOD/SCID Gamma mice (NSG), purchased from The Jackson Laboratory (JAX® Mice) at 7-8 weeks of age, were inoculated subcutaneously in the lower back with $5 \times 10^6$ NCI-N87 tumour cells in matrigel on experimental day 0. Tumours were measured every Monday, Wednesday, and Friday. Once tumors reach 150-200 mm$^3$ in size (experimental day 27), animals were assigned to one of 10 treatment groups by counterbalancing the average tumor size across groups. Animals were treated with their respective compound as indicated, and tumour measures continued every Monday, Wednesday, and Friday. Data shows animal results to experimental day 50 or until tumours reached 800 mm$^3$ in size.

Cell Preparation-Tissue Culture

NCI-N87 Cells

NCI-N87 human gastric carcinoma cells were derived from a liver metastasis of a well differentiated carcinoma of the stomach taken prior to cytotoxic therapy. The tumor was passaged as a xenograft in athymic nude mice for three passages before the cell line was established. NCI-N87 cells were obtained under MTA from the ATCC (Cat #CRL-5822) in 2013 and were tested negative at RADIL for *Mycoplasma* and mouse pathogens. (RADIL certificate #: 10556-2013)

Cells were started from a frozen vial of lab stock which was frozen down from ATCC original vial and kept in lab liquid nitrogen tanks. Cell cultures with passage #3 to #10 and a confluence of 80-90% were harvested for in vivo studies. NCI-N87 cells were grown in RPMI 1640 medium with 1.0 mM L-glutamine and 10% FBS at 37° C. in 5% CO2 environment. Cells were subcultured once or twice a week with the split ratio 1:3 or 1:4 and expanded. The medium was renewed once a week. Cell were frozen with 5% DMSO.

Cell Preparation—Harvesting for Implantation

Cells were rinsed briefly one time with Hanks Balanced Salt Solution without Ca, Mg. Fresh Trypsin/EDTA solution (0.25% trypsin with EDTA 4Na) was added, and the flask laid horizontally to ensure the cells were covered by trypsin/EDA, and then the extra trypsin/EDTA was aspirated. The cells were incubated at 37° C. for a few minutes. Cells were observed under an inverted microscope until cell layer is dispersed, fresh medium is then added. Then, 50 µL of cell suspension was collected and mix with trypan blue (1:1) and the cells counted and assessed for viability on a haemocytometer. Viability should be >90%. The cells were centrifuged at 125 RCF (1000 rpm) for 7 min and the supernatant aspirated off. The cells were resuspended in cold growth medium to 2 times the desired final concentration ($100 \times 10^6$/mL). The suspension was mixed (on ice) with matrigel (1:1). The resulting cell suspensions ($50 \times 10^6$ cells/mL) was used to deliver $5 \times 10^6$ cells in an injection volume of 100 µL per animal. All equipment coming into contact with matrigel (needles, syringes, pipette tips) were chilled prior to injection.

Tumour Cell Implantation—Subcutaneous (NCI-N87)

Prior to inoculation, approximately 2×2 cm area was shaved in the lower back region of each mouse and cleaned with alcohol. On Day 0, $5.0 \times 10^6$ tumour cells were implanted subcutaneously into the back of mice in a volume of 100 µL using a 27/28-gauge needle under Isoflurane anesthesia.

Animal Housing

Animals were housed in ventilated cages, 2 to 5 animals per cage, in a 12-hour light/dark cycle. Animals received sterile food and water ad libitum and housing and use of animals was performed in accordance with Canadian Council on Animal Care guidelines. Animals were handled aseptically, and cages changed once every 10-14 days.

Data Collection (Tumour Size)

Mice were monitored every Monday, Wednesday and Friday for tumour development. Dimensions of established tumours was measured with calipers. Tumour volumes was calculated according to the equation $L \times W^2/2$ with the length (mm) being the longer axis of the tumour. Animals were also weighed at the time of tumour measurement. Tumours were allowed to grow to a maximum of 800 mm$^3$.

Institutional Animal Care Committee

The methodology used was reviewed and approved by the University of British Columbia Animal Care Committee (ACC) prior to conducting the studies to ensure studies were planned in accordance with the Canadian Council on Animal Care guidelines. During the study the care, housing and use of animals was performed in accordance with the Canadian Council on Animal Care guidelines.

Analysis Methods

Tumour Volume X Experimental Day Growth Curves

Tumour volumes of each group across the treatment days were plotted. Growth curves were cutoff for each group at the time point when the first animal reached the tumour-size experimental endpoint (800 mm3), or at the last day of the study. Any animal that was withdrawn from the study prior to the group growth curve cutoff was removed entirely from the study.

Animal Exclusions

Any animal with ulcerating tumours, necessitating euthanasia of the animal, with tumour volume of 700 mm$^3$ or smaller were removed from the study and did not contribute to the data analysis (except for Days to Recurrence if the final tumour volume was >2.0 fold higher than on the treatment day).

Figure 16:
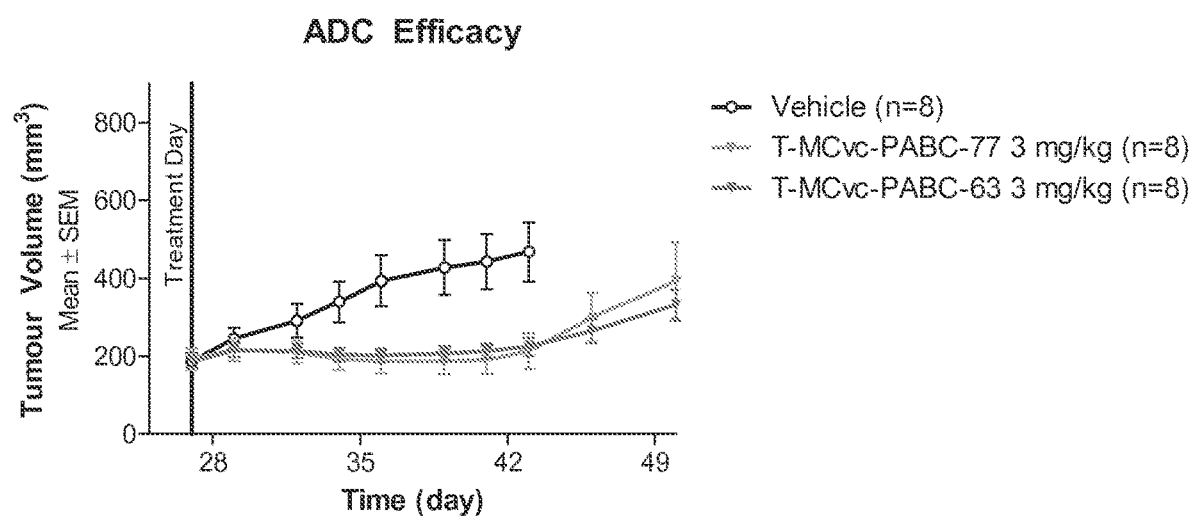
FIG. 16 shows the in vivo results of administration of antibody-drug conjugate T-MCvcPABC-63 at 3 mg/kg, or T-MCvcPABC-77 at 3 mg/kg, on tumour volume in female NOD/SCID Gamma mice with established tumours.
Figure 17:
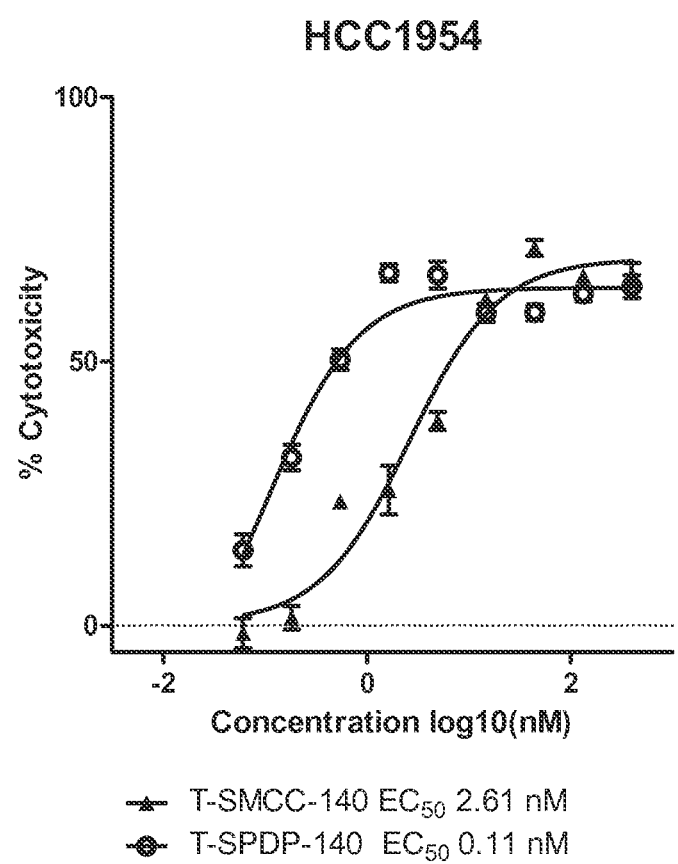
FIG. 17 shows a cell kill curve on HCC 1954 cells in vitro with the antibody-drug conjugates: T-SPDP-140 (Trastuzumab, LC-SPDP linker, Compound 140) and T-SMCC-140 (Trastuzumab, SMCC linker, Compound 140). Compound 140 is linked through the side chain of its N-terminal amino acid. $EC_{50}$ values are shown in the figure.
Figure 18:
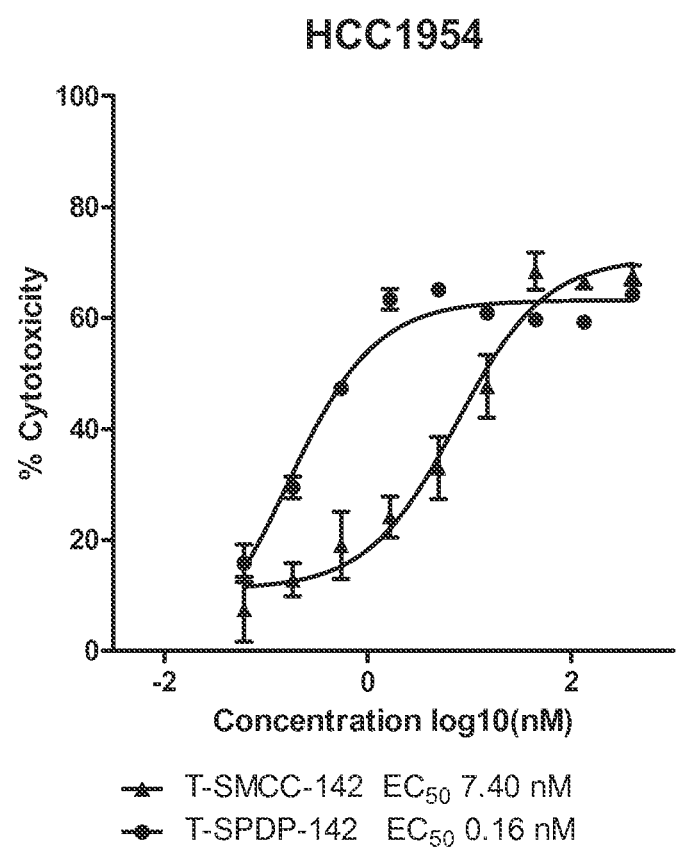
FIG. 18 shows a cell kill curve on HCC 1954 cells in vitro with the antibody-drug conjugates: T-SPDP-142 (Trastuzumab, LC-SPDP linker, Compound 142) and T-SMCC-142 (Trastuzumab, SMCC linker, Compound 142). Compound 142 is linked through the side chain of its N-terminal amino acid. $EC_{50}$ values are shown in the figure.
Figure 19:
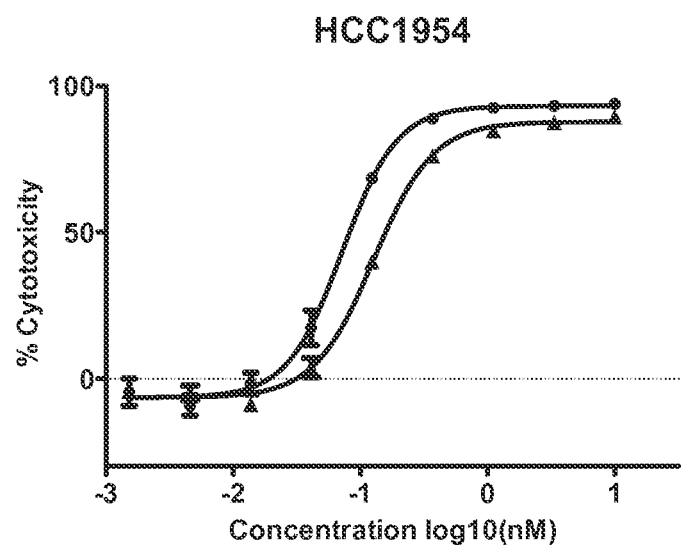
FIG. 19 shows a cell kill curve on HCC1954 cells in vitro with the antibody-drug conjugates: T-MCvcPABC-58, (Trastuzumab, MCvc PABC linker, Compound 58), and T-MCvcPABC-41, (Trastuzumab, MCvc PABC linker, Compound 41), and shows a cell kill curve on NCI-N87 cells in vitro with the antibody-drug conjugates: T-MCvcPABC-58, (Trastuzumab, MCvc PABC linker, Compound 58), and T-MCvcPABC-41, (Trastuzumab, MCvc PABC linker, Compound 41). Compound 41 is linked through the side chain of its N-terminal amino acid. Compound 58 is linked through the side chain of its N-terminal amino acid. $EC_{50}$ values are shown in the figure. $EC_{50}$ values are shown in the figure.
Figure 19:
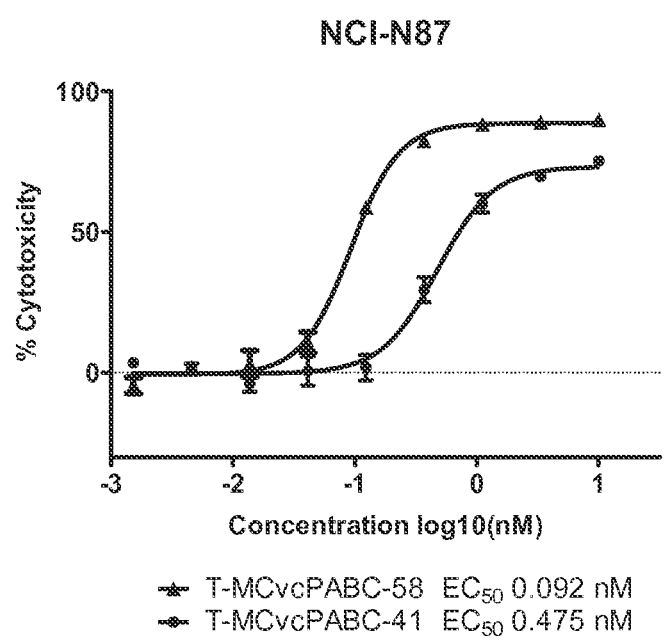

Example 6: Efficacy Comparison of Antibody Drug Conjugates in the NCI-N87 Tumour Model Using NOD SCID Gamma Mice Test articles were administered IV, with one administration. Dosages were as indicated in FIG. 16. "T" refers to Trastuzumab. Vehicle: 20 mM Sodium Citrate, 6.3% Trehalose, 0.02% Tween-20, pH 5, 4° C.

Procedure Overview

Twenty-four (24) female NOD/SCID Gamma mice (NSG), purchased from The Jackson Laboratory (JAX) Mice) at 7-8 weeks of age, were inoculated subcutaneously in the lower back with $5 \times 10^6$ NCI-N87 tumour cells in matrigel on experimental day 0. Tumours were measured every Monday, Wednesday, and Friday. Once tumors reach 150-200 mm$^3$ in size (experimental day 27), animals were assigned to one of 3 treatment groups by counterbalancing the average tumor size across groups. Animals were treated with their respective compound as outlined, and tumour measures continued every Monday, Wednesday, and Friday. Data shows animal results to experimental day 88 or until tumours reached 800 mm$^3$ in size.

Cell Preparation-Tissue Culture

NCI-N87 Cells

NCI-N87 human gastric carcinoma cells were derived from a liver metastasis of a well differentiated carcinoma of the stomach taken prior to cytotoxic therapy. The tumor was passaged as a xenograft in athymic nude mice for three passages before the cell line was established. NCI-N87 cells were obtained under MTA from the ATCC (Cat #CRL-5822) in 2013 and were tested negative at RADIL for *Mycoplasma* and mouse pathogens. (RADIL certificate #: 10556-2013)

Cells were started from a frozen vial of lab stock which was frozen down from ATCC original vial and kept in lab liquid nitrogen tanks. Cell cultures with passage #3 to #10 and a confluence of 80-90% were harvested for in vivo studies. NCI-N87 cells were grown in RPMI 1640 medium with 1.0 mM L-glutamine and 10% FBS at 37° C. in 5% CO2 environment. Cells were subcultured once or twice a week with the split ratio 1:3 or 1:4 and expanded. The medium was renewed once a week. Cell were frozen with 5% DMSO.

Cell Preparation—Harvesting for Implantation

Cells were rinsed briefly one time with Hanks Balanced Salt Solution without Ca, Mg. Fresh Trypsin/EDTA solution (0.25% trypsin with EDTA 4Na) was added, and the flask laid horizontally to ensure the cells were covered by trypsin/EDA, and then the extra trypsin/EDTA was aspirated. The cells were incubated at 37° C. for a few minutes. Cells were observed under an inverted microscope until cell layer is dispersed, fresh medium is then added. Then, 50 µL of cell suspension was collected and mix with trypan blue (1:1) and the cells counted and assessed for viability on a haemocytometer. Viability should be >90%. The cells were centrifuged at 125 RCF (1000 rpm) for 7 min and the supernatant aspirated off. The cells were resuspended in cold growth medium to 2 times the desired final concentration ($100 \times 10^6$/mL). The suspension was mixed (on ice) with matrigel (1:1). The resulting cell suspensions ($50 \times 10^6$ cells/mL) was used to deliver $5 \times 10^6$ cells in an injection volume of 100 µL per animal. All equipment coming into contact with matrigel (needles, syringes, pipette tips) were chilled prior to injection.

Tumour Cell Implantation—Subcutaneous (NCI-N87)

Prior to inoculation, approximately 2×2 cm area was shaved in the lower back region of each mouse and cleaned with alcohol. On Day 0, $5.0 \times 10^6$ tumour cells were implanted subcutaneously into the back of mice in a volume of 100 µL using a 27/28-gauge needle under Isoflurane anesthesia.

Animal Housing

Animals were housed in ventilated cages, 2 to 5 animals per cage, in a 12-hour light/dark cycle. Animals received sterile food and water ad libitum and housing and use of animals was performed in accordance with Canadian Council on Animal Care guidelines. Animals were handled aseptically, and cages changed once every 10-14 days.

Data Collection (Tumour Size)

Mice were monitored every Monday, Wednesday and Friday for tumour development. Dimensions of established tumours was measured with calipers. Tumour volumes were calculated according to the equation $L \times W^2/2$ with the length (mm) being the longer axis of the tumour. Animals were also weighed at the time of tumour measurement. Tumours were allowed to grow to a maximum of 800 mm$^3$.

Institutional Animal Care Committee

The methodology used was reviewed and approved by the University of British Columbia Animal Care Committee (ACC) prior to conducting the studies to ensure studies were planned in accordance with the Canadian Council on Animal Care guidelines. During the study the care, housing and use of animals was performed in accordance with the Canadian Council on Animal Care guidelines.

Analysis Methods

Tumour Volume X Experimental Day Growth Curves

Tumour volumes of each group across the treatment days were plotted. Growth curves were cutoff for each group at the time point when the first animal reached the tumour-size experimental endpoint (800 mm3), or at the last day of the study. Any animal that was withdrawn from the study prior to the group growth curve cutoff was removed entirely from the study.

Animal Exclusions

Any animal with ulcerating tumours, necessitating euthanasia of the animal, with tumour volume of 700 mm$^3$ or smaller were removed from the study and did not contribute to the data analysis (except for Days to Recurrence if the final tumour volume was >2.0 fold higher than on the treatment day).

All of the U.S. patents, U.S. patent application publications, U.S. patent applications, foreign patents, foreign patent applications and non-patent publications referred to in this specification are incorporated herein by reference, in their entirety to the extent not inconsistent with the present description.

From the foregoing it will be appreciated that, although specific embodiments of the disclosure have been described herein for purposes of illustration, various modifications may be made without deviating from the spirit and scope of the disclosure. Accordingly, the disclosure is not limited except as by the appended claims.

What is claimed is:

1. An antibody-drug conjugate comprising a targeting moiety (T), a linker (L) and a drug moiety (D), wherein the targeting moiety (T) is an antibody or antigen-binding antibody fragment and the drug moiety (D) is a compound of Formula (Ib):

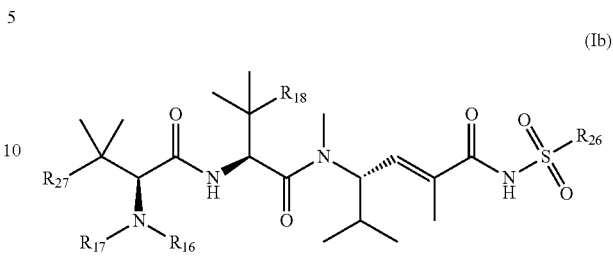

(Ib)

wherein:
   $R_{16}$ is selected from the group consisting of H and $C_{1-6}$ alkyl;
   $R_{17}$ is selected from the group consisting of H and $C_{1-6}$ alkyl;
   $R_{18}$ is $C_{1-6}$ alkyl;
   $R_{26}$ is selected from the group consisting of optionally substituted alkyl and optionally substituted aryl, and
   $R_{27}$ is

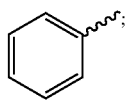

and
   wherein a C-terminus of the drug moiety (D) forms the point of attachment to the targeting moiety (T) via the linker (L).

2. The antibody-drug conjugate according to claim 1, wherein $R_{16}$ is H or methyl.

3. The antibody-drug conjugate according to claim 1, wherein $R_{17}$ is H or methyl.

4. The antibody-drug conjugate according to claim 1, wherein $R_{18}$ is methyl.

5. The antibody-drug conjugate according to claim 1, wherein $R_{16}$ is H, $R_{17}$ is methyl and $R_{18}$ is methyl.

6. The antibody-drug conjugate according to claim 1, wherein $R_{26}$ is optionally substituted alkyl or optionally substituted phenyl.

7. The antibody-drug conjugate according to claim 1, wherein drug moiety (D) is selected from:

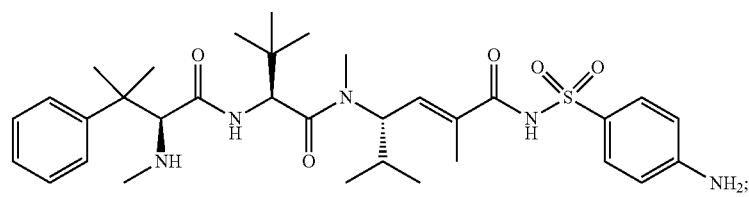

Compound 24

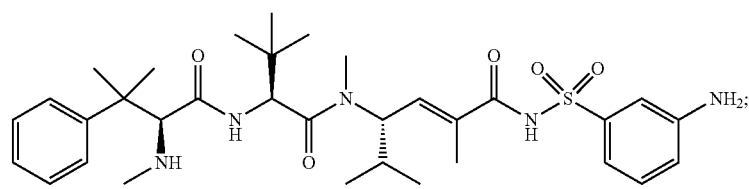

Compound 48

-continued

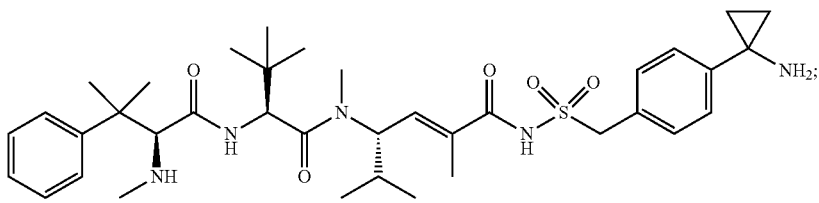

Compound 58

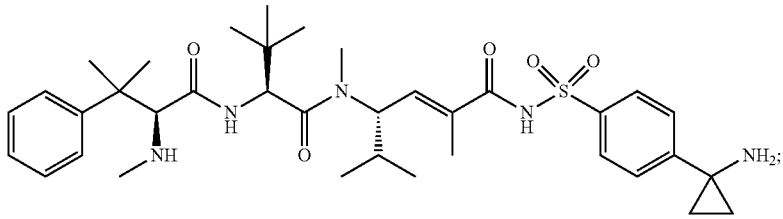

Compound 63

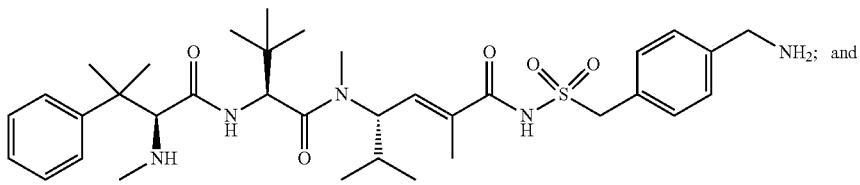

Compound 77

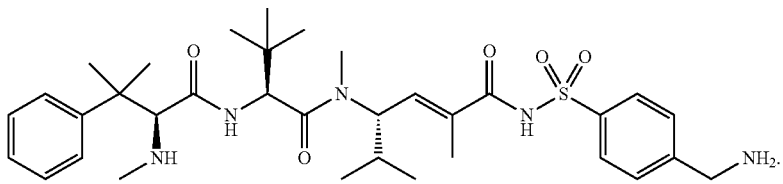

Compound 85

8. The antibody-drug conjugate according to claim 1, wherein drug moiety (D) is:

Compound 24

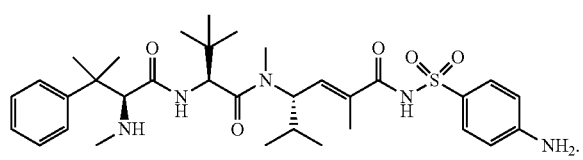

9. The antibody-drug conjugate according to claim 1, wherein linker (L) is a cleavable linker.

10. The antibody-drug conjugate according to claim 1, wherein linker (L) is joined to targeting moiety (T) by reaction of an electrophilic group on linker (L) with a nucleophilic group on targeting moiety (T).

11. The antibody-drug conjugate according to claim 10, wherein the electrophilic group is a maleimide and the nucleophilic group is a sulfhydryl group.

12. The antibody-drug conjugate according to claim 1, wherein targeting moiety (T) is a bispecific antibody or antigen-binding antibody fragment.

13. The antibody-drug conjugate according to claim 1, wherein the antibody or antigen-binding antibody fragment binds a cancer antigen.

14. The antibody-drug conjugate according to claim 8, wherein linker (L) is a cleavable linker.

15. The antibody-drug conjugate according to claim 8, wherein linker (L) is joined to targeting moiety (T) by reaction of an electrophilic group on linker (L) with a nucleophilic group on targeting moiety (T).

16. The antibody-drug conjugate according to claim 15, wherein the electrophilic group is a maleimide and the nucleophilic group is a sulfhydryl group.

17. The antibody-drug conjugate according to claim 8, wherein targeting moiety (T) is a bispecific antibody or antigen-binding antibody fragment.

18. The antibody-drug conjugate according to claim 8, wherein the antibody or antigen-binding antibody fragment binds a cancer antigen.

19. A pharmaceutical composition comprising the antibody-drug conjugate according to claim 1, and a pharmaceutically acceptable carrier, diluent or excipient.

20. A pharmaceutical composition comprising the antibody-drug conjugate according to claim 8, and a pharmaceutically acceptable carrier, diluent or excipient.

21. A method of inhibiting tumor growth in a subject, the method comprising administering to a subject in need thereof an effective amount of the antibody-drug conjugate according to claim 1.

22. The method according to claim 21, wherein the subject is a human.

23. A method of inhibiting tumor growth in a subject, the method comprising administering to a subject in need thereof an effective amount of the antibody-drug conjugate according to claim 8.

24. The method according to claim 23, wherein the subject is a human.

* * * * *